US012779218B2

(12) United States Patent
Neal, II et al.

(10) Patent No.: US 12,779,218 B2
(45) Date of Patent: Nov. 3, 2026

(54) DEVICES, SYSTEMS AND METHODS FOR THE TREATMENT OF ABNORMAL TISSUE

(71) Applicant: Galvanize Therapeutics, Inc., Redwood City, CA (US)

(72) Inventors: Robert E. Neal, II, Redwood City, CA (US); William S. Krimsky, Forest Hill, MD (US); Seth S. Gleiman, Guillford, CT (US); Nicholas S. Mercer, San Francisco, CA (US); Timothy J. O'Brien, Santa Clara, CA (US); Quim Castellvi, Barcelona (ES); Jonathan R. Waldstreicher, West Orange, NJ (US); Kevin J. Taylor, San Mateo, CA (US); Luis L. Mangual Arbelo, Sunnyvale, CA (US); Chiara Pastori, Hayward, CA (US); Ebtesam Nafie, Belmont, CA (US); Mukta S. Wagh, Sunnyvale, CA (US)

(73) Assignee: Galvanize Therapeutics, Inc., Redwood City, CA (US)

( * ) Notice: Subject to any disclaimer, the term of this patent is extended or adjusted under 35 U.S.C. 154(b) by 0 days.

(21) Appl. No.: 19/453,619

(22) Filed: Jan. 20, 2026

(65) Prior Publication Data

US 2026/0151621 A1 Jun. 4, 2026

Related U.S. Application Data

(63) Continuation-in-part of application No. 18/645,220, filed on Apr. 24, 2024, and a continuation of
(Continued)

(51) Int. Cl.
*A61N 1/36* (2006.01)
*A61B 17/00* (2006.01)

(52) U.S. Cl.
CPC .................... *A61N 1/36002* (2017.08); *A61B 2017/00154* (2013.01)

(58) Field of Classification Search
CPC .................. A61N 1/36002; A61B 2017/00154
See application file for complete search history.

(56) References Cited

U.S. PATENT DOCUMENTS

| | | | |
|---|---|---|---|
| 874,178 | A | 12/1907 | Forest |
| 4,249,541 | A | 2/1981 | Pratt |

(Continued)

FOREIGN PATENT DOCUMENTS

| | | | |
|---|---|---|---|
| AT | 306859 | B | 4/1973 |
| AU | 200048007 | | 11/2000 |

(Continued)

OTHER PUBLICATIONS

Al-Sakere, et al., Tumor Ablation with Irreversible Electroporation, *PLoS ONE*, 2(11):e1135. doi:10.1371/journal.pone.0001135 (Nov. 2007).

(Continued)

*Primary Examiner* — Catherine M Voorhees
(74) *Attorney, Agent, or Firm* — Greenberg Traurig, LLP; Christopher C. Bolten

(57) ABSTRACT

Devices, systems and methods are provided to treat damaged, diseased, abnormal, obstructive, cancerous or undesired tissue (e.g. a tumor, a benign tumor, a malignant tumor, a cyst, or an area of diseased tissue, etc) by delivering specialized pulsed electric field (PEF) energy to target tissue areas. The energy is delivered in a manner so as to be non-thermal (i.e. below a threshold for causing thermal ablation). Consequently, when extracellular matrices present, the extracellular matrices are preserved, and the targeted tissue maintains its structural architecture including blood vessels and lymphatics. Thus, sensitive structures, such as
(Continued)

biological lumens, blood vessels, nerves, etc, are preserved which are critical to maintaining the integrity and functionality of the tissue. The energy is delivered with the use of systems and devices advantageously designed for superior access to target tissue throughout the body, particularly in locations previously considered inaccessible to percutaneous approaches.

41 Claims, 41 Drawing Sheets

Related U.S. Application Data application No. 18/416,505, filed on Jan. 18, 2024, said application No. 18/645,220 is a continuation of application No. 17/941,815, filed on Sep. 9, 2022, now abandoned, said application No. 18/416,505 is a continuation-in-part of application No. 17/502,640, filed on Oct. 15, 2021, now Pat. No. 12,599,432, said application No. 17/941,815 is a continuation of application No. 16/914,072, filed on Jun. 26, 2020, now Pat. No. 11,471,208, said application No. 17/502,640 is a continuation of application No. PCT/US2020/028844, filed on Apr. 17, 2020, said application No. 16/914,072 is a continuation of application No. PCT/US2018/067501, filed on Dec. 26, 2018.

(60) Provisional application No. 63/502,877, filed on May 17, 2023, provisional application No. 63/480,440, filed on Jan. 18, 2023, provisional application No. 62/835,846, filed on Apr. 18, 2019, provisional application No. 62/610,430, filed on Dec. 26, 2017.

(56) References Cited

U.S. PATENT DOCUMENTS 4,822,470 A 4/1989 Chang
5,232,856 A 8/1993 Firth
5,304,120 A 4/1994 Crandell et al.
5,386,837 A 2/1995 Sterzer
5,507,724 A 4/1996 Hofmann et al.
5,601,588 A 2/1997 Tonomura et al.
5,683,384 A 11/1997 Gough et al.
5,704,908 A 1/1998 Hofmann et al.
5,833,710 A 11/1998 Jacobson
5,906,609 A 5/1999 Assa et al.
5,972,026 A 10/1999 Laufer et al.
6,009,347 A 12/1999 Hofmann
6,038,478 A 3/2000 Yuen et al.
6,041,252 A 3/2000 Walker et al.
6,078,490 A 6/2000 Walters
6,083,255 A 7/2000 Laufer et al.
6,107,699 A 8/2000 Swanson
6,120,493 A 9/2000 Hofmann
6,200,333 B1 3/2001 Laufer
6,219,577 B1 4/2001 Brown, III et al.
6,233,482 B1 5/2001 Hofmann et al.
6,248,056 B1 6/2001 Persson
6,261,831 B1 7/2001 Agee
6,273,907 B1 8/2001 Laufer
6,283,988 B1 9/2001 Laufer et al.
6,283,989 B1 9/2001 Laufer et al.
6,299,633 B1 10/2001 Laufer
6,326,177 B1 12/2001 Schoenbach et al.
6,366,808 B1 4/2002 Schroeppel et al.
6,411,852 B1 6/2002 Danek et al.
6,488,673 B1 12/2002 Laufer et al.
6,520,950 B1 2/2003 Hofmann et al.
6,569,149 B2 5/2003 Dev et al.
6,634,363 B1 10/2003 Danek et al.
6,678,558 B1 1/2004 Dimmer et al.
6,697,670 B2 2/2004 Chomenky et al.
6,733,485 B1 5/2004 Whitehurst et al.
6,738,663 B2 5/2004 Schroeppel et al.
6,770,070 B1 8/2004 Balbierz
6,795,728 B2 9/2004 Chornenky et al.
6,892,099 B2 5/2005 Jaafar et al.
6,994,706 B2 2/2006 Chornenky et al.
7,027,869 B2 4/2006 Danek et al.
7,054,685 B2 5/2006 Dimmer et al.
7,104,987 B2 9/2006 Biggs et al.
7,130,697 B2 10/2006 Chornenky et al.
7,171,263 B2 1/2007 Darvish
7,198,635 B2 4/2007 Danek et al.
7,200,445 B1 4/2007 Dalbec et al.
7,211,083 B2 5/2007 Chornenky et al.
7,255,693 B1 8/2007 Johnston et al.
7,264,002 B2 9/2007 Danek et al.
7,273,055 B2 9/2007 Danek et al.
7,344,533 B2 3/2008 Pearson et al.
7,395,112 B2 7/2008 Keisari et al.
7,412,284 B2 8/2008 Hofmann
7,412,285 B2 8/2008 Schroeppel et al.
7,425,212 B1 9/2008 Danek et al.
7,445,618 B2 11/2008 Eggers et al.
7,542,802 B2 6/2009 Danek et al.
7,556,624 B2 7/2009 Laufer et al.
7,565,205 B2 7/2009 Palti
7,565,206 B2 7/2009 Palti
7,594,925 B2 9/2009 Danek et al.
7,599,745 B2 10/2009 Palti
7,599,746 B2 10/2009 Palti
7,620,451 B2 11/2009 Demarais et al.
7,655,004 B2 2/2010 Long
7,680,543 B2 3/2010 Azure
7,708,768 B2 5/2010 Danek et al.
7,713,740 B2 5/2010 Jaroszeski et al.
7,722,606 B2 5/2010 Azure
7,740,017 B2 6/2010 Danek et al.
7,742,811 B2 6/2010 Schroeppel et al.
7,756,583 B2 7/2010 Demarais et al.
7,765,010 B2 7/2010 Chornenky et al.
7,770,584 B2 8/2010 Danek et al.
7,805,201 B2 9/2010 Palti
7,819,908 B2 10/2010 Ingenito
7,824,870 B2 11/2010 Kovalcheck et al.
7,837,679 B2 11/2010 Biggs et al.
RE42,016 E 12/2010 Chornenky et al.
7,853,331 B2 12/2010 Kaplan et al.
7,853,333 B2 12/2010 Demarais
7,854,734 B2 12/2010 Biggs et al.
7,879,610 B1 2/2011 Heller et al.
7,906,124 B2 3/2011 Laufer et al.
7,917,227 B2 3/2011 Palti
RE42,277 E 4/2011 Jaafar et al.
7,921,855 B2 4/2011 Danek et al.
7,931,647 B2 4/2011 Wizeman et al.
7,937,143 B2 5/2011 Demarais et al.
7,938,123 B2 5/2011 Danek et al.
7,938,824 B2 5/2011 Chornenky et al.
7,949,407 B2 5/2011 Kaplan et al.
7,959,628 B2 6/2011 Schaer et al.
7,992,572 B2 8/2011 Danek et al.
8,007,496 B2 8/2011 Rioux et al.
8,014,854 B2 9/2011 Schroeppel et al.
8,019,414 B2 9/2011 Palti
8,024,048 B2 9/2011 Schroeppel et al.
8,026,223 B1 9/2011 Heller et al.
RE42,835 E 10/2011 Chornenky et al.
8,048,067 B2 11/2011 Davalos et al.
RE43,009 E 12/2011 Chornenky et al.
8,105,324 B2 1/2012 Palanker et al.
8,109,926 B2 2/2012 Azure
8,114,070 B2 2/2012 Rubinsky et al.
8,120,207 B2 2/2012 Sanders et al.
8,131,371 B2 3/2012 Demarals et al.
8,145,316 B2 3/2012 Deem et al.
8,145,317 B2 3/2012 Demarais et al.
8,150,519 B2 4/2012 Demarais et al.
8,150,520 B2 4/2012 Demarais et al.

(56) References Cited

U.S. PATENT DOCUMENTS

| | | | |
|---|---|---|---|
| 8,161,978 | B2 | 4/2012 | Danek et al. |
| 8,181,656 | B2 | 5/2012 | Danek et al. |
| 8,221,411 | B2 | 7/2012 | Francischelli et al. |
| 8,231,603 | B2 | 7/2012 | Hobbs et al. |
| 8,235,983 | B2 | 8/2012 | Webster et al. |
| 8,244,345 | B2 | 8/2012 | Palti |
| 8,251,070 | B2 | 8/2012 | Danek et al. |
| 8,251,986 | B2 | 8/2012 | Chornenky et al. |
| 8,257,413 | B2 | 9/2012 | Danek et al. |
| 8,267,094 | B2 | 9/2012 | Danek et al. |
| 8,282,631 | B2 | 10/2012 | Davalos et al. |
| 8,292,882 | B2 | 10/2012 | Danek et al. |
| 8,298,222 | B2 | 10/2012 | Rubinsky et al. |
| 8,298,224 | B2 | 10/2012 | Danek et al. |
| 8,406,870 | B2 | 3/2013 | Palti |
| 8,425,505 | B2 | 4/2013 | Long |
| 8,428,710 | B2 | 4/2013 | Kuriyama et al. |
| 8,443,810 | B2 | 5/2013 | Danek et al. |
| 8,449,538 | B2 | 5/2013 | Long |
| 8,459,268 | B2 | 6/2013 | Danek et al. |
| 8,464,723 | B2 | 6/2013 | Danek et al. |
| 8,465,484 | B2 | 6/2013 | Davalos et al. |
| 8,465,486 | B2 | 6/2013 | Danek et al. |
| 8,480,667 | B2 | 7/2013 | Kaplan et al. |
| 8,500,713 | B2 | 8/2013 | Ferek-Petric |
| 8,504,147 | B2 | 8/2013 | Deem et al. |
| 8,512,334 | B2 | 8/2013 | Nuccitelli et al. |
| 8,521,274 | B2 | 8/2013 | Gutsol et al. |
| 8,534,291 | B2 | 9/2013 | Danek et al. |
| 8,540,710 | B2 | 9/2013 | Johnson et al. |
| 8,562,588 | B2 | 10/2013 | Hobbs et al. |
| 8,568,403 | B2 | 10/2013 | Soltesz et al. |
| 8,579,888 | B2 | 11/2013 | Hoey et al. |
| 8,584,681 | B2 | 11/2013 | Danek et al. |
| 8,600,494 | B2 | 12/2013 | Schroeppel et al. |
| 8,603,087 | B2 | 12/2013 | Rubinsky et al. |
| 8,620,423 | B2 | 12/2013 | Demarais et al. |
| 8,632,534 | B2 | 1/2014 | Pearson et al. |
| 8,634,929 | B2 | 1/2014 | Chornenky et al. |
| 8,636,726 | B1 | 1/2014 | Wells et al. |
| 8,640,711 | B2 | 2/2014 | Danek et al. |
| 8,647,338 | B2 | 2/2014 | Chornenky et al. |
| 8,652,130 | B2 | 2/2014 | Kreindel |
| 8,676,309 | B2 | 3/2014 | Deem et al. |
| 8,721,632 | B2 | 5/2014 | Hoey et al. |
| 8,733,367 | B2 | 5/2014 | Danek et al. |
| 8,740,895 | B2 | 6/2014 | Mayse et al. |
| 8,753,335 | B2 | 6/2014 | Moshe et al. |
| 8,774,922 | B2 | 7/2014 | Zarins et al. |
| 8,777,943 | B2 | 7/2014 | Mayse et al. |
| 8,802,643 | B1 | 8/2014 | Heller et al. |
| 8,814,860 | B2 | 8/2014 | Davalos et al. |
| 8,828,945 | B2 | 9/2014 | Laufer et al. |
| 8,888,769 | B2 | 11/2014 | Biggs et al. |
| 8,903,488 | B2 | 12/2014 | Callas et al. |
| 8,906,006 | B2 | 12/2014 | Chornenky et al. |
| 8,911,430 | B2 | 12/2014 | Hoey et al. |
| 8,911,439 | B2 | 12/2014 | Mayse et al. |
| 8,920,413 | B2 | 12/2014 | Danek et al. |
| 8,926,606 | B2 | 1/2015 | Davalos et al. |
| 8,927,518 | B1 | 1/2015 | Heller et al. |
| 8,944,071 | B2 | 2/2015 | Loomas et al. |
| 8,968,210 | B2 | 3/2015 | Mugan et al. |
| 8,974,417 | B2 | 3/2015 | Kimura et al. |
| 8,992,513 | B2 | 3/2015 | Delaney |
| 8,992,517 | B2 | 3/2015 | Davalos et al. |
| 9,005,189 | B2 | 4/2015 | Davalos et al. |
| 9,017,324 | B2 | 4/2015 | Mayse et al. |
| 9,027,564 | B2 | 5/2015 | Danek et al. |
| 9,033,976 | B2 | 5/2015 | Danek et al. |
| 9,037,230 | B2 | 5/2015 | Goldfarb et al. |
| 9,078,665 | B2 | 7/2015 | Moss et al. |
| 9,095,323 | B2 | 8/2015 | Chu et al. |
| 9,101,764 | B2 | 8/2015 | Nuccitelli et al. |
| 9,108,052 | B2 | 8/2015 | Jarrard |
| 9,125,666 | B2 | 9/2015 | Steinke et al. |
| 9,144,449 | B2 | 9/2015 | Burr et al. |
| 9,168,373 | B2 | 10/2015 | Nuccitelli et al. |
| 9,173,704 | B2 | 11/2015 | Hobbs et al. |
| 9,186,128 | B2 | 11/2015 | Mugan et al. |
| 9,198,733 | B2 | 12/2015 | Neal, II et al. |
| 9,199,091 | B2 | 12/2015 | Danek et al. |
| 9,211,155 | B2 | 12/2015 | Fruland et al. |
| 9,242,041 | B2 | 1/2016 | Kosik et al. |
| 9,259,235 | B2 | 2/2016 | Chierchia et al. |
| 9,265,563 | B2 | 2/2016 | Racz et al. |
| 9,272,132 | B2 | 3/2016 | Laufer et al. |
| 9,277,957 | B2 | 3/2016 | Long et al. |
| 9,283,374 | B2 | 3/2016 | Hollett et al. |
| 9,289,606 | B2 | 3/2016 | Paul et al. |
| 9,295,516 | B2 | 3/2016 | Pearson et al. |
| 9,301,796 | B2 | 4/2016 | Burr et al. |
| 9,308,043 | B2 | 4/2016 | Zarins et al. |
| 9,308,044 | B2 | 4/2016 | Zarins et al. |
| 9,314,620 | B2 | 4/2016 | Long et al. |
| 9,327,122 | B2 | 5/2016 | Zarins et al. |
| 9,332,973 | B2 | 5/2016 | McWeeney et al. |
| 9,339,328 | B2 | 5/2016 | Ortiz et al. |
| 9,339,618 | B2 | 5/2016 | Deem et al. |
| 9,358,024 | B2 | 6/2016 | Danek et al. |
| 9,375,268 | B2 | 6/2016 | Long |
| 9,414,881 | B2 | 8/2016 | Callas et al. |
| 9,439,726 | B2 | 9/2016 | Zarins et al. |
| 9,486,266 | B2 | 11/2016 | Soltesz et al. |
| 9,510,888 | B2 | 12/2016 | Lalonde |
| 9,526,568 | B2 | 12/2016 | Ohri et al. |
| 9,572,619 | B2 | 2/2017 | Laufer et al. |
| 9,598,691 | B2 | 3/2017 | Davalos |
| 9,610,067 | B2 | 4/2017 | Sekikawa |
| 9,610,364 | B1 | 4/2017 | Heller et al. |
| 9,629,912 | B2 | 4/2017 | Soikum et al. |
| 9,649,153 | B2 | 5/2017 | Mayse et al. |
| 9,649,154 | B2 | 5/2017 | Mayse et al. |
| 9,655,669 | B2 | 5/2017 | Palti et al. |
| 9,656,055 | B2 | 5/2017 | Weissberg et al. |
| 9,656,066 | B2 | 5/2017 | Nuccitelli et al. |
| 9,668,809 | B2 | 6/2017 | Mayse et al. |
| 9,675,406 | B2 | 6/2017 | Moss et al. |
| 9,675,412 | B2 | 6/2017 | Mayse et al. |
| 9,681,909 | B2 | 6/2017 | Bhargav et al. |
| 9,700,368 | B2 | 7/2017 | Callas et al. |
| 9,717,552 | B2 | 8/2017 | Cosman |
| 9,724,155 | B2 | 8/2017 | Nuccitelli et al. |
| 9,788,707 | B2 | 10/2017 | Tinkham et al. |
| 9,789,331 | B2 | 10/2017 | Danek et al. |
| 9,820,724 | B2 | 11/2017 | Mamiya |
| 9,820,797 | B2 | 11/2017 | Burr et al. |
| 9,833,617 | B2 | 12/2017 | Travers et al. |
| 9,867,648 | B2 | 1/2018 | Mulcahey et al. |
| 9,867,652 | B2 | 1/2018 | Sano et al. |
| 9,877,708 | B2 | 1/2018 | McWeeney et al. |
| 9,888,956 | B2 | 2/2018 | Model et al. |
| 9,895,189 | B2 | 2/2018 | Pearson |
| 9,931,161 | B2 | 4/2018 | Willis |
| 9,931,163 | B2 | 4/2018 | Danek et al. |
| 9,943,684 | B2 | 4/2018 | Nuccitelli et al. |
| 9,956,391 | B2 | 5/2018 | Weissberg et al. |
| 9,974,609 | B2 | 5/2018 | Hollett et al. |
| 9,987,081 | B1 | 6/2018 | Bowers et al. |
| 9,993,296 | B2 | 6/2018 | Ladtkow et al. |
| 9,999,465 | B2 | 6/2018 | Long et al. |
| 10,010,666 | B2 | 7/2018 | Rubinsky et al. |
| 10,016,232 | B1 | 7/2018 | Bowers et al. |
| D831,199 | S | 10/2018 | Holton et al. |
| D832,426 | S | 10/2018 | Holton et al. |
| 10,130,423 | B1 | 11/2018 | Viswanathan et al. |
| 10,136,943 | B1 | 11/2018 | Cosman, Jr. et al. |
| 10,143,512 | B2 | 12/2018 | Rubinsky et al. |
| 10,143,759 | B1 | 12/2018 | Heller et al. |
| 10,149,714 | B2 | 12/2018 | Mayse et al. |
| 10,154,869 | B2 | 12/2018 | Onik et al. |
| 10,154,874 | B2 | 12/2018 | Davalos et al. |
| 10,166,071 | B2 | 1/2019 | Sherman et al. |
| 10,172,673 | B2 | 1/2019 | Viswanathan et al. |

(56) References Cited

U.S. PATENT DOCUMENTS

| | | | |
|---|---|---|---|
| 10,238,447 | B2 | 3/2019 | Neal, II et al. |
| 10,245,105 | B2 | 4/2019 | Davalos et al. |
| 10,271,893 | B2 | 4/2019 | Stewart et al. |
| 10,292,755 | B2 | 5/2019 | Arena et al. |
| 10,322,286 | B2 | 6/2019 | Viswanathan et al. |
| 10,391,125 | B2 | 8/2019 | Nuccitelli et al. |
| 10,426,847 | B2 | 10/2019 | Pierce et al. |
| 10,448,989 | B2 | 10/2019 | Arena et al. |
| 10,471,254 | B2 | 11/2019 | Sano et al. |
| 10,499,980 | B2 | 12/2019 | Shuman et al. |
| 10,639,098 | B2 | 5/2020 | Cosman |
| 10,694,972 | B2 | 6/2020 | Davalos et al. |
| 10,702,337 | B2 | 7/2020 | Waldstreicher et al. |
| 10,722,322 | B2 | 7/2020 | Vazales |
| 10,779,887 | B2 | 9/2020 | Deem et al. |
| 10,849,678 | B2 | 12/2020 | Onik et al. |
| 10,874,451 | B2 | 12/2020 | Athos et al. |
| 10,939,958 | B2 | 3/2021 | Waldstreicher et al. |
| 10,945,714 | B2 | 3/2021 | Ralph |
| 11,039,819 | B2 | 6/2021 | Gonzalez |
| 11,051,871 | B2 | 7/2021 | Nuccitelli et al. |
| 11,052,246 | B2 | 7/2021 | Stewart et al. |
| 11,065,372 | B2 | 7/2021 | Stender et al. |
| 11,071,530 | B2 | 7/2021 | Wang et al. |
| 11,167,095 | B2 | 11/2021 | Ralph et al. |
| 11,324,543 | B2 | 5/2022 | Waldstreicher et al. |
| 11,369,433 | B2 | 6/2022 | Waldstreicher et al. |
| 11,382,681 | B2 | 7/2022 | Arena et al. |
| 11,471,208 | B2 * | 10/2022 | Waldstreicher .... A61B 18/1206 |
| 11,547,851 | B2 | 1/2023 | Krimsky et al. |
| 11,638,603 | B2 | 5/2023 | Sano et al. |
| 11,696,797 | B2 | 7/2023 | Onik |
| 11,723,712 | B2 | 8/2023 | Athos et al. |
| 11,737,810 | B2 | 8/2023 | Davalos et al. |
| 11,903,690 | B2 | 2/2024 | Davalos et al. |
| 11,938,317 | B2 | 3/2024 | Krimsky et al. |
| 11,952,568 | B2 | 4/2024 | Neal, II et al. |
| 12,059,197 | B2 | 8/2024 | Davalos et al. |
| 12,173,280 | B2 | 12/2024 | Neal, II et al. |
| 12,178,496 | B2 | 12/2024 | Jauregui Johnston et al. |
| 12,201,349 | B2 | 1/2025 | Pearson et al. |
| 12,349,967 | B2 | 7/2025 | Waldstreicher et al. |
| 12,403,305 | B2 | 9/2025 | Waldstreicher et al. |
| 12,458,433 | B2 | 11/2025 | Akagane et al. |
| 12,458,434 | B2 | 11/2025 | O'Brien et al. |
| 12,575,879 | B2 | 3/2026 | Waldstreicher et al. |
| 12,599,432 | B2 | 4/2026 | Gleiman et al. |
| 2001/0008016 | A1 | 7/2001 | Kotani et al. |
| 2001/0020166 | A1 | 9/2001 | Daly et al. |
| 2002/0010491 | A1 | 1/2002 | Schoenbach et al. |
| 2002/0022839 | A1 | 2/2002 | Stewart et al. |
| 2002/0103483 | A1 | 8/2002 | Edwards |
| 2002/0104318 | A1 | 8/2002 | Jaafar et al. |
| 2002/0115991 | A1 | 8/2002 | Edwards |
| 2002/0188242 | A1 | 12/2002 | Wu |
| 2002/0198567 | A1 | 12/2002 | Keisari et al. |
| 2003/0170898 | A1 | 9/2003 | Gundersen et al. |
| 2003/0199050 | A1 | 10/2003 | Mangano et al. |
| 2004/0029240 | A1 | 2/2004 | Acker |
| 2004/0044338 | A1 | 3/2004 | Lennox et al. |
| 2004/0047855 | A1 | 3/2004 | Ingenito |
| 2004/0068296 | A1 | 4/2004 | Palti |
| 2004/0102818 | A1 | 5/2004 | Hakky et al. |
| 2004/0158288 | A1 | 8/2004 | Keisari et al. |
| 2004/0176804 | A1 | 9/2004 | Palti |
| 2005/0010270 | A1 | 1/2005 | Laufer |
| 2005/0049542 | A1 | 3/2005 | Sigg et al. |
| 2005/0096584 | A1 | 5/2005 | Ferek-Petric |
| 2005/0096644 | A1 | 5/2005 | Hall et al. |
| 2005/0096647 | A1 | 5/2005 | Steinke et al. |
| 2005/0170510 | A1 | 8/2005 | Huang et al. |
| 2005/0171523 | A1 | 8/2005 | Rubinsky et al. |
| 2005/0171574 | A1 | 8/2005 | Rubinsky et al. |
| 2005/0171575 | A1 | 8/2005 | Dev et al. |
| 2005/0177150 | A1 | 8/2005 | Amoah et al. |
| 2005/0222646 | A1 | 10/2005 | Kroll et al. |
| 2005/0288730 | A1 | 12/2005 | Deem et al. |
| 2006/0008808 | A1 | 1/2006 | Yang et al. |
| 2006/0264752 | A1 | 11/2006 | Rubinsky et al. |
| 2006/0269531 | A1 | 11/2006 | Beebe et al. |
| 2006/0293725 | A1 | 12/2006 | Rubinsky et al. |
| 2006/0293731 | A1 | 12/2006 | Rubinsky et al. |
| 2007/0021803 | A1 | 1/2007 | Deem et al. |
| 2007/0025919 | A1 | 2/2007 | Deem et al. |
| 2007/0083239 | A1 | 4/2007 | Demarais et al. |
| 2007/0093802 | A1 | 4/2007 | Danek et al. |
| 2007/0106296 | A1 | 5/2007 | Laufer et al. |
| 2007/0106348 | A1 | 5/2007 | Laufer |
| 2007/0112349 | A1 | 5/2007 | Danek et al. |
| 2007/0118184 | A1 | 5/2007 | Danek et al. |
| 2007/0118190 | A1 | 5/2007 | Danek et al. |
| 2007/0123958 | A1 | 5/2007 | Laufer |
| 2007/0129720 | A1 | 6/2007 | Demarais et al. |
| 2007/0156135 | A1 | 7/2007 | Rubinsky et al. |
| 2007/0191904 | A1 | 8/2007 | Libbus et al. |
| 2007/0239213 | A1 | 10/2007 | Palti |
| 2008/0015571 | A1 | 1/2008 | Rubinsky et al. |
| 2008/0071264 | A1 | 3/2008 | Azure |
| 2008/0132884 | A1 | 6/2008 | Rubinsky et al. |
| 2008/0132885 | A1 | 6/2008 | Rubinsky et al. |
| 2008/0161801 | A1 | 7/2008 | Steinke et al. |
| 2008/0195174 | A1 | 8/2008 | Walker et al. |
| 2008/0200912 | A1 | 8/2008 | Long |
| 2008/0231337 | A1 | 9/2008 | Krishnaswamy et al. |
| 2008/0269586 | A1 | 10/2008 | Rubinsky et al. |
| 2008/0306570 | A1 | 12/2008 | Rezai et al. |
| 2008/0319372 | A1 | 12/2008 | Palti et al. |
| 2009/0043301 | A1 | 2/2009 | Jarrard et al. |
| 2009/0069797 | A1 | 3/2009 | Danek et al. |
| 2009/0118726 | A1 | 5/2009 | Auth et al. |
| 2009/0157002 | A1 | 6/2009 | Dumot et al. |
| 2009/0192504 | A1 | 7/2009 | Askew |
| 2009/0192505 | A1 | 7/2009 | Askew et al. |
| 2009/0192508 | A1 | 7/2009 | Laufer et al. |
| 2009/0247933 | A1 | 10/2009 | Maor et al. |
| 2009/0281477 | A1 | 11/2009 | Mikus et al. |
| 2009/0292342 | A1 | 11/2009 | Rubinsky et al. |
| 2009/0306644 | A1 | 12/2009 | Mayse et al. |
| 2009/0318914 | A1 | 12/2009 | Utley et al. |
| 2010/0004623 | A1 | 1/2010 | Hamilton, Jr. et al. |
| 2010/0023004 | A1 | 1/2010 | Francischelli et al. |
| 2010/0121270 | A1 | 5/2010 | Gunday et al. |
| 2010/0130975 | A1 | 5/2010 | Long |
| 2010/0147701 | A1 | 6/2010 | Field |
| 2010/0152725 | A1 | 6/2010 | Pearson et al. |
| 2010/0160906 | A1 | 6/2010 | Jarrard |
| 2010/0179530 | A1 | 7/2010 | Long et al. |
| 2010/0204688 | A1 | 8/2010 | Hoey et al. |
| 2010/0228248 | A1 | 9/2010 | Griffin |
| 2010/0240995 | A1 | 9/2010 | Nuccitelli et al. |
| 2010/0256628 | A1 | 10/2010 | Pearson et al. |
| 2010/0256630 | A1 | 10/2010 | Hamilton, Jr. et al. |
| 2010/0261994 | A1 | 10/2010 | Davalos et al. |
| 2010/0274236 | A1 | 10/2010 | Krimsky |
| 2010/0324616 | A1 | 12/2010 | Livnat et al. |
| 2011/0105726 | A1 | 5/2011 | Rosen et al. |
| 2011/0112527 | A1 | 5/2011 | Hamilton, Jr. et al. |
| 2011/0118732 | A1 | 5/2011 | Rubinsky et al. |
| 2011/0152855 | A1 | 6/2011 | Mayse et al. |
| 2011/0166565 | A1 | 7/2011 | Wizeman et al. |
| 2011/0190662 | A1 | 8/2011 | McWeeney |
| 2011/0196288 | A1 | 8/2011 | Kaplan et al. |
| 2011/0202052 | A1 | 8/2011 | Gelbart et al. |
| 2011/0208166 | A1 | 8/2011 | Dumot et al. |
| 2011/0288545 | A1 | 11/2011 | Beebe et al. |
| 2012/0098351 | A1 | 4/2012 | Ross |
| 2012/0109122 | A1 | 5/2012 | Arena et al. |
| 2012/0143120 | A1 | 6/2012 | Goldfarb et al. |
| 2012/0150172 | A1 | 6/2012 | Ortiz et al. |
| 2012/0197243 | A1 | 8/2012 | Sherman et al. |
| 2012/0220998 | A1 | 8/2012 | Long et al. |
| 2012/0220999 | A1 | 8/2012 | Long |
| 2012/0226101 | A1 | 9/2012 | Tinkham et al. |
| 2012/0226271 | A1 | 9/2012 | Callas et al. |

(56) References Cited

U.S. PATENT DOCUMENTS

| | | | |
|---|---|---|---|
| 2012/0277741 | A1 | 11/2012 | Davalos et al. |
| 2012/0310237 | A1 | 12/2012 | Swanson |
| 2012/0315704 | A1 | 12/2012 | Beebe et al. |
| 2012/0330299 | A1 | 12/2012 | Webster et al. |
| 2012/0330306 | A1 | 12/2012 | Long et al. |
| 2013/0006144 | A1 | 1/2013 | Clancy et al. |
| 2013/0023873 | A1 | 1/2013 | Danek et al. |
| 2013/0030425 | A1 | 1/2013 | Stewart et al. |
| 2013/0030430 | A1 | 1/2013 | Stewart et al. |
| 2013/0035747 | A1 | 2/2013 | Danek et al. |
| 2013/0184702 | A1 | 7/2013 | Neal, II et al. |
| 2013/0196441 | A1 | 8/2013 | Rubinsky et al. |
| 2013/0211402 | A1 | 8/2013 | Danek et al. |
| 2013/0218158 | A1 | 8/2013 | Danek et al. |
| 2013/0225996 | A1 | 8/2013 | Dillard et al. |
| 2013/0226167 | A1 | 8/2013 | Kaplan et al. |
| 2013/0253415 | A1 | 9/2013 | Sano et al. |
| 2013/0261389 | A1 | 10/2013 | Long |
| 2013/0261683 | A1 | 10/2013 | Soikum et al. |
| 2014/0018789 | A1 | 1/2014 | Kaplan et al. |
| 2014/0018790 | A1 | 1/2014 | Kaplan et al. |
| 2014/0025063 | A1 | 1/2014 | Kaplan et al. |
| 2014/0039489 | A1 | 2/2014 | Davalos et al. |
| 2014/0039491 | A1 | 2/2014 | Bakos et al. |
| 2014/0046322 | A1 | 2/2014 | Callas et al. |
| 2014/0052126 | A1 | 2/2014 | Long et al. |
| 2014/0058294 | A1 | 2/2014 | Gross et al. |
| 2014/0066913 | A1 | 3/2014 | Sherman |
| 2014/0074078 | A1 | 3/2014 | Kumar et al. |
| 2014/0081263 | A1 | 3/2014 | Mesallum |
| 2014/0107478 | A1 | 4/2014 | Seward et al. |
| 2014/0114378 | A1 | 4/2014 | Danek et al. |
| 2014/0121663 | A1 | 5/2014 | Pearson et al. |
| 2014/0128949 | A1 | 5/2014 | Hollett et al. |
| 2014/0148635 | A1 | 5/2014 | Danek et al. |
| 2014/0296844 | A1 | 10/2014 | Kevin et al. |
| 2014/0324036 | A1 | 10/2014 | Sachs et al. |
| 2014/0324037 | A1 | 10/2014 | Hoey et al. |
| 2014/0330332 | A1 | 11/2014 | Danek et al. |
| 2014/0341801 | A1 | 11/2014 | Laufer et al. |
| 2014/0378964 | A1 | 12/2014 | Pearson |
| 2015/0005766 | A1 | 1/2015 | Rioux et al. |
| 2015/0025605 | A1 | 1/2015 | Kaplan et al. |
| 2015/0038959 | A1 | 2/2015 | Biggs et al. |
| 2015/0039059 | A1 | 2/2015 | Mokelke et al. |
| 2015/0045788 | A1 | 2/2015 | Litscher et al. |
| 2015/0066005 | A1 | 3/2015 | Fan et al. |
| 2015/0066108 | A1 | 3/2015 | Shi et al. |
| 2015/0080884 | A1 | 3/2015 | Zarins et al. |
| 2015/0088120 | A1 | 3/2015 | Garcia et al. |
| 2015/0105775 | A1 | 4/2015 | Wizeman et al. |
| 2015/0112321 | A1 | 4/2015 | Cadouri |
| 2015/0119879 | A1 | 4/2015 | Jameson et al. |
| 2015/0141984 | A1 | 5/2015 | Loomas et al. |
| 2015/0150618 | A1 | 6/2015 | Onik et al. |
| 2015/0164584 | A1 | 6/2015 | Davalos et al. |
| 2015/0173943 | A1 | 6/2015 | Loomas et al. |
| 2015/0182282 | A1 | 7/2015 | Zemel et al. |
| 2015/0182560 | A1 | 7/2015 | Calle et al. |
| 2015/0201996 | A1 | 7/2015 | Rubinsky et al. |
| 2015/0223879 | A1 | 8/2015 | Danek et al. |
| 2015/0230855 | A1 | 8/2015 | Chornenky et al. |
| 2015/0258352 | A1 | 9/2015 | Lin et al. |
| 2015/0289923 | A1 | 10/2015 | Davalos et al. |
| 2015/0305794 | A1 | 10/2015 | Danek et al. |
| 2015/0313664 | A1 | 11/2015 | Jarrard |
| 2015/0320478 | A1 | 11/2015 | Cosman, Jr. et al. |
| 2015/0320479 | A1 | 11/2015 | Cosman, Jr. et al. |
| 2015/0320999 | A1 | 11/2015 | Nuccitelli et al. |
| 2015/0327944 | A1 | 11/2015 | Neal, II et al. |
| 2015/0342669 | A1 | 12/2015 | Flanagan et al. |
| 2016/0000499 | A1 | 1/2016 | Lennox et al. |
| 2016/0008016 | A1 | 1/2016 | Cioanta et al. |
| 2016/0008066 | A1 | 1/2016 | Kaplan et al. |
| 2016/0022349 | A1 | 1/2016 | Woloszko et al. |
| 2016/0030014 | A1 | 2/2016 | McWeeney et al. |
| 2016/0030016 | A1 | 2/2016 | McWeeney et al. |
| 2016/0038230 | A1 | 2/2016 | Danek et al. |
| 2016/0058493 | A1 | 3/2016 | Neal, II et al. |
| 2016/0066977 | A1 | 3/2016 | Neal, II et al. |
| 2016/0066990 | A1 | 3/2016 | Kaplan et al. |
| 2016/0074091 | A1 | 3/2016 | Amoah et al. |
| 2016/0081745 | A1 | 3/2016 | Rajagopalan et al. |
| 2016/0113703 | A1 | 4/2016 | Danek et al. |
| 2016/0128767 | A1 | 5/2016 | Azamian et al. |
| 2016/0166310 | A1* | 6/2016 | Stewart ............. A61B 18/1492 606/34 |
| 2016/0199131 | A1 | 7/2016 | Allison et al. |
| 2016/0206370 | A1 | 7/2016 | Fruland et al. |
| 2016/0235974 | A1 | 8/2016 | Holochwost et al. |
| 2016/0262601 | A1 | 9/2016 | Viebach et al. |
| 2016/0262795 | A1 | 9/2016 | Urbanski et al. |
| 2016/0287314 | A1 | 10/2016 | Arena et al. |
| 2016/0296269 | A1 | 10/2016 | Rubinsky et al. |
| 2016/0303293 | A1 | 10/2016 | Doyle et al. |
| 2016/0310211 | A1 | 10/2016 | Long |
| 2016/0324573 | A1 | 11/2016 | Mickelson et al. |
| 2016/0331441 | A1 | 11/2016 | Konings |
| 2016/0338758 | A9 | 11/2016 | Davalos et al. |
| 2016/0354142 | A1 | 12/2016 | Pearson et al. |
| 2016/0354145 | A1 | 12/2016 | Stern et al. |
| 2016/0361109 | A1 | 12/2016 | Weaver et al. |
| 2016/0367310 | A1* | 12/2016 | Onik ..................... A61B 18/14 |
| 2017/0000584 | A1 | 1/2017 | Blanco et al. |
| 2017/0035499 | A1 | 2/2017 | Stewart et al. |
| 2017/0049513 | A1 | 2/2017 | Cosman, Jr. et al. |
| 2017/0065330 | A1 | 3/2017 | Mickelsen et al. |
| 2017/0065339 | A1 | 3/2017 | Mickelsen |
| 2017/0065340 | A1 | 3/2017 | Long |
| 2017/0065343 | A1 | 3/2017 | Mickelsen |
| 2017/0087224 | A1 | 3/2017 | Quake |
| 2017/0105763 | A1 | 4/2017 | Karve et al. |
| 2017/0105793 | A1* | 4/2017 | Cao ....................... A61N 1/325 |
| 2017/0117603 | A1 | 4/2017 | Kreis et al. |
| 2017/0119465 | A1 | 5/2017 | Long et al. |
| 2017/0135723 | A1 | 5/2017 | Zarembinski |
| 2017/0156783 | A1 | 6/2017 | McKernon et al. |
| 2017/0189097 | A1 | 7/2017 | Viswanathan et al. |
| 2017/0189579 | A1 | 7/2017 | Davalos |
| 2017/0215939 | A1 | 8/2017 | Palti et al. |
| 2017/0215953 | A1 | 8/2017 | Long et al. |
| 2017/0216353 | A1 | 8/2017 | Nuccitelli et al. |
| 2017/0216585 | A1 | 8/2017 | Goldfarb et al. |
| 2017/0224363 | A1 | 8/2017 | Watanabe et al. |
| 2017/0239480 | A1 | 8/2017 | Zarins et al. |
| 2017/0246455 | A1 | 8/2017 | Athos et al. |
| 2017/0252090 | A1 | 9/2017 | Smith et al. |
| 2017/0266283 | A1 | 9/2017 | Soikum et al. |
| 2017/0266438 | A1 | 9/2017 | Sano et al. |
| 2017/0281934 | A1 | 10/2017 | Giladi et al. |
| 2017/0304002 | A1 | 10/2017 | Beebe et al. |
| 2017/0311789 | A1 | 11/2017 | Mulcahey et al. |
| 2017/0312021 | A1 | 11/2017 | Pilcher et al. |
| 2017/0319843 | A1 | 11/2017 | Beebe et al. |
| 2017/0319851 | A1 | 11/2017 | Athos et al. |
| 2017/0325894 | A1 | 11/2017 | Krimsky |
| 2017/0326361 | A1 | 11/2017 | Kreis et al. |
| 2017/0333104 | A1 | 11/2017 | Forde et al. |
| 2017/0333109 | A1 | 11/2017 | Gilbert |
| 2017/0333112 | A1 | 11/2017 | Nuccitelli et al. |
| 2017/0360326 | A1 | 12/2017 | Davalos et al. |
| 2018/0000895 | A1 | 1/2018 | Pierce et al. |
| 2018/0001056 | A1 | 1/2018 | Leeflang et al. |
| 2018/0008127 | A1 | 1/2018 | Tinkham et al. |
| 2018/0014868 | A1 | 1/2018 | O'Connor et al. |
| 2018/0028250 | A1 | 2/2018 | O'Connor |
| 2018/0028267 | A1 | 2/2018 | Onik et al. |
| 2018/0036058 | A1 | 2/2018 | Fan et al. |
| 2018/0042655 | A1 | 2/2018 | Burr et al. |
| 2018/0042674 | A1 | 2/2018 | Mickelsen |
| 2018/0042675 | A1 | 2/2018 | Long |
| 2018/0043153 | A1 | 2/2018 | Viswanathan et al. |
| 2018/0064488 | A1 | 3/2018 | Long et al. |
| 2018/0071014 | A1 | 3/2018 | Neal et al. |

(56) References Cited

U.S. PATENT DOCUMENTS

| | | | |
|---|---|---|---|
| 2018/0078755 | A1 | 3/2018 | Kreis et al. |
| 2018/0085160 | A1 | 3/2018 | Viswanathan et al. |
| 2018/0085575 | A1 | 3/2018 | Travers et al. |
| 2018/0104486 | A1 | 4/2018 | Yoon et al. |
| 2018/0110557 | A1 | 4/2018 | Muratori et al. |
| 2018/0110978 | A1 | 4/2018 | Beebe et al. |
| 2018/0125565 | A1 | 5/2018 | Sano et al. |
| 2018/0132922 | A1 | 5/2018 | Neal, II |
| 2018/0153467 | A1 | 6/2018 | Lichtenstein et al. |
| 2018/0153937 | A1 | 6/2018 | Nuccitelli et al. |
| 2018/0154142 | A1* | 6/2018 | Guo .................... A61B 18/1206 |
| 2018/0161086 | A1 | 6/2018 | Davalos et al. |
| 2018/0193082 | A1 | 7/2018 | Rubinsky et al. |
| 2018/0193088 | A1 | 7/2018 | Sutton et al. |
| 2018/0200510 | A1 | 7/2018 | Nuccitelli et al. |
| 2018/0221078 | A1 | 8/2018 | Howard et al. |
| 2018/0256240 | A1 | 9/2018 | Bloom et al. |
| 2018/0263685 | A1 | 9/2018 | Onik et al. |
| 2018/0289954 | A1 | 10/2018 | Hebb et al. |
| 2018/0303543 | A1 | 10/2018 | Stewart et al. |
| 2018/0311497 | A1 | 11/2018 | Viswanathan et al. |
| 2018/0344378 | A1 | 12/2018 | Wolf et al. |
| 2018/0360531 | A1 | 12/2018 | Holmes, Jr. et al. |
| 2019/0022333 | A1 | 1/2019 | Baillargeon et al. |
| 2019/0030328 | A1 | 1/2019 | Stewart et al. |
| 2019/0038171 | A1 | 2/2019 | Howard |
| 2019/0038895 | A1 | 2/2019 | Pianca et al. |
| 2019/0046791 | A1 | 2/2019 | Ebbers et al. |
| 2019/0059864 | A1 | 2/2019 | Gonzalez |
| 2019/0069950 | A1 | 3/2019 | Viswanathan et al. |
| 2019/0083169 | A1 | 3/2019 | Single et al. |
| 2019/0099214 | A1 | 4/2019 | Rubinsky et al. |
| 2019/0105408 | A1 | 4/2019 | Heller et al. |
| 2019/0117963 | A1 | 4/2019 | Travers et al. |
| 2019/0117969 | A1 | 4/2019 | Schmidt et al. |
| 2019/0126037 | A1 | 5/2019 | Ivorra Cano |
| 2019/0151015 | A1 | 5/2019 | Viswanathan et al. |
| 2019/0160283 | A1 | 5/2019 | Nuccitelli et al. |
| 2019/0201089 | A1 | 7/2019 | Waldstreicher et al. |
| 2019/0216899 | A1 | 7/2019 | Bright |
| 2019/0223938 | A1* | 7/2019 | Arena .................... A61N 1/327 |
| 2019/0223943 | A1* | 7/2019 | Forsyth .............. A61B 18/1477 |
| 2019/0232048 | A1 | 8/2019 | Latouche et al. |
| 2019/0239949 | A1 | 8/2019 | Nuccitelli et al. |
| 2019/0254735 | A1 | 8/2019 | Stewart et al. |
| 2019/0269826 | A1 | 9/2019 | Peyman |
| 2019/0269912 | A1 | 9/2019 | Viswanathan et al. |
| 2019/0275260 | A1 | 9/2019 | Ralph et al. |
| 2019/0282294 | A1 | 9/2019 | Davalos et al. |
| 2019/0299019 | A1 | 10/2019 | Chornenky et al. |
| 2019/0307781 | A1 | 10/2019 | Krex et al. |
| 2019/0328445 | A1 | 10/2019 | Sano et al. |
| 2019/0350971 | A1 | 11/2019 | Nuccitelli et al. |
| 2019/0351224 | A1 | 11/2019 | Sano et al. |
| 2019/0365362 | A1 | 12/2019 | Ralph |
| 2020/0000938 | A1 | 1/2020 | Pierce et al. |
| 2020/0009377 | A1 | 1/2020 | Chang et al. |
| 2020/0016067 | A1 | 1/2020 | Gotlib et al. |
| 2020/0038093 | A1 | 2/2020 | Onik |
| 2020/0046423 | A1 | 2/2020 | Viswanathan et al. |
| 2020/0046967 | A1 | 2/2020 | Ivey et al. |
| 2020/0060754 | A1 | 2/2020 | Shuman et al. |
| 2020/0060755 | A1 | 2/2020 | Shuman et al. |
| 2020/0078047 | A1 | 3/2020 | Lambe et al. |
| 2020/0129228 | A1 | 4/2020 | Henkes et al. |
| 2020/0260987 | A1 | 8/2020 | Davalos et al. |
| 2020/0275973 | A1 | 9/2020 | O'Brien et al. |
| 2020/0298008 | A1 | 9/2020 | Asirvatham |
| 2020/0323583 | A1 | 10/2020 | Qiao |
| 2020/0398048 | A1 | 12/2020 | Krimsky et al. |
| 2021/0022794 | A1 | 1/2021 | Viswanathan |
| 2021/0023362 | A1 | 1/2021 | Lorenzo et al. |
| 2021/0038280 | A1 | 2/2021 | Pikramenos |
| 2021/0052882 | A1* | 2/2021 | Wasson ................ A61N 1/0412 |
| 2021/0085777 | A1 | 3/2021 | Steinmetz et al. |
| 2021/0137410 | A1 | 5/2021 | O'Brien et al. |
| 2021/0146126 | A1 | 5/2021 | Waldstreicher et al. |
| 2021/0161582 | A1 | 6/2021 | Byrd et al. |
| 2021/0236815 | A1 | 8/2021 | Waldstreicher et al. |
| 2021/0236816 | A1 | 8/2021 | Waldstreicher et al. |
| 2021/0315639 | A1 | 10/2021 | Manucherhabadi et al. |
| 2021/0393327 | A1 | 12/2021 | Eyster et al. |
| 2022/0054188 | A1 | 2/2022 | Palushi et al. |
| 2022/0104875 | A1 | 4/2022 | Gleiman et al. |
| 2022/0161027 | A1 | 5/2022 | Aycock et al. |
| 2022/0233237 | A1 | 7/2022 | Adams et al. |
| 2022/0249157 | A1 | 8/2022 | Viswanathan et al. |
| 2022/0330886 | A1 | 10/2022 | Varadan et al. |
| 2022/0387095 | A1 | 12/2022 | Neal et al. |
| 2022/0395323 | A1 | 12/2022 | Waldstreicher et al. |
| 2023/0082389 | A1 | 3/2023 | Waldstreicher et al. |
| 2023/0149706 | A1 | 5/2023 | Krimsky et al. |
| 2023/0165629 | A1 | 6/2023 | Tehrani et al. |
| 2023/0172650 | A1 | 6/2023 | Castellvi et al. |
| 2023/0240746 | A1 | 8/2023 | Gundert et al. |
| 2023/0248414 | A1 | 8/2023 | Sano et al. |
| 2023/0405313 | A1 | 12/2023 | Pastori et al. |
| 2024/0032984 | A1 | 2/2024 | Castellvi et al. |
| 2024/0173557 | A1 | 5/2024 | Neal, II et al. |
| 2024/0180878 | A1 | 6/2024 | Spera |
| 2024/0216038 | A1 | 7/2024 | Girouard et al. |
| 2024/0277245 | A1 | 8/2024 | Davalos et al. |
| 2024/0350185 | A1 | 10/2024 | O'Brien et al. |
| 2024/0350187 | A1 | 10/2024 | Waldstreicher et al. |
| 2024/0390672 | A1* | 11/2024 | Neal .................. A61N 1/36002 |
| 2025/0032787 | A1 | 1/2025 | Krimsky et al. |
| 2025/0040985 | A1 | 2/2025 | Girouard et al. |
| 2025/0064510 | A1 | 2/2025 | Waldstreicher et al. |
| 2025/0213299 | A1 | 7/2025 | Nafie et al. |
| 2025/0261991 | A1 | 8/2025 | O'Brien et al. |
| 2025/0295442 | A1 | 9/2025 | Darwish et al. |
| 2026/0014371 | A1 | 1/2026 | Krimsky et al. |

FOREIGN PATENT DOCUMENTS

| | | | |
|---|---|---|---|
| AU | 2004235684 | A1 | 1/2005 |
| AU | 2015355241 | A1 | 6/2017 |
| AU | 2016246146 | A1 | 10/2017 |
| AU | 2020200688 | B2 | 7/2021 |
| CA | 2370223 | A1 | 10/2000 |
| CA | 2981867 | A1 | 10/2016 |
| CN | 1867299 | A | 11/2006 |
| CN | 101198287 | A | 6/2008 |
| CN | 101426551 | A | 5/2009 |
| CN | 101553180 | A | 10/2009 |
| CN | 101909649 | A | 12/2010 |
| CN | 102014779 | A | 4/2011 |
| CN | 102105115 | A | 6/2011 |
| CN | 102421386 | A | 4/2012 |
| CN | 102725021 | A | 10/2012 |
| CN | 103027745 | A | 4/2013 |
| CN | 103252016 | A | 8/2013 |
| CN | 103281978 | A | 9/2013 |
| CN | 103313671 | A | 9/2013 |
| CN | 103582463 | A | 2/2014 |
| CN | 103750899 | A | 4/2014 |
| CN | 103781433 | A | 5/2014 |
| CN | 103796603 | A | 5/2014 |
| CN | 104080418 | A | 10/2014 |
| CN | 104363849 | A | 2/2015 |
| CN | 104470454 | A | 3/2015 |
| CN | 104602634 | A | 5/2015 |
| CN | 104602754 | A | 5/2015 |
| CN | 104703557 | A | 6/2015 |
| CN | 105073051 | A | 11/2015 |
| CN | 105939686 | A | 9/2016 |
| CN | 107194119 | A | 9/2017 |
| CN | 107205772 | A | 9/2017 |
| CN | 107921258 | A | 4/2018 |
| CN | 108024803 | A | 5/2018 |
| CN | 108778172 | A | 11/2018 |
| CN | 108778173 | A | 11/2018 |
| CN | 109788979 | A | 5/2019 |
| CN | 110573104 | A | 12/2019 |

(56) References Cited

FOREIGN PATENT DOCUMENTS

| | | | |
|---|---|---|---|
| CN | 113558744 | A | 10/2021 |
| CO | 2017010662 | A2 | 3/2018 |
| DE | 60023283 | T2 | 7/2006 |
| DK | 0987989 | T3 | 10/2006 |
| EP | 1173103 | A2 | 1/2002 |
| EP | 0935482 | B1 | 5/2005 |
| EP | 1173103 | B1 | 10/2005 |
| EP | 1804905 | A1 | 7/2007 |
| EP | 1991303 | A2 | 11/2008 |
| EP | 2170198 | A1 | 4/2010 |
| EP | 2317951 | A1 | 5/2011 |
| EP | 2413833 | A1 | 2/2012 |
| EP | 2488251 | A2 | 8/2012 |
| EP | 2642937 | A2 | 10/2013 |
| EP | 2661236 | A1 | 11/2013 |
| EP | 2736432 | A1 | 6/2014 |
| EP | 2762195 | A2 | 8/2014 |
| EP | 2777579 | A1 | 9/2014 |
| EP | 2170198 | B1 | 4/2015 |
| EP | 1648555 | B1 | 9/2015 |
| EP | 2957248 | A1 | 12/2015 |
| EP | 1804905 | B1 | 2/2016 |
| EP | 2736432 | B1 | 3/2016 |
| EP | 3003461 | A2 | 4/2016 |
| EP | 2661236 | B1 | 8/2016 |
| EP | 3091925 | A1 | 11/2016 |
| EP | 3113605 | A1 | 1/2017 |
| EP | 3142584 | A1 | 3/2017 |
| EP | 3143124 | A1 | 3/2017 |
| EP | 3154464 | A1 | 4/2017 |
| EP | 3003470 | B1 | 8/2017 |
| EP | 3226794 | A1 | 10/2017 |
| EP | 3282953 | A1 | 2/2018 |
| EP | 3290082 | A2 | 3/2018 |
| EP | 3139997 | B1 | 9/2018 |
| EP | 3113605 | B1 | 10/2018 |
| EP | 3399931 | A1 | 11/2018 |
| EP | 3399933 | A1 | 11/2018 |
| EP | 3154463 | B1 | 3/2019 |
| EP | 3471631 | A1 | 4/2019 |
| EP | 2994045 | B1 | 5/2019 |
| EP | 3003461 | B1 | 5/2019 |
| EP | 3091921 | B1 | 6/2019 |
| EP | 3456278 | A3 | 6/2019 |
| EP | 3495018 | A1 | 6/2019 |
| EP | 3206613 | B1 | 7/2019 |
| EP | 3569144 | A1 | 11/2019 |
| ES | 2246853 | T3 | 3/2006 |
| ES | 2361460 | T3 | 6/2011 |
| IN | 200601622 | | 5/2007 |
| JP | H09285182 | A | 10/1997 |
| JP | 2001103741 | A | 4/2001 |
| JP | 2001506157 | A | 5/2001 |
| JP | 2002065626 | A | 3/2002 |
| JP | 2002541905 | A | 12/2002 |
| JP | 2003529401 | A | 10/2003 |
| JP | 2004516867 | A | 6/2004 |
| JP | 2006320176 | A | 11/2006 |
| JP | 2007504910 | A | 3/2007 |
| JP | 4242436 | B2 | 3/2009 |
| JP | 4243436 | B2 | 3/2009 |
| JP | 2010509032 | A | 3/2010 |
| JP | 2011519699 | A | 7/2011 |
| JP | 2011524785 | A | 9/2011 |
| JP | 2012515018 | A | 7/2012 |
| JP | 2013543745 | A | 12/2013 |
| JP | 2015128596 | A | 7/2015 |
| JP | 2015524732 | A | 8/2015 |
| JP | 2016195826 | A | 11/2016 |
| JP | 2017518805 | A | 7/2017 |
| JP | 2017529169 | A | 10/2017 |
| JP | 2019500170 | A | 1/2019 |
| JP | 2019524396 | A | 9/2019 |
| JP | 2020518335 | A | 6/2020 |
| JP | 2021500153 | A | 1/2021 |
| JP | 2021508533 | A | 3/2021 |
| JP | 2023536906 | A | 8/2023 |
| PT | 987989 | E | 11/2006 |
| WO | WO-1998014238 | A1 | 4/1998 |
| WO | WO-1999006101 | A1 | 2/1999 |
| WO | WO-2000062699 | A2 | 10/2000 |
| WO | WO-2001010319 | A1 | 2/2001 |
| WO | WO-2001055294 | A1 | 8/2001 |
| WO | WO-2002032333 | A1 | 4/2002 |
| WO | WO-2002098501 | A2 | 12/2002 |
| WO | WO-2003047684 | A2 | 6/2003 |
| WO | WO-2004037341 | A2 | 5/2004 |
| WO | WO-2004110371 | A2 | 12/2004 |
| WO | WO-2005044371 | A1 | 5/2005 |
| WO | WO-2005065284 | A2 | 7/2005 |
| WO | WO-2005065284 | A3 | 11/2005 |
| WO | WO-2005115535 | A2 | 12/2005 |
| WO | WO-2005032646 | A3 | 4/2006 |
| WO | WO-2006036706 | A1 | 4/2006 |
| WO | WO-2006052940 | A2 | 5/2006 |
| WO | WO-2006085150 | A2 | 8/2006 |
| WO | WO-2006116198 | A2 | 11/2006 |
| WO | WO-2006116608 | A2 | 11/2006 |
| WO | WO-2006131816 | A2 | 12/2006 |
| WO | WO-2007001747 | A2 | 1/2007 |
| WO | WO-2007001751 | A1 | 1/2007 |
| WO | WO-2007039799 | A3 | 7/2007 |
| WO | WO-2007100727 | A2 | 9/2007 |
| WO | WO-2007103070 | A2 | 9/2007 |
| WO | WO-2008034100 | A2 | 3/2008 |
| WO | WO-2008063195 | A1 | 5/2008 |
| WO | WO-2008087489 | A2 | 7/2008 |
| WO | WO-2009009398 | A1 | 1/2009 |
| WO | WO-2009137800 | A2 | 11/2009 |
| WO | WO-2009137819 | A1 | 11/2009 |
| WO | WO-2009154654 | A1 | 12/2009 |
| WO | WO-2010014480 | A1 | 2/2010 |
| WO | WO-2010022275 | A1 | 2/2010 |
| WO | WO-2010080974 | A1 | 7/2010 |
| WO | WO-2010093692 | A2 | 8/2010 |
| WO | WO-2010107947 | A1 | 9/2010 |
| WO | WO-2010117806 | A1 | 10/2010 |
| WO | WO-2010118387 | A1 | 10/2010 |
| WO | WO-2010141417 | A2 | 12/2010 |
| WO | WO-2010151277 | A1 | 12/2010 |
| WO | WO-2011047387 | A2 | 4/2011 |
| WO | WO-2011135294 | A1 | 11/2011 |
| WO | WO-2012071526 | A2 | 5/2012 |
| WO | WO-2012088149 | A2 | 6/2012 |
| WO | WO-2012118659 | A1 | 9/2012 |
| WO | WO-2013052501 | A1 | 4/2013 |
| WO | WO-2014025394 | A1 | 2/2014 |
| WO | WO-2014105964 | A1 | 7/2014 |
| WO | WO-2014181167 | A1 | 11/2014 |
| WO | WO-2014197240 | A2 | 12/2014 |
| WO | WO-2014197632 | A2 | 12/2014 |
| WO | WO-2014204978 | A1 | 12/2014 |
| WO | WO-2015085162 | A1 | 6/2015 |
| WO | WO-2015103530 | A1 | 7/2015 |
| WO | WO-2015103574 | A1 | 7/2015 |
| WO | WO-2015171921 | A2 | 11/2015 |
| WO | WO-2015175570 | A1 | 11/2015 |
| WO | WO-2015192018 | A1 | 12/2015 |
| WO | WO-2015192027 | A1 | 12/2015 |
| WO | WO-2016014264 | A1 | 1/2016 |
| WO | WO-2016036891 | A1 | 3/2016 |
| WO | WO-2016060983 | A1 | 4/2016 |
| WO | WO-2016061002 | A1 | 4/2016 |
| WO | WO-2016089781 | A1 | 6/2016 |
| WO | WO-2016100325 | A1 | 6/2016 |
| WO | WO-2016112359 | A1 | 7/2016 |
| WO | WO-2016123608 | A2 | 8/2016 |
| WO | WO-2016126778 | A1 | 8/2016 |
| WO | WO-2016149575 | A1 | 9/2016 |
| WO | WO-2016154473 | A1 | 9/2016 |
| WO | WO-2016164930 | A1 | 10/2016 |
| WO | WO-2016178697 | A1 | 11/2016 |
| WO | WO-2016179712 | A1 | 11/2016 |
| WO | WO-2016180934 | A1 | 11/2016 |

(56) References Cited

FOREIGN PATENT DOCUMENTS

WO WO-2016201264 A1 12/2016
WO WO-2017024123 A1 2/2017
WO WO-2017109261 A1 6/2017
WO WO-2017114001 A1 7/2017
WO WO-2017119934 A1 7/2017
WO WO-2017120169 A1 7/2017
WO WO-2017151260 A1 9/2017
WO WO-2017173089 A1 10/2017
WO WO-2017175116 A1 10/2017
WO WO-2017200954 A1 11/2017
WO WO-2017201394 A1 11/2017
WO WO-2017218734 A1 12/2017
WO WO-2018005511 A1 1/2018
WO WO-2018010659 A1 1/2018
WO WO-2018026985 A1 2/2018
WO WO-2018065806 A1 4/2018
WO WO-2018067999 A1 4/2018
WO WO-2018075946 A1 4/2018
WO WO-2018106672 A1 6/2018
WO WO-2018187244 A2 10/2018
WO WO-2018200800 A1 11/2018
WO WO-2018201037 A1 11/2018
WO WO-2019032474 A1 2/2019
WO WO-2019055512 A1 3/2019
WO WO-2019084011 A1 5/2019
WO WO-2019095604 A1 5/2019
WO WO-2019100016 A1 5/2019
WO WO-2019108540 A1 6/2019
WO WO-2019133606 A1 7/2019
WO WO-2019133608 A1 7/2019
WO WO-2019157359 A1 8/2019
WO WO-2019178500 A1 9/2019
WO WO-2019197973 A1 10/2019
WO WO-2020005186 A2 1/2020
WO WO-2020010188 A1 1/2020
WO WO-2020018662 A1 1/2020
WO WO-2020061192 A1 3/2020
WO WO-2020118383 A1 6/2020
WO WO-2020150709 A1 7/2020
WO WO-2020215007 A1 10/2020
WO WO-2021011733 A1 1/2021
WO WO-2021108292 A1 6/2021
WO WO-2021127558 A1 6/2021
WO WO-2021207385 A1 10/2021
WO WO-2022031797 A1 2/2022
WO WO-2022204479 A1 9/2022
WO WO-2022260723 A1 12/2022
WO WO-2022261418 A1 12/2022
WO WO-2023044124 A1 3/2023
WO WO-2023172773 A1 9/2023
WO WO-2023212250 A1 11/2023
WO WO-2023220419 A1 11/2023
WO WO-2024196823 A2 9/2024
WO WO-2024254966 A1 12/2024
WO WO-2025043024 A2 2/2025
WO WO-2025081663 A1 4/2025
WO WO-2025235871 A1 11/2025

OTHER PUBLICATIONS

Appelbaum L., et al., "US Findings after Irreversible Electroporation Ablation: Radiologic-pathologic Correlation," Radiology, Jan. 2012, vol. 262, No. 1, pp. 117-125.

Arena C.B., et al., "Chapter 10.13: Electroporation Therapy," Comprehensive Biomedical Physics, Springer, Editor: A. Brahme, 2014, vol. 10, pp. 269-287 (20 Pages), Retrieved from URL: http://dx.doi.org/10.1016/8978-0-444-53632-7.01016-9.

Arena C.B., et al., "High-frequency Irreversible Electroporation (H-FIRE) for Non-thermal Ablation without Muscle Contraction," Biomedical Engineering Online, Nov. 21, 2011, vol. 10, Article No. 102, pp. 1-20 (21 Pages).

Arena, et al., High-frequency irreversible electroporation (H-FIRE) for non-thermal ablation without muscle contraction, *BioMedical Engineering OnLine*, 10:102, http://www.biomedical-engineering-online.com/content/10/1/102 (Nov. 2011).

Bertacchini, et al., Design of an Irreversible Electroporation System for Clinical Use, *Technology in Cancer Research and Treatment*, 6(4):313-320 (Aug. 2007).

Bhonsle S., et al., "Characterization of Irreversible Electroporation Ablation with a Validated Perfused Organ Model," Journal of Vascular and Interventional Radiology, 2016, vol. 27, pp. 1913-1922 (12 Pages), Appendix A—Supplemental Materials and Methods.

Campelo S., et al., "An Evaluation of Irreversible Electroporation Thresholds in Human Prostate Cancer and Potential Correlations to Physiological Measurements," APL Bioengineering, 2017, vol. 1 (016101), pp. 016101-1-016101-10, Retrieved from URL: https://doi.org/10.1063/1.5005828.

Cerveri I., et al., "Variations in the Prevalence Across Countries of Chronic Bronchitis and Smoking Habits in Young Adults," The European Respiratory Journal, 2001, vol. 18, No. 1, pp. 85-92.

Charalambous P., et al., "The Efficacy and Safety of the Open Approach Irreversible Electroporation in the Treatment of Pancreatic Cancer: A Systematic Review," European Journal of Surgical Oncology: The Journal of the European Society of Surgical Oncology and the British Association of Surgical Oncology, 2020, vol. 46, No. 9, pp. 1565-1572 (27 Pages).

Cheetham J., et al., "Effects of Functional Electrical Stimulation on Denervated Laryngeal Muscle in a Large Animal Model," Artificial Organs, 2015, vol. 39, No. 10, pp. 876-885.

Criner G.G., "Chronic Bronchitis: The Case for an Unmet Medical Need," European Respiratory Society (ERS), 2017, 13 Pages.

Davalos, et al., Tissue Ablation with Irreversible Electroporation, *Annals of Biomedical Engineering*, 33(2):223-231 (Feb. 2005).

Davalos R.V., et al., "Implications and Considerations of Thermal Effects When Applying Irreversible Electroporation Tissue Ablation Therapy," The Prostate, Jul. 1, 2015, vol. 75, No. 10, pp. 1114-1118 (5 Pages).

Dean D.A., "Gene Electrotransfer to Lung," Clinical Aspects of Electroporation, Springer Science Business Media, LLC, Chapter 15, 2011, pp. 165-175.

Dev, et al., Medical Applications of Electroporation, *IEEE Transactions on Plasma Science*, 28(1):206-223 (Feb. 2000).

Dupuy D.E., et al., "Irreversible Electroporation in a Swine Lung Model," Cardiovascular and Interventional Radiology, 2011, vol. 34, No. 2, pp. 391-395.

Edd, et al., In Vivo Results of a New Focal Tissue Ablation Technique: Irreversible Electroporation, *IEEE Transactions on Biomedical Engineering*, 53(5):1409-1415 (Jun. 2006).

Edd J.F., et al., "In Vivo Results of a New Focal Tissue Ablation Technique: Irreversible Electroporation," IEEE Transactions on Biomedical Engineering, Jun. 2006, vol. 53, No. 5, pp. 1409-1415.

Eurostat Statistics Database: "Health at a Glance: Europe (2012 and 2014 Reports)," Dec. 3, 2014, 41 Pages, Retrieved from URL: http://www.oecd-ilibrary.org/social-issues-migration-health/health-at-a-glance-europe-2012_978926418.

Extended European Search Report for European Application No. 20792123.0, dated Dec. 21, 2022, 8 Pages.

Extended European Search Report for European Application No. 20840607.4, dated Jun. 27, 2023, 08 Pages.

Extended European Search Report for European Application No. 21785398.5, dated Apr. 4, 2024, 8 Pages.

Extended European Search Report for European Application No. 21853941.9, dated Jul. 23, 2024, 07 Pages.

Extended European Search Report for European Application No. 22210537.1, dated Apr. 26, 2023, 11 Pages.

Extended European Search Report for European Application No. 22820712.2, dated Apr. 7, 2025, 08 Pages.

Extended European Search Report for European Application No. 22821096.9, dated Aug. 6, 2025, 13 Pages.

Extended European Search Report for European Application No. 23174654.6, dated Jun. 23, 2023, 07 Pages.

Extended European Search Report for European Application No. 23178276.4, dated Jun. 26, 2023, 07 Pages.

Extended European Search Report for European Application No. 25166670.7, dated May 15, 2025, 8 Pages.

(56) References Cited

OTHER PUBLICATIONS

Extended European Search Report for European Application No. 25184327.2, dated Jul. 15, 2025, 08 Pages.
Extended European Search Report for European Application No. EP22776703.5, dated Dec. 23, 2024, 8 Pages.
Extended European Search Report for European Application No. EP22870831.9, dated Jun. 16, 2025, 10 Pages.
Faststats-Chronic Lower Respiratory Disease: "Chronic Obstructive Pulmonary Disease (COPD) Includes: Chronic Bronchitis and Emphysema," Centers for Disease Control and Prevention (CDC)/National Center for Health Statistics (NCHS), Jan. 16, 2021, pp. 1-2, [Retrieved on Feb. 4, 2021] Retrieved from URL: https://www.cdc.gov/nchs/fastats/copd.htm.
Fernandez-Bussy S., et al., "Histopathologic Results Post Bronchial Rheoplasty," American Thoracic Society, 2019, 17 Pages.
Fernandez-Bussy S., et al., "Histopathologic Results Post Bronchial Rheoplasty," American Thoracic Society, American journal of Respiratory and Critical Care Medicine, D94. COPD: Epidemiology and Therapy, 2019, vol. 199, Article No. A7043, 03 Pages.
Frandsen S.K., et al., "Calcium Electroporation in Three Cell Lines: A Comparison of Bleomycin and Calcium, Calcium Compounds, and Pulsing Conditions," Biochimica et Biophysica Acta, Mar. 2014, vol. 1840, No. 3, pp. 1204-1208 (5 Pages).
Garcia P.A., et al., "A Parametric Study Delineating Irreversible Electroporation from Thermal Damage Based on a Minimally Invasive Intracranial Procedure," BioMedical Engineering OnLine, Apr. 30, 2011, vol. 10, Article No. 34, 22 Pages, Retrieved from URL: http://www.biomedical-engineering-online.com/content/10/1/34.
Garcia P.A., et al., "An Experimental Investigation of Temperature Changes During Electroporation," URSI General Assembly and Scientific Symposium, Istanbul, Turkey, Aug. 13-20, 2011, 4 Pages.
Garcia P.A., et al., "Intracranial Nonthermal Irreversible Electroporation: In Vivo Analysis," The Journal of Membrane Biology, 2010, vol. 236, pp. 127-136.
Garcia P.A., et al., "Non-Thermal Irreversible Electroporation for Tissue Ablation," Chapter 3, Electroporation in Laboratory and Clinical Investigations, Editors: E. P. Spugnini and al Baldi, 2010, 22 Pages.
Global Strategy for the Diagnosis, Management, and Prevention of COPD: "Global Initiative for Chronic Obstructive Lung Disease," 2017, pp. 1-42.
International Search Report & Written Opinion dated Aug. 29, 2025 in Int'l PCT Patent Appl. Serial No. PCT/US2025/028619 (181001).
International Search Report and Written Opinion for International Application No. PCT/US2017/039527, dated Dec. 7, 2017, 22 Pages.
International Search Report and Written Opinion for International Application No. PCT/US2018/067501, dated Mar. 13, 2019, 14 Pages.
International Search Report and Written Opinion for International Application No. PCT/US2018/067504, dated Mar. 13, 2019, 13 Pages.
International Search Report and Written Opinion for International Application No. PCT/US2020/028844, dated Sep. 4, 2020, 13 Pages.
International Search Report and Written Opinion for International Application No. PCT/US2020/042260, dated Oct. 14, 2020, 12 Pages.
International Search Report and Written Opinion for International Application No. PCT/US2021/026221, dated Jul. 21, 2021, 21 Pages.
International Search Report and Written Opinion for International Application No. PCT/US2021/030911, dated Aug. 16, 2021, 10 Pages.
International Search Report and Written Opinion for International Application No. PCT/US2021/044469, dated Nov. 8, 2021, 17 Pages.
International Search Report and Written Opinion for International Application No. PCT/US2022/015217, dated May 6, 2022, 12 Pages.
International Search Report and Written Opinion for International Application No. PCT/US2022/021888, dated Jun. 16, 2022, 11 Pages.
International Search Report and Written Opinion for International Application No. PCT/US2022/032981, dated Aug. 29, 2022, 15 Pages.
International Search Report and Written Opinion for International Application No. PCT/US2022/044021, dated Jan. 11, 2023, 11 Pages.
International Search Report and Written Opinion for International Application No. PCT/US2023/020282, dated Jul. 21, 2023, 14 Pages.
International Search Report and Written Opinion for International Application No. PCT/US2023/022109, dated Aug. 15, 2023, 10 Pages.
International Search Report and Written Opinion for International Application No. PCT/US2023/060897, dated Jul. 7, 2023, 15 Pages.
International Search Report and Written Opinion for International Application No. PCT/US2024/020309, dated Jul. 29, 2024, 10 Pages.
International Search Report and Written Opinion for International Application No. PCT/US2024/043295, dated Oct. 30, 2024, 9 Pages.
Invitation to Pay Additional Fees for International Application No. PCT/US2023060897, dated May 15, 2023, 10 Pages.
Jourabchi, et al., Irreversible Electroporation (NanoKnife) in Cancer Treatment, *Gastrointestinal Intervention*, 3:8-18 (Feb. 2014).
Kim H.B., et al., "Physicochemical Factors That Affect Electroporation of Lung Cancer and Normal Cell Lines," Biochemical and Biophysical Research Communications, 2019, vol. 517, No. 4, pp. 703-708.
Kim V., et al., "Bronchial Rheoplasty Increases Distal Airway Volume in Chronic Bronchitis," European Respiratory Journal, 2019, vol. 54, Supplement. 63 (PA2040), 5 Pages, Abstract.
Kim V., et al., "The Chronic Bronchitic Phenotype of COPD: An Analysis of the COPD Gene Study," Chest, Sep. 2011, vol. 140, No. 3, pp. 626-633.
Krassowska, et al., Viability of Cancer Cells Exposed to Pulsed Electric Fields: The Role of Pulse Charge, *Annals of Biomedical Engineering*, 31:80-90 (2003).
Kundalia K., et al., "Margin Accentuation for Resectable Pancreatic Cancer Using Irreversible Electroporation E Results from the MACPIE-I Study," European Journal of Surgical Oncology, Oct. 2021, vol. 47, No. 10, pp. 2571-2578 (8 Pages).
Lee, et al., Advanced Hepatic Ablation Technique for Creating Complete Cell Death: Irreversible Electroporation,*Radiology*, 255(2) (Apr. 8, 2010).
Lu J., et al., "Sequence-Modified Antibiotic Resistance Genes Provide Sustained Plasmid-Mediated Transgene Expression in Mammals," Molecular Therapy, May 2017, vol. 25, No. 5, pp. 1187-1198.
Maor E., et al., "Irreversible Electroporation Attenuates Neointimal Formation after Angioplasty," IEEE Transactions on Biomedical Engineering, Sep. 2008, vol. 55, No. 9, pp. 2268-2274.
Maor E., et al., "The Effect of Irreversible Electroporation on Blood Vessels," Technology in Cancer Research and Treatment, Aug. 2007, vol. 6, No. 4, pp. 307-312.
Mercadal, et al., Avoiding nerve stimulation in irreversible electroporation: a numerical modeling study, *Phys. Med. Biol.*, 62(20):8060-8079 (Oct. 2004).
Miklavcic, et al., A validated model of in vitro electric field distribution in tissues for electrochemotherapy and for DNA electrotransfer for gene therapy, *Biochimica et Biophysica Acta*, 1523:73-83 (2000).
Miklavcic, et al., The effect of high frequency electric pulses on muscle contractions and antitumor efficiency in vivo for a potential use in clinical electrochemotherapy, *Bioelectrochemistry*, 65:121-128 (2005).

(56) References Cited

OTHER PUBLICATIONS

Miklovic T., et al., "A Comprehensive Characterization of Parameters Affecting High-frequency Irreversible Electroporation Lesions," Annals of Biomedical Engineering, 2017, vol. 45, pp. 2524-2534 (11 Pages).
Miller, et al., Cancer Cells Ablation with Irreversible Electroporation, *Technology in Cancer Research & Treatment*, 4(6):699-705 (Dec. 2005).
Mir, et al., Mechanisms of electrochemotherapy, *Advanced Drug Delivery Reviews*, 35:107-118 (1999).
Moore, et al., Early experience with PEF in the setting of recalcitrant stage IV lung cancer, Lung Cancer, 204:08575 (May 2025).
Napotnik, et al., Cell death due to electroporation—A Review, *Bioelectrochemistry*, 141:107871, pp. 1-18 (2021).
Neal II, R. E. et al., "The Feasibility of Irreversible Electroporation for the Treatment of Breast Cancer and Other Heterogeneous Systems," Annals of Biomedical Engineering, Dec. 2009, vol. 37, No. 12, pp. 2615-2625.
Neal II R.E., et al., "An "Off-the-Shelf" System for Intraprocedural Electrical Current Evaluation and Monitoring of Irreversible Electroporation Therapy," Cardio Vascular and Interventional Radiology, 2014, vol. 38, No. 3, pp. 736-741 (6 Pages).
Neal II R.E., et al., "Chapter 5.4: Clinical Implications of Irreversible Electroporation: Clinical and Preclinical Findings," Springer, Editors: H Akiyama and R Heller (In Press), 10 Pages.
Neal II R.E., et al., "Experimental Characterization and Numerical Modeling of Tissue Electrical Conductivity during Pulsed Electric Fields for Irreversible Electroporation Treatment Planning," IEEE Transactions on Biomedical Engineering, Apr. 2012, vol. 59, No. 4, pp. 1076-1085.
Neal II R.E., et al., "Hepatic Epithelioid Hemangioendothelioma Treated With Irreversible Electroporation and Antibiotics," Journal of Clinical Oncology, 2013, vol. 31, 5 Pages, Retrieved from URL: http://jco.ascopubs.org/cgl/dol/10.1200/JCO.2012.44.9736.
Neal II R.E., et al., "Improved Local and Systemic Anti-Tumor Efficacy for Irreversible Electroporation in Immunocompetent versus Immunodeficient Mice," PLOS ONE, May 24, 2013, vol. 8, No. 5 (e64559), 10 Pages, DOI:10.1371/journal.pone.0064559.
Neal II R.E., et al., "In Vitro and Numerical Support for Combinatorial Irreversible Electroporation and Electrochemotherapy Glioma Treatment," Annals of Biomedical Engineering, 2013, vol. 42, 13 Pages, DOI: 10.1007/s10439-013-0923-2.
Neal II R.E., et al., "In vivo Characterization and Numerical Simulation of Prostate Properties for Non-Thermal Irreversible Electroporation Ablation," The Prostate, 2014, vol. 17, No. 10 (22760), 11 Pages.
Neal II R.E., et al., "In Vivo Irreversible Electroporation Kidney Ablation: Experimentally Correlated Numerical Models," IEEE Transactions on Biomedical Engineering, 2013, 10 Pages, DOI: 10.1109/TBME.2014.2360374.
Neal II R.E., et al., "Spectrum of Imaging and Characteristics for Liver Tumors Treated With Irreversible Electroporation," Journal of Biomedical Science and Engineering, 2012, vol. 5, pp. 813-818.
Neal II R.E., et al., "The Effects of Metallic Implants on Electroporation Therapies: Feasibility of Irreversible Electroporation for Brachytherapy Salvage," CardioVascular and Interventional Radiology, 2013, vol. 36, No. 6, pp. 1638-1645 (08 Pages).
Neal II R.E., et al., "Treatment of Breast Cancer through the Application of Irreversible Electroporation Using a Novel Minimally Invasive Single Needle Electrode," Breast Cancer Research and Treatment, Aug. 2010, vol. 123, No. 1, pp. 295-301 (13 Pages).
Neal II R.E., et al., "Successful Treatment of a Large Soft Tissue Sarcoma with Irreversible Electroporation," Journal of Clinical Oncology, May 1, 2011, vol. 29, No. 13, pp. e372-e377, DOI: 10.1200/JCO.2010.33.0902.
Novickij V., et al., "High Frequency Electroporation Efficiency is Under Control of Membrane Capacitive Charging and Voltage Potential Relaxation," Bioelectrochemistry, 2018, vol. 119, pp. 92-97.
O'Brien T.J., et al., "Effects of Internal Electrode Cooling on Irreversible Electroporation Using a Perfused Organ Model," International Journal of Hyperthermia, 2019, vol. 35, No. 1, pp. 44-55 (12 Pages).
Reddy V.Y., et al., "Pulsed Field Ablation of Paroxysmal Atrial Fibrillation: 1-year Outcomes of Impulse, PEFCAT, and PEFACT II," The Journal of the American College of Cardiology (JAAC): Clinical Electrophysiology, May 2021, vol. 7, No. 5, pp. 614-627.
Ricke J., et al., "Irreversible Electroporation (IRE) Fails to Demonstrate Efficacy in a Prospective Multicenter Phase II Trial on Lung Malignancies: The ALICE Trial," Cardiovascular and Interventional Radiology, 2015, vol. 38, No. 2, pp. 401-408.
Rogers, et al., Strength-Duration Curve for an Electrically Excitable Tissue Extended Down to Near 1 Nanosecond, *IEEE Transactions on Plasma Science*, 32(4):1587-1599 (Aug. 2004).
Rossmeisl J.H., Jr., et al., "Safety and Feasibility of the Nanoknife System for Irreversible Electroporation Ablative Treatment of Canine Spontaneous Intracranial Gliomas," Journal of Neurosurgery, Jul. 3, 2015, vol. 123, No. 4, pp. 1008-1025 (18 Pages).
Rubinsky B., et al., "Irreversible Electroporation: A New Ablation Modality—Clinical Implications," Technology in Cancer Research & Treatment, Feb. 2007, vol. 6, No. 1, pp. 1-12.
Rubinsky, et al., Optimal Parameters for the Destruction of Prostate Cancer Using Irreversible Electroporation, *The Journal of Urology*, 180:2668-2674 (Dec. 2008).
Sano M.B., et al., "Burst and Continuous High Frequency Irreversible Electroporation Protocols Evaluated in a 3D Tumor Model," Physics in Medicine and Biology, Jul. 6, 2018, vol. 63, No. 13 (135022), pp. 1-18.
Sano M.B., et al., "Towards the Creation of Decellularized Organ Constructs Using Irreversible Electroporation and Active Mechanical Perfusion," BioMedical Engineering OnLine, 2010, vol. 9, No. 83, 16 Pages, Retrieved from URL: http://www.biomedical-engineering-online.com/content/9/1/83.
Scheffer H.J., et al., "The Influence of a Metal Stent on the Distribution of Thermal Energy during Irreversible Electroporation," PLOS ONE, Feb. 4, 2016, vol. 11, No. 2 (e0148457), 13 Pages, DOI:10.1371/journal.pone.0148457.
Schoenbach K.H., et al., "Bioelectrics," Springer, Editors: H. Akiyama, R. Heller, 2017, 491 Pages, ISBN 978-4-431-56093-7, ISBN 978-4-431-56095-1 (eBook), DOI: 10.1007/978-4-431-56095-1.
SHAH P.L., et al., "Epithelial Resurfacing: The Bronchial Skin Peel," American Journal of Respiratory and Critical Care Medicine, Sep. 1, 2020, Vo,. 202, No. 5, pp. 641-642.
SHAH P.L., et al., "Epithelial Resurfacing: The Bronchial Skin Peel," American Thoracic Society, May 22, 2020, pp. 1-8 (9 Pages).
Tang P.S., et al., "Acute Lung Injury and Cell Death: How Many Ways Can Cells Die," American Journal of Physiology Lung Cellular and Molecular Physiology, Jan. 18, 2008, vol. 294, No. 4, pp. L632-L641.
Thomson K.R., et al., "Introduction to Irreversible Electroporation-Principles and Techniques," Techniques in Vascular and Interventional Radiology, 2015, vol. 18, No. 3, pp. 128-134.
Timmer F.E.F., et al., "Irreversible Electroporation for Locally Advanced Pancreatic Cancer," Techniques in Vascular and Interventional Radiology, Jun. 2020, vol. 23, No. 2 (100675), pp. 1-9.
Tri J.A., et al., "Electroporation Ablation of Bronchial Smooth Muscle Cells: A Novel Non-thermal Asthma Therapy," Pulmonary and Critical Care Medicine, 2016, vol. 1, No. 4, pp. 1-4.
Valipour A., et al., "Bronchial Rheoplasty for Treatment of Chronic Bronchitis Twelve-Month Results from a Multicenter Clinical Trial," American Journal of Respiratory and Critical Care Medicine, 2019, vol. 202, No. 5, 27 Pages.
Valipour A., et al., "Bronchial Rheoplasty for Treatment of Chronic Bronchitis Twelve-Month Results from a Multicenter Clinical Trial," Journal of Respiratory and Critical Care Medicine, Sep. 1, 2020, vol. 202, No. 5, pp. 681-689.
Valipour A., et al., "Bronchial Rheoplasty Treatment for Chronic Bronchitis Using the Rheox System: 12-Month Results of a Prospective, Multi-Center Study," American Thoracic Society, Aug. 5-10, 2020, 1 Page, Abstract.

(56) References Cited

OTHER PUBLICATIONS

Valipour A., et al., "First-in-Human Results of Bronchial Rheoplasty: An endobronchial Treatment for Chronic Bronchitis (CB)," American Thoracic Society, 2019, pp. 1-20.
Valipour A., et al., "First-in-Human Results of Bronchial Rheoplasty: An Endobronchial Treatment for Chronic Bronchitis (CB)," D 94. COPD: Epidemiology and Therapy, Mini Symposium, May 22, 2019, 5 Pages, Abstract.
Valipour A., et al., "Late Breaking Abstract—Bronchial Rheoplasty for Treatment of Chronic Bronchitis: 6 Month Results from a Prospective Multi-Center Study," Abstract, European Respiratory Journal, 2019, vol. 54, Supplement. 63 (RCT448), pp. 1-5.
Valipour A., et al., "Late Breaking Abstract—First-in-Human Results of Bronchial Rheoplasty: An Endobronchial Treatment for Chronic Bronchitis (CB)," European Respiratory Journal, 2018, vol. 52, Supplement. 62 (OA2162), 6 Pages.
Verma A., et al., "Primer on Pulsed Electrical Field Ablation: Understanding the Benefits and Limitations," Circulation: Arrhythmia and Electrophysiology, Sep. 2021, vol. 14, No. 9 (e010086), pp. 1-16.
Vollmer, Robin T., Tumor Length In Prostate Cancer, *American Journal of Clinical Pathology*, 130(1):77-82 (Jul. 2008).
Wandel A., et al., "Optimizing Irreversible Electroporation Ablation with a Bipolar Electrode," The Journal of Vascular and Interventional Radiology, Sep. 2016, vol. 27, No. 9, pp. 1441-1450 (12 Pages).
Xie F., et al., "Ablation of Myocardial Tissue with Nanosecond Pulsed Electric Fields," PLoS One, Dec. 14, 2015, vol. 10, No. 12, Article No. e0144833, pp. 1-15.
Yavin H., et al., "Pulsed Field Ablation Using a Lattice Electrode for Focal Energy Delivery, Biophysical Characterization, Lesion Durability, and Safety Evaluation," Circulation: Arrhythmia and Electrophysiology, Jun. 2020, vol. 13, No. 6, pp. 529-538, E-Publication: May 6, 2020.
Extended EP Search Report dated Mar. 4, 2026 in EP Patent Appl. Serial No. 23797314.4 (123001).
Gowrishankar, et al., Electrical behavior and por accumulation in a multicellular model for conventional and supra-electroporation, Biochem. Biophys. Res. Commun., 349(2):643-653 (Oct. 2006).
Ibey, et al., Plasma Membrane Permeabilization by Trains of Ultrashort Electric Pulses, Bioelectrochemistry, 79(1):114-121 (Aug. 2010).
Kim, et al., Technical Feasibility and Safety of Image-Guided Biphasic Monopolar Pulsed Electric Field Ablation of Metastatic and Primary Malignancies, J. Vasc. Interv. Radiol., 35:1644-1654 (2024).
Reddy, et al., Pulsed Field Ablation For Pulmonary Vein Isolation in Atrial Fibrillation, Journal of the American College of Cardiology, 74(3):315-326 (Jul. 2019).
Schoenbach, et al., Bioelectric Effects of Intense Nanosecond Pulses, IEEE Transactions on Dielectrics & Electrical Insulation, 14(5):1088-1109 (2007).
Weaver, et al., Theory of electroporation: A Review, Bioelectrochemistry and Bioenergetics, 41(2):135-160 (Dec. 1996).
Wendler, et al., A prospective Phase 2a pilot study investigating focal percutaneous irreversible electroporation (IRE) ablation by NanoKnife in patients with localised renal cell carcinoma (RCC) with delayed interval tumour resection (IRENE trial), Contemporary Clinical Trials, 43:10-19 (May 2015).
Xuzhang, et al., Cisplatin-induced Pyroptosis Enhances the Efficacy of PD-L1 Inhibitor in Small-Cell Lung Cancer via GSDME/IL12/CD4Tem Axis, International Journal of Biological Sciences, 20(2):537-553 (2024).

* cited by examiner

| Parameter | Relative Change | Treatment Size | Muscle Contraction | Temperature Rise | Treatment Delivery Time | Electrical Arcing Risk |
|---|---|---|---|---|---|---|
| Electrode Style | Monopolar | ↓ | ↑ | ↓ | = | ↓ |
| Voltage | ↑ | ↑ | ↑ | ↑ | = | ↑ |
| Waveform | Biphasic | ↓ | ↓ | = | = | ↓ |
| Fundamental Frequency | ↑ | ↓ | ↓ | = | = | = |
| Packet Duration | ↑ | ↑ | ↑ | ↑ | = | ↑ |
| Number of Packets | ↑ | ↑ | = | ↑ | ↑ | = |
| Packet Delivery Rate | ↑ | = | = | ↑ | ↓ | = |

FIG. 3

Tumor growth and survival for unresected tumors groups

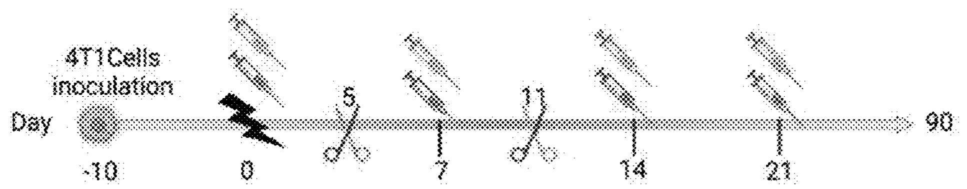

Fig. 37A

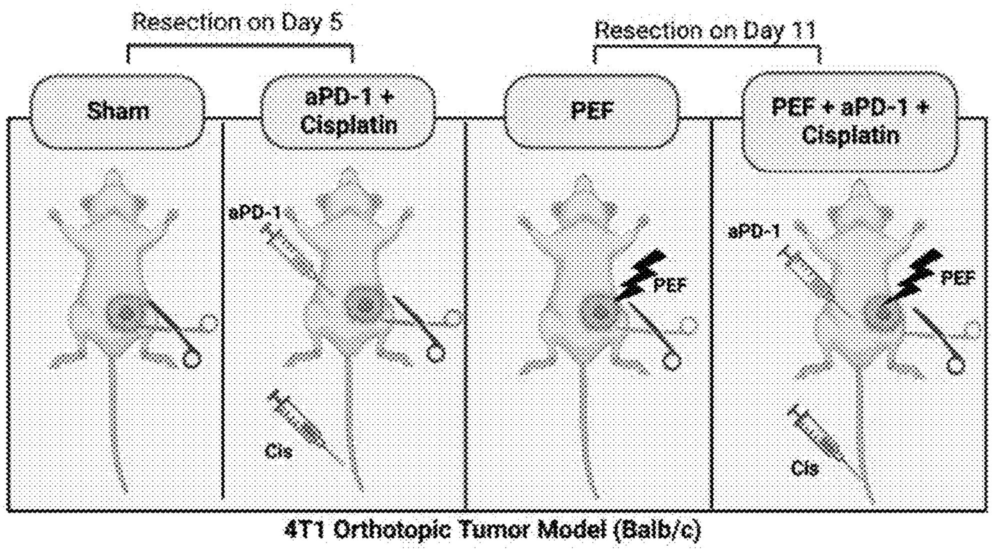

Fig. 37B

4T1 cells were inoculated in the 4th mammary fat pad of Balb/c mice. PEF was delivered to selected groups when the tumor reached 5mm in size (Day 0). On the same day, selected groups received anti PD-1 (i.p) and/or Cisplatin (i.v). The resection of the primary tumor was done on day 5 for the Sham group and the aPD-1 + Cisplatin group; on day 11 for PEF and PEF + aPD-1 + Cisplatin groups. Cisplatin and aPD-1 were administered also on day 7, day 14 and day 21. Upon resection of primary tumors, the mice were monitored up to the 90 days or euthanized due to extensive metastatic tumor burden.

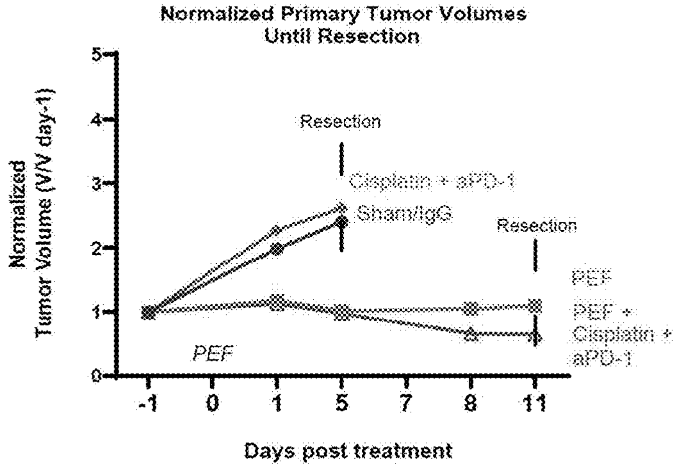

Fig. 38

DEVICES, SYSTEMS AND METHODS FOR THE TREATMENT OF ABNORMAL TISSUE

CROSS-REFERENCE TO RELATED APPLICATIONS

This application is a continuation of U.S. patent application Ser. No. 18/416,505, filed Jan. 18, 2024, which claims priority to U.S. Provisional Patent Application No. 63/502,877, filed on May 17, 2023, and U.S. Provisional Patent Application No. 63/480,440, filed Jan. 18, 2023, the entire contents of each of which are incorporated herein by reference. U.S. patent application Ser. No. 18/416,505, filed Jan. 18, 2024, is also a continuation-in-part of U.S. patent application Ser. No. 17/502,640, filed Oct. 15, 2021, which is a continuation of PCT/US2020/028844, filed Apr. 17, 2020, which claims priority to U.S. Provisional Patent Application No. 62/835,846, filed Apr. 18, 2019, the entire contents of each of which are incorporated herein by reference. This application is also a continuation-in-part of U.S. patent application Ser. No. 18/645,220, filed Apr. 24, 2024, which is a continuation of U.S. patent application Ser. No. 17/941,815, filed Sep. 9, 2022, which is a continuation of U.S. patent application Ser. No. 16/914,072, filed Jun. 26, 2020, now U.S. Pat. No. 11,471,208, which is a continuation of PCT/US2018/067501, filed Dec. 26, 2018, which claims priority to U.S. Provisional Patent Application No. 62/610,430, filed Dec. 26, 2017, the entire contents of each of which are incorporated herein by reference.

BACKGROUND

Abnormal tissue can take a variety of different forms, such as damaged, diseased, obstructive, cancerous or undesired tissue. In some instances, the abnormal tissue is a tumor, such as a benign tumor or a malignant tumor, a cyst, or an area of diseased tissue. One of the most troublesome types of abnormal tissue is related to cancer.

Cancer is a group of diseases characterized by the uncontrolled growth and spread of abnormal cells. If the spread is not controlled, it can result in death. Although the causes of cancer are not completely understood, numerous factors are known to increase the disease's occurrence, including many that are modifiable (e.g., tobacco use and excess body weight) and others that are not (e.g., inherited genetic mutations). These risk factors may act, simultaneously or in sequence, to initiate and/or promote cancer growth. More than 1.8 million new cancer cases are expected to be diagnosed in 2020 and about 606,520 Americans are expected to die of cancer in 2020, which translates to about 1,660 deaths per day. Cancer is the second most common cause of death in the US, exceeded only by heart disease.

Lung, liver and pancreatic cancers are among the cancers having the lowest survival rates. Lung cancer is the leading cause of cancer death, more than colorectal, breast, and prostate combined. The overall change in 5-yr survival rate for all stages combined has only slightly improved over time: 1970's (approx. 13%), 2010's (approx. 17.2%), 2019 (approx. 21.7%). Liver cancer incidence rates have more than tripled since 1980, while the death rates have more than doubled during this time. Some progress has occurred in survival for patients with liver cancer, but 5-year survival remains low, even for those diagnosed at the localized stage. Pancreatic cancer is expected to be the 2nd leading cause of cancer-related death in 2020. The 5-yr survival rate for all stages is 9% and has not substantially improved over 40 years. These outcomes have endured despite the evolution of conventional therapies.

Some cancers are characterized by abnormal activation of tyrosine kinases, a type of enzyme, due to mutations, translocations, or amplifications in one or more genes. There are two main types of tyrosine kinases: receptor tyrosine kinases (RTKs) and non-receptor tyrosine kinases (NRTKs). RTKs are located on the cell surface and are activated by binding of a specific ligand, such as a growth factor (i.e EGF) or hormone. NRTKs are located within the cell and are activated by various intracellular signals. Both types of tyrosine kinases play important roles in cellular signaling. Abnormal activation of tyrosine kinases is implicated in tumorigenesis, progression, invasion, and metastasis of malignancies.

Consequently, tyrosine kinases have been targeted for treatment of such cancers. Antineoplastic tyrosine kinase inhibitors are a class of drugs used to identify and attack these types of cancer cells while causing less damage to normal cells. Antineoplastic tyrosine kinase inhibitors work by blocking the action of the enzymes, tyrosine kinases, that are responsible for the activation of proteins and are part of many cell functions, including cell signaling, growth, and division. However, almost all patients that receive tyrosine kinase inhibitors (TKI) develop resistance to the drugs and the tumors eventually come back. Cancer cells can acquire mutations or bypass signaling pathways, making them resistant to the effects of TKIs. This can result in disease progression and limit the effectiveness of the treatment.

Many types of cancers are not successfully cured or recur at a later point in time. Recurrence typically occurs because the original treatment did not successfully eliminate all of the cancer cells and those left behind proliferated. In some instances, the cancer cells spread to other parts of the body in undetectable amounts, known as micrometastases. When these micrometastases are not overcome by the body, they grow to detectable levels and require additional treatment. And, ultimately, many patients lose their battle with cancer.

Consequently, improved therapies are needed that more successfully treat cancers and reduce or prevent their recurrence, along with improved therapies for all types of abnormal tissue. At least some of these objectives will be met by the present invention.

SUMMARY

Described herein are embodiments of apparatuses, systems and methods for treating target tissue. Likewise, the invention relates the following numbered clauses:

1. A system for treating a mass of undesired tissue cells within a body of a patient comprising:

- an instrument comprising a shaft having a proximal end and a distal end, and at least one energy delivery body disposed near the distal end of the shaft, wherein the distal end of the shaft is configured to be advanced into a luminal structure of the body of the patient and positioned so that the at least one energy delivery body is able to deliver non-thermal energy to the mass of undesired tissue cells; and
- a generator in electrical communication with the at least one energy delivery body, wherein the generator includes at least one energy delivery algorithm configured to provide an electric signal of the non-thermal energy deliverable to the mass of undesired tissue so as to destroy at least a portion of the mass of undesired tissue.

2. A system as in clause 1, wherein the mass of undesired tissue cells comprises a tumor, a benign tumor, a malignant tumor, a cyst, or an area of diseased tissue.

3. A system as in any of the above clauses, wherein the at least a portion of the mass of undesired tissue is located within a wall of the luminal structure.

4. A system as in clause 3, wherein the at least one energy delivery algorithm is configured to provide an electric signal of the non-thermal energy deliverable to the mass of undesired tissue so as to destroy at least a portion of the mass of undesired tissue while maintaining patency of the luminal structure.

5. A system as in any of clauses 1-2, wherein the at least a portion of the mass of undesired tissue is located external to a wall of the luminal structure.

6. A system as in clause 5, wherein the at least one energy delivery algorithm is configured to provide an electric signal of the non-thermal energy deliverable to the mass of undesired tissue so as to destroy at least a portion of the mass of undesired tissue while maintaining a collage structure supporting the luminal structure through which the non-thermal energy passed.

7. A system as in any of clauses 1-2, wherein the at least a portion of the mass of undesired tissue is located within a lumen of the luminal structure.

8. A system as in any of the above clauses, wherein the energy delivery body comprises an expandable structure configured to be expanded within the luminal structure so that the expandable structure is able to deliver the non-thermal energy to the mass of undesired tissue cells.

9. A system as in clause 8, wherein the expandable structure comprises a basket-shaped electrode.

10. A system as in any of the above clauses, wherein the energy delivery body comprises a paddle configured to be positioned against an inner surface of the luminal structure so that the paddle is able to deliver the non-thermal energy to the mass of undesired tissue cells.

11. A system as in any of clauses 1-2, wherein the at least one energy delivery body is able to deliver the non-thermal energy to a depth of up to 3 cm from an exterior of the wall of the luminal structure.

12. A system as in any of clauses 1-2, wherein the at least a portion of the mass of undesired tissue is located external to a wall of the luminal structure, and wherein the energy delivery body comprises a probe configured to penetrate a wall of the luminal structure and deliver the non-thermal energy to the mass of undesired tissue cells.

13. A system as in clause 12, wherein the probe is advanceable from the distal end of the shaft.

14. A system as in any of clauses 12-13, wherein the probe includes a probe tip, wherein the probe tip is able to be advanced up to 8 cm from the distal end of the shaft.

15. A system as in any of clauses 12-14, wherein the distal end of the shaft is configured to be advanced up to 20 cm beyond the wall of the luminal structure.

16. A system as in clause 12, wherein the probe comprises a plurality of probe elements, wherein at least one probe element is capable of delivering the non-thermal energy to the mass of undesired tissue cells.

17. A system as in clause 16, wherein at least two probe elements are capable of delivering the non-thermal energy and at least one of the at least two probe elements is independently selectable for receiving the non-thermal energy for delivery.

18. A system as in clause 17, wherein each of the at least two probe elements are capable of simultaneously delivering the non-thermal energy in different amounts.

19. A system as in clause 12, wherein the probe comprises a plurality of probe elements, wherein each probe element is capable of delivering the non-thermal energy to the mass of undesired tissue cells.

20. A system as in clause 12, wherein the probe comprises a plurality of probe elements, wherein at least one probe element is individually advanceable from the shaft.

21. A system as in any of clauses 12-20, wherein the probe comprises a conductive tube extending from the proximal end of the shaft to the distal end of the shaft.

22. A system as in clause 21, further comprising an energy plug configured to electrically connect the probe to the generator, wherein the energy plug includes a conductive wire configured to engage the conductive tube.

23. A system as in any of clauses 12-20, wherein the probe comprises a probe tip disposed near the distal end of the shaft and a conductive wire extending from the proximal end of the shaft to the probe tip.

24. A system as in clause 12, wherein the probe comprises a probe tip and a conductive element configured to extend beyond the probe tip, wherein the conductive element is configured to deliver the non-thermal energy to the mass of undesired tissue cells.

25. A system as in any of the above clauses, wherein the at least one energy delivery body is configured to transmit the non-thermal energy to a return electrode positioned outside the body of the patient so as to deliver the non-thermal energy to the mass of undesired tissue cells disposed therebetween.

26. A system as in any of the above clauses, wherein the non-thermal energy comprises a series of biphasic pulses delivered in packets.

27. A system as in any of the above clauses, wherein the distal end of the shaft is configured to be advanced through an endoscope.

28. A system as in any of the above clauses, wherein the luminal structure comprises a blood vessel, an esophagus, a stomach, a pancreatic duct, a biliary duct, a small intestine, a large intestine, a colon, a rectum, a bladder, a urethra, a urinary collecting duct, a uterus, a vagina, a fallopian tube, a ureter, a renal tubule, a spinal canal, a spinal cord, an airway, a nasal cavity, a mouth, a heart chamber, a heart lumen, a kidney lumen, and an organ lumen.

29. A system as in any of the above clauses, wherein the shaft further comprises a delivery lumen configured to deliver a fluid to the mass of undesired tissue cells.

30. A system for treating a mass of undesired tissue cells within a body of a patient comprising:

an instrument comprising a shaft having a proximal end and a distal end, and an energy delivery body disposed near the distal end of the shaft, wherein the distal end of the shaft is configured to be advanced into the body near the mass so that the at least one energy delivery body is able to deliver non-thermal energy to the mass of undesired tissue cells;

a return electrode positionable at a distance from the at least one energy delivery body so that the at least one energy delivery body functions in a monopolar fashion; and a generator in electrical communication with the at least one energy delivery body, wherein the generator includes at least one energy delivery algorithm configured to provide an electric signal of the non-thermal energy deliverable from the energy delivery body to the return electrode so as to destroy at least a portion of the mass of undesired tissue.

31. A system as in clause 30, wherein the mass of undesired tissue cells comprises a tumor, a benign tumor, a malignant tumor, a cyst, or an area of diseased tissue.

32. A system as in any of clauses 30-31, wherein the at least a portion of the mass of undesired tissue is located within a wall of a luminal structure.

33. A system as in clause 32, wherein the at least one energy delivery algorithm is configured to provide an electric signal of the non-thermal energy deliverable to the mass of undesired tissue so as to destroy at least a portion of the mass of undesired tissue while maintaining patency of the luminal structure.

34. A system as in any of clauses 30-31, wherein the at least a portion of the mass of undesired tissue is located near a wall of a luminal structure.

35. A system as in clause 34, wherein the at least one energy delivery algorithm is configured to provide an electric signal of the non-thermal energy deliverable to the mass of undesired tissue so as to destroy at least a portion of the mass of undesired tissue while maintaining a collage structure supporting the luminal structure.

36. A system as in any of clauses 30-31, wherein the at least a portion of the mass of undesired tissue is located within a lumen of a luminal structure.

37. A system as in any of clauses 30-36, wherein the energy delivery body comprises an expandable structure configured to be expanded so that the expandable structure is able to deliver the non-thermal energy to the mass of undesired tissue cells.

38. A system as in clause 37, wherein the expandable structure comprises a basket-shaped electrode.

39. A system as in any of clauses 30-36, wherein the energy delivery body comprises a paddle configured to be positioned near the mass of undesired tissue cells so that the paddle is able to deliver the non-thermal energy to the mass of undesired tissue cells.

40. A system as in any of clauses 30-39, wherein the at least one energy delivery body is able to deliver the non-thermal energy to a radius of up to 3 cm from an exterior surface of the at least one energy delivery body.

41. A system as in any of clauses 30-36, the energy delivery body comprises a probe configured to penetrate tissue and deliver the non-thermal energy to the mass of undesired tissue cells.

42. A system as in clause 41, wherein the probe is advanceable from the distal end of the shaft.

43. A system as in clause 42, wherein the probe includes a probe tip, wherein the probe tip is able to be advanced up to 8 cm from the distal end of the shaft.

44. A system as in clause 41, wherein the distal end of the shaft is configured to be advanced into tissue up to 20 cm.

45. A system as in clause 41, wherein the probe comprises a plurality of probe elements, wherein at least one probe element is capable of delivering the non-thermal energy to the mass of undesired tissue cells.

46. A system as in clause 45, wherein at least two probe elements are capable of delivering the non-thermal energy and at least one of the at least two probe elements is independently selectable for receiving the non-thermal energy for delivery.

47. A system as in clause 46, wherein each of the at least two probe elements are capable of simultaneously delivering the non-thermal energy in different amounts.

48. A system as in clause 41, wherein the probe comprises a plurality of probe elements, wherein each probe element is capable of delivering the non-thermal energy to the mass of undesired tissue cells.

49. A system as in clause 41, wherein at least one probe element is individually advanceable from the shaft.

50. A system as in clause 41, wherein the probe comprises a conductive tube extending from the proximal end of the shaft to the distal end of the shaft.

51. A system as in clause 50, further comprising an energy plug configured to electrically connect the probe to the generator, wherein the energy plug includes a conductive wire configured to engage the conductive tube.

52. A system as in clause 41, wherein the probe comprises a probe tip disposed near the distal end of the shaft and a conductive wire extending from the proximal end of the shaft to the probe tip.

53. A system as in clause 41, wherein the probe comprises a probe tip and a conductive element configured to extend beyond the probe tip, wherein the conductive element is configured to deliver the non-thermal energy to the mass of undesired tissue cells.

54. A system as in any of clauses 30-53, wherein the non-thermal energy comprises a series of biphasic pulses delivered in packets.

55. A system as in any of clauses 30-54, wherein the distal end of the shaft is configured to be advanced through an endoscope.

56. A system as in any of clauses 30-55, wherein the distal end of the shaft is configured to be advanced into a luminal structure comprising a blood vessel, an esophagus, a stomach, a pancreatic duct, a biliary duct, a small intestine, a large intestine, a colon, a rectum, a bladder, a urethra, a urinary collecting duct, a uterus, a vagina, a fallopian tube, a ureter, a renal tubule, a spinal canal, a spinal cord, an airway, a nasal cavity, a mouth, a heart chamber, a heart lumen, a kidney lumen, and an organ lumen.

57. A system as in any of clauses 30-56, wherein the shaft further comprises a delivery lumen configured to deliver a fluid to the mass of undesired tissue cells.

58. A system as in any of clauses 30-57, wherein shaft is configured to be advanced percutaneously through skin of the patient.

59. A system as in any of clauses 30-57, further comprising a percutaneous needle and wherein the shaft is configured to be advanced through the percutaneous needle.

60. An instrument for delivering energy to target tissue near a luminal structure in a body comprising:

- a shaft having a proximal end and a distal end, wherein the distal end is configured to be advanced into the luminal structure; and
- a probe having a probe tip advanceable from the distal end of the shaft, wherein the probe tip is configured to penetrate a wall of the luminal structure near the target tissue and insert into the target tissue so as to deliver energy to the target tissue.

61. An instrument as in clause 60, wherein the probe tip is able to be advanced up to 8 cm from the distal end of the shaft.

62. An instrument as in any of clauses 60-61, wherein the distal end of the shaft is configured to be advanced through the wall of the luminal structure.

63. An instrument as in clause 62, wherein the distal end of the shaft is configured to be advanced up to 20 cm beyond the wall of the luminal structure.

64. An instrument as in any of clauses 60-63, wherein the probe comprises a plurality of probe elements, wherein at least one probe element is capable of delivering the energy to the target tissue.

65. An instrument as in clause 64, wherein at least two probe elements are capable of delivering the non-thermal energy and at least one of the at least two probe elements is independently selectable for receiving the energy for delivery.

66. An instrument as in clause 65, wherein each of the at least two probe elements are capable of simultaneously delivering the non-thermal energy in different amounts.

67. An instrument as in clause 64, wherein at least one probe element is individually advanceable from the shaft.

68. An instrument as in clause 64, wherein at least one probe element is capable of receiving the energy so that energy is delivered a bipolar fashion between the at least one probe element delivering the energy and the at least one probe element receiving the energy.

69. An instrument as in clause 60, wherein the probe comprises a plurality of probe elements, wherein each probe element is capable of delivering the energy.

70. An instrument as in any of clauses 60-69, wherein the instrument includes an energy delivery body disposed long the shaft.

71. An instrument as in clause 70, wherein the energy delivery body is configured to deliver energy to the target tissue from within the luminal structure.

72. An instrument as in clause 70, wherein the energy delivery body comprises an electrode having a basket shape.

73. An instrument as in clause 70, wherein the energy delivery body comprises an electrode having a disk shape.

74. An instrument as in clause 73, wherein the disk shape is disposed so that its diameter is substantially perpendicular to a longitudinal axis of the shaft.

75. An instrument as in clause 74, wherein the probe tip is substantially concentric with the electrode having the disk shape.

76. An instrument as in clause 70, wherein instrument is configured so that the energy delivery body delivers different energy than the probe tip.

77. A instrument as in any of clauses 60-76, further comprising a handle disposed near the proximal end of the shaft, wherein the handle is configured to electrically couple with a pulse waveform generator so that energy from the pulse waveform generator is delivered to the probe tip.

78. An instrument as in clause 77, wherein the probe comprises a conductive component extending from the proximal end of the shaft to the distal end of the shaft which transmits the energy from the handle to the probe tip.

79. An instrument as in clause 78, wherein the conductive component comprises a tubular shaft.

80. An instrument as in clause 78, wherein the conductive component comprises a conductive wire.

81. An instrument as in clause 77, wherein the handle is configured to receive a connection wire that joins with the conductive component so that the energy is transmitted through the connection wire to the conductive component.

82. An instrument as in clause 60, wherein the distal end of the shaft is configured to pass through a percutaneous needle.

83. An instrument as in clause 60, wherein the shaft is configured to be advanced percutaneously through skin of the patient.

84. An instrument as in any of clauses 60-83, wherein the target tissue comprises a tumor, a benign tumor, a malignant tumor, a cyst, or an area of diseased tissue 85. A system for delivering energy to target tissue near a luminal structure in a body comprising:

an instrument comprising a shaft having a proximal end and a distal end, wherein the distal end is configured to be advanced into the luminal structure, and a probe having a probe tip advanceable from the distal end of the shaft, wherein the probe tip is configured to penetrate a wall of the luminal structure near the target tissue and insert into the target tissue so as to deliver energy to the target tissue; and a generator in electrical communication with the at least one energy delivery body, wherein the generator includes at least one energy delivery algorithm configured to provide an electric signal of the non-thermal energy deliverable from the probe tip so as to treat at least a portion of the target tissue.

86. A system as in clause 85, further comprising a return electrode positionable at a distance from the probe so that the probe functions in a monopolar fashion.

87. A method of treating target tissue cells within a body of a patient, wherein the target tissue cells reside outside of a luminal structure of the body comprising:

advancing a distal end of an instrument into the luminal structure of the body, wherein the instrument includes an energy delivery body disposed near its distal end; and delivering non-thermal energy from the energy delivery body to the target tissue cells residing outside of the luminal structure, wherein the non-thermal energy treats the target tissue cells while maintaining an extra-cellular matrix of the luminal structure.

88. A method as in clause 87, wherein the target tissue cells reside up to 8 cm away from an exterior of the luminal structure.

89. A method as in any of clauses 87-88, wherein treats comprises destroys.

90. A method as in any of clauses 87-88, wherein treats comprises increases the vulnerability of the target tissue cells to premature death.

91. A method as in any of clauses 87-88, wherein treats comprises increases the uptake of agents by the target tissue cells.

92. A method as in any of clauses 87-91, further comprising expanding the energy delivery body within the luminal structure.

93. A method as in clause 92, wherein the energy delivery body comprises a basket-shaped electrode configured to be expanded so as to reside near or against an interior surface of the luminal structure, wherein the basket-shaped electrode delivers the non-thermal energy.

94. A method as in clause 87, wherein delivering the non-thermal energy from the energy delivery body comprises delivering the non-thermal energy circumferentially from the energy delivery body to an inner circumference of the luminal structure.

95. A method as in clause 87, wherein additional target tissue cells reside within a wall of the luminal structure and wherein delivering the non-thermal energy from the energy delivery body to the target tissue cells residing outside of the luminal structure includes delivering the non-thermal energy from the energy delivery body to the additional target tissue cells residing within the wall of the luminal structure.

96. A method as in clause 87, further comprising penetrating a wall of the luminal structure with the energy delivery body.

96. A method as in clause 96, further comprising passing at least a portion of the energy delivery body through a wall of the luminal structure so that the at least a portion of the energy delivery body resides outside of the luminal structure.

98. A method as in clause 97, wherein the at least a portion of the energy delivery body comprises a probe tip, and wherein passing the at least a portion of the energy delivery body through the wall of the luminal structure comprises advancing a probe tip from the distal end of the instrument.

99. A method as in clause 98, wherein passing the at least a portion of the energy delivery body through the wall of the luminal structure comprises advancing a plurality of probe elements from the distal end of the instrument.

100. A method as in clause 99, wherein advancing the plurality of probe elements comprises individually advancing at least one of the plurality of probe elements form the distal end of the instrument.

101. A method as in clause 99, wherein delivering the non-thermal energy comprises delivering the non-thermal energy to at least one of the plurality of probe elements.

102. A method as in clause 87, wherein the instrument includes another energy delivery body disposed near the distal end of the instrument, and wherein advancing the distal end of the instrument into the luminal structure comprises positioning the another energy delivery body within the luminal structure.

103. A method as in any of clauses 87-102, further comprising delivering an additional therapy to the patient, wherein the additional therapy comprises radiotherapy, chemotherapy, immunotherapy, targeted therapy, focal therapy, gene therapy, plasmid therapy or a combination of any of these.

104. A method as in clause 103, wherein focal therapy comprises delivery of energy to cause thermal ablation, energy to cause cryotherapy, energy to cause irreversible electroporation or energy to cause reversible electroporation.

105. A method as in clause 103, wherein delivering an additional therapy comprises surgically removing a portion of tissue near or including at least some of the target tissue cells.

106. A method as in any of clauses 103-105, wherein delivering the non-thermal energy occurs prior to delivering the additional therapy.

107. A method as in any of clauses 103-105, wherein delivering the non-thermal energy occurs after delivering the additional therapy.

108. A method as in any of clauses 103-105, wherein delivering the non-thermal energy occurs during a treatment session of delivering the additional therapy.

109. A method as in any of clauses 87-102, further comprising delivering chemotherapy, and wherein delivering the non-thermal energy comprises delivering sufficient non-thermal energy to synergistically increase the effect of the chemotherapy.

110. A method as in any of clauses 87-102, further comprising delivering radiotherapy, and wherein delivering the non-thermal energy comprises delivering sufficient non-thermal energy to synergistically increase the effect of the radiotherapy.

111. A method as in any of clauses 87-110, wherein the delivering the non-thermal energy comprises delivering the non-thermal energy in a manner which causes an abscopal effect by the patient.

112. A method as in any of clauses 87-111, further comprising positioning a return electrode on the patient and wherein delivering the non-thermal energy comprises delivering the non-thermal energy in a monopolar fashion while utilizing the return electrode.

113. A method as in any of clauses 87-112, wherein the target tissue cells comprise a tumor, a benign tumor, a malignant tumor, a cyst, or an area of diseased tissue.

114. A method as in any of clauses 87-113, further comprising inserting the distal end of the instrument through an endoscope.

115. A method of treating a patient having a tumor at least partially within a portion of wall of a luminal structure, the method comprising:

advancing a distal end of an instrument into the luminal structure, wherein the instrument includes an energy delivery body disposed near its distal end; and delivering non-thermal energy from the energy delivery body so that the non-thermal energy destroys at least some of the tumor.

116. A method as in clause 115, wherein the non-thermal energy destroys at least some of the tumor while maintaining physiological function of the luminal structure.

117. A method as in any of clauses 115-116, wherein the luminal structure comprises a blood vessel, an esophagus, a stomach, a pancreatic duct, a biliary duct, a small intestine, a large intestine, a colon, a rectum, a bladder, a urethra, a urinary collecting duct, a uterus, a vagina, a fallopian tube, a ureter, a renal tubule, a spinal canal, a spinal cord, an airway, a nasal cavity, a mouth, a heart chamber, a heart lumen, a kidney lumen, and an organ lumen.

118. A method as in any of clauses 115-117, further comprising expanding the energy delivery body within the luminal structure.

119. A method as in clause 118, wherein the energy delivery body comprises a basket-shaped electrode configured to be expanded so as to reside near or against an interior surface of the luminal structure, wherein the basket-shaped electrode delivers the non-thermal energy.

120. A method as in clause 118, wherein delivering the non-thermal energy from the energy delivery body comprises delivering the non-thermal energy circumferentially from the energy delivery body to an inner circumference of the luminal structure.

121. A method as in any of clauses 115-117, further comprising penetrating a wall of the luminal structure with the energy delivery body.

122. A method as in clause 121, further comprising passing at least a portion of the energy delivery body through the wall of the luminal structure so that the at least a portion of the energy delivery body resides outside of the luminal structure.

123. A method as in any of clauses 115-122, wherein the instrument includes another energy delivery body disposed near its distal end, the method further comprising passing at least a portion of the another energy delivery body through the wall of the luminal structure so that the at least a portion of the another energy delivery body resides outside of the luminal structure.

124. A method as in clause 123, wherein the energy delivery body and the another energy delivery body function in a bipolar manner to deliver the non-thermal energy to the tumor therebetween.

125. A method as in clause 115, further comprising positioning a return electrode on the patient and wherein delivering the non-thermal energy comprises delivering the non-thermal energy in a monopolar fashion while utilizing the return electrode.

126. A method as in any of clauses 115-125, further comprising delivering an additional therapy to the patient, wherein the additional therapy comprises radiotherapy, chemotherapy, immunotherapy, targeted therapy, focal therapy, gene therapy, plasmid therapy, or a combination of any of these.

127. A method as in clause 126, wherein focal therapy comprises delivery of energy to cause thermal ablation, energy to cause cryotherapy, energy to cause irreversible electroporation or energy to cause reversible electroporation.

128. A method as in clause 126, wherein delivering an additional therapy comprises surgically removing a portion of tissue near or including at least some of the tumor.

129. A method as in any of clauses 115-128, wherein delivering the non-thermal energy occurs prior to delivering the additional therapy.

130. A method as in any of clauses 115-128, wherein delivering the non-thermal energy occurs after delivering the additional therapy.

131. A method as in any of clauses 115-128, wherein delivering the non-thermal energy occurs during a treatment session of delivering the additional therapy.

132. A method as in any of clauses 115-125, further comprising delivering chemotherapy, and wherein delivering the non-thermal energy comprises delivering sufficient non-thermal energy to synergistically increase the effect of the chemotherapy.

133. A method as in any of clauses 115-132, wherein the delivering the non-thermal energy comprises delivering the non-thermal energy in a manner which causes an abscopal effect by the patient.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3 provides a table illustrating various example effects of parameter changes.

FIGS. 37A-37B is a schematic of a study design.

FIG. 38 provides a graph that shows the average tumor growth for each experimental group until the day of resection.

DETAILED DESCRIPTION

Specific embodiments of the disclosed devices, systems, and methods will now be described with reference to the drawings. Nothing in this detailed description is intended to imply that any particular component, feature, or step is essential to the invention.

I. Overview

Devices, systems and methods are provided to treat damaged, diseased, abnormal, obstructive, cancerous or undesired tissue (e.g. a tumor, a benign tumor, a malignant tumor, a cyst, or an area of diseased tissue, etc) by delivering specialized pulsed electric field (PEF) energy to target tissue areas. The energy is delivered in a manner so as to be non-thermal (i.e. below a threshold for causing thermal ablation). Consequently, when extracellular matrices are present, the extracellular matrices are preserved, and the targeted tissue maintains its structural architecture including blood vessels and lymphatics. Thus, sensitive structures, such as biological lumens, blood vessels, nerves, etc, are able to be preserved which are critical to maintaining the integrity and functionality of the tissue. This provides a number of benefits. To begin, this allows for the treatment of tissues that are often considered untreatable by conventional methods. Target tissues that are near sensitive structures are typically unresectable by surgical methods due to the inability to thoroughly and effectively surgically separate the tissue from the sensitive structures. Likewise, many conventional non-surgical therapies are contraindicated due to the potential for damage to the sensitive structures by the therapy or because the therapies are deemed ineffective due to the proximity of the sensitive structures. In addition, the ability to treat tissue near sensitive structures also provides a more comprehensive treatment in that malignant margins are not left near sensitive structures. Once tissue is treated, the survival of the structural architecture also allows for the natural influx of biological elements, such as components of the immune system, or for the introduction of various agents to further the therapeutic treatment. This provides a number of treatment benefits as will be described in more detail in later sections.

Figure 1:
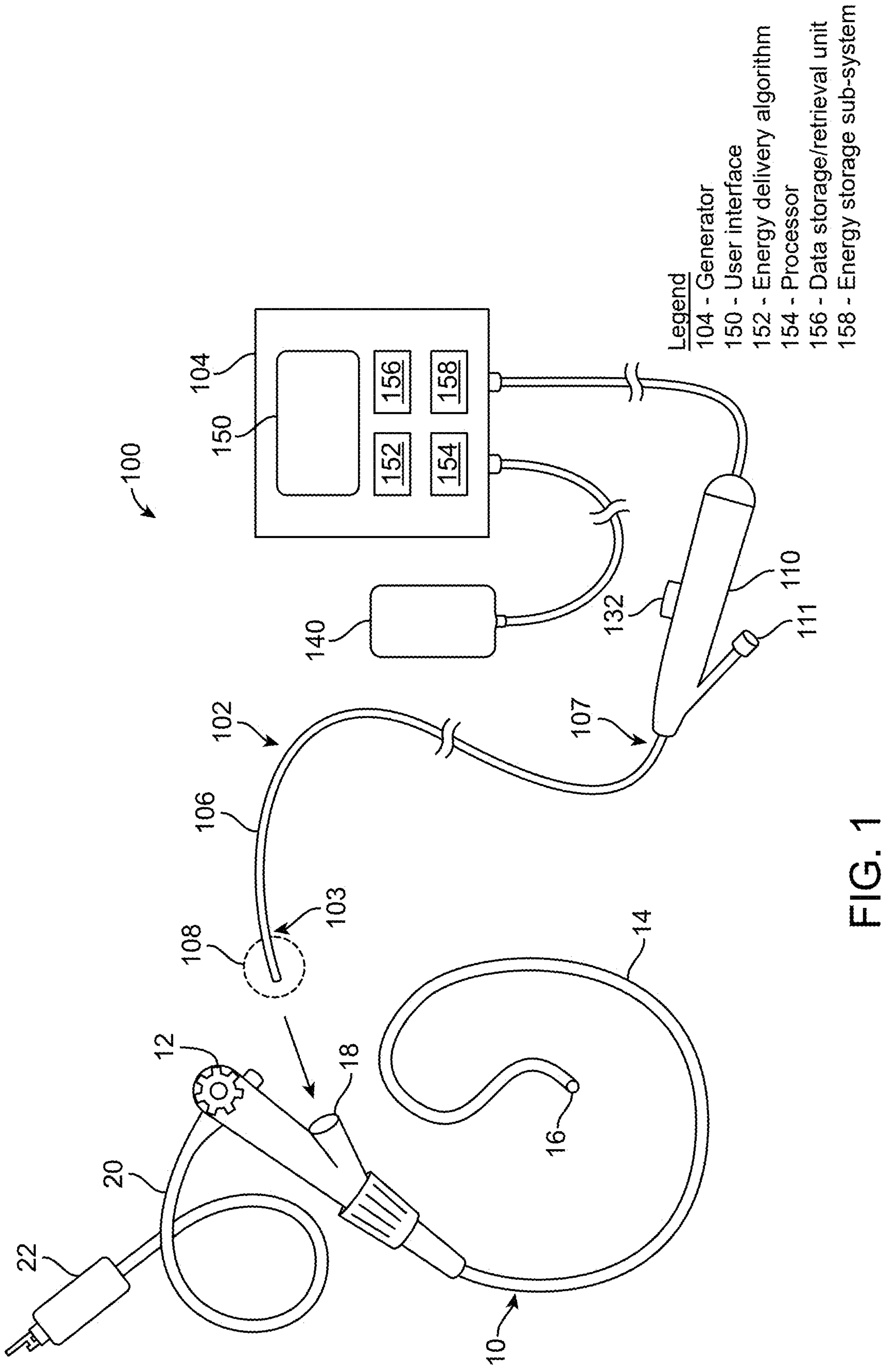
FIG. 1 provides an overview illustration of an example therapeutic system 100 for use in delivering specialized PEF energy.

The energy is delivered with the use of systems and devices advantageously designed for superior access to target tissue throughout the body, particularly in locations previously considered inaccessible to percutaneous approaches. Such access is typically minimally invasive and relies on endoluminal approaches, though it may be appreciated that other approaches, such as percutaneous, laparoscopic or open surgical approaches, may be used in some situations, if desired. FIG. 1 provides an overview illustration of an example therapeutic system 100 for use in delivering the specialized PEF energy. In this embodiment, the system 100 comprises an elongate instrument 102 comprising a shaft 106 having a distal end 103 and a proximal end 107. The instrument 102 includes an energy delivery body 108 which is generically illustrated as a dashed circle near the distal end 103 of the shaft 106. It may be appreciated that the energy delivery body 108 may take a variety of forms having structural differences which encumber the drawing of a single representation, however individual example embodiments will be described and illustrated herein. The energy delivery body 108 may be mounted on or integral with an exterior of the shaft 106 so as to be externally visible. Or, the energy delivery body 108 may be housed internally within the shaft 106 and exposed by advancing from the shaft 106 or retracting the shaft 106 itself. Likewise, more than one energy delivery body 108 may be present and may be external, internal or both. In some embodiments, the shaft 106 is comprised of a polymer, such as an extruded polymer. It may be appreciated that in some embodiments, the shaft 106 is comprised of multiple layers of material with different durometers to control flexibility and/or stiffness. In some embodiments, the shaft 106 is reinforced with various elements such as individual wires or wire braiding. In either case, such wires may be flat wires or round wires. Wire braiding has a braid pattern and in some embodiments the braid pattern is tailored for desired flexibility and/or stiffness. In other embodiments, the wire braiding that reinforces the shaft 106 may be combined advantageously with multiple layers of material with different durometers to provide additional control of flexibility and/or stiffness along the length of the shaft.

In any case, each energy delivery body 108 comprises at least one electrode for delivery of the PEF energy. Typically, the energy delivery body 108 comprises a single delivery electrode and operates in a monopolar arrangement which is achieved by supplying energy between the energy delivery body 108 disposed near the distal end 103 of the instrument 102 and a return electrode 140 positioned upon the skin of the patient. It will be appreciated, however, that bipolar energy delivery and other arrangements may alternatively be used. When using bipolar energy delivery, the instrument 102 may include a plurality of energy delivery bodies 108 configured to function in a bipolar manner or may include a single energy delivery body 108 having multiple electrodes configured to function in a bipolar manner. The instrument 102 typically includes a handle 110 disposed near the proximal end 107. The handle 110 is used to maneuver the instrument 102, and typically includes an actuator 132 for manipulating the energy delivery body 108. In some embodiments, the energy delivery body 108 transitions from a closed or retracted position (during access) to an open or exposed position (for energy delivery) which is controlled by the actuator 132. Thus, the actuator 132 typically has the form of a knob, button, lever, slide or other mechanism. It may be appreciated that in some embodiments, the handle 110 includes a port 111 for introduction of liquids, agents, substances, tools or other devices for delivery through the instrument 102. Example liquids include suspensions, mixtures, chemicals, fluids, chemotherapy agents, immunotherapy agents, micelles, liposomes, embolics, nanoparticles, drug-eluting particles, genes, plasmids, and proteins, to name a few.

The instrument 102 is in electrical communication with a generator 104 which is configured to generate the PEF energy. In this embodiment, the generator 104 includes a user interface 150, one or more energy delivery algorithms 152, a processor 154, a data storage/retrieval unit 156 (such as a memory and/or database), and an energy-storage subsystem 158 which generates and stores the energy to be delivered. In some embodiments, the user interface 150 on the generator 104 is used to select the desired treatment algorithm 152. In other embodiments, the algorithm 152 is automatically selected by the generator 104 based upon information obtained by one or more sensors, which will be described in more detail in later sections. A variety of energy delivery algorithms may be used. In some embodiments, one or more capacitors are used for energy storage/delivery, however any other suitable energy storage element may be used. In addition, one or more communication ports are typically included.

As illustrated in FIG. 1, the distal end 103 of the instrument 102 is typically advanceable through a delivery device, such as an endoscope 10. Endoscopes 10 typically comprise a control body 12 attached to an elongate insertion tube 14 having a distal tip 16. The endoscope 10 has an interior lumen accessible by a port 18 into which the distal end 103 of the instrument 102 passes. The shaft 106 of the instrument 102 advanceable through the interior lumen and exits out of the distal tip 16. Imaging is achieved through the endoscope 10 with the use of a light guide tube 20 having an endoscopic connector 22 which connects to a light and energy source. The distal tip 16 of the endoscope may be outfitted with visualization technologies including but not limited to video, ultrasound, laser scanning, etc. These visualization technologies collect signals consistent with their design and transmit the signal either through the length of the shaft over wires or wirelessly to a video processing unit. The video processing unit then processes the video signals and displays the output on a screen. It may be appreciated that the endoscope 10 is typically specific to the anatomical location to which it is being used, such as gastroscopes (upper GI endoscopy, which includes the stomach, esophagus, and small intestine (duodenum)), colonoscopes (large intestine), bronchoscopes (lungs), laryngoscopes (larynx), cystoscopes (urinary tract), duodenoscopes (small intestine), enteroscopes (digestive system), ureteroscopes (ureter), hysteroscopes (cervix, uterus), etc. It may be appreciated that in other embodiments, the instrument 102 is deliverable through a catheter, sheath, introducer, needle or other delivery system.

Endoluminal access allows treatment of target tissue from within various lumens in the body. Lumens are the spaces inside of tubular-shaped or hollow structures within the body and include passageways, canals, ducts and cavities to name a few. Example luminal structures include blood vessels, esophagus, stomach, small and large intestines, colon, bladder, urethra, urinary collecting ducts, uterus, vagina, fallopian tubes, ureters, kidneys, renal tubules, spinal canal, spinal cord, and others throughout the body, as well as structures within and including such organs as the lung, heart and kidneys, to name a few. In some embodiments, the target tissue is accessed via the nearby luminal structure. In some instances, a treatment instrument 102 is advanced through various luminal structures or branches of a luminal system to reach the target tissue location. For example, when accessing a target tissue site via a blood vessel, the treatment instrument 102 may be inserted remotely and advanced through various branches of the vasculature to reach the target site. Likewise, if the luminal structure originates in a natural orifice, such as the nose, mouth, urethra or rectum, entry may occur through the natural orifice and the treatment instrument 102 is then advanced through the branches of the luminal system to reach the target tissue location. Alternatively, a luminal structure may be entered near the target tissue via cut-down or other methods. This may be the case when accessing luminal structures that are not part of a large system or that are difficult to access otherwise.

Once a target tissue area has been approached endoluminally, energy can be delivered to the target tissue in a variety of ways. In one arrangement, an energy delivery body 108 is positioned within a body lumen and energy is delivered to the target tissue that is has entered the body lumen, through at least a portion of the lumen wall to target tissue either within the lumen wall and/or at least partially surrounding the lumen wall or through the lumen wall to target tissue outside and nearby the lumen wall. In another arrangement, the energy delivery body 108 is advanced through the lumen wall and inserted within or near target tissue outside of the lumen wall. It may be appreciated that such arrangements may be combined, involving at least two energy delivery bodies 108, one positioned within the body lumen and one extending through the wall of the body lumen. In some embodiments, each of the energy delivery bodies 108 function in a monopolar manner (e.g. utilizing a return electrode placed at a distance). In other embodiments, at least some of the energy delivery bodies 108 function in a bipolar manner (e.g. utilizing an energy delivery body 108 as a return electrode). Optionally, each of two energy delivery bodies 108 may be positioned on opposite sides of a lumen wall and function in a bipolar manner so as to treat tissue therebetween (e.g. within the lumen wall). Since the lumen itself is preserved throughout the treatment, these delivery options are possible and allow treatment of tissue in, on or nearby the lumen itself. Such delivery of therapy allows access to previously inaccessible tissue, such as tumors or diseased tissue that has invaded lumen walls or has wrapped at least partially around a body lumen, too close to be surgically removed or treated with conventional focal therapies. Many conventional focal therapies, such as treatment with thermal energy, damage or destroy the structure of the lumen walls due to thermal protein coagulation, etc. In particular, bowel injuries caused by radiofrequency ablation are one of the most feared complications and have been associated with mortality due to sepsis and abscess formation. Consequently, most physicians will defer radiofrequency ablation in tumors adjacent to bowel. Other conventional focal therapies are ineffective near particular body lumens. For example, cryotherapy relies on sufficient cooling of tissue which is compromised by flow through body lumens, such a blood through the vasculature, which reduces the cooling effects. Such endoluminal access is also less invasive than other types of treatment, such as percutaneous delivery of energy involving the placement of numerous needle probes through the skin and deeply into tissues and organs. Since natural openings in the body are utilized, less wound healing is incurred along with reduced possible points of infection. Likewise, locations deep within the body can be access along with locations that are difficult to otherwise access from the outside, such as locations behind other organs or near great vessels, etc. It may be appreciated that a variety of anatomical locations may be treated with the systems and methods described herein. Examples include luminal structures themselves, soft tissues throughout the body located near luminal structures and solid organs accessible from luminal structures, including but not limited to liver, pancreas, gall bladder, kidney, prostate, ovary, lymph nodes and lymphatic drainage ducts, underlying musculature, bony tissue, brain, eyes, thyroid, etc. It may also be appreciated that a variety of tissue locations can be accessed percutaneously.

The endoscopic approach also lends itself to monopolar energy delivery. As mentioned, monopolar delivery involves the passage of current from the energy delivery body 108 (near the distal end of the instrument 102) to the target tissue and through the patient to a return pad 140 positioned against the skin of the patient to complete the electric current circuit. Thus, in some embodiments, the instrument 102 includes only one energy delivery body 108 or electrode. This allows the instrument 102 to have a low profile so as to be positionable within smaller body lumens. This also allows deep penetration of tissue surrounding the energy delivery body 108. Likewise, when penetrating the lumen wall with such devices, only one penetration is needed per treatment due to the use of only one energy delivery body 108. It may be appreciated that additional penetrations may occur due to various device designs or treatment protocols, however in some embodiments, the monopolar delivery design reduces the invasiveness of the procedure, simplifies the device and treatment design and provides superior treatment zones in target tissue.

In contrast, bipolar delivery involves the passage of current through target tissue between two electrodes either on the same energy delivery body 108, on different energy delivery bodies 108 or by other arrangements. Most conventional energy therapies are bipolar and are typically percutaneous. Such therapies involve multiple penetrations of the skin, increasing discomfort, prolonging healing and adding complexity to the procedure. It may be appreciated that although the systems described herein may be utilized in a variety of formats, including bipolar and percutaneous arrangements, the device features will typically be combined in a manner that reduces overall invasiveness and provides better outcomes.

The devices, systems and methods described herein may be used on their own or in combination with other treatments. Such combinatory treatment may be applicable to cancer treatment in particular. For example, the PEF treatment described herein may be used in combination with a variety of non-surgical therapies, neoadjuvant and adjuvant therapies such as radiotherapy, chemotherapy, targeted therapy/immunotherapy, focal therapy, gene therapy, plasmid therapy, to name a few. Example focal therapies include microwave ablation, radiofrequency ablation, cryoablation, high intensity focused ultrasound (HIFU), and other pulsed electric field ablation therapies. Such combination may condition the tissue for improved responsiveness and in some cases a synergistic response that is greater than either of the therapies alone. In addition, the PEF treatments described herein may lead to an abscopal effect due to the nature of the therapy.

II. Energy Algorithms

The PEF energy is provided by one or more energy delivery algorithms 152. In some embodiments, the algorithm 152 prescribes a signal having a waveform comprising a series of energy packets wherein each energy packet comprises a series of high voltage pulses. In such embodiments, the algorithm 152 specifies parameters of the signal such as energy amplitude (e.g., voltage) and duration of applied energy, which is comprised of the number of packets, number of pulses within a packet, and the fundamental frequency of the pulse sequence, to name a few. Additional parameters may include switch time between polarities in biphasic pulses, dead time between biphasic cycles, and rest time between packets, which will be described in more detail in later sections. There may be a fixed rest period between packets, or packets may be gated to the cardiac cycle and are thus variable with the patient's heart rate. There may be a deliberate, varying rest period algorithm or no rest period may also be applied between packets. A feedback loop based on sensor information and an auto-shutoff specification, and/or the like, may be included.

Figure 2A:
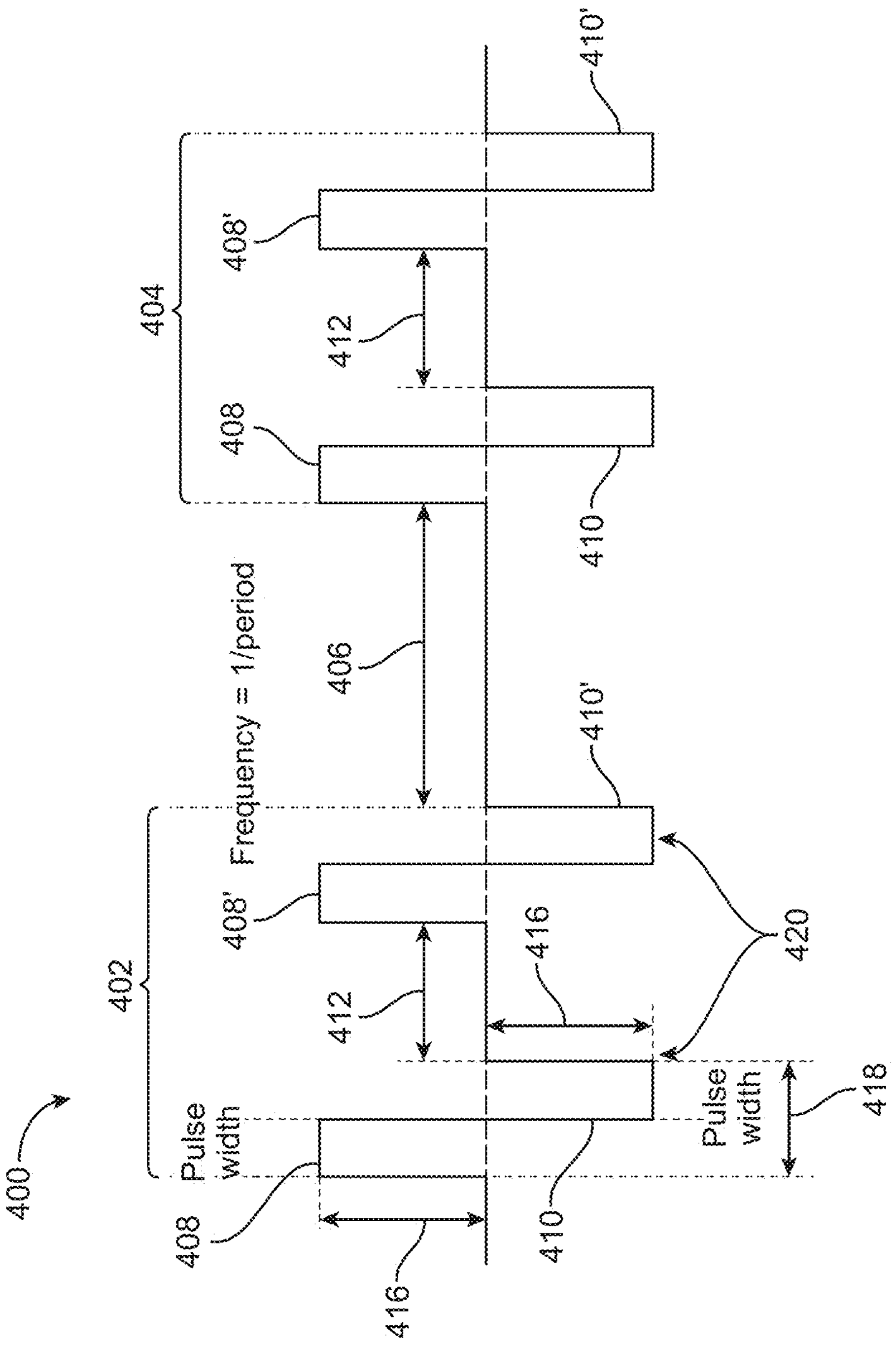
FIG. 2A illustrates an embodiment of a waveform of a signal prescribed by an energy delivery algorithm.

FIG. 2A illustrates an embodiment of a waveform 400 of a signal prescribed by an energy delivery algorithm 152. Here, two packets are shown, a first packet 402 and a second packet 404, wherein the packets 402, 404 are separated by a rest period 406. In this embodiment, each packet 402, 404 is comprised of a first biphasic cycle 418 (comprising a first positive pulse peak 408 and a first negative pulse peak 410) and a second biphasic cycle (comprising a second positive pulse peak 408' and a second negative pulse peak 410'). The first and second biphasic pulses are separated by dead time 412 (i.e., a pause) between each pulse. In this embodiment, the biphasic pulses are symmetric so that the set voltage 416 is the same for the positive and negative peaks. Here, the biphasic, symmetric waves are also square waves such that the magnitude and time of the positive voltage wave is approximately equal to the magnitude and time of the negative voltage wave. When using a bipolar configuration, portions of the wall W cells facing the negative voltage wave undergo cellular depolarization in these regions, where a normally negatively charged cell membrane region briefly turns positive. Conversely, portions of the wall W cells facing the positive voltage wave undergo hyperpolarization in which the cell membrane region's electric potential becomes extremely negative. It may be appreciated that in each positive or negative phase of the biphasic pulse, portions of the wall W cells will experience the opposite effects. For example, portions of cell membranes facing the negative voltage will experience depolarization, while the portions 180° to this portion will experience hyperpolarization. In some embodiments, the hyperpolarized portion faces the dispersive or return electrode 140.

A. Voltage

The voltages used and considered may be the tops of square-waveforms, may be the peaks in sinusoidal or saw-tooth waveforms, or may be the RMS voltage of sinusoidal or sawtooth waveforms. In some embodiments, the energy is delivered in a monopolar fashion and each high voltage pulse or the set voltage 416 is between about 500 V to 10,000 V, particularly about 3500 V to 4000 V, about 3500 V to 5000 V, about 3500 V to 6000 V, including all values and subranges in between including about 3000 V, 3500 V, 4000 V, 4500 V, 5000 V, 5500 V, 6000 V to name a few. Voltages delivered to the tissue may be based on the setpoint on the generator 104 while either taking in to account the electrical losses along the length of the instrument 102 due to inherent impedance of the instrument 102 or not taking in to account the losses along the length, i.e., delivered voltages can be measured at the generator or at the tip of the instrument.

It may be appreciated that the set voltage 416 may vary depending on whether the energy is delivered in a monopolar or bipolar fashion. In bipolar delivery, a lower voltage may be used due to the smaller, more directed electric field. The bipolar voltage selected for use in therapy is dependent on the separation distance of the electrodes, whereas the monopolar electrode configurations that use one or more distant dispersive pad electrodes may be delivered with less consideration for exact placement of the catheter electrode and dispersive electrode placed on the body. In monopolar electrode embodiments, larger voltages are typically used due to the dispersive behavior of the delivered energy through the body to reach the dispersive electrode, on the order of 10 cm to 100 cm effective separation distance. Conversely, in bipolar electrode configurations, the relatively close active regions of the electrodes, on the order of 0.5 mm to 10 cm, including 1 mm to 1 cm, results in a greater influence on electrical energy concentration and effective dose delivered to the tissue from the separation distance. For instance, if the targeted voltage-to-distance ratio is 3000 V/cm to evoke the desired clinical effect at the appropriate tissue depth (1.3 mm), if the separation distance is changed from 1 mm to 1.2 mm, this would result in a necessary increase in treatment voltage from 300 to about 360 V, a change of 20%.

B. Frequency

It may be appreciated that the number of biphasic cycles per second of time is the frequency when a signal is continuous. In some embodiments, biphasic pulses are utilized to reduce undesired muscle stimulation, particularly cardiac muscle stimulation. In other embodiments, the pulse waveform is monophasic and there is no clear inherent frequency. Instead, a fundamental frequency may be considered by doubling the monophasic pulse length to derive the frequency. In some embodiments, the signal has a frequency in the range 100 kHz-1 MHz, more particularly 100 kHz-1000 kHz. In some embodiments, the signal has a frequency in the range of approximately 100-600 kHz which typically penetrates the lumen wall so as to treat or affect particular cells somewhat deeply positioned, such as submucosal cells or smooth muscle cells. In some embodiments, the signal has a frequency in range of approximately 600 kHz-1000 kHz or 600 kHz-1 MHz which typically penetrates the lumen wall so as to treat or affect particular cells somewhat shallowly, such as epithelial or endothelial cells. It may be appreciated that at some voltages, frequencies at or below 100-250 kHz may cause undesired muscle stimulation. Therefore, in some embodiments, the signal has a frequency in the range of 400-800 kHz or 500-800 kHz, such as 500 kHz, 550 kHz, 600 kHz, 650 kHz, 700 kHz, 750 kHz, 800 kHz. In particular, in some embodiments, the signal has a frequency of 600 kHz. In addition, cardiac synchronization is typically utilized to reduce or avoid undesired cardiac muscle stimulation during sensitive rhythm periods. It may be appreciated that even higher frequencies may be used with components which minimize signal artifacts.

C. Voltage-Frequency Balancing

The frequency of the waveform delivered may vary relative to the treatment voltage in synchrony to retain adequate treatment effect. Such synergistic changes would include the decrease in frequency, which evokes a stronger effect, combined with a decrease in voltage, which evokes a weaker effect. For instance, in some cases the treatment may be delivered using 3000 V in a monopolar fashion with a waveform frequency of 800 kHz, while in other cases the treatment may be delivered using 2000 V with a waveform frequency of 400 kHz.

When used in opposing directions, the treatment parameters may be manipulated in a way that makes it too effective, which may increase muscle contraction likelihood or risk effects to undesirable tissues, such as cartilage for airway treatments. For instance, if the frequency is increased and the voltage is decreased, such as the use of 2000 V at 800 kHz, the treatment may not have sufficient clinical therapeutic benefit. Opposingly, if the voltage was increased to 3000 V and frequency decreased to 400 kHz, there may be undesirable treatment effect extent to collateral sensitive tissues. In some cases, the over-treatment of these undesired tissues could result in morbidity or safety concerns for the patient, such as destruction of cartilaginous tissue in the airways sufficient to cause airway collapse, or destruction of smooth muscle in the GI tract sufficient to cause interruption of normal peristaltic motion. In other cases, the overtreatment of the untargeted or undesirable tissues may have benign clinical outcomes and not affect patient response or morbidity if they are overtreated.

D. Packets

As mentioned, the algorithm 152 prescribes a signal having a waveform comprising a series of energy packets wherein each energy packet comprises a series of high voltage pulses. The cycle count 420 is half the number of pulses within each biphasic packet. Referring to FIG. 2A, the first packet 402 has a cycle count 420 of two (i.e. four biphasic pulses). In some embodiments, the cycle count 420 is set between 1 and 100 per packet, including all values and subranges in between. In some embodiments, the cycle count 420 is up to 5 pulses, up to 10 pulses, up to 25 pulses, up to 40 pulses, up to 60 pulses, up to 80 pulses, up to 100 pulses, up to 1,000 pulses or up to 2,000 pulses, including all values and subranges in between.

The packet duration is determined by the cycle count, among other factors. Typically, the higher the cycle count, the longer the packet duration and the larger the quantity of energy delivered. In some embodiments, packet durations are in the range of approximately 50 to 1000 microseconds, such as 50 μs, 60 μs, 70 μs, 80 μs, 90 μs, 100 μs, 125 μs, 150 μs, 175 μs, 200 μs, 250 μs, 100 to 250 μs, 150 to 250 μs, 200 to 250 μs, 500 to 1000 μs to name a few. In other embodiments, the packet durations are in the range of approximately 100 to 1000 microseconds, such as 150 μs, 200 μs, 250 μs, 500 μs, or 1000 μs.

The number of packets delivered during treatment, or packet count, typically includes 120 to 280 packets including all values and subranges in between.

Example parameter combinations include:

| Voltage | Frequency | Packet duration | Minimum # of Packets | Penetration |
|---|---|---|---|---|
| 3500 V | 500 kHz | 250 μs | 200 | 0.1-1 cm |
| 5000 V | 5 kHz | 200 μs | 10-20 | 0.5-2 cm |
| 6000 V | 300 kHz | 500 μs | 100 | 3-5 cm |
| 3000 V | 500 kHz | 250 μs | 25-50 | 0.5-2 cm |
| 2500 V | 300 kHz | 150 μs | 100 | 0.5-2 cm |
| 2500 V | 500 kHz | 100 μs | 50 | 0.5 cm |
| 2500 V | 600 kHz | 100 μs | 20 | 0.05-0.1 cm |

E. Rest Period

In some embodiments, the time between packets, referred to as the rest period 406, is set between about 0.1 seconds and about 5 seconds, including all values and subranges in between. In other embodiments, the rest period 406 ranges from about 0.001 seconds to about 10 seconds, including all values and subranges in between. In some embodiments, the rest period 406 is approximately 1 second. In particular, in some embodiments the signal is synced with the cardiac rhythm so that each packet is delivered synchronously within a designated period relative to the heartbeats, thus the rest periods coincide with the heartbeats. In other embodiments wherein cardiac synchronization is utilized, the rest period 406 may vary, as the rest period between the packets can be influenced by cardiac synchronization, as will be described in later sections.

F. Switch Time and Dead Time

Figure 2B:
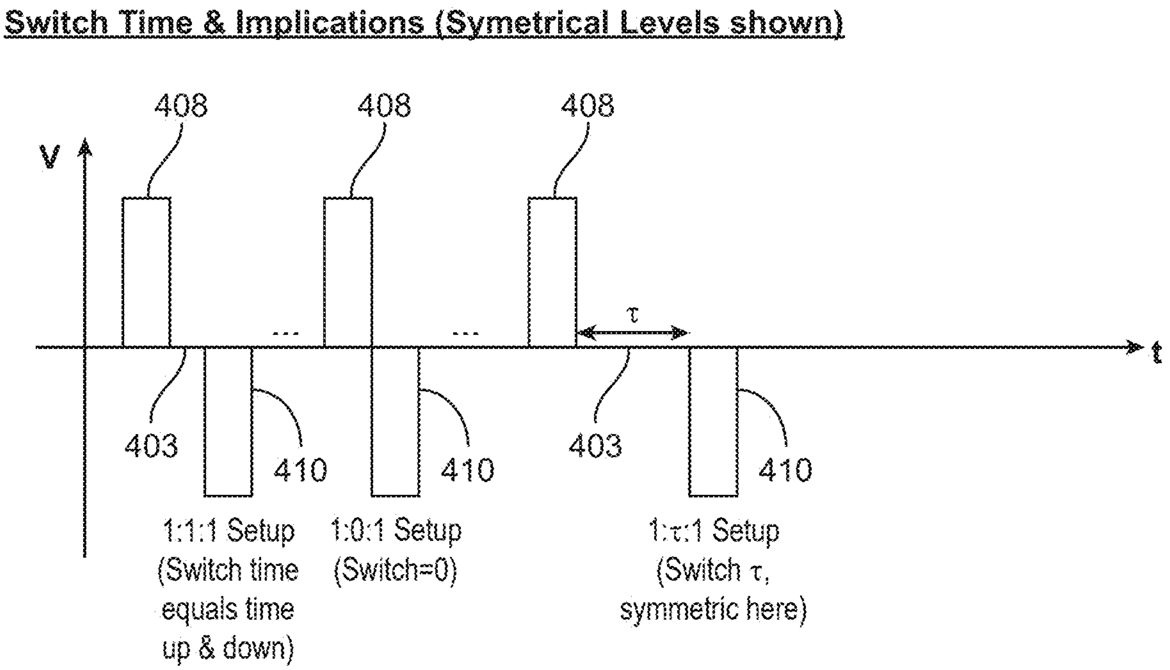
FIG. 2B illustrates various examples of biphasic pulses having a switch time therebetween.
Figure 2C:
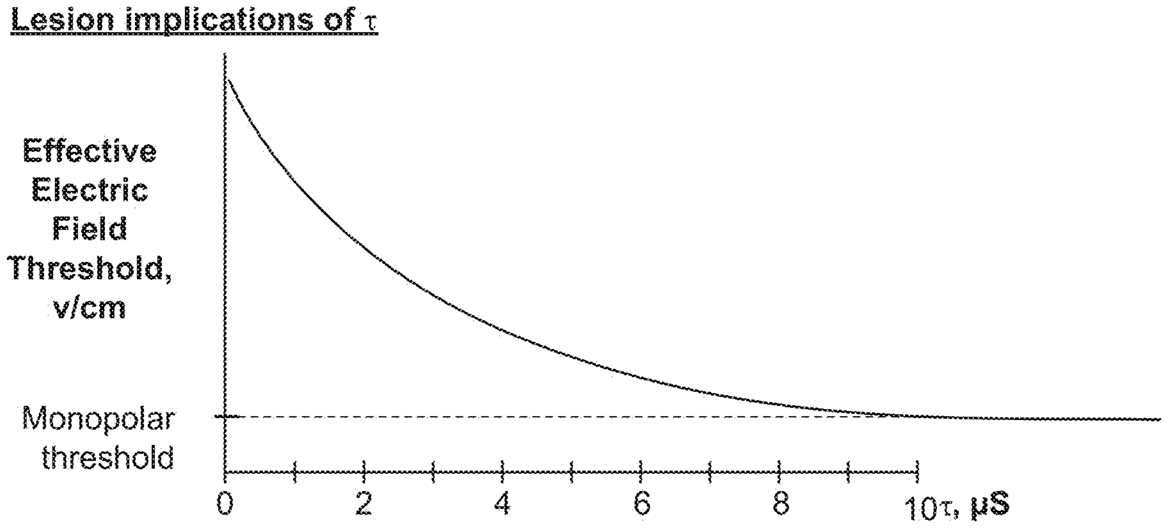
FIG. 2C illustrates the relationship between effective electric field threshold and pulse length

A switch time is a delay or period of no energy that is delivered between the positive and negative peaks of a biphasic pulse, as illustrated in FIGS. 2B-2C. FIG. 2B illustrates various examples of biphasic pulses (comprising a positive peak 408 and a negative peak 410) having a switch time 403 therebetween (however when the switch time 403 is zero, it does not appear). In some embodiments, the switch time ranges between about 0 to about 1 microsecond, including all values and subranges in between. In other embodiments, the switch time ranges between 1 and 20 microseconds, including all values and subranges in between. In other embodiments, the switch time ranges between about 2 to about 8 microsecond, including all values and subranges in between. FIG. 2C illustrates the relationship between effective electric field threshold and switch time.

Delays may also be interjected between each cycle of the biphasic pulses, referred as "dead-time". Dead time occurs within a packet, but between biphasic pulses. This is in contrast to rest periods which occur between packets. In other embodiments, the dead time 412 is in a range of approximately 0 to 0.5 microseconds, 0 to 10 microseconds, 2 to 5 microseconds, 0 to 20 microseconds, about 0 to about 100 microseconds, or about 0 to about 100 milliseconds, including all values and subranges in between. In some embodiments, the dead time 412 is in the range of 0.2 to 0.3 microseconds. Dead time may also be used to define a period between separate, monophasic, pulses within a packet.

Delays, such as switch times and dead times, are introduced to a packet to reduce the effects of biphasic cancellation within the waveform. Biphasic cancellation is a term used to refer to the reduced induction of cellular modulation in response to biphasic waveforms versus monophasic waveforms, particularly when switch times and dead times are small, such as below 10 μs. One explanation for this phenomenon is provided here, though it may be appreciated that there are likely other biological, physical, or electrical characteristics or alterations that result in the reduced modulation from biphasic waveforms. When cells are exposed to the electromotive force induced by the electric field presence, there is electrokinetic movement of ions and solutes within the intracellular and extracellular fluids. These charges accumulate at dielectric boundaries such as cell and organelle membranes, altering the resting transmembrane potentials (TMPs). When the electric field is removed, the driving force that generated the manipulated TMPs is also eliminated, and the normal biotransport and ionic kinetics operating with concentration gradients begin to restore normative distributions of the solutes. This induces a logarithmic decay of the manipulated TMP on the membranes. However, if rather than eliminating the electric field, the electric field polarity is retained but with a reversed polarity, then there is a new electromotive force actively eliminating the existing TMP that was induced, followed by the accumulation of a TMP in the opposite polarity. This active depletion of the initially manipulated TMP considerably restricts the downstream effects cascade that may occur to the cell, weakening the treatment effect from the initial electric field exposure. Further, where the subsequent electric field with reversed polarity must first "undo" the original TMP manipulation generated, and then begin accumulating its own TMP in the opposite polarity; the final TMP reached by the second phase of the electric field is not as strong as the original TMP, assuming identical durations of each phase of the cycle. This reduces the treatment effects generated from each phase of the waveform resulting in a lower treatment effect than that generated by either pulse in the cycle would achieve alone. This phenomenon is referred as biphasic cancellation. For packets with many cycles, this pattern is repeated over the entire set of cycles and phase changes within the cycles for the packet. This dramatically limits the effect from the treatment. When cell behavior is modulated as a result of the pulsed electric fields by mechanisms other than purely transmembrane potential manipulation, it may be appreciated that the effects of biphasic cancellation are less pronounced, and thus the influence of switch times and dead times on treatment outcome are reduced.

Thus, in some embodiments, the influence of biphasic cancellation is reduced by introducing switch time delays and dead time. In some instances, the switch time and dead time are both increased together to strengthen the effect. In other instances, only switch time or only dead time are increased to induce this effect.

It may be appreciated that typically appropriate timing is for the relaxation of the TMP to complete after 5× the charging time-constant, T. For most cells, the time constant may be approximated as 1 μs. Thus, in some embodiments the switch time and the dead time are both set to at least 5 μs to eliminate biphasic cancellation. In other embodiments, the reduction in biphasic cancellation may not require complete cell relaxation prior to reversing the polarity, and thus the switch time and the dead time are both set at 0.5 μs to 2 μs. In other embodiments, the switch time and the dead time are set to be the same length as the individual pulse lengths, since further increases in these delays may only offer diminishing returns in terms of increased treatment effect and the collateral increase in muscle contraction. In this way, the combination of longer-scale pulse durations (>500 ns) and stacked pulse cycles with substantial switch time and dead time delays, it is possible to use biphasic waveforms without the considerably reduced treatment effect that occurs due to biphasic cancellation. In some cases, the tuning of these parameters may be performed to evoke stronger treatment effects without a comparably proportional increase in muscle contraction. For example, using 600 kHz waveform with switch time=dead time=1.66 microseconds (2× the duration as the pulses), may be used to retain the reduction in muscle contraction versus monophasic pulse waveforms, but with the retention of stronger treatment effects.

In some embodiments, the switch time duration is adjusted such that the degree of therapy effect relative to distant cell effects is optimized for the target of the therapy. In some embodiments, the switch time duration or dead time duration is minimized to decrease distant muscle cell contractions, with lesser local therapy effect. In other embodiments, the switch time duration is extended to increase the local therapy effect, with potential additional distant muscle cell contractions. In some embodiments, the switch time or dead time duration are extended to increase the local therapy effect, and the use of neuromuscular paralytics are employed to control the resulting increase in muscle contraction. In some embodiments, switch time duration is 10 ns to 2 μs, while in other embodiments, the switch time duration is 2 μs to 20 μs. In some instances, when cell modulation is targeted in a way where transmembrane potential manipulation is not the primary mechanism needed to evoke the targeted treatment effects, the switch time and dead time delays are minimized to less than 0.1 μs or to 0 μs. This elimination of delays minimizes the peripheral, non-targeted treatment effects such as skeletal muscle contraction or cardiac muscle action potential and contraction.

Another benefit of utilizing switch time and the dead time delays to increase treatment effects for biphasic waveforms is a reduction in generator demands, whereby the introduction of pauses will enable stronger treatment effects without requiring asymmetric/unbalanced pulse waveforms. In this case, unbalanced waveforms are described as those that are monophasic, or have an unbalanced duration or voltage or combination in one polarity relative to the other. In some cases, unbalanced means that the integral of the positive portions of the waveform are not equal to the integral of the negative portions of the waveform. Generators capable of delivering unbalanced waveforms have a separate set of design considerations that are accounted for thereby increasing potential generator complexity.

G. Waveforms

Figure 2D:
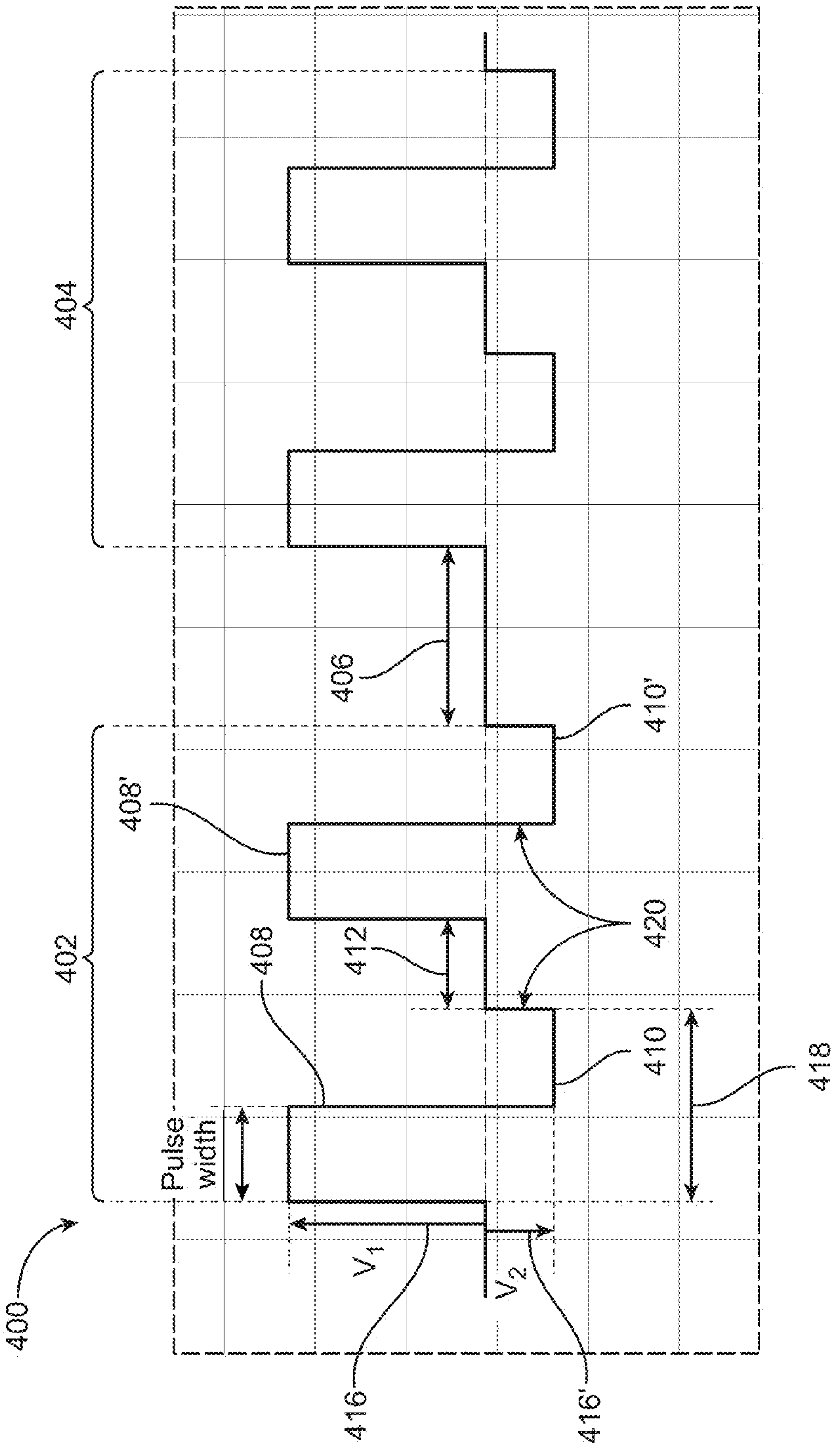
FIG. 2D illustrates an example waveform prescribed by another energy delivery algorithm wherein the waveform has voltage imbalance.
Figure 2E:
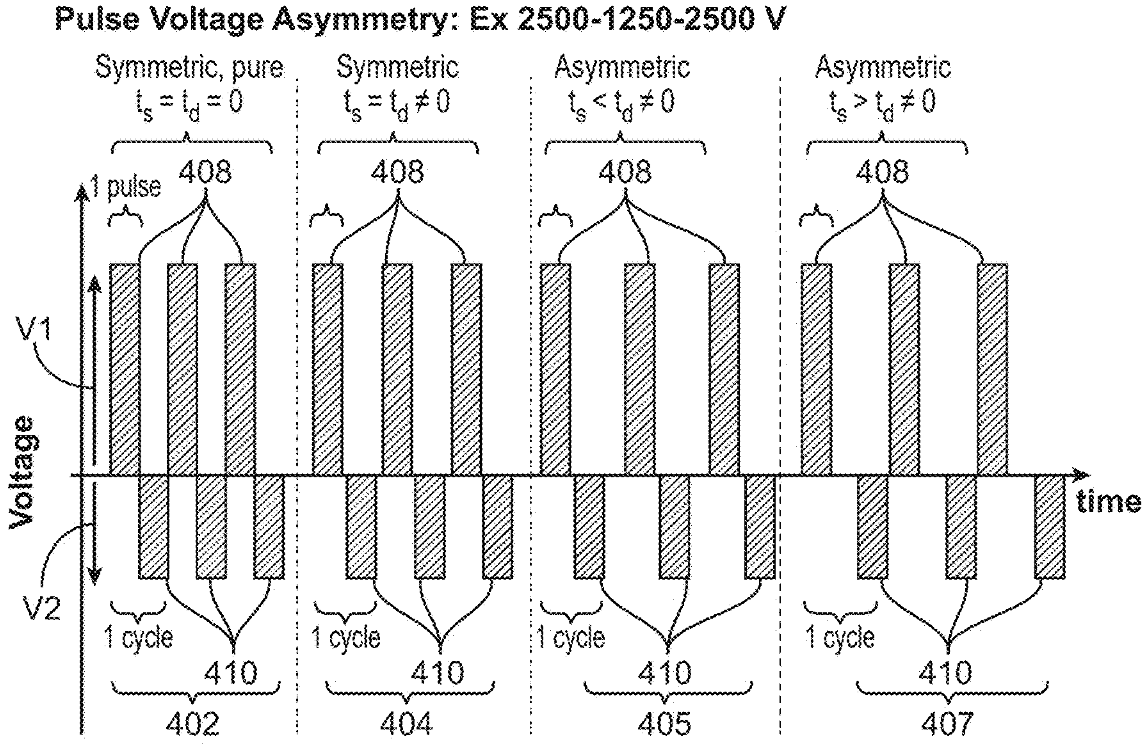
FIG. 2E illustrates further examples of waveforms having unequal voltages.

FIG. 2A illustrates an embodiment of a waveform 400 having symmetric pulses such that the voltage and duration of pulse in one direction (i.e., positive or negative) is equal to the voltage and duration of pulse in the other direction. FIG. 2D illustrates an example waveform 400 prescribed by another energy delivery algorithm 152 wherein the waveform 400 has voltage imbalance. Here, two packets are shown, a first packet 402 and a second packet 404, wherein the packets 402, 404 are separated by a rest period 406. In this embodiment, each packet 402, 404 is comprised of a first biphasic cycle (comprising a first positive pulse peak 408 having a first voltage V1 and a first negative pulse peak 410 having a second voltage V2) and a second biphasic cycle (comprising a second positive pulse peak 408' having first voltage V1 and a second negative pulse peak 410' having a second voltage V2). Here the first voltage V1 is greater than the second voltage V2. The first and second biphasic cycles are separated by dead time 412 between each pulse. Thus, the voltage in one direction (i.e., positive or negative) is greater than the voltage in the other direction so that the area under the positive portion of the curve does not equal the area under the negative portion of the curve. This unbalanced waveform may result in a more pronounced treatment effect as the dominant positive or negative amplitude leads to a longer duration of same charge cell membrane charge potential. In this embodiment, the first positive peak 408 has a set voltage 416 (V1) that is larger than the set voltage 416' (V2) of the first negative peak 410. FIG. 2E illustrates further examples of waveforms having unequal voltages. Here, four different types of packets are shown in a single diagram for condensed illustration. The first packet 402 is comprised of pulses having unequal voltages but equal pulse widths, along with no switch times and dead times. Thus, the first packet 402 is comprised of four biphasic pulses, each comprising a positive peak 408 having a first voltage V1 and a negative peak 410 having a second voltage V2). Here the first voltage V1 is greater than the second voltage V2. The second packet 404 is comprised of pulses having unequal voltages but symmetric pulse widths (as in the first pulse 402), with switch times equal to dead times. The third packet 405 is comprised of pulses having unequal voltages but symmetric pulse widths (as in the first pulse 402), with switch times that are shorter than dead times. The fourth packet 407 is comprised of pulses having unequal voltages but symmetric pulse widths (as in the first pulse 402), with switch times that are greater than dead times. It may be appreciated that in some embodiments, the positive and negative phases of biphasic waveform are not identical, but are balanced, where the voltage in one direction (i.e., positive or negative), is greater than the voltage in the other direction but the length of the pulse is calculated such that the area under the curve of the positive phase equals the area under the curve of the negative phase.

In some embodiments, imbalance includes pulses having pulse widths of unequal duration. In some embodiments, the biphasic waveform is unbalanced, such that the voltage in one direction is equal to the voltage in the other direction, but the duration of one direction (i.e., positive or negative) is greater than the duration of the other direction, so that the area under the curve of the positive portion of the waveform does not equal the area under the negative portion of the waveform.

Figure 2F:
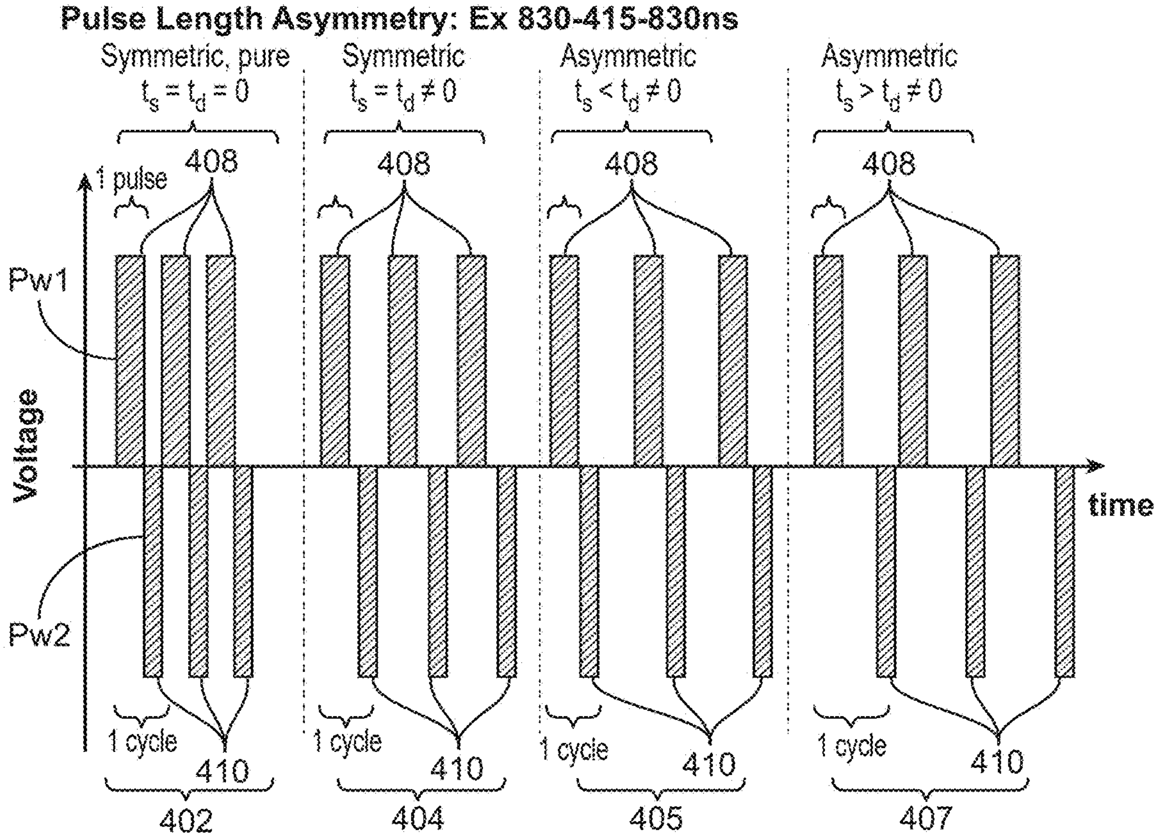
FIG. 2F illustrates further examples of waveforms having unequal pulse widths.

FIG. 2F illustrates further examples of waveforms having unequal pulse widths. Here, four different types of packets are shown in a single diagram for condensed illustration. The first packet 402 is comprised of pulses having equal voltages but unequal pulse widths, along with no switch times and dead times. Thus, the first packet 402 is comprised of four biphasic pulses, each comprising a positive peak 408 having a first pulse width PW1 and a negative peak 410 having a second pulse width PW2). Here the first pulse width PW1 is greater than the second pulse width PW2. The second packet 404 is comprised of pulses having equal voltages but unequal pulse widths (as in the first pulse 402), with switch times equal to dead times. The third packet 405 is comprised of pulses having equal voltages but unequal pulse widths (as in the first pulse 402), with switch times that are shorter than dead times. The fourth packet 407 is comprised of pulses having equal voltages but unequal pulse widths (as in the first pulse 402), with switch times that are greater than dead times.

Figure 2G:
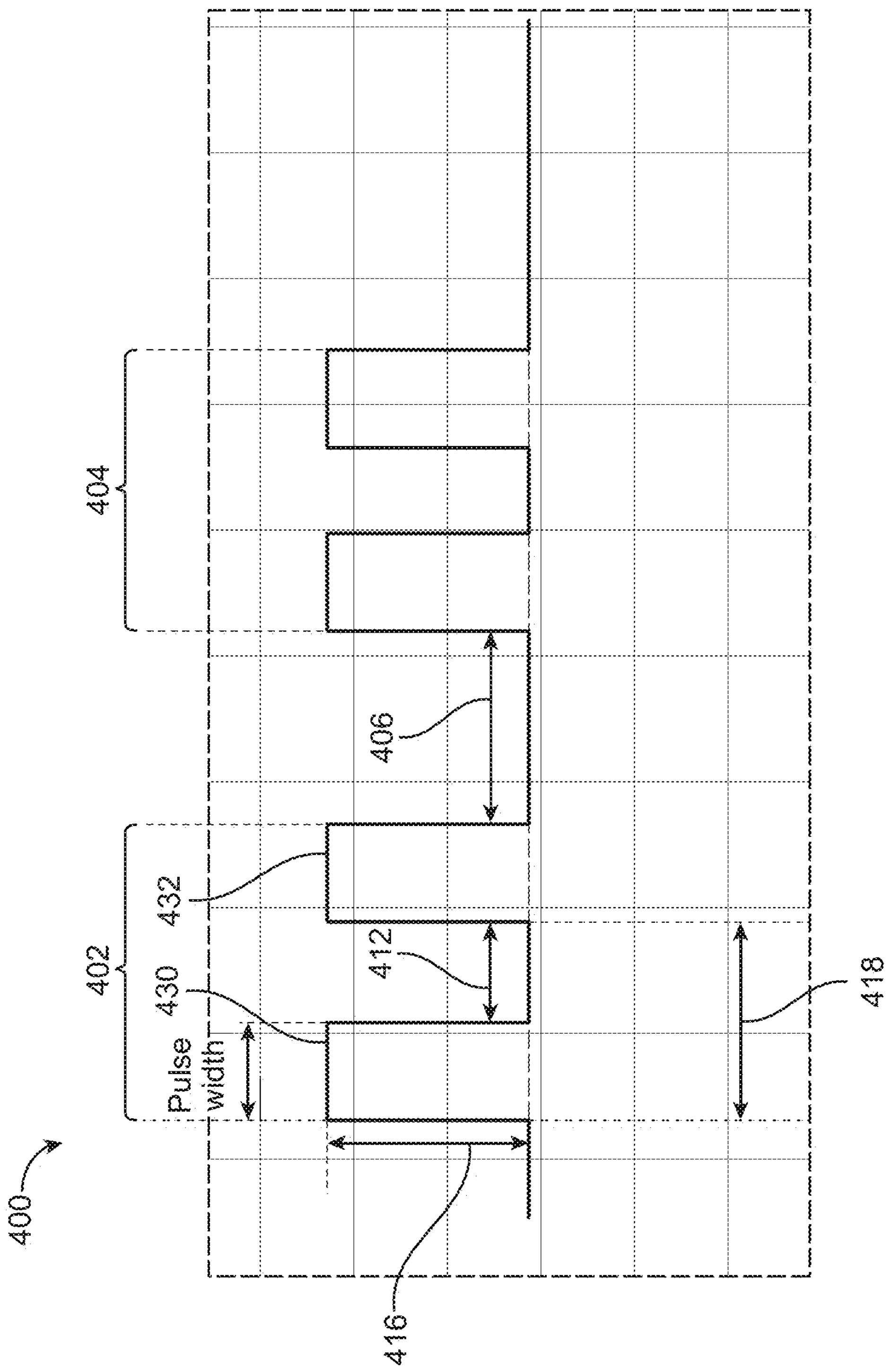
FIG. 2G illustrates an example waveform prescribed by another energy delivery algorithm wherein the waveform is monophasic.

FIG. 2G illustrates an example waveform 400 prescribed by another energy delivery algorithm 152 wherein the waveform is monophasic, a special case of imbalance whereby there is only a positive or only a negative portion of the waveform. Here, two packets are shown, a first packet 402 and a second packet 404, wherein the packets 402, 404 are separated by a rest period 406. In this embodiment, each packet 402, 404 is comprised of a first monophasic pulse 430 and a second monophasic pulse 432. The first and second monophasic pulses 430, 432 are separated by dead time 412 between each pulse. This monophasic waveform could lead to a more desirable treatment effect as the same charge cell membrane potential is maintain for longer durations. However, adjacent muscle groups will be more stimulated by the monophasic waveform, compared to a biphasic waveform.

Figure 2H:
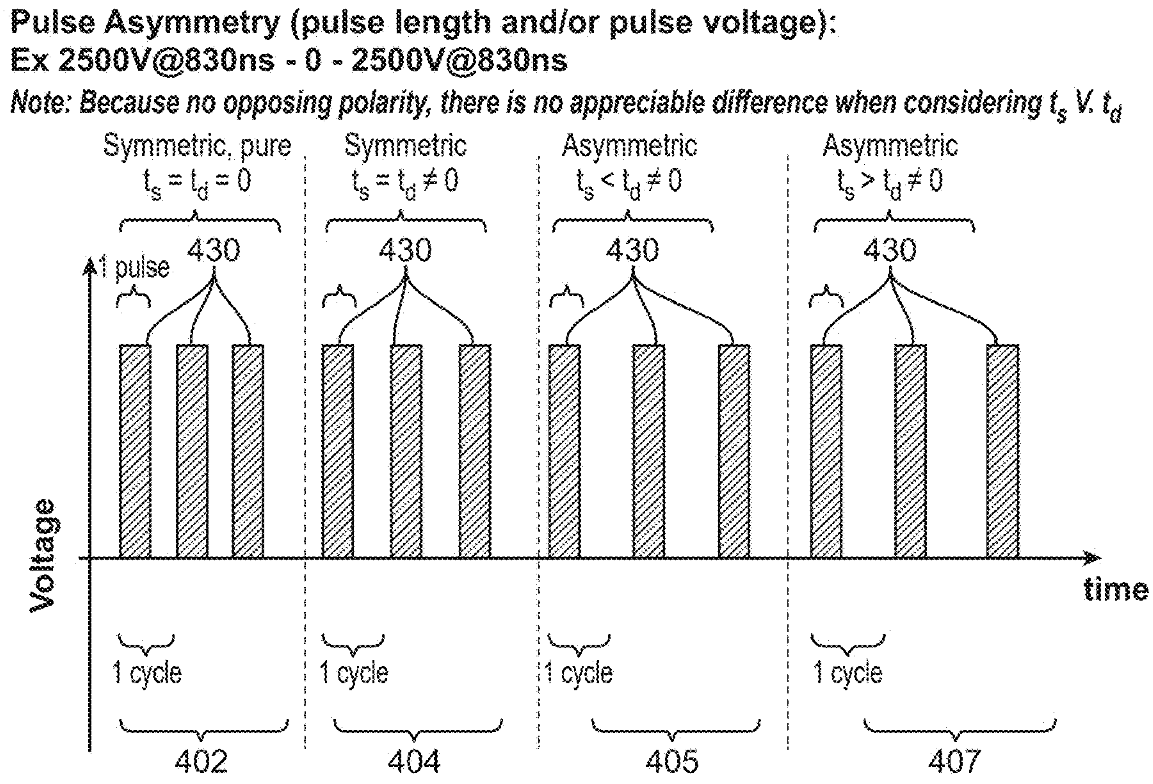
FIG. 2H illustrates further examples of waveforms having monophasic pulses.

FIG. 2H illustrates further examples of waveforms having monophasic pulses. Here, four different types of packets are shown in a single diagram for condensed illustration. The first packet 402 is comprised of pulses having identical voltages and pulse widths, with no switch times (because the pulses are monophasic) and a dead time equal to the active time. In some cases, there may be less dead time duration than the active time of a given pulse. Thus, the first packet 402 is comprised of three monophasic pulses 430, each comprising a positive peak. In instances where the dead time is equal to the active time, the waveform may be considered unbalanced with a fundamental frequency representing a cycle period of 2× the active time and no dead time. The second packet 404 is comprised of monophasic pulses 430 having equal voltages and pulse widths (as in the first packet 402), with larger dead times. The third packet 405 is comprised of monophasic pulses 430 having equal voltages and pulse widths (as in the first packet 402), and even larger dead times. The fourth packet 407 is comprised of monophasic pulses 430 having equal voltages and pulse widths (as in the first packet 402), with yet larger dead times.

Figure 2I:
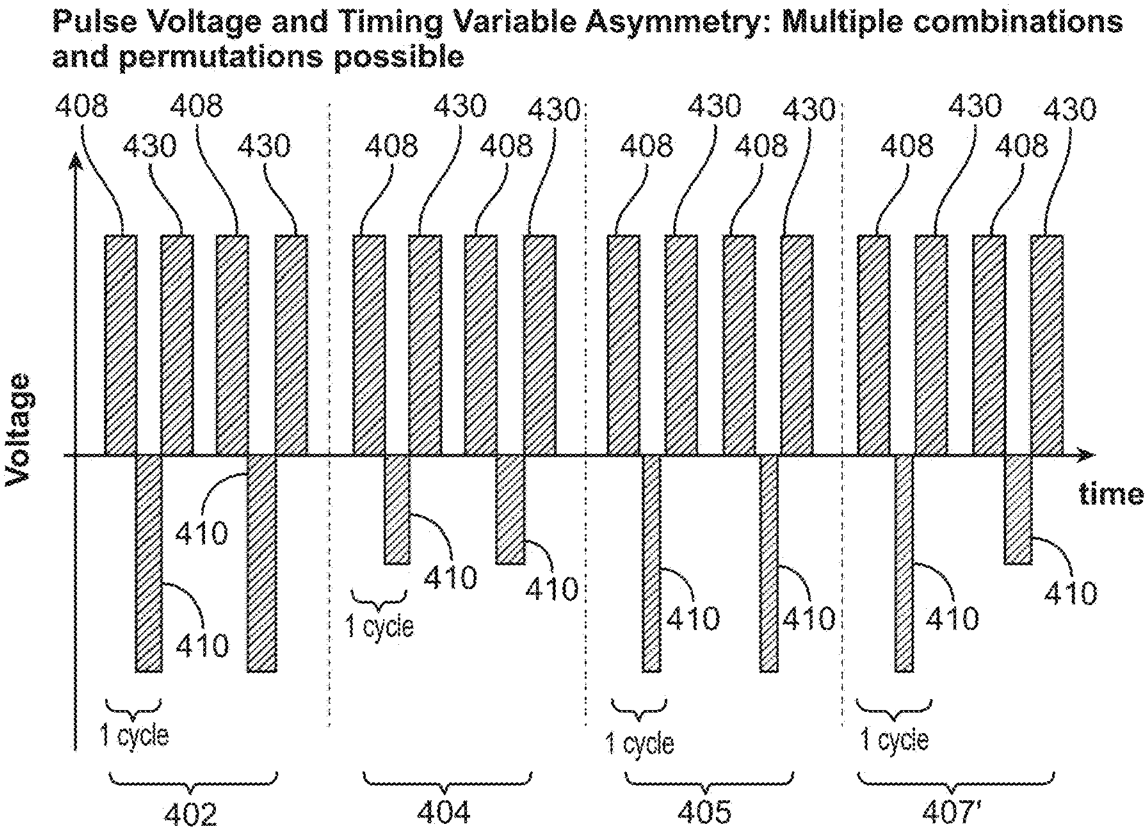
FIG. 2I illustrates further examples of waveforms having such phase imbalances.
Figure 2J:
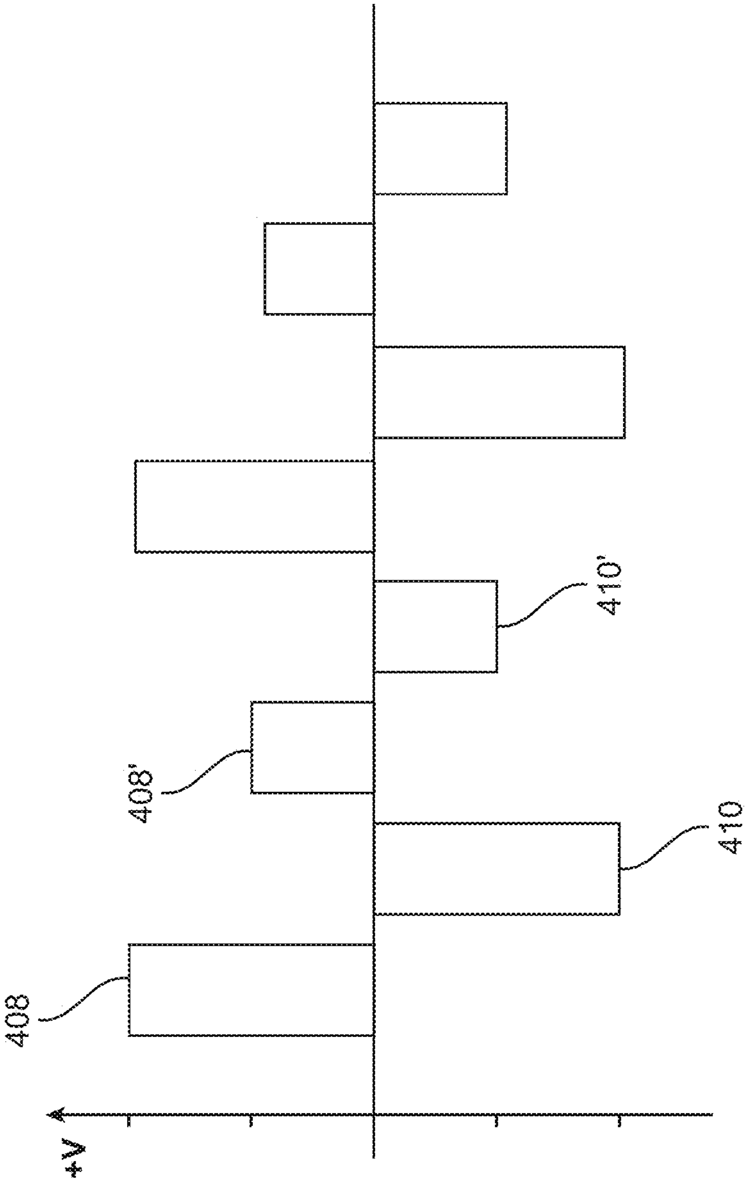
FIG. 2J illustrates an example of a waveform having imbalances in both positive and negative voltages.
Figure 21:
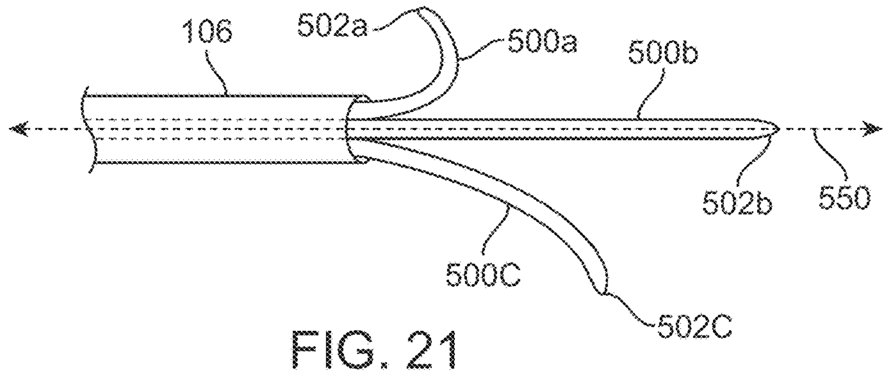
FIG. 21 illustrates an embodiment of a probe having probe elements that extended different distances from the shaft and have the different curvatures.

In some embodiments, an unbalanced waveform is achieved by delivering more than one pulse in one polarity before reversing to an unequal number of pulses in the opposite polarity. FIG. 2I illustrates further examples of waveforms having such phase imbalances. Here, four different types of packets are shown in a single diagram for condensed illustration. The first packet 402 is comprised of four cycles having equal voltages and pulse widths, however, opposite polarity pulses are intermixed with monophasic pulses. Thus, the first cycle comprises a positive peak 408 and a negative peak 410. The second cycle is monophasic, comprising a single positive pulse with no subsequent negative pulse 430. This then repeats. The second packet 404 is comprised of intermixed biphasic and monophasic cycles (as in the first packet 402), however the pulses have unequal voltages. The third packet 405 is comprised of intermixed biphasic and monophasic cycles (as in the first packet 402), however the pulses have unequal pulse widths. The fourth packet 407 is comprised of intermixed biphasic and monophasic pulses (as in the first packet 402), however the pulses have unequal voltages and unequal pulse widths. Thus, multiple combinations and permutations are possible. FIG. 21 illustrates an example of a waveform having imbalances in both positive and negative voltages. Here a packet is shown having a first positive pulse peak 408 and a first negative pulse peak 410 having a greater voltage than a second positive pulse peak 408' and a second negative pulse peak 410'. These differing cycles repeat throughout the packet.

Regarding the utility of unequal waveforms, the unbalanced TMP manipulation achieved reduces the implications of biphasic cancellation. There is a correlative relationship between the degree of imbalance, approaching a monopolar waveform as fully unbalanced, and the intensity of TMP manipulation. This will result in proportional relationship between the extent of treatment effect as well as the degree of muscle contraction. Thus, approaching more unbalanced waveforms will enable stronger treatment effects at the same voltage and frequency (if applicable) for biphasic waveforms than those produced from purely balanced biphasic waveforms. For example, the treatment effect evoked by a 830 ns-415 ns-830 ns-etc pulse length sequence within a packet will have the pulse constituting the second half of the cycle being half the duration of the original phase. This will restrict the induction of TMP manipulation by the second phase of the cycle, but will also generate less reversed TMP, enabling a stronger effect from the original polarity in the subsequent cycle at the original length. In another example, the "positive" portion of the waveform may be 2500V, with the "negative" portion being 1500V (2500-1250-2500-etc V), which will induce comparable effects on TMP polarization as that which was described for the pulse duration imbalance. In both of these cases, the manipulation of the opposing polarity intensity will result in cumulative stronger TMP manipulation for the positive pulse in the cycle. This will thus reduce the effects of biphasic cancellation and will generate stronger treatment effects than a protocol of 830-830-830 ns or 2500-2500-2500V, despite the deposition of less total energy delivered to the tissue. In this way, it is possible to deliver less total energy to the tissue but evoke the desired treatment effect when TMP manipulations are integral to the treatment mechanism of action.

Extended further, the fully unbalanced waveforms would not include any opposite polarity component but may still include brief portions of pulses delivered in just the positive phase. An example of this is a packet that contains 830 ns of positive polarity, an 830 ns pause with no energy delivered, followed by another 830 ns of positive polarity, and so forth. The same approach is true whether considering the pulse length imbalance or the voltage imbalance, as the absence of a negative pulse is equivalent to setting either of these parameters to zero for the "negative" portion.

However, appropriate treatment delivery considers that the advantages offered by biphasic waveforms, namely the reduction of muscle contraction, resulting from biphasic cancellation will likewise be reduced. Therefore, the appropriate treatment effect extent is balanced against the degree of acceptable muscle contraction. For example, an ideal voltage imbalance may be 2500-1000-2500- . . . V, or 2500-2000-2500- . . . V; or 830-100-830- . . . ns, or 830-500-830- . . . ns.

H. Waveform Shapes

Figure 2K:
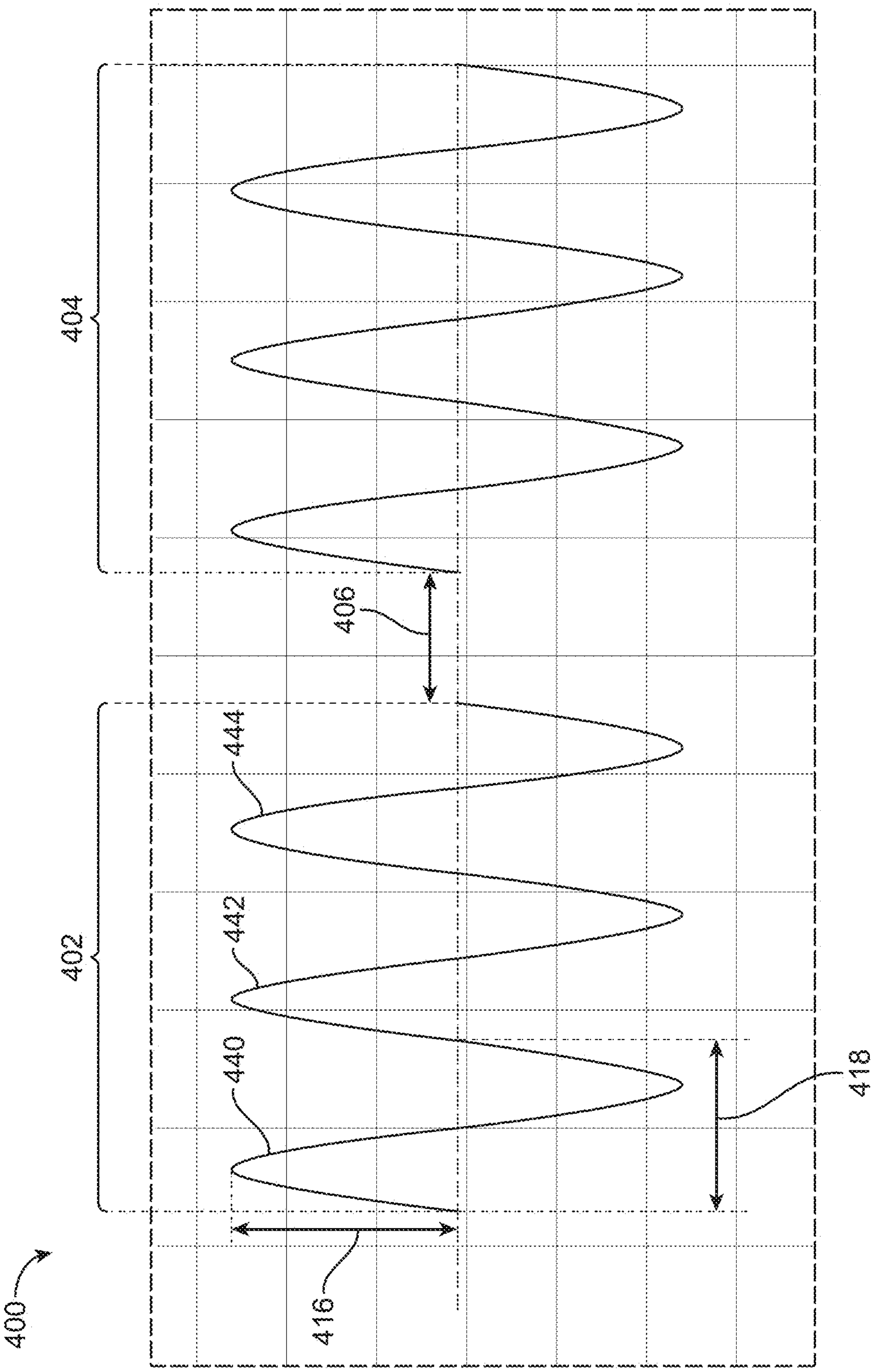
FIG. 2K illustrates an example waveform prescribed by another energy delivery algorithm wherein the pulses are sinusoidal in shape rather than square.

FIG. 2K illustrates an example waveform 400 prescribed by another energy delivery algorithm 152 wherein the pulses are sinusoidal in shape rather than square. Again, two packets are shown, a first packet 402 and a second packet 404, wherein the packets 402, 404 are separated by a rest period 406. In this embodiment, each packet 402, 404 is comprised three biphasic pulses 440, 442, 444. And, rather than square waves, these pulses 440, 442, 444 are sinusoidal in shape. One benefit of a sinusoidal shape is that it is balanced or symmetrical, whereby each phase is equal in shape. Balancing may assist in reducing undesired muscle stimulation. It may be appreciated that in other embodiments the pulses have decay-shaped waveforms.

Energy delivery may be actuated by a variety of mechanisms, such as with the use of an actuator 132 on the instrument 102 or a foot switch operatively connected to the generator 104. Such actuation typically provides a single energy dose. The energy dose is defined by the number of packets delivered and the voltage of the packets. Each energy dose delivered to the target tissue maintains the temperature at or in the target tissue below a threshold for thermal ablation, particularly thermal ablation or denaturing of stromal proteins in the basement membrane or deeper submucosal extracellular protein matrices. In addition, the doses may be titrated or moderated over time so as to further reduce or eliminate thermal build up during the treatment procedure. Instead of inducing thermal damage, defined as protein coagulation at sites of danger to therapy, the energy dose provides energy at a level which induces treatment of the condition, such as cancer, without damaging sensitive tissues.

It may be appreciated that manipulation of the various parameters (e.g. voltage, fundamental frequency, number of pulses per packet, number of packets, and various delays, etc.) have a variety of influences on the resultant lesion and on the body itself. In some instances, parameter changes can balance each other wherein the effect of change in one or more parameters can be balanced by a change in one or more different parameter values leading to the same or similar result. In other instances, parameter values can be tuned to create or generate different effects, such as different lesion characteristics (e.g. the presence, size and/or properties of the different zones) and/or different effects on the body. These effects on the body may be immediate, such as muscle stimulation, or delayed, such as the generation of a particular immune response.

FIG. 3 provides a table illustrating various example effects of parameter changes. Typically, the electrode style is monopolar as opposed to bipolar. In monopolar arrangements, one or more delivery electrodes are positioned near the target tissue site and at least one remote return electrode is positioned against the patient's skin. By utilizing a monopolar electrode configuration, muscle contraction intensity increases. To counteract this effect, generally a biphasic waveform or waveform comprised of sufficiently short individual pulse durations comprising a packet with appropriate delays between the pulses, so as to offset the degree in muscle contraction. This waveform variety results in treatment effect decreases, but the decrease is more subtle than the muscle contraction reduction, thus resulting in still valid PEF therapeutic applications. Monopolar configurations also decrease the risk of electrical arcing compared to bipolar or multipolar configurations, wherein all effector electrodes are placed within a similar region that may permit electrical arcing between them. Typically, the waveform utilizes biphasic pulses as opposed to monophasic pulses. The use of biphasic pulses decreases the treatment size, decreases muscle contraction and also decreases arcing risk. Thus, the use of biphasic pulses counters the increase in muscle contraction due to the monopolar electrode style. Since both monopolar electrode style and biphasic pulses reduce treatment size, treatment size can be increased by changing other variables. For example, an increase in voltage, packet duration and number of packets increases the treatment size. However, increasing these parameters have a variety of other effects. For example, increasing the voltage and increasing the packet duration each increase muscle contraction, temperature rise and risk of electrical arcing. Increasing the fundamental frequency can lower the muscle contraction but it also reduces the treatment size. Likewise, increasing the number of packets increases the treatment size but also increases the temperature rise and the treatment delivery time. The treatment delivery time can be lowered by increasing the packet delivery rate, however, this increases the temperature rise. Therefore, managing the influences of various parameter changes is a complex endeavor. This is further complicated by the increments in which these changes are made. Once considering the number of parameters and increments in which they can be changed as related to the PEF waveform and dose itself, the set of combinations in staggering in volume. This is further compounded by the influence of electrode geometry, such as where a large electrode delivering a particular electrical voltage will have different characteristics than a smaller electrode, or monopolar versus bipolar and multipolar arrangements (and the separation distances between electrodes in these arrangements). These characteristics also include the temperature rise, treatment effect size, electrical current delivered, muscle contraction, electrical arcing risk, and time required to attain coverage of a targeted treatment effect size. Furthermore, certain conditioning solutions provided to the patient may specifically be used to target and reduce the induced muscle contraction. For instance, neuromuscular blockade with pancuronium bromide, vecuronium, succynlcholine, and other blockades may be used. This reduction in muscle contraction may be used to facilitate treatment doses with lower frequencies, longer packet durations, or higher voltages to attain larger treatment effects while maintaining acceptably safe muscle contractions.

Thus, determining the appropriate parameter values for a particular outcome involves a high level of manipulation and skill. In addition, determining what particular outcome is desired also involves a high level of skill. For example, the presence, type and size of the various zones in a resultant lesion that culminates in a desired clinical outcome has not been previously known. The methods, systems and devices described herein provide both the specific parameter values and the characteristics of the desired resultant lesions that culminate in the desired clinical outcomes. Thus, the specialized energy delivered to the target tissue, typically cancerous or otherwise undesired, is generated from an algorithm 152 of the generator 104 that produces a waveform according to these parameter values.

In one embodiment, the treatment dose is provided by a waveform that is produced from a combination of parameter values that includes the following: voltage=3000V, fundamental frequency=400 kHz, number of biphasic pulses (i.e., cycles) per packet=40 cycles, inter-cycle delay=1000 microseconds, number of packets=100 packets and inter-packet delay=3 seconds. For this combination, the dose delivery time is approximately 5-6 minutes. This treatment time is substantially shorter than treatment times using conventional energy such as microwave (10 minutes), RF (20 minutes), or cryoablation (30-40 minutes). In some instances, this dose produces a lesion size of approximately $1\times1\times1$ cm$^3$+0.3 cm in any direction. The characteristics of the resultant lesion will be described hereinbelow.

In addition to manipulating the parameter values to generate desired lesion zones, parameter values were further manipulated to maximize lesion size while ensuring patient safety, a desirable treatment time, reduced electrical arcing risk, reduced muscle contraction, and reduced temperature rise, to name a few. Extensive studies were undertaken to determine the parameters for the desired dose. Studies included evaluating the following parameter combinations:

TABLE 1

| No. | Voltage, V | Fundamental Frequency, kHz | Cycles, count | Inter-Cycle Delay, μs | Packets, count | Inter-Packet Delay, s |
|---|---|---|---|---|---|---|
| 1 | 2500 V | 400 kHz | 40 cycles | 1000 μs | 100 packets | 3 second |
| 2 | 2500 V | 400 kHz | 60 cycles | 1000 μs | 100 packets | 3 second |
| 3 | 3000 V | 400 kHz | 40 cycles | 1000 μs | 100 packets | 3 second |
| 4 | 3000 V | 400 kHz | 60 cycles | 1000 μs | 100 packets | 3 second |
| 5 | 3300 V | 400 kHz | 60 cycles | 1000 μs | 100 packets | 3 second |
| 6 | 2500 V | 400 kHz | 40 cycles | 500 μs | 100 packets | 3 second |
| 7 | 2500 V | 400 kHz | 60 cycles | 500 μs | 100 packets | 3 second |
| 8 | 3000 V | 400 kHz | 40 cycles | 500 μs | 100 packets | 3 second |
| 9 | 3000 V | 400 kHz | 60 cycles | 500 μs | 100 packets | 3 second |
| 10 | 3300 V | 400 kHz | 60 cycles | 500 μs | 100 packets | 3 second |

Thus, the refined dose of specialized energy described herein generates a treatment lesion (e.g. 10 mm in diameter) with minimal thermal volume, particularly in comparison to lesions generated by conventional pulsed electric field technology. In some embodiments, the treatment duration is 5 minutes. The refined dose provided by the specialized waveforms maximizes the PEF treatment effect zone while minimizing thermal effects. At this specifically-tuned dosing, the PEF energy causes release of tumor antigens, stimulates the body's innate and adaptive immune response such as due to enhanced release of neo-antigens, stimulated immunogenic cell death (e.g. necroptosis, pyroptosis, etc.), and enhanced sensitivity to antigens due to limited encapsulation and scarring of the treated area. In addition, in some embodiments the specialized energy disrupts the immunosuppressive tumor immune microenvironment (TME). Thus, embodiments of the treatment systems maximize antigen release and increase the immune response.

III. Intra-Luminal Placement and Energy Delivery

As mentioned previously, in one arrangement, an energy delivery body 108 is positioned within a body lumen and energy is delivered to or through the lumen wall to target tissue either within the lumen, within the lumen wall, at least partially surrounding the lumen wall or outside the lumen wall. Thus, the target tissue is able to be treated from an energy delivery body 108 positioned within a body lumen.

The treatment devices and systems described in this section are configured for luminal access and delivery of therapeutic energy toward the luminal walls so as to treat the nearby target tissue. The therapeutic energy is generally characterized by high voltage pulses which allow for removal of target tissue with little or no destruction of critical anatomy, such as tissue-level architectural proteins among extracellular matrices. This prevents dangerous collateral effects, such as stenosis, thrombus formation or fistulization, to name a few, and also allows for regeneration of healthy new luminal tissue within days of the procedure. Examples of systems which provide this type of therapeutic treatment include the pulmonary tissue modification systems (e.g., energy delivery catheter systems) described in commonly assigned patent applications including international patent application number PCT/US2017/039527 titled "GENERATOR AND A CATHETER WITH AN ELECTRODE AND A METHOD FOR TREATING A LUNG PASSAGEWAY," which claims priority to U.S. provisional application Nos. 62/355,164 and 62/489,753, international patent application number PCT/US2018/067501 titled "METHODS, APPARATUSES, AND SYSTEMS FOR THE TREATMENT OF DISORDERS" which claims priority to U.S. Provisional Application No. 62/610,430, and international patent application number PCT/US2018/067504 titled "OPTIMIZATION OF ENERGY DELIVERY FOR VARIOUS APPLICATIONS" which claims priority to Provisional Patent Application No. 62/610,430 filed Dec. 26, 2017 and U.S. Provisional Patent Application No. 62/693,622 filed Jul. 3, 2018, all of which are incorporated herein by reference for all purposes.

Figure 4B:
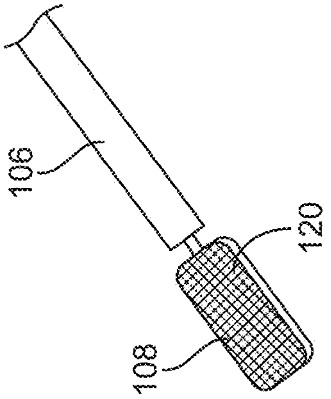
FIG. 4B illustrates an energy delivery body having a paddle shape.
Figure 4A:
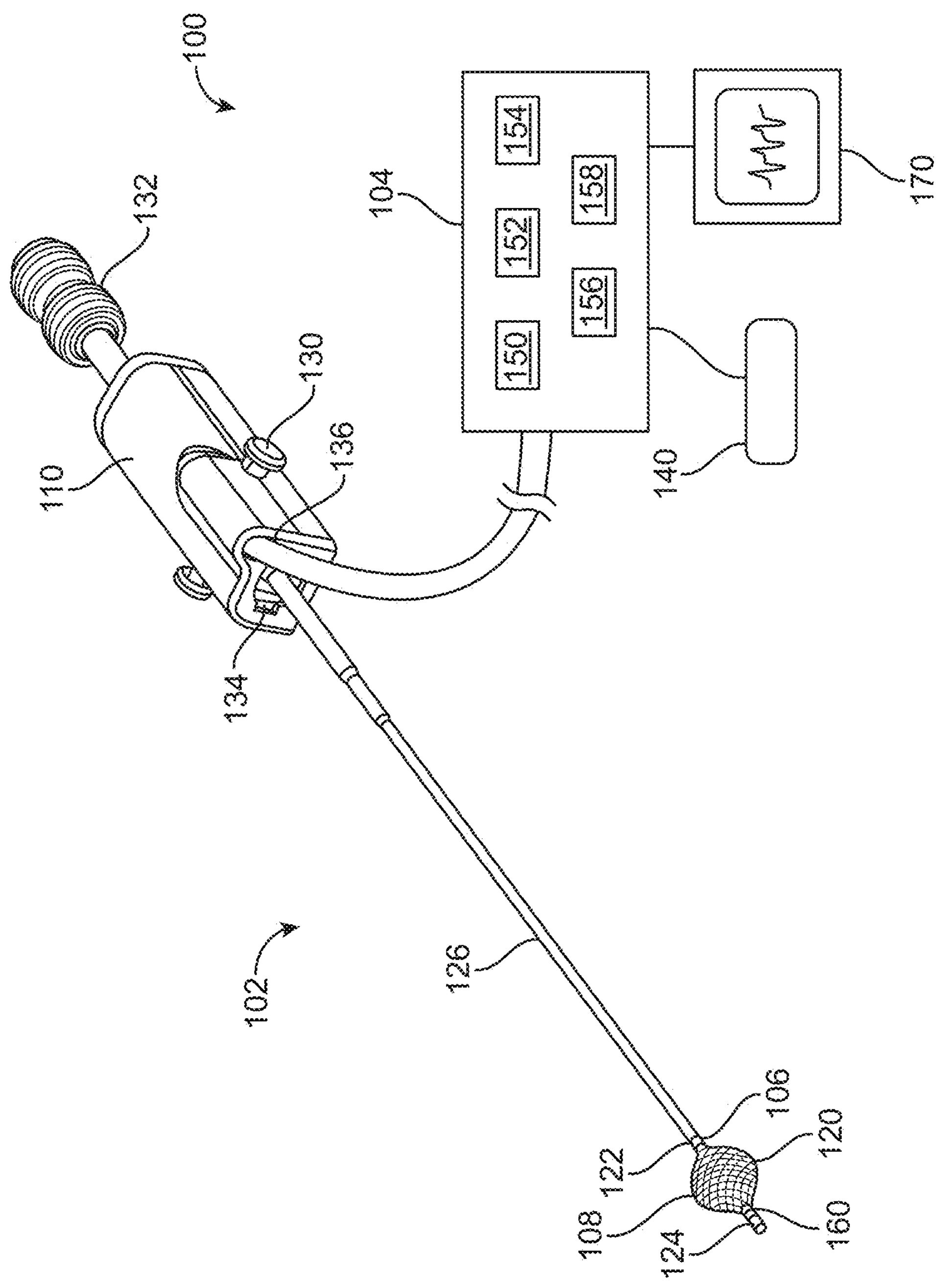
FIG. 4A illustrates an embodiment of a therapeutic system that delivers energy intra-luminally.

FIG. 4A illustrates an embodiment of a therapeutic energy delivery catheter or instrument 102. In this embodiment, the instrument 102 has an elongate shaft 106 with at least one energy delivery body 108 near its distal end and a handle 110 at its proximal end. The instrument 102 is connectable to a generator 104 as part of a treatment system 100. Connection of the instrument 102 to the generator 104 provides electrical energy to the energy delivery body 108, among other features. In this embodiment, the energy delivery body 108 includes a plurality of wires or ribbons 120, constrained by a proximal end constraint 122 and a distal end constraint 124, and forms a spiral-shaped basket serving as an electrode. In an alternative embodiment, the wires or ribbons are straight instead of formed into a spiral-shape (i.e., configured to form a straight-shaped basket). In still another embodiment, the energy delivery body 108 is laser cut from a tube. It may be appreciated that a variety of other designs may be used. For example, FIG. 4B illustrates an energy delivery body 108 having a paddle shape. In this embodiment, the energy delivery body 108 is comprised of a plurality of wires or ribbons 120 arranged so as to form a flat pad or paddle. Such an energy delivery body 108 is flexible so as to be retracted into the shaft 106. Referring back to FIG. 4A, in this embodiment the energy delivery body 108 is self-expandable and delivered to a targeted area in a collapsed configuration. This collapsed configuration can be achieved, for example, by placing a sheath 126 over the energy delivery body 108. The instrument shaft 106 (within the sheath 126) terminates at the proximal end constraint 122, leaving the distal end constraint 124 essentially axially unconstrained and free to move relative to the shaft 106 of the instrument 102. Advancing the sheath 126 over the energy delivery body 108 allows the distal end constraint 124 to move forward, thereby lengthening/collapsing and constraining the energy delivery body 108.

As shown in this example, the instrument 102 includes a handle 110 at its proximal end. In some embodiments, the handle 110 is removable, such as by pressing a handle removal button 130. In this embodiment, the handle 110 includes an energy delivery body manipulation knob or actuator 132 wherein movement of the actuator 132 causes expansion or retraction/collapse of the basket-shaped electrode. In this example, the handle 110 also includes a working port snap 134 for optional connection with an endoscope or other type of visualization device and a cable plug-in port 136 for connection with the generator 104. It may be appreciated that a variety of types of visualization may be used, including angiography (optionally including markers), computed tomography, optical coherence tomography, ultrasound, and direct video visualization, to name a few.

In this embodiment, the therapeutic energy delivery instrument 102 is connectable with the generator 104 along with a dispersive (return) electrode 140 applied externally to the skin of the patient P. Thus, in this embodiment, monopolar energy delivery is achieved by supplying energy between the energy delivery body 108 disposed near the distal end of the instrument 102 and the return electrode 140. It will be appreciated, however, that bipolar energy delivery and other arrangements may alternatively be used. When using bipolar energy delivery, the therapeutic energy delivery instrument 102 may differ in overall design, such as to include a plurality of energy delivery bodies 108, or may appear similar in overall design, such as to include a single energy delivery body 108 which is configured to function in a bipolar manner. In some instances, bipolar energy delivery allows for the use of a lower voltage to achieve the treatment effect, as compared to monopolar energy delivery. In a bipolar configuration, the positive and negative poles are close enough together to provide a treatment effect both at the electrode poles and in-between the electrode poles. This can spread the treatment effect over a larger, shallower surface area thus requiring a lower voltage to achieve the treatment effect, compared to monopolar. Likewise, this lower voltage may be used to reduce the depth of penetration. In addition, lower voltage requirements may obviate the use of cardiac synchronization in particular cases if the delivered voltage is low enough to avoid stimulation of the cardiac muscle cells.

In this embodiment, the generator 104 includes a user interface 150, one or more energy delivery algorithms 152, a processor 154, a data storage/retrieval unit 156 (such as a memory and/or database), and an energy-storage sub-system 158 which generates and stores the energy to be delivered. In some embodiments, one or more capacitors are used for energy storage/delivery, however any other suitable energy storage element may be used. In addition, one or more communication ports are included.

In some embodiments, the generator 104 includes three sub-systems: 1) a high-energy storage system, 2) a high-voltage, medium-frequency switching amplifier, and 3) the system controller, firmware, and user interface. The system controller includes a cardiac synchronization trigger monitor that allows for synchronizing the pulsed energy output to the patient's cardiac rhythm. The generator takes in alternating current (AC) mains to power multiple direct current (DC) power supplies. The generator's controller can cause the DC power supplies to charge a high-energy capacitor storage bank before energy delivery is initiated. At the initiation of therapeutic energy delivery, the generator's controller, high-energy storage banks and a bi-phasic pulse amplifier can operate simultaneously to create a high-voltage, medium frequency output.

It will be appreciated that a multitude of generator electrical architectures may be employed to execute the energy delivery algorithms. In particular, in some embodiments, advanced switching systems are used which are capable of directing the pulsed electric field circuit to the energy delivering electrodes separately from the same energy storage and high voltage delivery system. Further, generators employed in advanced energy delivery algorithms employing rapidly varying pulse parameters (e.g., voltage, frequency, etc.) or multiple energy delivery electrodes may utilize modular energy storage and/or high voltage systems, facilitating highly customizable waveform and geographical pulse delivery paradigms. It should further be appreciated that the electrical architecture described herein above is for example only, and systems delivering pulsed electric fields may or may not include additional switching amplifier components.

The user interface 150 can include a touch screen and/or more traditional buttons to allow for the operator to enter patient data, select a treatment algorithm (e.g., energy delivery algorithm 152), initiate energy delivery, view records stored on the storage/retrieval unit 156, and/or otherwise communicate with the generator 104. The user interface 150 can include a voice-activated mechanism to enter patient data or may be able to communicate with additional equipment in the suite so that control of the generator 104 is through a secondary separate user interface.

In some embodiments, the user interface 150 is configured to receive operator-defined inputs. The operator-defined inputs can include a duration of energy delivery, one or more other timing aspects of the energy delivery pulse, power, and/or mode of operation, or a combination thereof. Example modes of operation can include (but are not limited to): system initiation and self-test, operator input, algorithm selection, pre-treatment system status and feedback, energy delivery, post energy delivery display or feedback, treatment data review and/or download, software update, or any combination or subcombination thereof.

In some embodiments, the system 100 also includes a mechanism for acquiring an electrocardiogram (ECG), such as an external cardiac monitor 170. Example cardiac monitors are available from AccuSync Medical Research Corporation. In some embodiments, the external cardiac monitor 170 is operatively connected to the generator 104. The cardiac monitor 170 can be used to continuously acquire an ECG signal. External electrodes 172 may be applied to the patient P to acquire the ECG. The generator 104 analyzes one or more cardiac cycles and identifies the beginning of a time period during which it is safe to apply energy to the patient P, thus providing the ability to synchronize energy delivery with the cardiac cycle. In some embodiments, this time period is within milliseconds of the R wave (of the ECG QRS complex) to avoid induction of an arrhythmia, which could occur if the energy pulse is delivered on a T wave. It will be appreciated that such cardiac synchronization is typically utilized when using monopolar energy delivery, however it may be utilized as part of other energy delivery methods.

In some embodiments, the processor 154, among other activities, modifies and/or switches between the energy-delivery algorithms, monitors the energy delivery and any sensor data, and reacts to monitored data via a feedback loop. In some embodiments, the processor 154 is configured to execute one or more algorithms for running a feedback control loop based on one or more measured system parameters (e.g., current), one or more measured tissue parameters (e.g., impedance), and/or a combination thereof.

The data storage/retrieval unit 156 stores data, such as related to the treatments delivered, and can optionally be downloaded by connecting a device (e.g., a laptop or thumb drive) to a communication port. In some embodiments, the device has local software used to direct the download of information, such as, for example, instructions stored on the data storage/retrieval unit 156 and executable by the processor 154. In some embodiments, the user interface 150 allows for the operator to select to download data to a device and/or system such as, but not limited to, a computer device, a tablet, a mobile device, a server, a workstation, a cloud computing apparatus/system, and/or the like. The communication ports, which can permit wired and/or wireless connectivity, can allow for data download, as just described but also for data upload such as uploading a custom algorithm or providing a software update.

The data storage/retrieval unit 156 can be, for example, a random access memory (RAM), a memory buffer, a hard drive, a database, an erasable programmable read-only memory (EPROM), an electrically erasable read-only memory (EEPROM), a read-only memory (ROM), flash memory, and/or so forth. The data storage/retrieval unit 156 can store instructions to cause the processor 154 to execute modules, processes and/or functions associated with the system 100.

Some embodiments the data storage/retrieval unit 156 comprises a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) can be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as ASICs, Programmable Logic Devices (PLDs), Read-Only Memory (ROM) and Random-Access Memory (RAM) devices. Other embodiments described herein relate to a computer program product, which can include, for example, the instructions and/or computer code discussed herein.

Examples of computer code include, but are not limited to, micro-code or micro-instructions, machine instructions, such as produced by a compiler, code used to produce a web service, and files containing higher-level instructions that are executed by a computer using an interpreter. For example, embodiments can be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

In some embodiments, the system 100 can be communicably coupled to a network, which can be any type of network such as, for example, a local area network (LAN), a wide area network (WAN), a virtual network, a telecommunications network, a data network, and/or the Internet, implemented as a wired network and/or a wireless network. In some embodiments, any or all communications can be secured using any suitable type and/or method of secure communication (e.g., secure sockets layer (SSL)) and/or encryption. In other embodiments, any or all communications can be unsecured.

As described herein, a variety of energy delivery algorithms 152 are programmable, or can be pre-programmed, into the generator 104, such as stored in memory or data storage/retrieval unit 156. Alternatively, energy delivery algorithms can be added into the data storage/retrieval unit to be executed by processor 154. The processor 154 can be, for example, a general-purpose processor, a field programmable gate array (FPGA), an application specific integrated circuit (ASIC), a digital signal processor (DSP), and/or the like. The processor 154 can be configured to run and/or execute application processes and/or other modules, processes and/or functions associated with the system 100, and/or a network associated with the system 100. As used herein the term “module” refers to any assembly and/or set of operatively-coupled electrical components that can include, for example, a memory, a processor, electrical traces, optical connectors, software (executing in hardware), and/or the like. For example, a module executed in the processor can be any combination of hardware-based module (e.g., a FPGA, an ASIC, a DSP) and/or software-based module (e.g., a module of computer code stored in memory and/or executed at the processor) capable of performing one or more specific functions associated with that module.

Each of these algorithms 152 may be executed by the processor 154. In some embodiments, the instrument 102 includes one or more sensors 160 that can be used to determine temperature, impedance, resistance, capacitance, conductivity, permittivity, and/or conductance, to name a few. It may be appreciated that one or more sensors 160 may be disposed in a variety of locations, particularly depending on the parameter being sensed. For example, a sensor may be located along an energy delivery body 108, along an interior of the instrument, along the shaft 106, along an element that protrudes from the instrument 120, etc. Multiple sensors 160 may be present for sensing the same parameter at multiple sites, sensing different parameters at different sites, or sampling parameters at different sites to compile a single metric value measurement (e.g. average temperature, average voltage exposure, average conductivity, etc). One or more sensors 160 may alternatively or additionally be located on a separate device. Sensor data can be used to plan the therapy, monitor the therapy and/or provide direct feedback via the processor 154, which can then alter the energy-delivery algorithm 152. For example, impedance measurements can be used to determine not only the initial dose to be applied but can also be used to determine the need for further treatment, or not.

It will be appreciated that the system 100 can include an automated treatment delivery algorithm that could dynamically respond and adjust and/or terminate treatment in response to inputs such as temperature, impedance at various voltages or AC frequencies, treatment duration or other timing aspects of the energy delivery pulse, treatment power and/or system status.

In some embodiments, imaging is achieved with the use of a commercially available system, such as an endoscope connected with a separate imaging screen. It will be appreciated that imaging modalities can be incorporated into the instrument 102 or used alongside or in conjunction with the instrument 102. The imaging modality can be mechanically, operatively, and/or communicatively coupled to the instrument 102 using any suitable mechanism.

As mentioned previously, one or more energy delivery algorithms 152 are programmable, or can be pre-programmed, into the generator 104 for delivery to the patient. The one or more energy delivery algorithms 152 specify electric signals which provide energy delivered to the lumen walls which are non-thermal (e.g. below a threshold for thermal ablation; below a threshold for inducing coagulative thermal damage), reducing or avoiding inflammation, and/or preventing denaturation of stromal proteins in the luminal structures. In general, the algorithm 152 is tailored to affect tissue to a pre-determined depth and/or to target specific types of cellular responses to the energy delivered. It may be appreciated that depth and/or targeting may be affected by parameters of the energy signal prescribed by the one or more energy delivery algorithms 152, the design of the instrument 102 (particularly the one or more energy delivery bodies 108), and/or the choice of monopolar or bipolar energy delivery. Typically, depths of up to 0.01 cm, up to 0.02 cm, 0.01-0.02 cm, up to 0.03 cm, 0.03-0.05 cm, up to 0.05 cm, up to 0.08 cm, up to 0.09 cm, up to 0.1 cm, up to 0.2 cm, up to 0.5 cm, up to 0.7 cm, up to 1.0 cm, up to 1.5 cm, up to 2.0 cm, up to 2.5 cm, up to 3.0 cm, up to 3.5 cm, up to 4.0 cm, up to 4.5 cm, or up to 5.0 cm, to name a few. These depths may be larger for circumferentially focal targets, or they may exist for entire circumferential depths through the lumen and parenchymal tissue.

Figure 5:
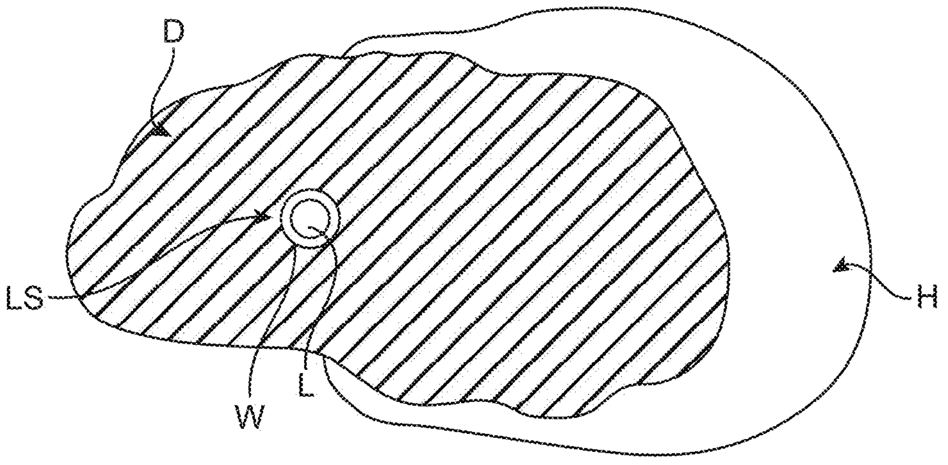
FIG. 5 illustrates an embodiment of an instrument advanced within the lumen of the luminal structure so that the energy delivery body is desirably positioned therein.
Figure 6:
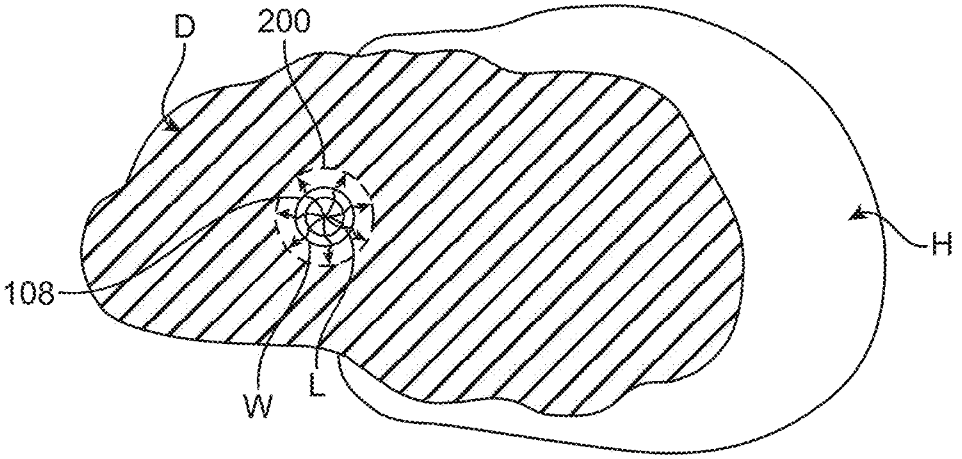
FIG. 6 illustrates an energy delivery body expanded and delivering energy to the lumen wall.

FIGS. 5-8 illustrate an example method of treatment. In particular, FIG. 5 illustrates abnormal or diseased tissue D, such as a tumor, alongside healthy tissue H. In this example, the diseased tissue D surrounds a luminal structure LS having a lumen wall W and interior lumen L. This luminal structure LS is used to access the diseased tissue D and treat a portion of the diseased tissue D near the luminal structure LS. FIG. 6 illustrates an embodiment of an instrument 102 advanced within the lumen L so that the energy delivery body 108 is desirably positioned therein. The energy delivery body 108 is then expanded, as illustrated in FIG. 6 so as to effectively deliver energy to the wall W (e.g. expanded so as to contact the lumen wall W). It may be appreciated that in some embodiments, depending on the type of anatomy, the energy delivery body 108 may not contact the wall W itself and may alternatively contact a substance or other entity along the wall W, such a saline, blood, mucus, etc, which is able to conduct or otherwise transfer the energy to the wall W. Energy is then delivered according to one or more energy delivery algorithms 152, as illustrated in FIG. 6 by wavy arrows extending radially outwardly from the lumen L. The energy penetrates the wall W and a distance into the diseased tissue D, the boundary of which is indicated by a dashed line 200 around the periphery of the luminal structure LS. It may be appreciated that the distance into the diseased tissue may vary based on parameter values, treatment times and type of tissue, to name a few. It may also be appreciated that larger or smaller treatment depths may be achieved than illustrated herein.

The delivered energy treats the diseased tissue D as appropriate. In the case of cancer, the cancerous cells are destroyed, eliminated, killed, removed, etc., while maintaining non-cancerous, non-cellular elements, such as collagen, elastin, and matrix proteins. These non-cellular elements maintain the structure of the walls W of the luminal structure allowing for and encouraging normative cellular regeneration. Therefore, the integrity and mechanical properties of the luminal structures are maintained while abnormal or diseased cells and tissues are sufficiently eliminated. It may be appreciated that in some instances, the energy kills the cells directly, such as via accumulated generalized cellular injury and irrecoverable disruption of cellular homeostasis. This creates an area around the luminal structure that is free of diseased tissue. The remaining diseased tissue may then be surgically removed or removed by other methods that are typically unable to safely treat tissue close to lumens.

Figure 7:
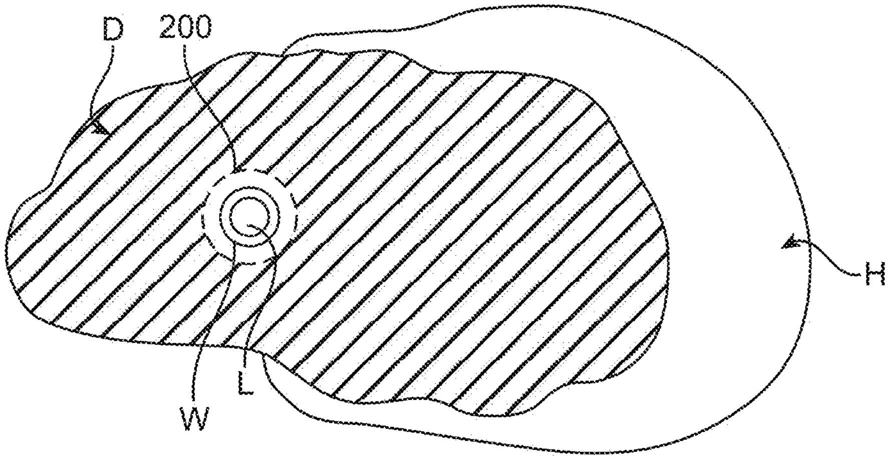
FIG. 7 illustrates a luminal structure after the catheter has been removed and energy delivery is complete.

FIG. 7 illustrates the instrument 102 removed from the luminal structure LS after energy delivery is complete. In this embodiment, a margin or segment of treated tissue (within dashed line 200) surrounds the luminal structure LS. Thus, in this embodiment wall W is treated with the energy along with tissue surrounding the wall W at a depth or distance. It may be appreciated that the penetration distance into the surrounding tissue may vary. Likewise, in some embodiments, wall W of the luminal structure LS is treated with minimal or no penetration into the diseased tissue D. This may be beneficial when the main concern is that the tumor or disease resides within the luminal structure LS, within the wall W and/or penetrates the wall W from within the body lumen. However, the creation of a margin of treated tissue around the luminal structure LS is often desired to allow the diseased tissue D to be safely resected without disturbing the luminal structure LS.

Figure 8:
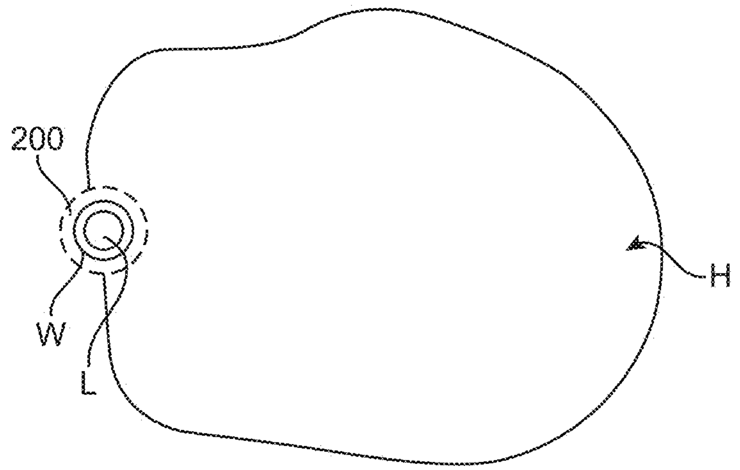
FIG. 8 illustrates resection of the diseased tissue up to the treated tissue, indicated by dashed line.

FIG. 8 illustrates resection of the diseased tissue D up to the treated tissue, indicated by dashed line 200. As a result, the patient is successfully free of the diseased tissue D while keeping the luminal structure LS intact. Thus, previously unresectable tumors and diseased tissue may become resectable, permitting treatments with curative intent in instances where there was previously no such option or where the option was too unreliable and/or too complicated to implement. It may be appreciated that such methods may be used or modified to achieve other treatment goals. Such treatment may be used to restore function to the tissue, with or without debulking of the tissue. Such treatment may be used to reduce or eliminate pain. Such treatment may be the sole treatment or may be used in combination with other treatments, such as surgery, other energy modalities, pharmacologic-based therapeutics and other approaches, such as to address remaining tissue regions. For example, such treatment may be undertaken in advance of a resection or ablation treatment, or pharmacologic-based treatment, or radiotherapy treatment, such as 2 hours prior, 1 day prior, 3 days prior, 7 days prior, 14 days prior, 28 days prior 60 days prior, 90 days prior or more. Alternatively, such treatment may be undertaken during the same procedure as the resection or ablation treatment as well as after surgical resection and/or debulking. It may be appreciated that such treatment may occur over a single session or achieved over a series of multiple treatment deliveries.

It may be appreciated, that in some instances, the area of diseased tissue D is small in relation to the ablation zone created by the therapy so that the entire area of diseased tissue D may be successfully treated.

In some instances, the energy encourages macromolecule uptake in the targeted cells for gene, drug or other bioactive compound transfection.

It may be appreciated that treatments may also utilize a combination of these effects, such as directly killing the most superficial cells while rendering the deeper targeted cells more susceptible to treatment or effects from the uptake of some adjuvant material or additional therapy. In addition, it may be appreciated that treatments may also utilize a combination of these effects, such as directly killing the deeper targeted cells while rendering the most superficial cells more susceptible to treatment or effects form the uptake of some adjuvant material or additional therapy.

Thus, the treatment is minimally invasive, quickly and easily executable, and has relatively low sensitivity to electrode placement (e.g. due to the monopolar arrangement) therefore allowing technicians of various skill levels to achieve high levels of consistency as well as successful outcomes. In some embodiments, the monopolar arrangement is possible without the need for muscular paralytics due to the waveform characteristics of the energy used. This can mitigate muscle contractions from motor neuron and skeletal muscle depolarization to an acceptable level, with or without a neuromuscular paralytic. Thus, it becomes possible to implement monopolar-directed treatment delivery through a lumen out to a distant pad, producing a more predictable and desirable treatment zone. It may be appreciated that paralytics may optionally be used depending on the type of energy and the depth of penetration desired.

Figure 9A:
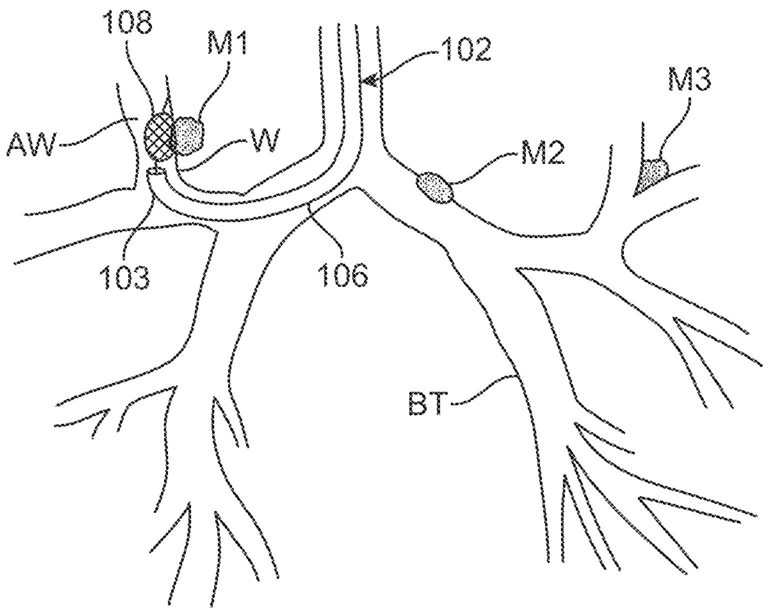
FIGS. 9A-9C illustrate examples of masses of undesired tissue located along airways of a bronchial tree.
Figure 9B:
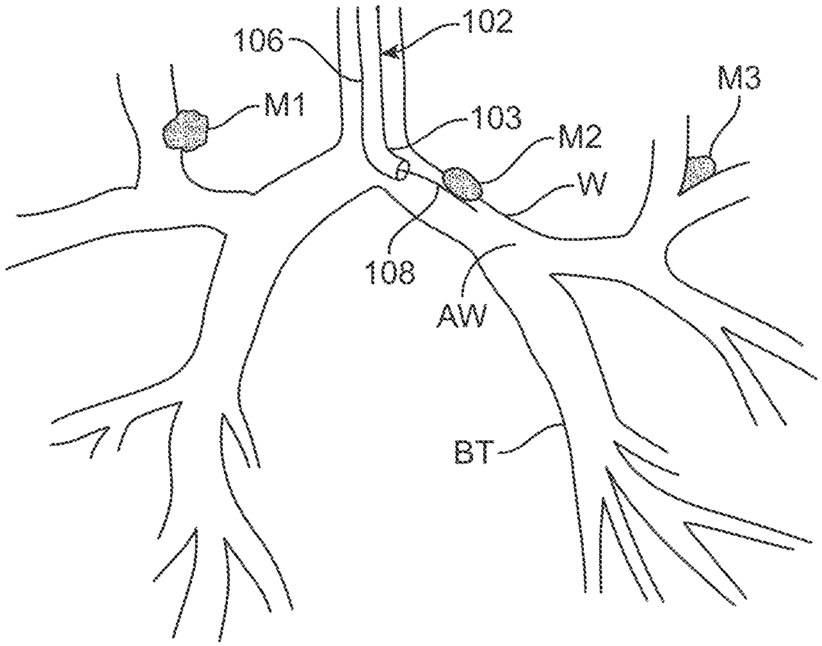
Figure 9C:
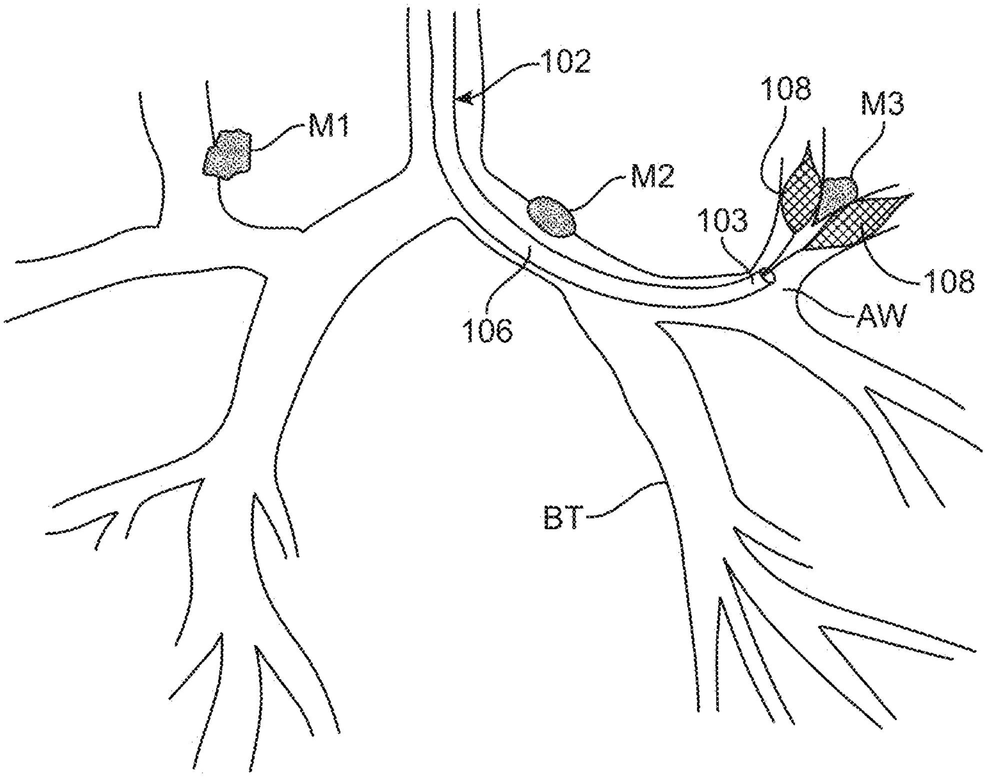

FIGS. 9A-9C illustrate examples of masses of undesired tissue located along airways of a bronchial tree BT. Such masses may be a tumor, a benign tumor, a malignant tumor, a cyst, or an area of diseased tissue, to name a few. In this example, a first mass M1 is illustrated on the left side of the bronchial tree BT. This first mass M1 is located next to the airway AW and has grown into the wall W of the airway AW and encroached into the lumen of the airway. FIG. 9A illustrates an instrument 102 advanced into the bronchial tree BT so that its distal end 103 is positioned near the first mass M1. An energy delivery body 108 is then advanced from the shaft 106 of the instrument 102. In this embodiment, the energy delivery body 108 comprises an electrode having a basket shape. The energy delivery body 108 is expanded so as to contact the first mass M1 and the wall W. Energy is then provided thereto so as to treat the first mass M1. In this embodiment, such treatment is monopolar and leads to destruction of the first mass M1 while maintaining the extracellular matrix, and therefore structural integrity, of the wall W. In this example, a second mass M2 is illustrated on the right side of the bronchial tree BT. This second mass M2 is located in the wall W of the airway AW with portions extending into the body lumen and outside of the airway AW. FIG. 9B illustrates an instrument 102 advanced into the bronchial tree BT so that its distal end 103 is positioned near the second mass M2. An energy delivery body 108 is then advanced from the shaft 106 of the instrument 102. In this embodiment, the energy delivery body 108 comprises an electrode having a basket shape. However, in this instance, the energy delivery body 108 is not expanded and remains in a collapsed configuration. The energy delivery body 108 is placed in contact with the second mass M2. Energy is then provided thereto so as to treat the second mass M2. In this embodiment, such treatment is monopolar and leads to destruction of the second mass M2 while maintaining the extracellular matrix, and therefore structural integrity, of the wall W. In this example, a third mass M3 is illustrated on the far right side of the bronchial tree BT. This third mass M3 is located at a bifurcation, between two airways AW. FIG. 9C illustrates an instrument 102 advanced into the bronchial tree BT so that its distal end 103 is positioned near the third mass M3. In this embodiment, two energy delivery bodies 108 are advanced from the shaft 106 of the instrument 102. In this embodiment, the energy delivery bodies 108 each comprises an electrode having a basket shape. The energy delivery bodies 108 are placed into separate airways of the bifurcation so that the third mass M3 is disposed therebetween. Energy is then provided thereto so as to treat the third mass M3. It may be appreciated that such treatment may be monopolar or each of the two energy delivery bodies 108 may serve as a pole to deliver the energy in a bipolar fashion to the third mass M3. In either case, such treatment leads to destruction of the third mass M3 while maintaining the extracellular matrix, and therefore structural integrity, of the wall W.

Figure 10A:
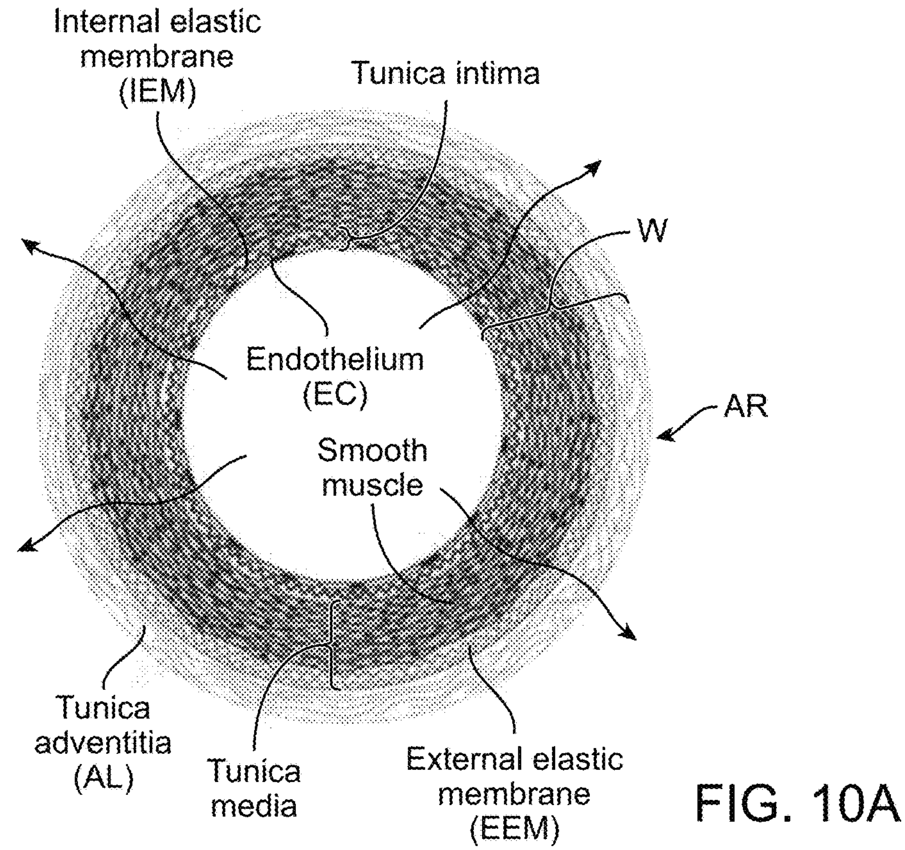
FIG. 10A illustrates a cross-section of an artery having a wall.
Figure 10B:
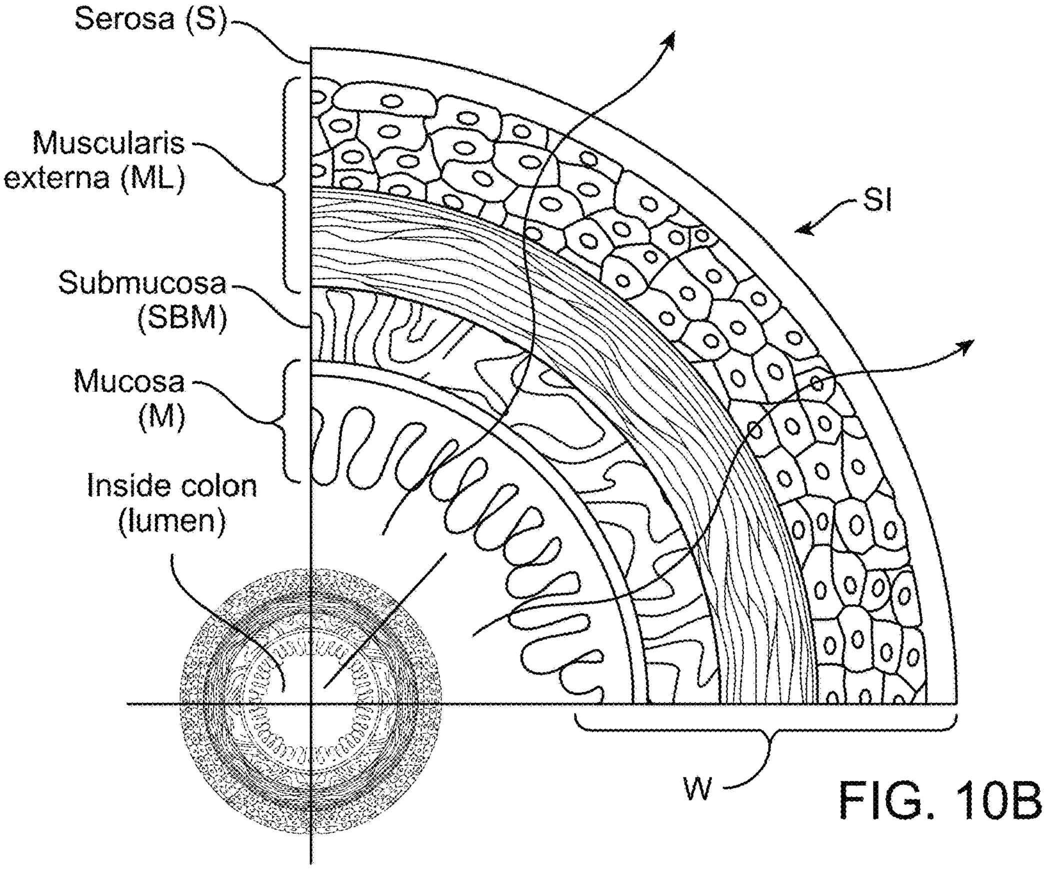
FIG. 10B illustrates a cross-section of a gastrointestinal luminal structure, in particular a colon having a wall.
Figure 10C:
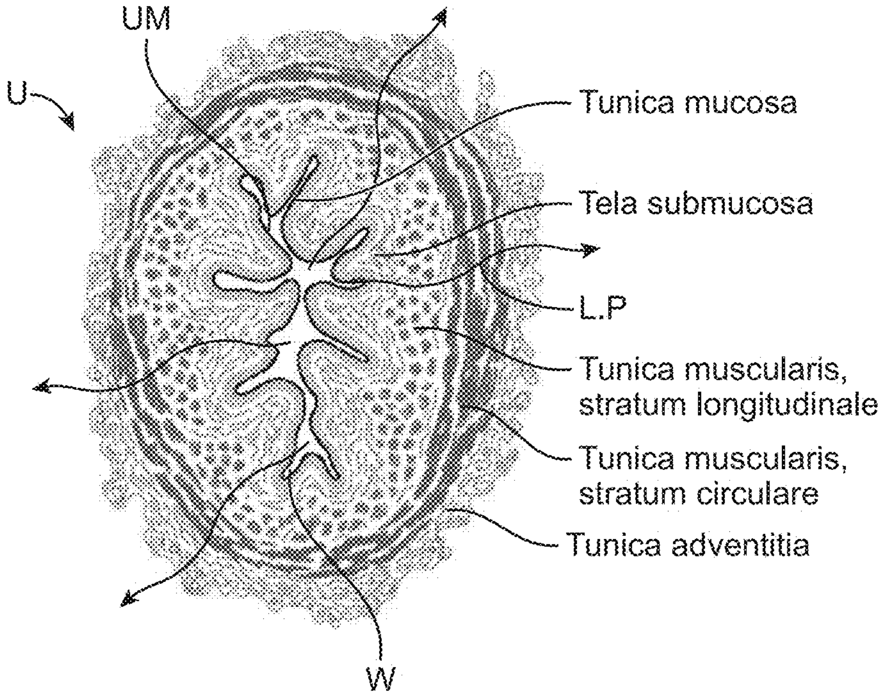
FIG. 10C illustrates a cross-section of a ureter having a wall.

FIGS. 10A-10C illustrate cross-sections of example luminal structures for illustrative purposes. In each example, energy is schematically illustrated as wavy arrows penetrating through the cross-sectional layers to the surrounding tissue. For clarity purposes, the device is not shown. FIG. 10A illustrates a cross-section of an artery AR having a wall W. Here, the wall W is comprised of a plurality of layers including endothelial cells EC, an internal elastic membrane IEM, smooth muscle cells, an external elastic membrane EEM and an adventitial layer AL. The endothelial cells EC are anchored on the underlying basement membrane or internal elastic membrane IEM which is a thin sheet-like structure containing mainly laminin, type IV collagen, nidogen, perlecan, type XV and type XVIII collagens, fibronectin, the heparin sulfate proteoglycan perlecan, and other macromolecules. At least twenty extracellular proteins have been identified from basement membrane preparations. Most of these proteins, if not all, have tissue-specific functions. Underneath the internal elastic membrane IEM is several layers of contractile vascular smooth muscle cells [SM] in concentric lamellar units composed of elastic fibers and smooth muscle cells [SM] separated by interlaminar matrix collagens, microfibrils, proteoglycans, glycoproteins, and ground substance. Arteries, for example, have more collagens and elastin than veins. Outside the smooth muscle cell SM layer of large vessels is an adventitial layer extending beyond the external elastic laminae and interstitial matrix that contains fibrillar type I and III collagen, chondroitin sulfate and dermatan sulfate proteoglycans, fibronectin, and many other extracellular matrix proteins.

Therapeutic energy passes through these layers killing or altering cells yet maintaining non-cellular elements, such as collagen, elastin, and matrix proteins. As mentioned, these non-cellular elements maintain the structure of the walls W allowing and encouraging normative cellular regeneration. Therefore, the luminal structures are maintained while abnormal or diseased cells and tissues are sufficiently eliminated.

Similarly, FIG. 10B illustrates a cross-section of a gastrointestinal luminal structure, in particular a small intestine SI having a wall W. Here, the wall W is made up of four layers of specialized tissue—from the lumen outwards: mucosa M, submucosa SBM, muscular layer ML and serosa S (if the tissue is intraperitoneal)/adventitia (if the tissue is retroperitoneal)—these last two tissue types differ slightly in form and function according to the part of the gastrointestinal tract they belong. The epithelium, the most exposed part of the mucosa, is a glandular epithelium with many goblet cells. Goblet cells secrete mucus, which lubricates the passage of food along and protects the intestinal wall from digestive enzymes. In the small intestine, villi are folds of the mucosa that increase the surface area of the intestine. The villi contain a lacteal, a vessel connected to the lymph system that aids in the removal of lipids and tissue fluids. Microvilli are present on the epithelium of a villus and further increase the surface area over which absorption can take place. Numerous intestinal glands as pocket-like invaginations are present in the underlying tissue. In the large intestines, villi are absent and a flat surface with thousands of glands is observed. Underlying the epithelium is the lamina propria, which contains myofibroblasts, blood vessels, nerves, and several different immune cells, and the muscularis mucosa which is a layer of smooth muscle that aids in the action of continued peristalsis and catastalsis along the gut. The submucosa contains nerves including the submucous plexus (Meissner's plexus), blood vessels and elastic fibers with collagen, that stretches with increased capacity but maintains the shape of the intestine. Surrounding this is the muscular layer, which comprises both longitudinal and circular smooth muscle that also helps with continued peristalsis and the movement of digested material out of and along the gut. In between the two layers of muscle lies the myenteric plexus (Auerbach's plexus). Lastly, there is the serosa/adventitia which is made up of loose connective tissue and coated in mucus so as to prevent any friction damage from the intestine rubbing against other tissue.

Again, therapeutic energy passes through these layers killing or altering cells yet maintaining non-cellular elements. Likewise, these non-cellular elements maintain the structure of the walls W allowing and encouraging normative cellular regeneration. Therefore, the luminal structures are maintained while abnormal or diseased cells and tissues are sufficiently eliminated.

And lastly, FIG. 10C illustrates a cross-section of a ureter U having a wall W. The ureter is lined by urothelium UM, a type of transitional epithelium that is capable of responding to stretches in the ureters. The transitional epithelium may appear as a columnar epithelia when relaxed, and squamous epithelia when distended. Below the epithelium, a lamina propria LP exists. The lamina propria is made up of loose connective tissue with many elastic fibers interspersed with blood vessels, veins and lymphatics. The ureter is surrounded by two muscular layers, an inner longitudinal layer of muscle, and an outer circular or spiral layer of muscle. Such illustrations show that luminal structures share similarity in structure, at least with the inclusion of both cellular components and non-cellular structural components. Therefore, the therapeutic energy delivered to the wall W will have a similar effect in regard to killing or altering cells yet maintaining non-cellular elements. The non-cellular elements maintain the structure of the walls W allowing and encouraging normative cellular regeneration. Therefore, the luminal structures are maintained while abnormal or diseased cells and tissues are sufficiently eliminated.

Figure 11:
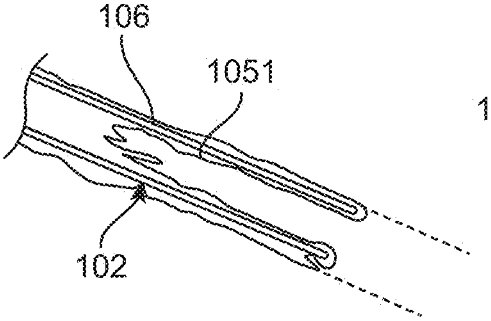
FIGS. 11-12 illustrate an embodiment of an energy delivery body comprising an inflatable member which is closed at one end and attached to the distal end of a catheter at its other end.
Figure 12:
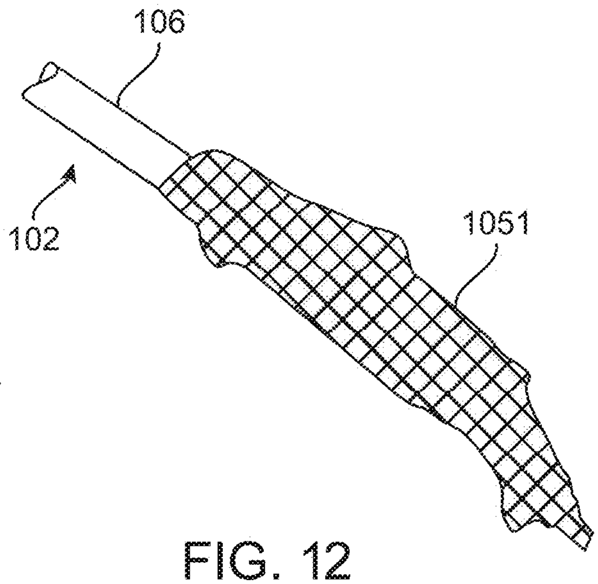

In some embodiments, the instrument 102 has a flexible and conforming energy delivery body 108 which may assist in treating uneven surfaces, such as the mucosal layer M of the small intestine SI and the urothelium UM of the ureter U. In some embodiments, as illustrated in FIG. 11-12, the energy delivery body 108 comprises an inflatable member 1051 which is closed at one end and attached to the distal end of a catheter 102 at its other end. Thus, in these embodiments, the inflatable member 1051 appears as a continuous "balloon" having a single open end which is attached to the distal end of the instrument 102. FIG. 11 illustrates the inflatable member 1051 retracted into the shaft 106 of the catheter 102 so that the inflatable member 1051 is turned inside out. This allows for compact storage of the inflatable member 1051 within the shaft 106. Upon deployment, the inflatable member 1051 is expanded distally of the shaft 106, turning the inflatable member 1051 right side out as illustrated in FIG. 11.

Figure 13:
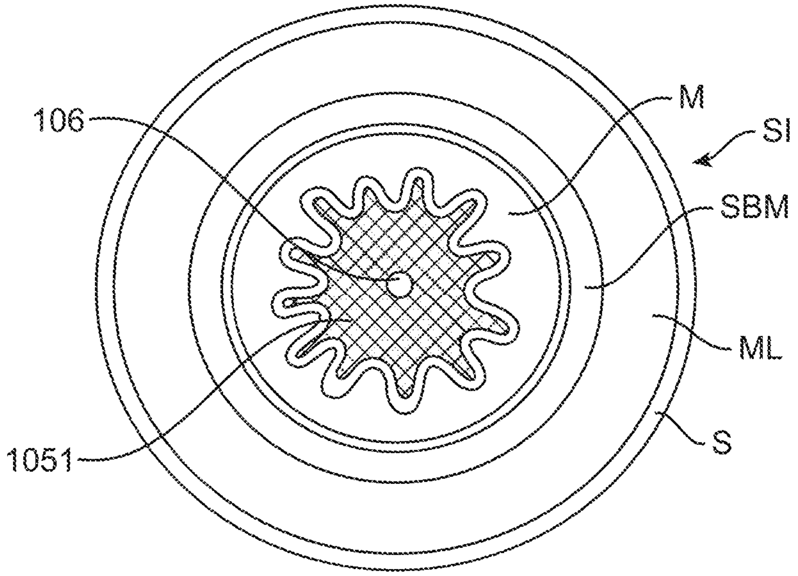
FIG. 13 is a cross-sectional illustration of an example small intestine having a conformable energy delivery body positioned therein.

In some embodiments, the inflatable member 1051 is configured to inflate in a manner which extends portions of the inflatable member 1051 into the folds of the luminal structure, such as the small intestine SI, so as to create finger-like projections as illustrated in FIG. 13. FIG. 13 is a cross-sectional illustration of an example small intestine SI having an uneven surface along the mucosal layer M. The inflatable member 1051 of FIGS. 10-11 is shown inflated therein wherein the inflatable member 1051 forms finger-like projections into the folds or villi.

Figures 14A, 14B, 14C:
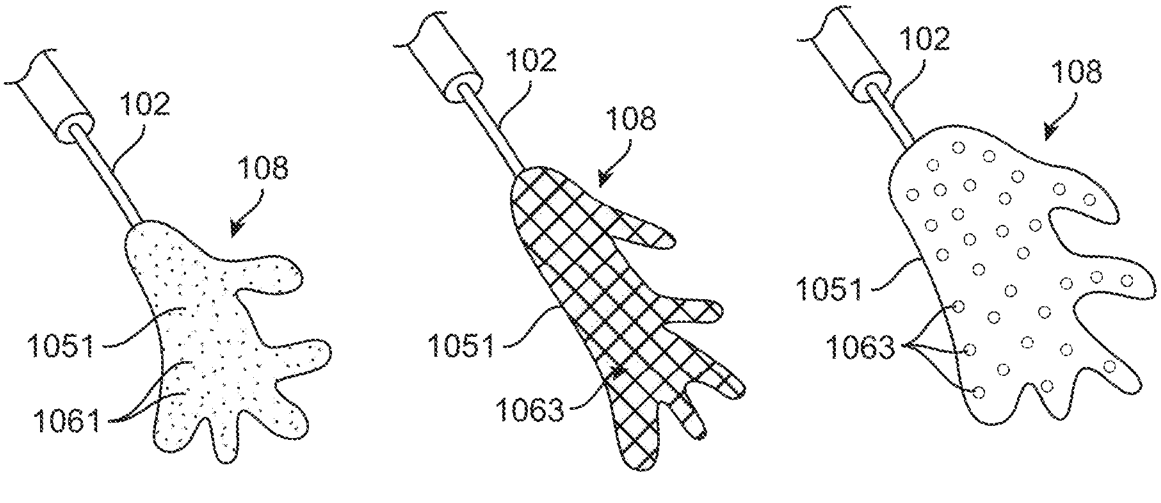
FIG. 14A illustrates a conformable inflatable member having thin electrode traces which cross at activation points.
FIG. 14B illustrates an embodiment of a conformable inflatable member surrounded by a compliant braid which acts as the electrode.
FIG. 14C illustrates an embodiment of a conformable inflatable member having activation points arranged so as to function in a multi-polar manner.

In some embodiments, such as illustrated in FIG. 14A, the inflatable member 1051 includes very thin electrode traces which cross at activation points 1061 providing a "speckled" appearance. Here, the inflatable member 1051 is configured to be used in a monopolar arrangement. However, in other embodiments the inflatable member 1051 is arranged so that the activation points 1061 function in a bipolar manner or in a multipolar manner with the use of a dispersive external pad. FIG. 14B illustrates an embodiment wherein the inflatable member 1051 is surrounded by a compliant braid 1063 which acts as the electrode. In some instances, the compliant braid 1063 is embedded in the inflatable member 1051 and in other instances the compliant braid 1063 is separate wherein the inflatable member 1051 inflates to deploy the compliant braid 1063. FIG. 14C illustrates an embodiment wherein the inflatable member 1051 includes activation points 1061 arranged so as to function in a multi-polar manner.

In some embodiments, energy may be delivered to uneven surfaces, such as including folds and/or villi, simultaneously with the use of a liquid electrode. In some embodiments, the liquid electrode is comprised of existing conductive solutions in the luminal structures, such as mucus. In other embodiments, the liquid electrode is comprised of a conductive solution that is delivered to the luminal structure, particularly into the targeted region. Typically, such a conductive solution comprises hypertonic saline, calcium, or other components and is delivered to an upstream segment so as to reach many of the downstream folds. The treatment delivery would then be performed either via a catheter 102 having an energy delivery body 108 as described hereinabove or a catheter having a simple electrode configured to activate the conductive solution (e.g. a dull probe). In some embodiments, the conductive solution is then removed and in other embodiments the conductive solution is left behind to be resorbed. It may be appreciated that in some embodiments the conductive solution is comprised of a hypertonic solution, isotonic solution, or specialty conductive solution (e.g. calcium, silver, etc) that compounds the treatment effect.

In some embodiments, the liquid electrode is comprised of a conductive solution that is disposed within the energy delivery body 108. For example, in some embodiments, the energy delivery body 108 comprises a braided wire electrode forming a basket shape and a porous expandable member (e.g. a balloon with laser-drilled holes) that is disposed within the braided wire electrode basket. Inflation of the expandable member deploys the braided wire electrode basket and allows the conductive solution to weep from the porous expandable member. In a blood-filled environment, such as in the vasculature, blood circulating therearound will interact with the conductive solution weeping from the porous expandable member, thereby creating a virtual electrode. Thus, the conductive solution forms the second pole of the electrical circuit to create a bipolar electrode configuration. In another embodiment, a second pole electrode is added to the distal tip of the catheter to act as the return pole of the bipolar circuit. The second pole electrode may be comprised of any suitable conductive material, such as a platinum metal tip. In a blood-filled environment, such as in the vasculature, blood circulating therearound will interact with the second pole electrode thereby turning the local blood into a virtual electrode to complete the circuit. These embodiments allow for localized bipolar delivery of energy for treatment of tissue while diminishing effects on the integrity of adjacent structures and a need for cardiac synchronization.

Figure 15:
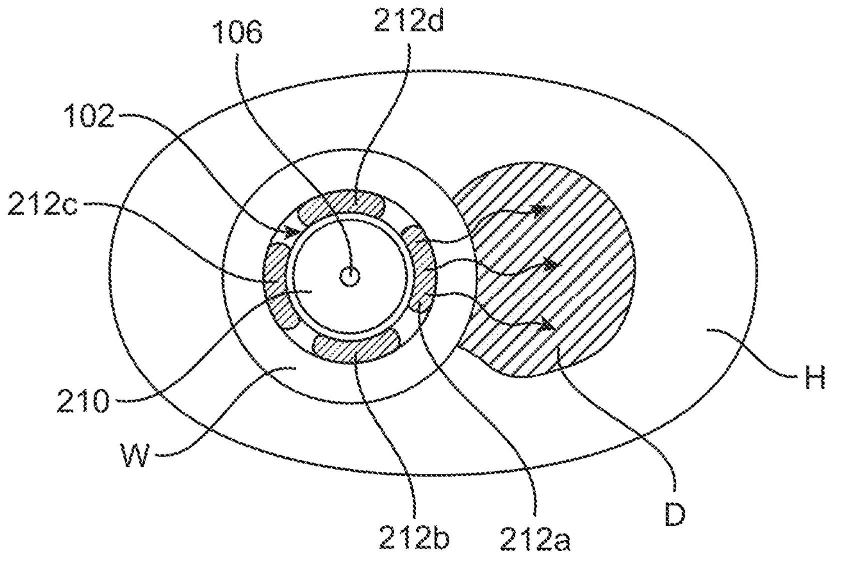
FIG. 15 illustrates the use of an energy delivery catheter configured to provide focal therapy.

In some embodiments, such as illustrated in FIG. 15, the energy delivery catheter or instrument 102 is configured to provide focal therapy, such as according to international patent application number PCT/US2018/067504 titled "OPTIMIZATION OF ENERGY DELIVERY FOR VARIOUS APPLICATIONS" which claims priority to Provisional Patent Application No. 62/610,430 filed Dec. 26, 2017 and U.S. Provisional Patent Application No. 62/693,622 filed Jul. 3, 2018, all of which are incorporated herein by reference for all purposes. In this embodiment, the instrument 102 again has an elongate shaft 106 with at least one energy delivery body 108 near its distal end and a handle 110 at its proximal end. In this embodiment, the energy delivery body 108 comprises an expandable member 210, such as an inflatable balloon, having at least one electrode 212 mounted thereon or incorporated therein. The energy delivery body 108 is delivered to a targeted area in a collapsed configuration. This collapsed configuration can be achieved, for example, by placing a sheath 126 over the energy delivery body 108, which maintains the collapsed configuration allowing smooth delivery. When deployment is desired, the sheath 126 is retracted or the instrument 102 advanced to allow the energy delivery body 108 to expand.

In this embodiment, the electrode 212 has the form of a pad having a relatively broad surface area and thin cross-section. The pad shape provides a broader surface area than other shapes, such as a wire shape. The electrode 212 is connected with a conduction wire which electrically connects the electrode 212 with the generator 104. In this embodiment, the electrode 212 has four electrodes 212*a*, 212*b*, 212*c*, 212*d*, however it will be appreciated that the energy delivery body 208 can have any number of electrodes 212, such as one, two, three, four, five, six, seven, eight, nine, ten or more. The electrodes 212 may be comprised of flexible circuit pads or other materials attached to the expandable member 210 or formed into the expandable member 210. The electrodes 212 may be distributed radially around the circumference of the expandable member 210 and/or they may be distributed longitudinally along the length of the expandable member 210. Such designs may facilitate improved deployment and retraction qualities, easing user operation and compatibility with standard introducer lumens as well as achieve greater field consistency over a non-uniform surface.

Focal therapy may be particularly useful when treating tumors or diseased tissue D that is near a localized segment of the wall W of the luminal structure LS, as illustrated in FIG. 15. In use, the instrument 102 is advanced into a body passageway or lumen L, such as over a guidewire, to the diseased segment along the length of the lumen L. When, for example, a first electrode 212*a* is energized and the other electrodes 212*b*, 212*c*, 212*d* are not energized, all of the energy flows along a first electrical pathway (indicated by wavy arrows) to the dispersive electrode 140. This provides a predictable pathway in which any naturally occurring preference in current flow is overcome by the induced current flow through the first electrical pathway. This increases treatment effect in the tissue area through which the first electrical pathway flows and is sufficient to treat the localized diseased tissue.

It may be appreciated that in some embodiments focal therapy is utilized to treat diseased tissue that is not localized but has surrounded a majority or all of the circumferential lumen of the luminal structure. In such instances, energy may be delivered to the entire diseased region in segmental sections, either circumferentially or longitudinally, such as by energizing various electrodes in a predetermined pattern and/or with a predetermined pattern of energy parameters. It may also be appreciated in some embodiments various electrodes are energized at differing voltage levels with respect to a dispersive (return) electrode 140 applied externally to the skin of the patient. Manipulation of the voltage levels manipulates the electric field distribution, thus shaping the treatment area.

It may be appreciated that in some embodiments the energy delivery body 108 comprises an electrode pair able to function in a bipolar manner. In such embodiments, the electrode pair may operate independently or concurrently with monopolar energy delivery. It may also be appreciated that in some embodiments a multipolar arrangement may be used. In such embodiments, the multipolar arrangement may operate independently or concurrently with monopolar energy delivery.

Figure 16:
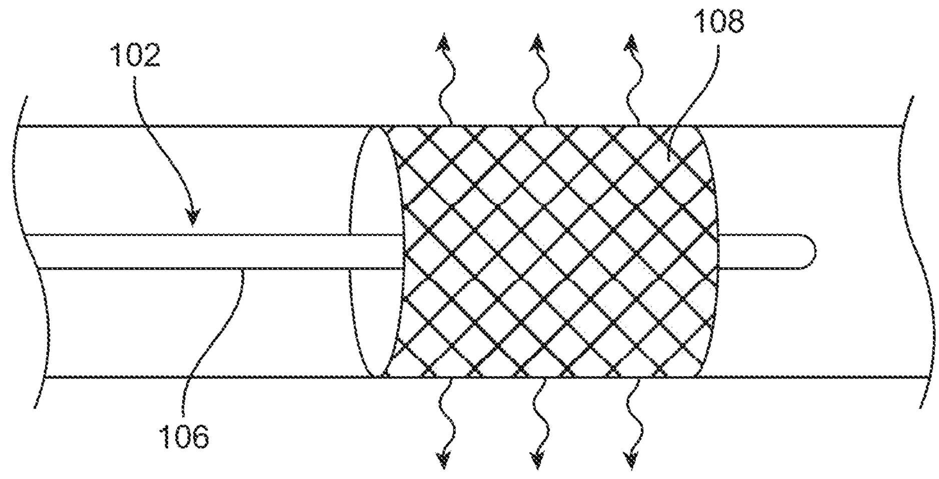
FIG. 16 illustrates an embodiment wherein the energy delivery body has the form of a stent.

It may be appreciated that, in some embodiments, energy is delivered to a luminal structure in conjunction with a structural therapy, such as stenting, of the lumen. In such embodiments, the energy delivery body 108 may have a form related to the structural therapy. For example, in some embodiments, such as illustrated in FIG. 16, the energy delivery body 108 has the form of a stent. Stents are typically considered a tubular support placed temporarily or permanently inside of a lumen, such as a blood vessel, canal, or duct, to aid healing or relieve an obstruction. In some embodiments, energy is delivered by the stent, such as indicated by wavy arrows in FIG. 16. It may be appreciated that in some embodiments the stent remains in place after the therapy and is left behind as an implant.

IV. Extra-Luminal Placement and Energy Delivery

Figures 17A, 17B:
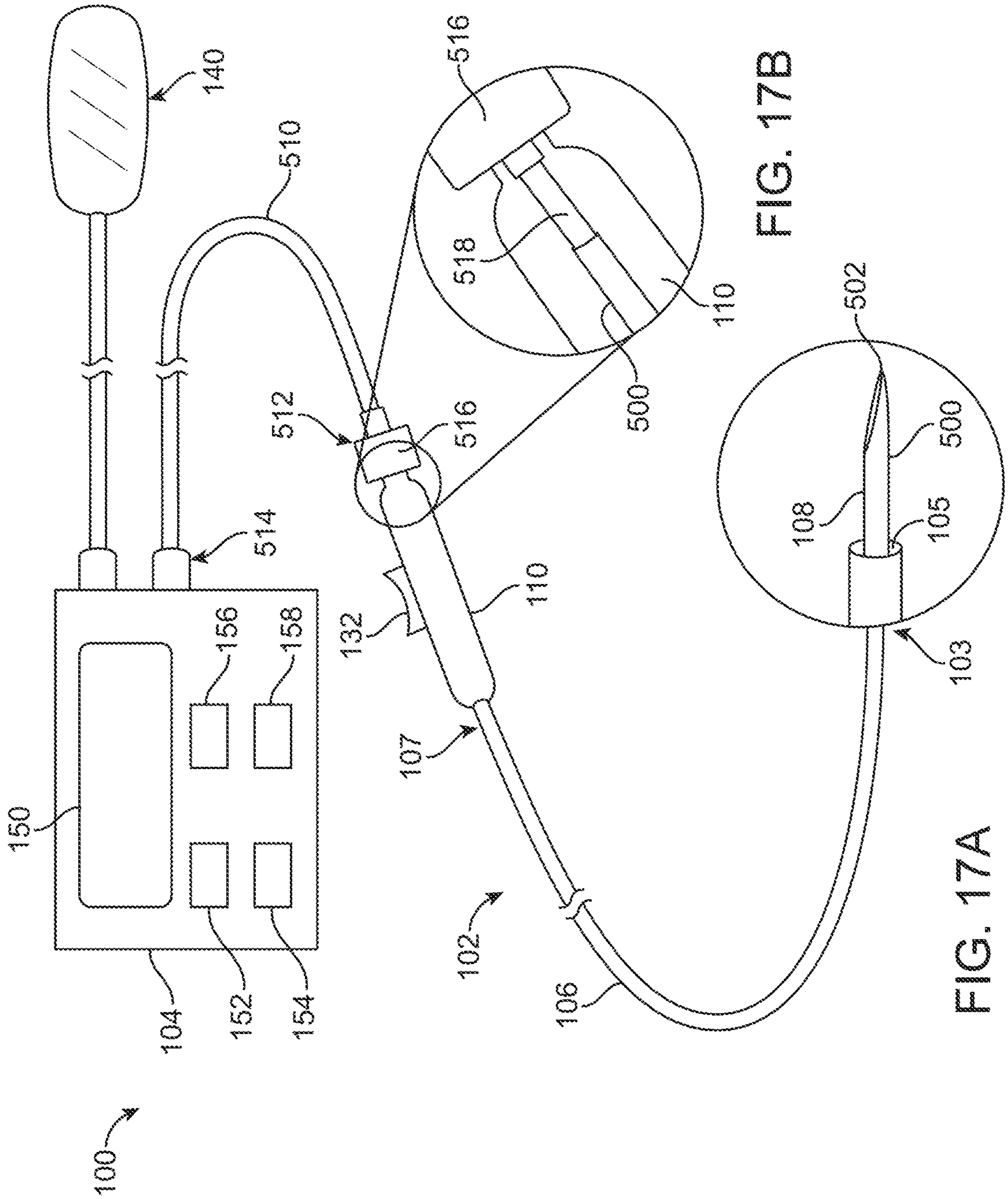
FIGS. 17A-17B illustrates an embodiment of a therapeutic system that delivers energy extra-luminally.

FIGS. 17A-17B illustrate another embodiment of a treatment system 100. Here, the system 100 is configured to treat target tissue that is located at least partially outside of a body lumen wherein treatment may benefit from originating the treatment energy at a distance from the body lumen. In this embodiment, the system 100 comprises an elongate instrument 102 connectable with a generator 104. It may be appreciated that many of the system components described above are utilized in this embodiment of the system 100, such as particular aspects of the instrument 102, generator 104 and other accessories. Therefore, such description provided above is applicable to the system 100 described herein below. The main differences are related to the energy delivery body 108.

Here, the instrument 102 comprises a shaft 106 having a distal end 103, a proximal end 107 and at least one lumen 105 extending at least partially therethrough. Likewise, the instrument 102 also includes at least one energy delivery body 108. In this embodiment, an energy delivery body 108 has the form of a probe 500 that is disposed within the lumen 105 of the shaft 106. The probe 500 has a probe tip 502 that is advanceable through the lumen 105 and extendable from the distal end 103 of the shaft 106 (expanded in FIG. 17A to show detail). In this embodiment, the tip 502 has a pointed shape configured to penetrate tissue, such as to resemble a needle. Thus, in this embodiment, the probe tip 502 is utilized to penetrate the lumen wall W and surrounding tissue so that it may be inserted into the target tissue external to the body lumen. Thus, the probe 500 has sufficient flexibility to be endoluminally delivered yet has sufficient column strength to penetrate the lumen wall W and target tissue. In some embodiments, the instrument 102 has markings to indicate to the user the distance that the probe tip 502 has been advanced so as to ensure desired placement. In some embodiments, the probe extends from the distal end 103 of the shaft 106 approximately less than 0.5 cm, 0.5 cm, 1 cm, 2 cm, 3 cm, 4 cm, 5 cm, 6 cm, 7 cm, 8 cm or more than 8 cm. In some embodiments, the probe extends 1-3 cm or 2-3 cm from the distal end of the shaft 106. In some embodiments, the probe is 18 gauge, 19 gauge, 20 gauge, 21 gauge, 22 gauge, 23 gauge, 24 gauge, or 25 gauge. In some embodiments, the probe 500 is comprised of a conductive material so as to serve as an electrode. Thus, the electrode would have the size of the exposed probe. Example materials include stainless steel, nitinol, cobalt-chromium alloy, copper, and gold. Thus, in these embodiments, the PEF energy is transmittable through the probe 500 to the probe tip 502. Consequently, the shaft 106 is comprised of an insulating material or is covered by an insulating sheath. Example insulating materials include polyimide, silicone, polytetrafluoroethylene, and polyether block amide. The insulating material may be consistent or varied along the length of the shaft 106 or sheath. Likewise, in either case, the insulating material typically comprises complete electrical insulation. However, in some embodiments, the insulating material allows for some leakage current to penetrate.

When the probe 500 is energized, the insulting shaft 106 protects the surrounding tissue from the treatment energy and directs the energy to the probe tip 502 (and any exposed portion of the probe 500) which is able to deliver treatment energy to surrounding tissue. Thus, the tip 502 acts as a delivery electrode and its size can be selected based on the amount of exposed probe 500. Larger electrodes can be formed by exposing a greater amount of the probe 500 and smaller electrodes can be formed by exposing less. In some embodiments, the exposed tip 502 (measured from its distal end to the distal edge of the insulating shaft) during energy delivery has a length of 0.1 cm, 0.2 cm, 0.3 cm, 0.4 cm, 0.5 cm, 0.6 cm, 0.7 cm, 0.8 cm, 0.9 cm, 1 cm, 2 cm, 3 cm, greater than 3 cm, up to 8 cm, less than or equal to 0.1 cm, less than or equal to 0.3 cm, less than or equal to 0.5 cm, less than or equal to 1 cm, 0.2-0.3 cm, 0.1-0.5 cm, 0.1-1 cm, and all ranges and subranges therebetween. In addition to changing the size of the electrode, the tip 502 is retractable into the shaft 106 to allow for atraumatic endoscopic delivery and is then advanceable as desired to reach the target tissue. In this embodiment, advancement and retraction are controlled by an actuator 132 (e.g. knob, button, lever, slide or other mechanism) on a handle 110 attached to the proximal end 107 of the shaft 106. It may be appreciated that the shaft 106 itself may be advanced toward the target tissue, with or without advancing the probe from the distal end 103 of the shaft 106. In some embodiments, the distal end of the shaft 106 is advanced up to 20 cm into the tissue, such as from an external surface of a luminal structure or from an external surface of the body of the patient.

The handle 110 is connected to the generator 104 with the use of a specialized energy plug 510. The energy plug 510 has a first end 512 that connects to the handle 110 and a second end 514 the connects to the generator 104. The connection of the first end 512 with the handle 110 is expanded for detail in FIG. 17B. In this embodiment, the first end 512 has an adapter 516 that includes a connection wire 518 extending therefrom. The connection wire 518 is insertable into the proximal end of the probe 500 within the handle 110. This allows the energy to be transferred from the generator 104, through the connection wire 518 to the probe 500. Thus, the probe 500 is able to be electrified throughout its length, however only the exposed tip 502 delivers energy to the tissue due to the presence of the insulated shaft 106.

Figure 18A:
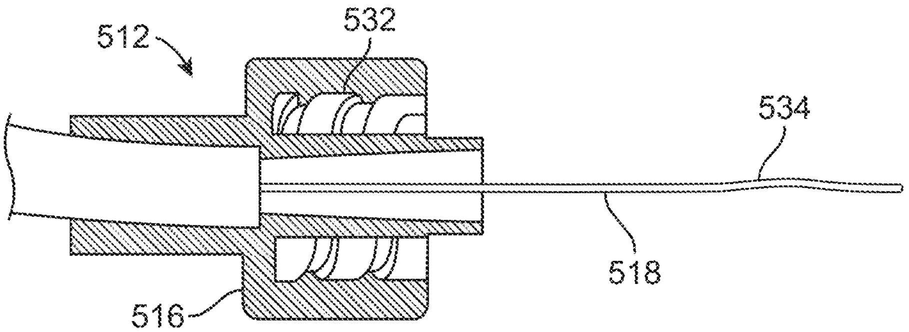
FIGS. 18A-18C illustrate an example of the connection between the energy plug and the handle.
Figure 18B:
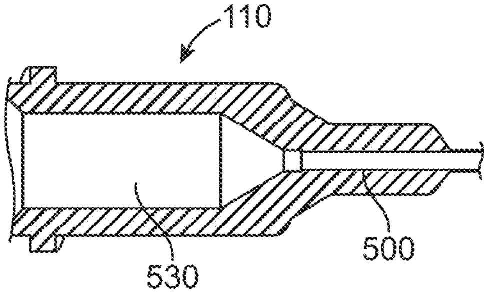
Figure 18C:
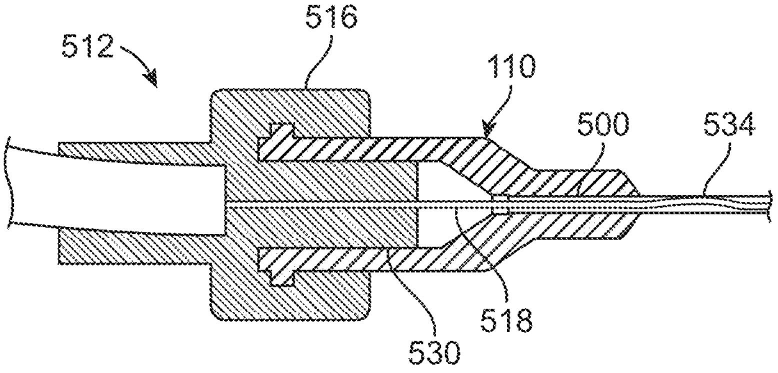

FIGS. 18A-18C illustrate an example of the connection between the energy plug 510 and the handle 110. As mentioned previously, in this embodiment, the first end 512 of the energy plug 510 has an adapter 516 that includes a connection wire 518 extending therefrom. The connection wire 518 is conductive and is typically comprised of copper, aluminum, stainless steel, or nitinol. Thus, energy from the generator 104 is able to be transmitted from the generator 104, through the plug 510 and to the connection wire 518. In this embodiment, the adapter 516 is joinable with the handle 110 so that the connection wire 518 is inserted into the handle 110. As illustrated in FIGS. 18A-18B, the handle 110 has a cavity 530 into which the connection wire 518 is insertable. The cavity 530 guides the connection wire 518 into the proximal end of the probe 500, wherein the probe 500 has a hollow configuration, at least near its proximal end, so as to receive the connection wire 518. As the connection wire 518 is advanced into the probe 500, the adapter 516 engages with the handle 110. In this embodiment, the adapter 516 has threads 532 so as to hold the handle 110 in engagement, as illustrated in FIG. 18C. In this embodiment, the connection wire 518 includes at least one bend or kink 534. Therefore, when the connection wire 518 is coaxially positioned within the probe 500, the kink 534 draws the connection wire away from the coaxial axis and contacts the probe 500. It is this contact that allows the energy to be transmitted from the connection wire 518 to the probe 500.

Figure 19B:
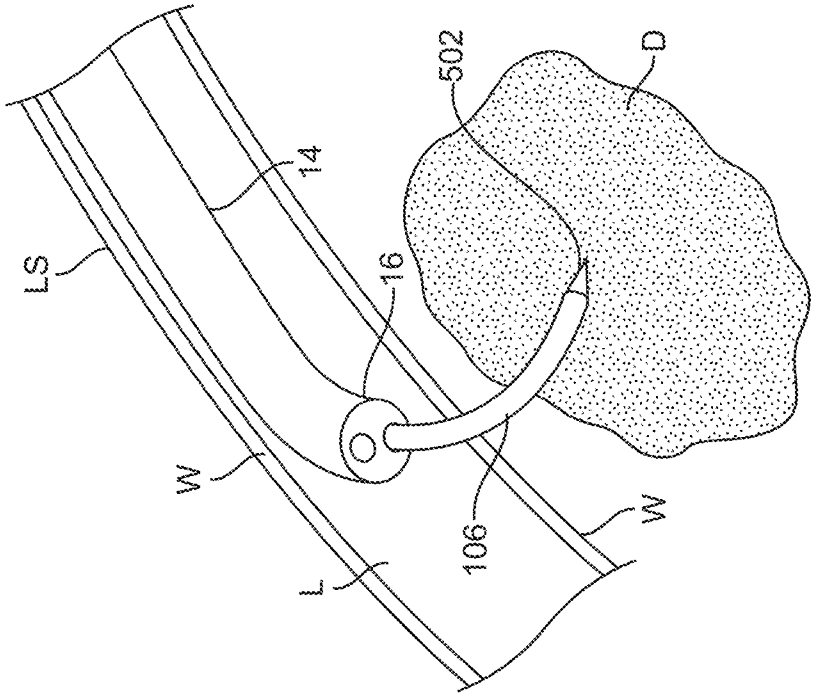
FIGS. 19A-19C illustrate an example method of extra-luminal treatment.
Figure 19A:
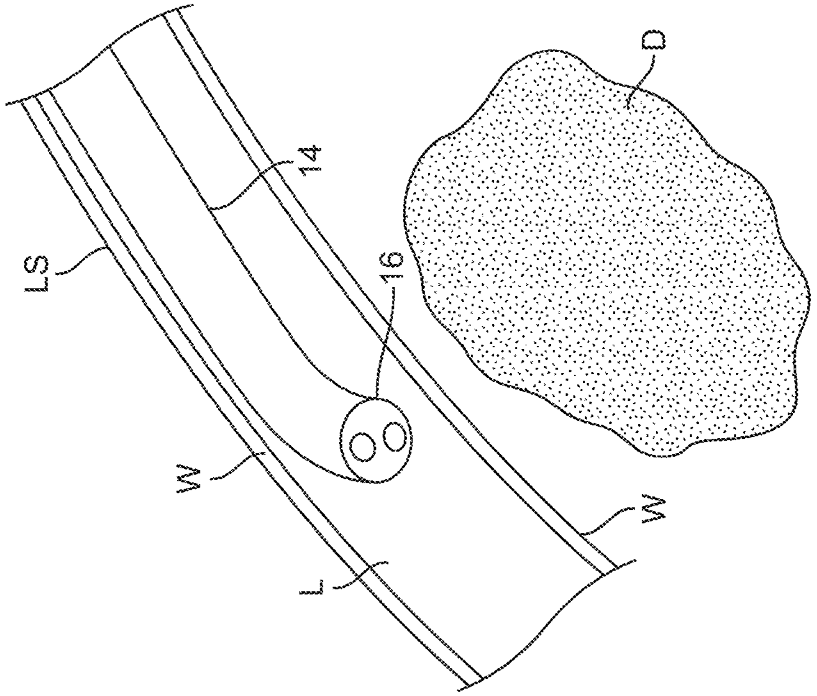
Figure 19C:
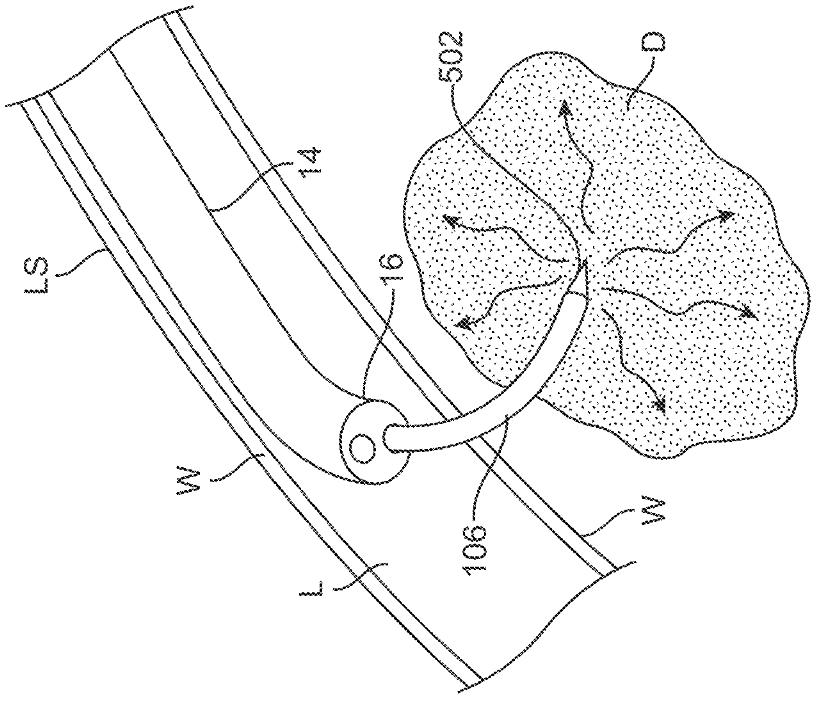

FIGS. 19A-19C illustrate an example method of treatment. FIG. 19A illustrates abnormal or diseased tissue D, such as a tumor, near a luminal structure LS. In this example, the diseased tissue D is near the luminal structure LS but spaced a distance from the lumen wall W. This luminal structure LS is used to access and the diseased tissue D and extra-luminally treat the diseased tissue D near the luminal structure LS. In this embodiment, the elongate insertion tube 14 of an endoscope 10 is advanced into the luminal structure LS and its distal tip 16 is steered toward the lumen wall W, beyond which lies the diseased tissue D. Once desirably positioned, the treatment instrument 150 is advanced through a lumen in the insertion tube 14 so that the distal end 103 of the shaft 106 extends beyond the tip 16 of the endoscope 10, as illustrated in FIG. 18B. In this embodiment, the probe tip 502 assists in penetrating the wall W and the shaft 106 is advanced across the wall W until the probe tip 502 is desirably positioned within the diseased tissue D. Referring to FIG. 19C, in this embodiment, the probe tip 502 is then advanced from the shaft 106 so as to create a desired delivery electrode size. Energy is then delivered according to one or more energy delivery algorithms 152, through the probe 500 to the diseased tissue D, as illustrated in FIG. 19C by wavy arrows extending radially outwardly from the probe tip 502. It may be appreciated that the distance into the diseased tissue may vary based on parameter values, treatment times and type of tissue, to name a few. It may also be appreciated that larger or smaller treatment depths may be achieved than illustrated herein.

The delivered energy treats the diseased tissue D as appropriate. In the case of cancer, the cancerous cells are destroyed, eliminated, killed, removed, etc., while maintaining non-cancerous, non-cellular elements, such as collagen, elastin, and matrix proteins. These non-cellular elements maintain the structure of the tissue allowing for and encouraging normative cellular regeneration. Likewise, any energy reaching the walls W of the nearby luminal structure LS preserve the integrity and mechanical properties of the luminal structure LS. It may be appreciated that in some instances, the energy kills the cells in the diseased tissue D directly, such as via accumulated generalized cellular injury and irrecoverable disruption of cellular homeostasis. Any remaining diseased tissue may then be surgically removed or removed by other methods that are typically unable to safely treat tissue close to luminal structures.

A. Alternative Probe Designs

It may be appreciated that the probe 500 may have a variety of forms and structures. In some embodiments, the probe 500 is hollow, such as having a tubular shape. In such embodiments, the probe 500 may be formed from a hypotube or metal tube. Such tubes can be optimized for desired push and torque capabilities, kink performance, compression resistance and flexibility to ensure consistent and reliable steerability to the target treatment site. Likewise, such tubes can include custom engineered transitions, such as laser cutting and skive features, along with optional coatings to optimize produce performance. In some embodiments, the tube has a sharp point with multiple cutting edges to form the probe tip 502. In other embodiments, the tube has a blunt atraumatic tip. In some embodiments, the probe 500 is solid, such as having a rod shape. These probes can also be optimized and customized similarly to hypotubes. In some embodiments, the solid probe 500 has a sharp point with a symmetric or asymmetric cut to form the probe tip 502. In other embodiments, the solid probe 502 has a blunt atraumatic tip.

It may be appreciated that the probe 500 may include a lumen for delivery of fluids or agents. Such a lumen may be internal or external to the probe. Likewise, fluid or agents may be delivered directly from the shaft 106, such as through a lumen therein or a port located along the shaft 106.

Figure 20:
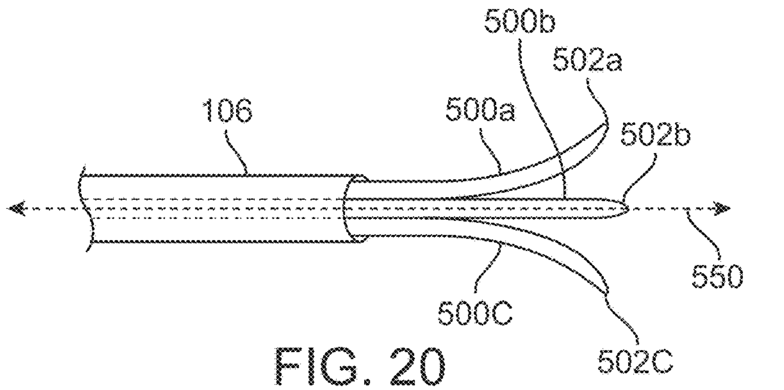
FIG. 20 illustrates an embodiment of a probe having three probe elements, each having a respective probe tip.

In some embodiments, the probe 500 is comprised of multiple probe elements, wherein each probe element has similar features and functionality to an individual probe 500 as described above. Thus, in some embodiments they may be considered separate probes, however for simplicity they will be described as probe elements making up a single probe 500 since they are passed through the same shaft 106 of the instrument 102. FIG. 20 illustrates an embodiment having three probe elements 500*a*, 500*b*, 500*c*, each having a respective probe tip 502*a*, 502*b*, 502*c*. The probe elements 500*a*, 500*b*, 500*c* extend from the shaft 106 in varying directions from a central axis 550, for example along the axis 550 and curving radially away from the axis 550 in opposite directions. This allows the tips 502*a*, 502*b*, 502*c* to be positioned in an array of locations throughout an area of diseased tissue D. Consequently, a larger ablation zone can be created. This may be desired when the area of diseased tissue D is larger, when treating multiple targets or when a target has imprecise location information. It may be appreciated that the probe elements 500*a*, 500*b*, 500*c* may be deployed independently or simultaneously. Likewise, the tips 502*a*, 502*b*, 502*c* may be energized independently or simultaneously. The energy delivered by the tips 502*a*, 502*b*, 502*c* may be provided by the same energy delivery algorithm 152 or different energy delivery algorithms 152, therefore delivering the same or different energies. The probe elements 500*a*, 500*b*, 500*c* may function in a monopolar manner or in a bipolar manner between pairs of probe elements. Likewise, it may be appreciated that the probe elements 500*a*, 500*b*, 500*c* may function in a combination of monopolar and bipolar manners.

It may be appreciated that any number of probe elements may be present, including one, two, three, four, five, six, seven, eight, nine, ten or more. Likewise, the probe elements may be extended the same or different distances from the shaft 106 and may have the same or different curvatures. In FIG. 21, three probe elements 500*a*, 500*b*, 500*c* are illustrated extending different distances from the shaft 106, wherein one probe element 500*a* is extended the shortest distance, another probe element 500*b* is extended the furthest distance and yet another probe element 500*c* is extended therebetween. These probe elements 500*a*, 500*b*, 500*c* also are illustrated as having different curvatures, extending radially outwardly from the central axis 550. Here, the one probe element 500*a* has the greatest curvature, the another probe element 500*b* has no curvature and the yet another probe element 500*c* has a curvature therebetween. In another embodiment, the probe elements to not have any curvature and exit from the shaft 106 in a linear fashion. Typically, the probe elements are pre-curved so that advancement of the probe tip from the shaft 106 allows the probe element to assume its pre-curved shape. Thus, in some embodiments, a variety of curvatures can be utilized by advancing the probe tips differing amounts from the shaft 106.

Figure 22:
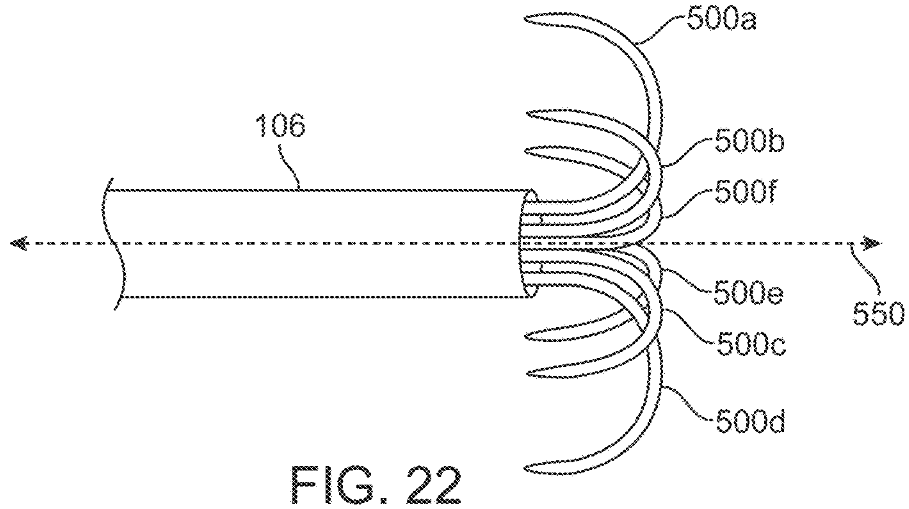
FIG. 22 illustrates an embodiment of a probe having probe elements curve that radially outwardly in a flower or umbrella shape.

In some embodiments, the probe elements curve radially outwardly in a flower or umbrella shape, as illustrated in FIG. 22. Here, a plurality of probe elements 500*a*, 500*b*, 500*c*, 500*d*, 500*e*, 500*f* extend radially outwardly from the central axis 550 in a flower shape and curve around so that their respective tips are ultimately oriented in a proximal direction. In some embodiments, the elements 500*a*, 500*b*, 500*c*, 500*d*, 500*e*, 500*f* are of equal length and are equally spaced to form a symmetrical arrangement. In other embodiments, the elements 500*a*, 500*b*, 500*c*, 500*d*, 500*e*, 500*f* have differing lengths and/or have differing spacing to form a myriad of arrangements.

Figure 23:
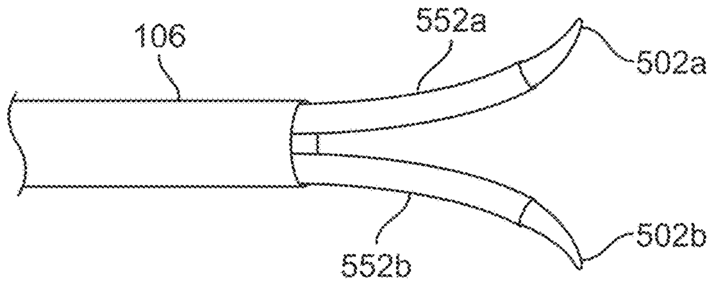
FIG. 23 illustrates an embodiment of a probe comprising two probe elements extending from a shaft wherein each probe element is at least partially covered by a respective insulating sheath, leaving the tips exposed.

It may be appreciated that the size of the probe tip 502 capable of transmitting energy may be further adjusted with the use of an insulating sheath 552 that extends at least partially over the probe. As mentioned previously, the size of the active portion of the probe tip 502 may be adjusted based on its extension from the shaft 106. However, this may be further refined, particularly when a plurality of probe elements are present, with the use of insulating sheaths 552 covering portions of the individual probe elements. FIG. 23 illustrates an embodiment of a probe comprising two probe elements 500*a*, 500*b* extending from a shaft 106. Here, each probe element 500*a*, 500*b* is at least partially covered by a respective insulating sheath 552*a*, 552*b*, leaving the tips 502*a*, 502*b* exposed. In some embodiments, the sheaths 552*a*, 552*b* are individually advanceable so that the size of each probe tip 502*a*, 502*b* is individually selectable. This may be beneficial when the tips 502*a*, 502*b* are deployed into different portions of the target tissue desiring different amounts of energy delivery. This may also be beneficial when delivering a concentration of energy to a location that is at an angular distance from the central axis of the shaft 106. Together, the ability to vary the number of probe elements, the shape and length of the probe elements, the arrangement of the probe elements and the size of the delivery area on the probe tips, allows for a wide variety of lesion shapes, sizes and intensities to be formed.

It may be appreciated that any of the probe elements described herein may have the same structure and features as any of the probes describe herein. For example, the probe elements may be constructed of the same materials, have the same functionality and have a sharp or atraumatic tip. Likewise, it may be appreciated that any of the probe elements may be deployed independently or simultaneously and may be energized independently or simultaneously. The energy delivered may be provided by the same energy delivery algorithm 152 or different energy delivery algorithms 152, therefore delivering the same or different energies. Any of the probe elements may function in a monopolar manner or in a bipolar manner between pairs of probe elements. Likewise, it may be appreciated that the probe elements may function in a combination of monopolar and bipolar manners.

Figure 24:
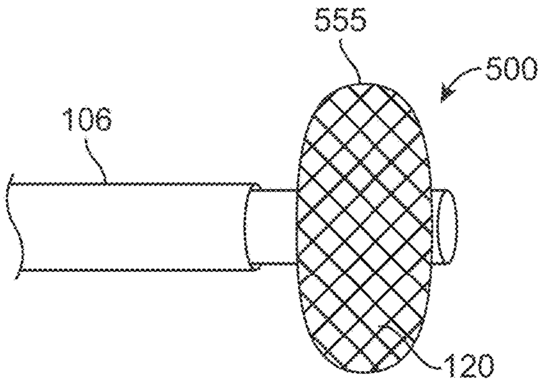
FIG. 24 illustrates an embodiment of a probe comprising a plurality of wires or ribbons to form a basket.
Figure 25:
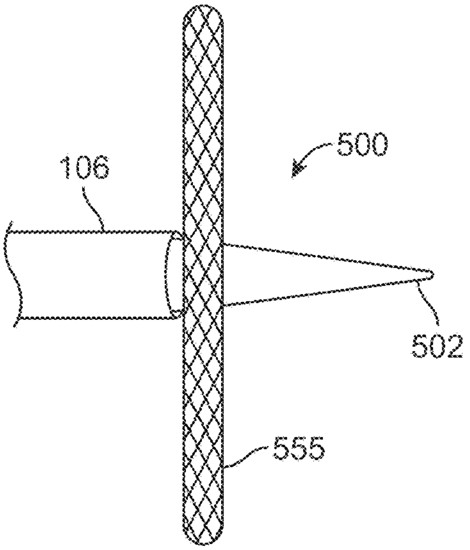
FIG. 25 provides a side view illustration of a probe comprising a basket having a disk shape.
Figure 26A:
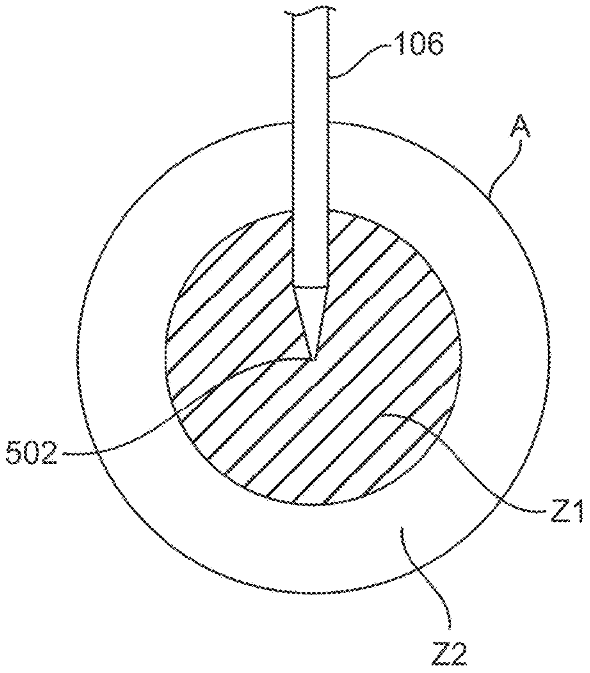
FIG. 26A illustrates an embodiment of a probe positioned within a target tissue area creating a first ablation zone surrounding the probe tip.
Figure 26B:
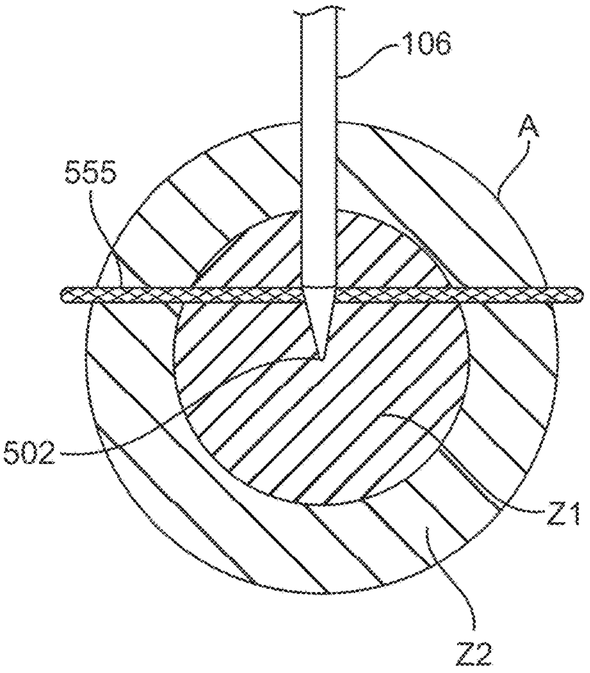
FIG. 26B illustrates the embodiment of the probe FIG. 26A with the addition of a disk-shaped basket forming a second ablation zone that is larger than the first ablation zone.

As stated previously, in many of these extra-luminal delivery embodiments, the energy delivery body 108 has the form of a probe 500 that is disposed within the lumen 105 of the shaft 106. In some embodiments, the probe 500 comprises a plurality of wires or ribbons 120 and forms a basket 555 serving as an electrode, as illustrated in FIG. 24. It may be appreciated that alternatively the basket 555 can be laser cut from a tube. It may be appreciated that a variety of other designs may be used. Typically, the basket 555 is delivered to a targeted area in a collapsed configuration and then expanded for use. Such expansion can form the basket 555 into an oblong shape, an oval or elliptical shape, a round shape or a disk shape, to name a few. In some embodiments, the basket 555 is configured to form a disk shape, as illustrated in FIG. 24 (side view). In this embodiment, probe 500 comprises both a disk-shaped basket 555 and a pointed probe tip 502, wherein the probe tip 502 is concentric to the disk-shaped basket 555. Such arrangement may assist in creating larger lesions. For example, FIG. 26A illustrates an embodiment of a probe tip 502 positioned within a target tissue area A. Energy transmitted from the probe tip 502 creates a first ablation zone Z1 surrounding the tip 502. In this example, the first ablation zone Z1 is smaller than the target tissue area A. However, with the addition of the disk-shaped basket 555, as illustrated in FIG. 26B, energy is also delivered from the basket 555 forming a second ablation zone Z2 that is larger than the first ablation zone Z1. In some embodiments, the first and second ablation zones Z1, Z2 overlap so that the first ablation zone Z1 resides entirely within the second ablation zone Z2. This provides an additive effect of the two ablations within the first ablation zone Z1. In other embodiments, the disk-shaped basket 555 delivers energy only or primarily from its outer perimeter or rim, such as by insulating or masking the central region of the basket 555. In such embodiments, the first ablation zone Z1 and the second ablation zone Z2 do not substantially overlap. When the energy provided by the basket 555 and the probe tip 502 are the same, this arrangement may allow an even expansion of the first ablation zone Z1 to the size of the second ablation zone Z1 (i.e. forming a consistent lesion). When the energy provided by the basket 555 and the probe tip 502 are different, this may allow different types of lesions to be formed in the first ablation zone Z1 and the second ablation zone Z2.

It may be appreciated that in some embodiments, the probe 500 may include two or more baskets 555 that are spaced apart so as to allow target tissue to be positioned therebetween. In such instances, energy can be delivered from the two or more baskets 555 in a monopolar fashion, or in a bipolar fashion wherein two baskets have opposite polarities so that energy is transferred between them, treating the tissue therebetween.

It may be appreciated that in some embodiments, the probe 500 is fixed in relation to the shaft 106. Likewise, in some embodiments, the probe 500 does not extend throughout the length of the shaft 106. For example, in some embodiments, the probe 500 is shortened and resides near the distal end 103 of the shaft 106 where a probe tip 502 extends from the shaft 106. In such embodiments, energy is transmitted to the shortened probe 500 by a conductive wire or other apparatus that extends through the shaft 106 to the shortened probe 500. In some instances, this may allow the shaft 106 to have altered physical characteristics, such as increased flexibility.

Figure 27:
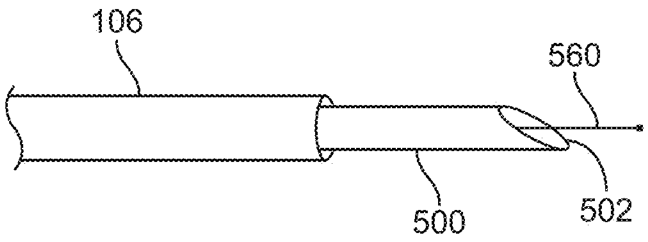
FIG. 27 illustrates an energy delivery body comprising a conductive element passing through a probe and extending therefrom.

It may be appreciated that, in some embodiments, the energy delivery body 108 comprises conductive element 560, such as a wire or filament, that passes through the probe 500 and extends therefrom, such as illustrated in FIG. 27. In this embodiment, the probe 500 is not conductive and simply provides a tip 502 to assist in penetrating tissue and to deliver the conductive element 560. It may be appreciated that the conductive element 560 has suitable strength to be advanced beyond the probe tip 502 so as to be inserted into target tissue. Energy is delivered from the generator 104 to the conductive element 560 which delivers the energy to the tissue. In some embodiments, the conductive element 560 has a length 0.5 cm, 0.5 cm, 1 cm, 2 cm, 3 cm, 1-3 cm, 2-3 cm or greater than 3 cm from the probe tip. In some embodiments, the conductive element 560 has a diameter of 0.010 inches, 0.011 inches, 0.012 inches, 0.013 inches, 0.014 inches, 0.015 inches. Use of such a conductive element 560 may be beneficial when higher concentrations of energy are desired to be delivered at a particular tissue location.

It may be appreciated that in some embodiments, the instrument 102 does not include a probe 500 and the one or more electrode bodies 108 are mounted on or integral with the shaft 106. In such embodiments, the one or more electrode bodies 108 may have the form of a band electrode, a basket electrode, or any other suitable shaped electrode. In such embodiments, the shaft 106 is advanced into the target tissue and energy is delivered from the one or more electrode bodies 108.

V. Manipulation of Instrument and Visualization

As described herein above, the instrument 102 is typically delivered through an endoscope 10 or other delivery device which is steered through the luminal structures by conventional methods. This may culminate in positioning one or more energy delivery bodies 108 within a body lumen (intra-luminal placement) or positioning one or more energy delivery bodies 108 outside of a body lumen (extra-luminal placement). In either case, the shaft 106 of the instrument 102 is advanced from the endoscope or delivery device to its desired position. Such positioning may be achieved manually, such as with manual manipulation of the handle 110 (e.g. with one hand or two), and/or positioning may be controlled or assisted with a variety of mechanisms, such as electromechanical servo-based controls (e.g. robotics), actuated through the handle 110 or the user interface 150.

In some embodiments, the distal end 103 of the shaft 106 may be steered in one or more planes. This includes side to side movement, up and down movement or angular movement in relation to a central longitudinal axis of the shaft 106 as it exits the endoscope or delivery device. In some embodiments, the distal end 103 of the shaft 106 is able to rotate in relation to the endoscope or delivery device. As mentioned, such steering may be achieved manually or with electromechanical controls, either via the handle 110 and/or the user interface 150. Likewise, in embodiments having probes and/or probe elements, the probes/probe elements may be advanced, steered, manipulated or positioned in a similar manner, either independently or simultaneously in relation to each other and/or in relation to the shaft 106.

Steering and positioning of the shaft 106 can be assisted by a variety of design features. For example, in some embodiments, flexibility of the shaft 106 is enhanced through a series of designed cuts along its length. Such cuts may vary along the length to incur variance in flexibility, such as increased flexibility along the distal end 103 of the shaft 106. Likewise, the probe 500 itself may be enhanced for flexibility, such as having notches machined along its length to confer additional steerability or flexibility. This may be particularly the case with the use of solid probes 500.

Typically, the instrument 102 is visualized within the body during placement with the use of one or more visualization systems including but not limited to white light visualization from the endoscope, ultrasound visualization from the endoscope or external ultrasound system, fluoroscopy, cone beam computed tomography, or any other X-Ray visualization system. In some embodiments, the instrument 102 has an integrated or embedded electromagnetic (EM) sensor that provides tracking in electromagnetic fields. In other embodiments, the instrument 102 has an integrated or embedded sensing system that measures changes in shaft shape such as Fiber-Bragg Grating sensor. In other embodiments, the instrument 102 and/or applicator 108 is coated with an echogenic coating that allows for enhanced visualization in ultrasound fields. In other embodiments, the instrument 102 has surface preparation or treatments that allows for enhanced visualization in ultrasound fields. In yet other embodiments, the instrument 102 has one or more designs imprinted into its surface that allows for enhanced visualization in ultrasound fields. In still other embodiments, the instrument 102 is enhanced with integrated ultrasound. For example, in some embodiments the shaft 106 includes one or more Piezoelectric Micromachined Ultrasonic Transducers (PMUT), Capacitive Micromachined Ultrasonic Transducers (CMUT) or lead zirconate titanate (PZT)-based ultrasound transducers, such as in an array circumferentially positioned around the shaft 106. In still other embodiments, the instrument 102 is at least partially comprised of metal that is radio-opaque and visible under X-Ray, fluoroscopy, cone beam computed tomography (CBCT), and/or magnetic resonance imaging (MRI). In other embodiments, the shaft is comprised partially of fluoro-visible material such as tungsten powder or paste. In other embodiments, a combination of these sensors, coatings, surface treatments, imprints or materials to enhance visualization.

VI. Sensing

In some embodiments, one or more sensors are included in the system 100 to measure one or more system or tissue parameters. Example sensors include temperature sensors, impedance sensors, resistance sensors, surface conductance sensors, membrane potential sensors, capacitance sensors, and/or force/pressure sensors, or combinations thereof. Thus, parameters measured by sensors can include impedance, membrane potential or capacitance, and/or temperature, to name a few. Sensors can be used for (a) obtaining a baseline measure, (b) measuring a parameter during the delivery of energy, and/or (c) measuring a parameter following energy delivery, among others.

Sensor information can be used as feedback to the system 100 in order to, as non-limiting examples, determine proper deployment of energy delivery bodies 108, drive a therapeutic algorithm 152, and/or stop energy delivery for safety reasons. Sensors can also be used to sense when an adequate treatment is achieved. An algorithm 152 within the generator 104 can also use the sensed data to automatically titrate the therapeutic algorithm 152 such that the target tissue treatment is achieved. Said another way, one or more parameters and/or aspects of the therapeutic algorithm can be modified based on the sensor data in an iterative manner. For example, in some embodiments, the power and/or energy duration can be increased or decreased based on the sensor data. Thus, in some embodiments, the system 100 includes one or more sensors which may optionally provide real-time information that can be used to modify the treatment during the treatment session. It may be appreciated that in some embodiments, energy delivery bodies 108 having or functioning as electrodes may be used as sensors. These include some probes 500 and probe elements.

In some embodiments, the instrument 102 includes one or more sensors to provide force feedback to the user during positioning of the instrument 102. Example sensors include force sensor based on fiber Bragg grating (FBG). An FBG is a microstructure typically a few millimeters in length that can be photo inscribed in the core of a single mode fiber. The FBG has unique characteristics to perform as a sensor. For example, when the fiber is stretched or compressed, the FBG will measure strain. This happens because the deformation of the optical fiber leads to a change in the period of the microstructure and of the Bragg wavelength. Such force sensors may be constructed to measure force in one, two or three dimensions. It may be appreciated that other types of force sensors may be used. Such force sensors may be used to sense the curvature of the shaft 106 and/or probe 500 during delivery. Or such force sensors may be used to provide a variety of force feedback to assist in advancing or redirecting the instrument during placement of the one or more energy delivery bodies 108.

In some embodiments, the system 100 includes one or more sensors to measure tissue impedance. In some embodiments, such tissue impedance information is used to generate approximate mapping of tissue treatment areas before, during and after treatment. In other embodiments, such tissue impedance information is provided as feedback to the generator 104 during treatment. Thus, the energy delivery algorithm 152 can be modified or a different algorithm 152 can be selected based on the feedback information so as to change the energy delivered. In other embodiments, an alert is provided to the user. In either case, this may be triggered when the tissue impedance crosses a predetermined threshold, optionally for a predetermined period of time.

In some embodiments, impedance measurements can be made prior to, during or after applying energy in order to define which energy delivery algorithm 152 to apply and/or the need to apply additional energy to the target location. In some embodiments, pre-treatment impedance measurements can be used to determine the settings of various signal parameters. In other embodiments, sensors can be used to determine if the energy-delivery algorithm should be adjusted.

In some embodiments, the impedance measurement is performed as follows. A short duration, low voltage signal is delivered to the energy delivery body 108 via a generator (e.g., the generator 104) once positioned at a targeted area within a lung passageway. Based on the measured electrical current feedback received by the generator 104, the generator 104 performs a calculation using the set voltage and actual current to calculate the impedance. The calculated impedance is compared to impedance values that are considered acceptable for the measured impedance. Then, the energy delivery algorithm 152 is modified or tailored based upon the measured impedance. Parameters that can be adjusted include, but are not limited to, voltage, frequency, rest period, cycle count, dead time, packet count or number of packets, or a combination thereof. Thus, a feedback control loop can be configured to modify a parameter of energy delivery based on the measured one or more system or tissue parameters.

In some embodiments, one or more impedance sensors are used to monitor the electrical properties of the tissue. Impedance values can be regarded as an indicator of tissue state. In some embodiments, impedance is measured at different frequencies to provide an impedance spectrum. This spectrum characterizes the frequency dependent, or reactive, component of impedance. Tissue has both resistive and reactive components; these are components of complex impedance. Reactance is the frequency dependent component of impedance that includes tissue capacitance and inductance. Changes in the state of the tissue can result in changes to overall impedance as well as to changes in the resistive or reactive components of complex impedance. Measurement of complex impedance involves the conduction of a low voltage sensing signal between two electrodes. The signal can include but not be limited to a sine wave. Changes in complex impedance, including changes in resistance or reactance, can reflect the state of treated tissue and therefore be used as indicators that treatment is affecting tissue, not affecting tissue, and or that treatment can be complete. Impedance values can also change depending on the contact conditions between the sensors and airway tissue. In this way, sensors can also be used to determine the state of contact between electrodes and the tissue.

In some instances, the generator 104 instructs the user that additional energy delivery at the target location is not needed. Optionally, the generator 104 displays a specific message and/or emits a specific sound alerting the operator as to which energy delivery algorithm 154 has been selected, or that treatment is complete at that target location. Thus, the generator 104 can be configured to automatically select the appropriate algorithm for a particular measured impedance or shut off the delivery of energy signals if the treatment is determined to be completed. Further, impedance or other sensors can be used to determine that a treatment should be automatically stopped due to a safety concern.

In some embodiments, the system 100 includes one or more sensors to measure temperature. Example sensors include a temperature sensor based on fiber Bragg grating (FBG). Sensitivity to temperature is intrinsic to a fiber Bragg grating. In this case, the main contributor to Bragg wavelength change is the variation of the silica refraction index induced by the thermo-optic effect. There is also a lesser contribution from the thermal expansion which alters the period of the microstructure. It may be appreciated that other types of temperature sensors may be used. In some embodiments, potential thermal damage can be calculated based on feedback from one or more temperature sensors and aspects of the energy in use, such as waveform parameters. Thus, in some embodiments, the system 100 includes software that calculates such potential thermal damage and such information is provided as feedback to the generator 104 during treatment. Thus, the energy delivery algorithm 152 can be modified or a different algorithm 152 can be selected based on the feedback information so as to change the energy delivered. In other embodiments, an alert is provided to the user. In other embodiments, approximate local perfusion at the treatment site may be calculated based on feedback from one or more temperature sensors measuring temperature at the treatment site in combination with the core temperature of the patient (measured either by a temperature sensor of the system 100 or other mechanisms). Thus, in some embodiments, the system 100 includes software that calculates such local perfusion at the treatment site and such information is provided as feedback to the generator 104 during treatment. Thus, the energy delivery algorithm 152 can be modified or a different algorithm 152 can be selected based on the feedback information so as to change the energy delivered.

In some embodiments, one or more temperature sensors are disposed along the surface of one or more energy delivery bodies 108 so as to contact the tissue and ensure that the tissue is not being heated above a pre-defined safety threshold. Thus, the one or more temperature sensors can be used to monitor the temperature of the tissue during treatment. In one embodiment, temperature changes that meet pre-specified criterion, such as temperature increases above a threshold (e.g., 40° C., 45° C., 50° C., 60° C., 65° C.) value, can result in changes to energy delivery parameters (e.g. modifying the algorithm) in an effort to lower the measured temperature or reduce the temperature to below the pre-set threshold. Adjustments can include but not be limited to increasing the rest period or dead time, or decreasing the packet count. Such adjustments occur in a predefined step-wise approach, as a percentage of the parameter, or by other methods.

In other embodiments, one or more temperature sensors monitor the temperature of the tissue and/or electrode, and if a pre-defined threshold temperature is exceeded (e.g., 65° C.), the generator 104 alters the algorithm to automatically cease energy delivery. For example, if the safety threshold is set at 65° C. and the generator 104 receives the feedback from the one or more temperature sensors that the temperature safety threshold is being exceeded, the treatment can be stopped automatically.

In some embodiments, the system 100 includes one or more sensors to measure pH. In some embodiments, such pH information is used to provide information about the microenvironment of the target treatment area, such as before, during and after treatment. When utilized during treatment, the pH information can be provided as feedback to the generator 104 so that the energy delivery algorithm 152 can be modified or a different algorithm 152 can be selected based on the feedback information. In other embodiments, an alert is provided to the user. Thus, energy delivered can be changed in real time. In either case, this may be triggered when the information crosses a predetermined threshold, optionally for a predetermined period of time.

It may be appreciated that the sensors may be located in various locations throughout the system 100. For example, one or more sensors may be attached to or embedded in the shaft 106 of the instrument 102. Additionally or alternatively, one or more sensors may be attached or embedded in the probe 500 or various probe elements. Likewise, if other accessories are utilized, one or more sensors may be located on the accessory and communicated to the system 100.

VII. Alternative Delivery Approaches

As mentioned previously, in most embodiments, access is minimally invasive and relies on endoluminal approaches. However, it may be appreciated that other approaches, such as percutaneous, laparoscopic or open surgical approaches, may be used in some situations.

In some embodiments, when accessing percutaneously, the shaft 106 of the instrument 102 is passed through a delivery device that penetrates the skin layer into the underlying tissue. In some embodiments, the delivery device comprises a needle that is inserted through the skin and directed toward the target tissue. The shaft 106 is then advanced through the needle. In some embodiments, the probe tip 502 is shaped to assist in penetrating tissue, such as a pointed shape. Thus, the shaft 106 may be advanced through tissue to the desired location therein. Once desirably positioned, energy is delivered through the probe tip 502 to treat the target tissue. It may be appreciated that the probe tip 502 may also be advanced from the shaft 106 into the tissue and/or a conductive element 560 may be advanced into the tissue wherein the energy is delivered from the conductive element 560.

In other embodiments, when accessing percutaneously, the shaft 106 of the instrument 102 is rigid so as to be able to penetrate the skin layer without the use of a delivery device. In such embodiments, the probe tip 502 is typically shaped to assist in penetrating tissue, such as a pointed shape. Thus, the shaft 106 itself is advanced into the tissue to the desired location therein. Once desirably, positioned, energy is delivered through the probe tip 502 to treat the target tissue. It may be appreciated that the probe tip 502 may also be advanced from the shaft 106 into the tissue and/or a conductive element 560 may be advanced into the tissue wherein the energy is delivered from the conductive element 560.

In laparoscopic approaches, the shaft 106 of the instrument 102 is passed through a laparoscope which has been inserted through a small incision. These small incisions provide reduced pain, reduced hemorrhaging and shorter recovery time in comparison to open surgery. In some embodiments, the probe tip 502 is shaped to assist in penetrating tissue, such as a pointed shape. Thus, the shaft 106 may be advanced through tissue to the desired location therein. Once desirably positioned, energy is delivered through the probe tip 502 to treat the target tissue.

In open surgical approaches, the shaft 106 of the instrument 102 may also be passed through a delivery device or the instrument 102 may penetrate the tissue directly. In either case, once desirably positioned, energy is delivered through the probe tip 502 to treat the target tissue.

VIII. Cardiac Synchronization

Figure 28:
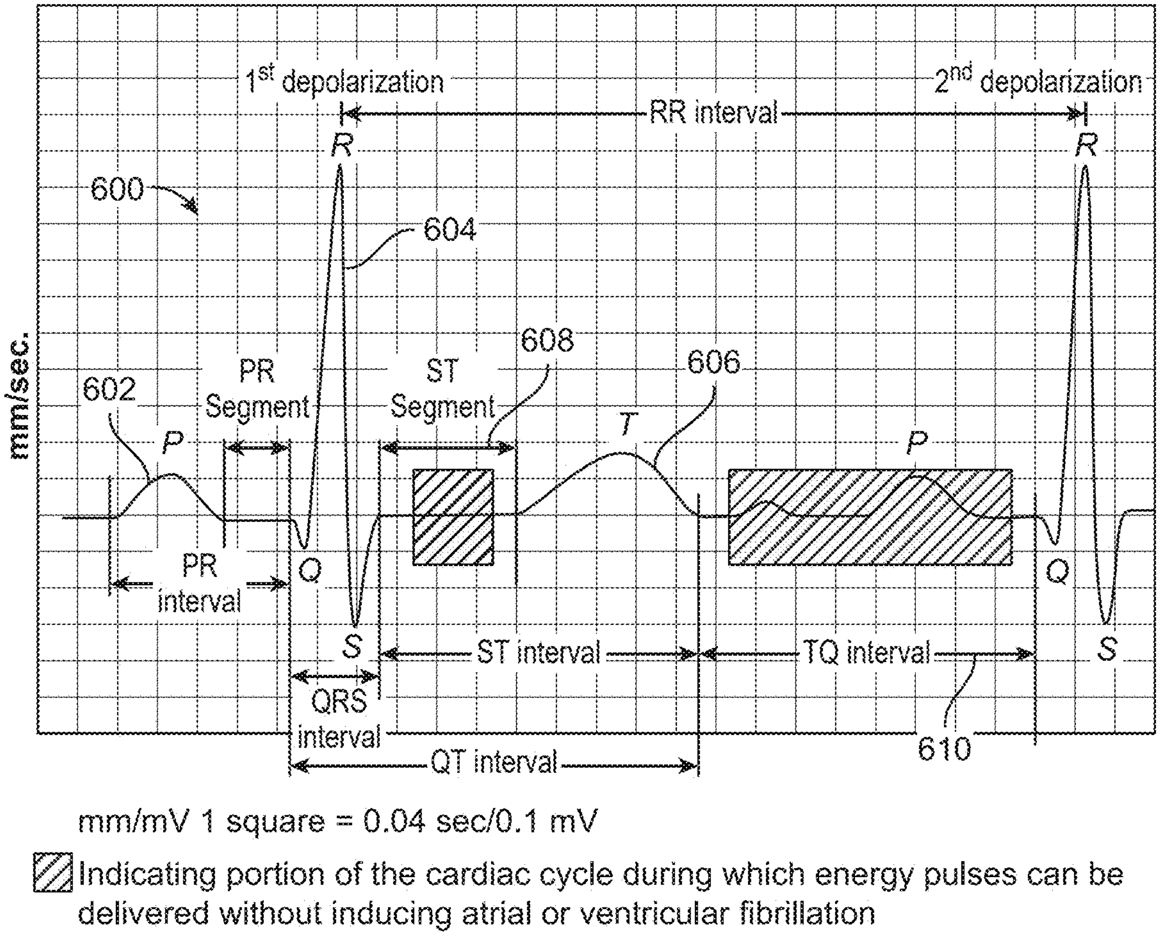
FIG. 28 is a graph illustrating portions of a sample electrocardiogram (ECG) trace of a human heart highlighting periods wherein it is desired to deliver energy pulses to the lung passageway via the energy delivery body.

In some embodiments, the energy signal is synchronized with the patient's cardiac cycle to prevent induction of cardiac arrhythmias. Thus, the patient's cardiac cycle is typically monitored with the use of an electrocardiogram (ECG). Referring to FIG. 28, a typical ECG trace 600 includes a repeating cycle of a P wave 602 representing atrial depolarization, a QRS complex 604 representing ventricular depolarization and atrial repolarization, and a T wave 606 representing ventricular repolarization. To safely deliver energy within the airway in close proximity to the heart, synchronization between energy delivery and the patient's cardiac cycle is employed to reduce the risk of cardiac arrhythmia. High voltage energy can trigger a premature action potential within the cardiac muscle as the delivered energy increases the cardiac muscle cell membrane permeability allowing ion transport, which can induce cardiac arrhythmias, especially ventricular fibrillation. To avoid cardiac arrhythmias, the electrical energy is delivered to the airway in a fashion that is outside the "vulnerable period" of the cardiac muscle. Within one cardiac cycle (heartbeat), the vulnerable period of the ventricular muscle is denoted on an ECG by the entire T wave 606. Typically, for ventricular myocardium, the vulnerable period coincides with the middle and terminal phases of the T wave 606. However, when high energy pulses are delivered in close proximity to the ventricle, the vulnerable period can occur several milliseconds earlier in the heartbeat. Therefore, the entire T wave can be considered to be within the vulnerable period of the ventricles.

The remaining parts of a cardiac cycle are the P wave 602 and the QRS complex 604, which both include periods when atrial or ventricular muscle is refractory to high voltage energy stimuli. If high voltage energy pulses are delivered during the muscle's refractory period, arrhythmogenic potential can be minimized. The ST segment 608 (interval between ventricular depolarization and repolarization) of the first cardiac cycle and the TQ interval 610 (interval including the end of the first cardiac cycle and the mid-point of the second cardiac cycle) are the periods where high voltage energy can be delivered without induction of cardiac arrhythmia due to the cardiac muscle depolarized state (refractory period). FIG. 28 includes shaded boxes that indicate example portions of the cardiac cycle during which energy can be applied safely.

It may be appreciated that in some embodiments, components for acquiring the electrocardiogram 170 are integrally formed as part of the generator 104. If the cardiac monitor is limited to acquiring up to a 5-lead ECG, and it may be beneficial to incorporate additional leads into the system. This would further eliminate the need to use the communications port 167 to receive cardiac sync pulses. Rather, the processor 154 can be configured to detect the R-waves directly and to assess the integrity of the entire QRS complex.

IX. Imaging

Methods associated with imaging that can be useful include: (a) detecting diseased target tissue, (b) identifying areas to be treated, (c) assessing areas treated to determine how effective the energy delivery was, (d) assessing target areas to determine if areas were missed or insufficiently treated, (e) using pre- or intra-procedural imaging to measure a target treatment depth and using that depth to choose a specific energy delivery algorithm to achieve tissue effects to that depth, (f) using pre or intra-procedural imaging to identify a target cell type or cellular interface and using that location or depth to choose a specific energy delivery algorithm to achieve tissue effects to that target cell type or cellular interface, and/or (g) using pre-, intra-, or post-procedural imaging to identify the presence or absence of a pathogen with or without the presence of inflamed tissue.

In some embodiments, confocal laser endomicroscopy (CLE), optical coherence tomography (OCT), ultrasound, static or dynamic CT imaging, X-ray, magnetic resonance imaging (MRI), and/or other imaging modalities can be used, either as a separate apparatus/system, or incorporated/integrated (functionally and/or structurally) into the treatment system 100 by either incorporating into the instrument 102 or a separate device. The imaging modality (or modalities) can be used to locate and/or access various sections of target tissue. In some embodiments, the targeted depth of treatment can be measured and used to select a treatment algorithm 152 sufficient to treat to the targeted depth. At least one energy delivery body can then be deployed at the target tissue site and energy delivered to affect the target tissue. The imaging modality (or modalities) can be used before, during, between, and/or after treatments to determine where treatments have or have not been delivered or whether the energy adequately affected the airway wall. If it is determined that an area was missed or that an area was not adequately affected, the energy delivery can be repeated followed by imaging modality (or modalities) until adequate treatment is achieved. Further, the imaging information can be utilized to determine if specific cell types and or a desired depth of therapy was applied. This can allow for customization of the energy delivery algorithm for treating a wide variety of patient anatomies.

In some embodiments, access via a body lumen is visualized with one or more appliances inserted into the body. Likewise, in some embodiments, one or more of a variety of imaging modalities (e.g., CLE, OCT) are used either along with direct visualization, or instead of direct visualization. As an example, a bronchoscope can be delivered via the mouth to allow for direct visualization and delivery of the instrument 102, while an alternate imaging modality can be delivered via another working channel of the bronchoscope, via the nose, or adjacent to the bronchoscope via the mouth. In some embodiments, the imaging modality (e.g., direct visualization, CLE, and/or OCT) is incorporated into the instrument 102 with appropriate mechanisms to connect the imaging modality to either the system generator 104 or commercially available consoles.

X. Treatments

As mentioned previously, the devices, systems and methods described herein are provided to treat damaged, diseased, abnormal, obstructive, cancerous or undesired tissue by delivering specialized pulsed electric field (PEF) energy to target tissue areas. Such therapies may be used on their own wherein the undesired cells are destroyed, eliminated, killed, removed, etc., while maintaining non-cellular elements, such as collagen, elastin, and matrix proteins. These non-cellular elements maintain the structure of the tissue allowing for and encouraging normative cellular regeneration. Therefore, the integrity and mechanical properties of the tissue, and any nearby luminal structures, are maintained while abnormal or diseased cells and tissues are sufficiently eliminated. In such instances, the therapy may resolve the issue in a single treatment or may involve follow up treatments.

Figure 29:
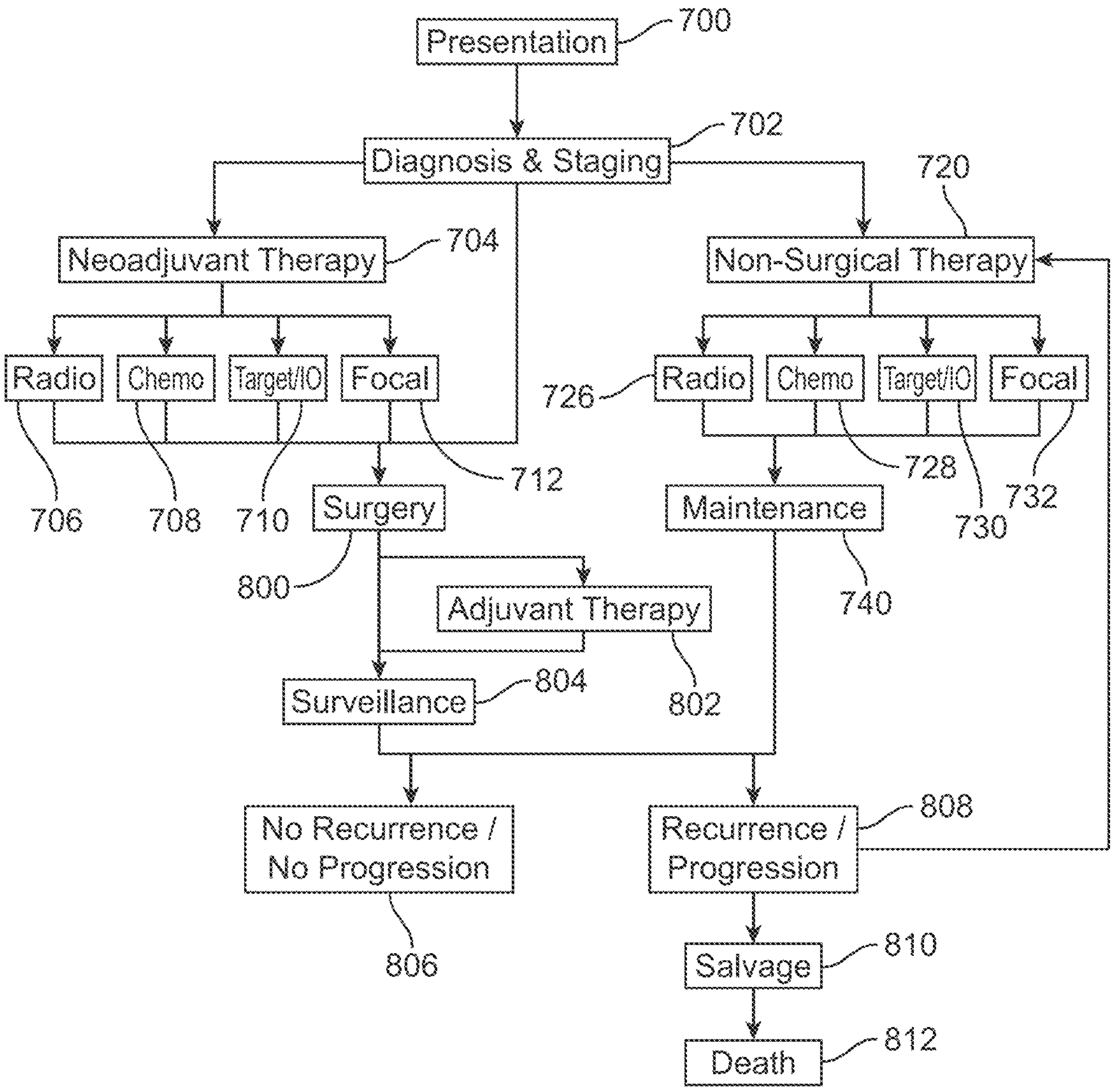
FIG. 29 provides a flowchart of example care path options for a cancer patient.

However, in some instances, the medical issue involves a variety of treatment options, of which the treatments provided by the systems 100 described herein are utilized in combination with other treatments. This may be particularly the case when treating cancer. FIG. 29 provides a flowchart of example care path options for a cancer patient. Cancer is typically discovered either through related symptoms or through unrelated testing wherein cancer is identified (step 700). Once discovered, a diagnosis is made as to the type of cancer and its stage (step 702). Stage refers to the extent of the cancer, such as how large the tumor is, and if it has spread. When the cancer is described by the TNM system, numbers are provided after each letter that give more details about the cancer—for example, T1N0MX or T3N1M0. The following table explains the meaning of the letters and numbers:

| T (primary tumor) | |
|---|---|
| T0 | No primary tumor |
| Tis | Carcinoma in situ (squamous or adenocarcinoma) |
| T1 | Tumor ≤3 cm |
| T1mi | Minimally invasive adenocarcinoma |
| T1a | Superficial spreading tumor in central airways* |
| T1a | Tumor ≤1 cm |
| T1b | Minor >1 but ≤2 cm |
| T1c | Tumor >2 but ≤3 cm |
| T2 | Tumor >3 but ≤5 cm or tumor involving: visceral pleura†, main bronchus (not carina), atelectasis to hilum† |
| T2a | Tumor >3 but ≤4 cm |
| T2b | Tumor >4 but ≤5 cm |
| T3 | Tumor >5 but ≤7 cm or invading chest wall. pericardium. phrenic nerve; or separate tumor nodule(s) in the same lobe |
| T4 | Tumor >7 cm or tumor invading: mediastinum. diaphragm, heart, great vessels, recurrent laryngeal nerve, carina, trachea, esophagus, spine; or tumor nodule(s) in a different ipsilateral lobe |
| N (regional lymph nodes) | |
| N0 | No regional node metastasis |
| N1 | Metastasis in ipsilateral pulmonary or hilar nodes |
| N2 | Metastasis in ipsilateral mediastinal or subcarinal nodes |
| N3 | Metastasis in contralateral mediastinal, hilar, or supraclavicular nodes |
| M (distant metastasis) | |
| M0 | No distant metastasis |
| M1a | Malignant pleural or pericardial effusion‡ or pleural or pericardial nodules or separate tumor nodule(s) in a contralateral lobe |
| M1b | Single extrathoracic metastasis |
| M1c | Multiple extrathoracic metastases (1 or >1 organ) |

*Superficial spreading tumor of any size but confirmed to the tracheal or bronchial wall.
†Atelectasis or obstructive pneumonitis extending to hilum; such tumors are classified as T2a if >3 and ≤4 cm, T2b if >3 and ≤5 cm.
‡Pleural effusions are excluded that are cytologically negative, nonbloody, transudative, and clinically judged not to be due to cancer.

The diagnosis and staging are used to plan the best treatment option for the patient. Typically, there are two main pathways of treatment for cancer patients, surgical treatments (left branch of flowchart) and non-surgical treatments (right branch of flowchart).

Surgery (step 800) can be utilized alone as a treatment option. However, it is often provided as a primary treatment in conjunction with neoadjuvant therapy (step 704) and/or adjuvant therapy (step 802). Neoadjuvant therapies are delivered before the primary treatment, to help reduce the size of a tumor or kill cancer cells that have spread. Adjuvant therapies are delivered after the primary treatment, to destroy remaining cancer cells. Neoadjuvant and adjuvant therapies benefit many, but not all, cancer patients. The type and stage of a patient's cancer often dictate whether he or she is a candidate for additional treatment. For example, if surgery determines that cancer is found in a large number of lymph nodes, the risk rises that cancer cells may be left behind and adjuvant therapy may help. Also, because certain cancers result from specific mutations that carry a high risk of recurrence, adjuvant therapy may benefit patients with these cancers more than those with cancers that have a lower recurrence risk. In some cases, neoadjuvant therapy may be more helpful than adjuvant therapy. For example, if neoadjuvant therapy is given before surgery, the physician can assess the response to see if the tumor is indeed shrinking. The treatment can then be adjusted accordingly, which may mean fewer treatments. Neoadjuvant therapy may also serve as a tool for determining the patient's response to treatment. If the tumor responds to the neoadjuvant therapy before surgery, it is known that the patient is more than likely to do well. Many times, both neoadjuvant and adjuvant therapies may be prescribed.

FIG. 29 illustrates a variety of different types of neoadjuvant therapies: radiotherapies (step 706), chemotherapy (step 708), targeted therapy/immunotherapy (step 710), and focal therapy (step 720). Example focal therapies include microwave ablation, radiofrequency ablation, cryoablation, high intensity focused ultrasound (HIFU), and pulsed electric field ablation, such as described herein.

Radiation therapy or radiotherapy (step 706), often abbreviated RT, RTx, XRT, or SBRT (also known as CyberKnife), is a therapy using ionizing radiation that is normally delivered by a linear accelerator. Radiation therapy is commonly applied to cancerous tumors because of its ability to control cell growth. Ionizing radiation works by damaging the DNA of cancerous tissue leading to cellular death. To spare normal tissues (such as skin or organs which radiation must pass through to treat the tumor), shaped radiation beams are aimed from several angles of exposure to intersect at the tumor, providing a much larger absorbed dose there than in the surrounding, healthy tissue.

It may be appreciated that since radiotherapy relies on damaging DNA to kill cells, the cells do not die immediately. Over time, the damage leads to cell death, leaving scarred tissue behind. In some instances, pulsed electric field ablation provided by the systems 100 described herein, are used in conjunction with radiotherapy to provide improved outcomes. For example, in some instances, the target tissue is treated with PEF energy provided by the systems 100 described herein, before, during and/or after radiotherapy. Such treatment disrupts cellular homeostasis, which can initiate an apoptotic-like effect which leads to permanent cell death or priming of the cells for more effective damage by the radiotherapy. Since cell death is delayed in radiotherapy, application of PEF energy after radiotherapy can also increase cell death rate. Thus, such combinatory treatment can lead to more effective treatment and better outcomes.

Chemotherapy (step 708) is typically a systemic therapy that is introduced into the bloodstream, so it is, in principle, able to address cancer at any anatomic location in the body. Traditional chemotherapeutic agents are cytotoxic by means of interfering with cell division but cancer cells vary widely in their susceptibility to these agents. To a large extent, chemotherapy can be thought of as a way to damage or stress cells, which may then lead to cell death if apoptosis is initiated. Many of the side effects of chemotherapy can be traced to damage to normal cells that divide rapidly and are thus sensitive to anti-mitotic drugs, particularly cells in the bone marrow, digestive tract and hair follicles. Chemotherapy may also be administered locally to the tumor tissue.

In some instances, pulsed electric field ablation provided by the systems 100 described herein, are used in conjunction with chemotherapy to provide improved outcomes. For example, in some instances, the target tissue is treated with PEF energy provided by the systems 100 described herein, before, during and/or after chemotherapy. Such treatment disrupts cellular homeostasis, which can initiate an apoptotic-like effect which leads to permanent cell death or priming of the cells for more effective damage by the chemotherapy. Such priming provides a synergy between the PEF treatment and the chemotherapy leading to outcomes that exceed either treatment alone. Thus, such combinatory treatment can lead to more effective treatment and greatly improved responses.

Targeted therapies/immunotherapy (step 710) are types of targeted cancer therapies. Targeted therapies are drugs or other substances that block the growth and spread of cancer by interfering with specific molecules or molecular targets that are involved in the growth, progression, and spread of cancer. Targeted therapies differ from standard chemotherapy in several ways. For example, targeted therapies act on specific molecular targets that are associated with cancer, whereas most standard chemotherapies act on all rapidly dividing normal and cancerous cells. Targeted therapies are deliberately chosen or designed to interact with their target, whereas many standard chemotherapies were identified because they kill cells. Targeted therapies are often cytostatic (i.e. block tumor cell proliferation), whereas standard chemotherapy agents are cytotoxic (i.e. kill tumor cells). Targeted therapies are a cornerstone of precision medicine, a form of medicine that uses information about a person's genes and proteins to prevent, diagnose, and treat disease.

Immunotherapy is a type of biological therapy. Biological therapy is a treatment that uses substances made from living organisms to treat cancer. Several types of immunotherapy are used to treat cancer. One example is immune checkpoint inhibitors. Checkpoints are a normal part of the immune system and keep immune responses from being too strong. Therefore, by blocking or inhibiting them, these drugs allow immune cells to respond more strongly to cancer. In T-cell transfer therapy, immune cells are taken from the tumor. Those that are most active against the cancer are selected or modified to better attack the cancer cells, grown in large batches, and put back into the patient intravenously. This treatment boosts the natural ability of the T cells to fight cancer. In this treatment, immune cells are taken from your tumor. In another immunotherapy, monoclonal antibodies designed to bind to specific targets on cancer cells. Some monoclonal antibodies mark cancer cells so that they will be better seen and destroyed by the immune system. Monoclonal antibodies may also be called therapeutic antibodies. Further, immune system modulators have been developed that enhance the body's immune response against cancer. Some of these agents affect specific parts of the immune system, whereas others affect the immune system in a more general way.

In some instances, pulsed electric field ablation provided by the systems 100 described herein, are used in conjunction with targeted therapies and immunotherapies to provide improved outcomes. For example, in some instances, the target tissue is treated with PEF energy provided by the systems 100 described herein, before or during these therapies. When the PEF energy causes cell death, the cell membranes are ruptured and the internal cellular components are released. This exposes the DNA and other cellular components so as to be more easily identified by the immune system, targeted therapies and immunotherapies. Thus, such combinatory treatment can lead to more effective treatment and better outcomes.

Focal therapies (step 712) have also been used as neoadjuvant therapies. Focal therapies rely largely on local delivery of energy to kill cells. As mentioned, example focal therapies include radiofrequency ablation (RFA), microwave ablation (MWA), High-Intensity Focused Ultrasound (HIFU), cryoablation, and pulsed electric field ablation, such as described herein. MWA, RFA and HIFU are conventional therapies that rely on thermal energy. RFA and MWA are treatments that use image guidance to place a needle through the skin into a tumor, such as within the chest to treat lung cancer. In RFA, high-frequency electrical currents are passed through an electrode, creating a small region of heat. In MWA, microwaves are created from the needle to create a small region of heat. HIFU uses an ultrasound transducer, similar to the ones used for diagnostic imaging, but with much higher energy. The transducer focuses sound waves to generate heat at a single point within the body and destroy the target tissue. The tissue can raise to 150° F. in just 20 seconds. This process is repeated as many times as is necessary until the target tissue is destroyed. HIFU can also be operated in a non-thermal manner.

In each case, heat is intended to destroy the cancer cells. It is known that thermal energy destroys not only the cells but the collagen support structure by coagulation necrosis. Therefore, thermal energy cannot be used near sensitive or critical structures, such as body lumens. Likewise, thermal energy is limited in its range, effectiveness and ability to be repeated. For example, once tissue has been thermally ablated it is difficult or undesired to overlap or re-treat the tissue because the tissue has become necrosed and difficult to penetrate. For all of these reasons, pulsed electric field ablation provided by the systems 100 described herein, may be used in conjunction with RFA, MWA and HIFU therapies to treat tissue areas that are inaccessible or contraindicated for thermal treatments and/or to improve the effectiveness of these conventional therapies. Thus, in some instances, tissue is treated with PEF energy provided by the systems 100 described herein, before, during or after these conventional thermal therapies.

Other focal therapies do not rely on heat to kill cancer cells. For example, cryoablation utilizes extreme cold temperatures to kill cancer cells. During cryoablation, a thin needle (cryoprobe) is inserted through the skin and directly into the cancerous tumor. A gas is pumped into the cryoprobe in order to freeze the tissue. Then the tissue is allowed to thaw. The freezing and thawing process is repeated several times during the same treatment session. The intracellular and/or extracellular ice crystals formed in the process cause the cells to rupture. Like thermal energy, cryotherapy has limitations. To begin, the size of the lesions are restricted and the treatment times are extended. Further, the therapy is limited in locations to which it can be applied. For example, some locations cannot be reached with current technologies, such as the lymph nodes. Likewise, although luminal structures are preserved, cryotherapy is not suitable for use near many luminal structures due to interference with the cooling process which leaves the therapy ineffective. For all of these reasons, pulsed electric field ablation provided by the systems 100 described herein, may be used in conjunction with cryotherapy to treat tissue areas that are inaccessible or contraindicated treatments and/or to improve the effectiveness of these conventional therapies.

Likewise, non-thermal energy has been used to treat tumors by mechanisms other than heating. In particular, irreversible electroporation (IRE) has been used for the treatment of cancerous tumors. Percutaneous IRE is performed with a system called NanoKnife® that utilizes probes inserted through the skin to deliver energy to tumor cells. The technique uses a non-thermal energy to create permanent nanopores in the cell membrane. After delivering a sufficient number of high voltage pulses, the cells within the electrical field will be irreversibly damaged and die. Like other such therapies, percutaneous IRE has limitations. As in other cases, the therapy is limited in locations to which it can be applied. Some locations cannot be reached with a percutaneous approach or are suitable for treatment with the NanoKnife®. Thus, pulsed electric field ablation provided by the systems 100 described herein, may be used in conjunction with other non-thermal treatments to treat tissue areas that are inaccessible or contraindicated for such treatments and/or to improve the effectiveness of these therapies.

It may be appreciated that pulsed electric field ablation provided by the systems 100 described herein may be used alone as a non-adjuvant therapy. Such PEF ablation may cause sufficient tissue destruction and cellular death so as to render the cancer treated and the patient cured. In addition, immune system priming due to the presence of highly antigenetic tumor cellular components resulting from the deposition of such PEF energy in the targeted tissue could induce the abscopal effect. The abscopal effect is a theory regarding the use of a local treatment in one area that results in cancer shrinking in an untreated area. This is particularly beneficial when treating metastatic cancers. When the PEF energy causes cell death, the cell membranes are ruptured and the internal cellular components are released. This exposes the DNA and other cellular components so as to be more easily identified by the immune system. These components are carried to the lymph system which also assists in identification. Thus, the treatment acts as a vaccine in some regard, generating a systemic immune response.

Likewise, it may be appreciated that any of the neoadjuvant therapies may be used in any combination, including combinations of more than two therapies.

Referring again to FIG. 29, once neoadjuvant therapy has been provided, surgery (step 800) is provided for those on the surgical care path. It may be appreciated that some patients will receive surgery (step 800) directly after diagnosis and staging (step 702), skipping neoadjuvant therapy altogether. After surgery, some patients may be considered cured and will undergo surveillance (step 804) to monitor the patient for signs of cancer recurrence. Other patients will undergo adjuvant therapy (step 802) to destroy any remaining cancer cells. Adjuvant therapy may comprise any of the treatments described herein above in relation to neoadjuvant therapy, such as radiotherapies, chemotherapy, targeted therapy/immunotherapy, either alone or in combination with pulsed electric field ablation provided by the systems 100 described herein. Likewise, adjuvant therapy may comprise any of the treatments described herein above in relation to focal therapy, such as radiofrequency ablation (RFA), microwave ablation (MWA), High-Intensity Focused Ultrasound (HIFU), cryoablation, pulsed electric field ablation provided by the systems 100 described herein and other pulsed electric field ablations, or any combination of these. It may be appreciated that any of the adjuvant therapies may be used in any combination, including combinations of more than two therapies. After adjuvant therapies, patients will undergo surveillance (step 804) to monitor the patient for signs of cancer recurrence. Some patients will not have a recurrence and will be considered cured (step 806).

Unfortunately, some patients will have cancer recurrence (step 808). Typically, these patients will be treated with non-surgical therapy options. Referring to FIG. 29, non-surgical therapy (step 720) is offered as a first line of therapy for patients unsuited or contraindicated to surgery or for patients who have a cancer recurrence. As illustrated in the flowchart, non-surgical therapy may comprise any of the treatments described herein above in relation to neoadjuvant therapy, such as radiotherapies (step 726), chemotherapy (step 728), targeted therapy/immunotherapy (step 730), either alone or in combination with pulsed electric field ablation provided by the systems 100 described herein. Likewise, non-surgical therapy may comprise any of the treatments described herein above in relation to focal therapy (step 732), such as radiofrequency ablation (RFA), microwave ablation (MWA), High-Intensity Focused Ultrasound (HIFU), cryoablation, pulsed electric field ablation provided by the systems 100 described herein and other pulsed electric field ablations, or any combination of these. It may be appreciated that any of the non-surgical therapies may be used in any combination, including combinations of more than two therapies. After such therapy, the patient will typically undergo maintenance procedures (step 740) to keep the cancer at bay.

A portion of these patients will have no recurrence or progression and will ultimately be considered cured (step 806). Those with recurrence may have additional non-surgical therapies. Others will be given salvage therapy (step 810), treatments that are given after the cancer has not responded to other treatments. And, ultimately some patients will succumb to the cancer (step 812).

It may be appreciated the pulsed electric field ablation treatments provided by the systems 100 described herein, either alone or optionally in combination with other therapies, provides additional benefits beyond the immediate success of the therapy. For example, in some instances, the PEF ablation treatments provided by the systems 100 induce an abscopal effect. The abscopal effect is a theory regarding the use of a local treatment in one area that results in cancer shrinking in an untreated area. This is particularly beneficial when treating metastatic cancers. When the PEF energy causes cell death, the cell membranes are ruptured and the internal cellular components are released. This exposes the DNA and other cellular components so as to be more easily identified by the immune system. These components are carried to the lymph system which also assists in identification. Thus, the treatment acts as a vaccine in some regard, generating a systemic immune response. This may be further accentuated when utilizing targeted therapies and immunotherapies.

XI. Combined Therapy

Devices, systems and methods are provided to treat damaged, diseased, abnormal, obstructive, cancerous or undesired tissue (e.g. a tumor, a benign tumor, a malignant tumor, a cyst, or an area of diseased tissue, etc) by delivering specialized pulsed electric field (PEF) energy to target tissue areas in combination with one or more agents. In some embodiments, such agents comprise tyrosine kinase inhibitors (TKIs). Although some patients may be receiving a traditional treatment plan of tyrosine kinase inhibitors alone, combination with the PEF energy does not diminish the effects of the traditional treatment plan. To the contrary, such combination can provide improved outcomes by sensitizing the tissue to immunotherapy. Such tissue typically does not respond well to immunotherapy, however treatment with PEF causes the tissue to have improved results. Thus, patients can receive PEF energy in addition to traditional therapy with TKIs, to prevent or delay resistance to TKIs or to provide further treatment once the tissue has developed resistance to TKIs under traditional therapy. Therefore, patients suffering from cancers characterized by abnormal activation of tyrosine kinases can receive improved treatment with more successful outcomes.

Particular types of cancers characterized by abnormal activation of tyrosine kinases include non-small cell lung cancer, gastrointestinal stromal tumors (a type of tumor that grows in the wall of the stomach and the intestine), mastocytosis (a disorder characterized by mast cell proliferation and accumulation within various organs, most commonly the skin), renal cell carcinoma (cancer that begins in the cells of the kidneys), mantle cell lymphoma (fast-growing cancer that begins in the cells of the immune system), chronic lymphocytic leukemia (a type of cancer that begins in the white blood cells), and small lymphocytic lymphoma (a cancer of the immune system), hepatocellular carcinoma, and thyroid cancer, to name a few.

The PEF energy and delivery has been optimized to provide advanced treatment of target tissue areas, including destruction of undesired tissue and generation of improved inflammatory and immune responses. These various types of treatment are controlled by a variety of factors including the electrode geometry, the dose of PEF energy delivered, the time the energy is delivered over, and the waveform of the PEF energy itself. The PEF energy is delivered in the form a dose which is considered to be one application of the specialized energy. Each dose creates a lesion in the target tissue area. In some embodiments, the desired outcome is achieved with the delivery of a single dose. This achievement reduces treatment time and reduces any complications which may arise by providing additional doses, such as related to repositioning of the energy delivery device or retreatment of the same tissue area. The specific parameter values which define the waveform of the energy cause the waveform to be configured to deliver the desired effects with one dose. It may be appreciated that additional doses may be delivered to the target tissue if desired or the energy may be delivered to additional target tissues that may or may not include the original target tissue.

The devices, systems and methods described herein utilize a specific dose of specialized PEF energy to generate lesions having various zones, wherein manipulation of the zones provides benefits which culminate in a more comprehensive and therefore successful treatment of the patient, particularly when treating cancer and other diseases. The zones emanate from the delivery electrode radially outwardly, such as in rings. Each zone has differing cellular effects and therefore differing effects on the overall outcome of the treatment. In some instances, the zones include a cavitation zone, a thermal zone, a PEF zone, an inflammatory zone and an immune response zone.

Figure 30A:
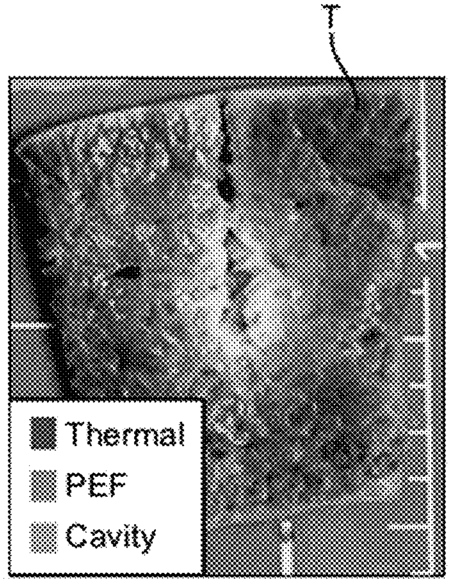
FIGS. 30A-30B illustrate tissue lesions resulting from a study focusing on the effects of the addition of inter-cycle and inter-packet delays within the energy waveform on the local tissue characteristics.
Figure 30B:
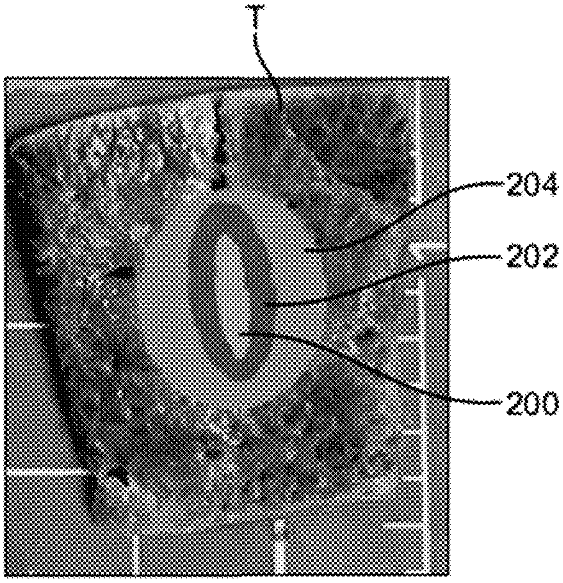

FIG. 30A illustrates an actual tissue lesion in tissue T created by delivering specialized energy to a porcine liver kept viable using a machine perfused organ preservation model. FIG. 30B illustrates the lesion demarcated with zones for clarity. The energy waveform generated a very small cavitation zone 200 (in this example, likely not an actual cavity but a needle tract from positioning the energy delivery body (needle) therein, however a cavitation zone 200 would typically be located here), a thermal zone 202, and a PEF zone 204. It may be appreciated that an inflammatory zone and/or immune response zone would be located around the PEF zone, thus following the edge of the PEF zone. The presence and size of the zones may be manipulated by the waveform, particularly the parameter values. It may be appreciated that in these examples a lesion is generated by a single dose or a single application of energy. The on-time of energy and its application during this dose is dependent on the waveform, more particularly the waveform parameters.

Typically, the zones are manipulated to eliminate or reduce the cavitation zone, eliminate or reduce the thermal zone and maximize the PEF zone along with a potential inflammatory zone and immune response zone. The size or amount of the zones are particularly generated so that their combination elicits an increase in the adaptive immune response of the patient, such as by promoting a cascade of increased recruitment for Tregs, CD4, CD8, and other adaptive immune cell types. These lesion classifications (i.e. zones) can be measured grossly, but also monitored in real-time based on the tissue properties (i.e. tissue density, impedance change, etc.) and perhaps most importantly, via imaging modalities such as CT, etc.

The PEF energy is deliverable with a variety of different TKIs that act on the following: epidermal growth factor receptor (EGFR), anaplastic lymphoma kinase (ALK) gene, ROS1 fusion protein, human epidermal growth factor receptor (HER2), neurotrophic tyrosine receptor kinase (NTRK) gene, vascular endothelial growth factor receptor (VEGFR), rearranged during transfection receptor (RET), mesenchymal-epithelial transition factor (MET), mitogen-activated protein kinase (MEK), fibroblast growth factor receptors (FGFR), platelet-derived growth factor receptor alpha (PDGFR), and proto-oncogene c-KIT (KIT), to name a few. TKIs that have been approved by the FDA for the treatment of various cancers include imatinib, dasatinib, nilotinib, ponatinib, sunitinib, pazopanib, cabozantinib, and larotrectinib, all of which are deliverable with PEF energy per the methods and devices described here. TKIs are typically superior to traditional chemotherapy in selectivity, efficacy, and safety by acting on specific targets involved in proliferation and differentiation of cancer cells with minimal activity on normal cells.

In some embodiments, PEF energy is delivered with a TKI that is an EGFR inhibitor. EGFR inhibitors are a type of targeted therapy that block the activity of the epidermal growth factor receptor (EGFR), a protein that plays a key role in cell growth and division. EGFR is overexpressed or mutated in certain types of cancer, such as non-small cell lung cancer (NSCLC), and these inhibitors can be used to treat these cancers. EGFR inhibitors, a subclass of tyrosin kinase inhibitors (TKIs), are small molecules that can penetrate the cell membrane and target the intracellular domain of the EGFR protein. They work by inhibiting the enzymatic activity of the EGFR tyrosine kinase, thereby blocking downstream signaling pathways that promote cancer cell growth and division. Examples of EGFR TKIs include gefitinib, erlotinib, afatinib, osimertinib, and dacomitinib.

In other embodiments, PEF energy is delivered with a KI (kinase inhibitor) for KRAS, Kirsten rat sarcoma viral oncogene homolog. It is one of a group of genes involved in a pathway called the epidermal growth factor receptor (EGFR) pathway. This complex signaling pathway involves numerous components that relay signals from outside of the cell to within the cell to help regulate cell growth, division, survival and death. KRAS mutations are present in approximately 25% of NSCLC cases and are more common in current or former smokers with adenocarcinoma histology.

In other embodiments, PEF energy is delivered with a KI for BRAF. BRAF is a human gene that encodes a protein called B-Raf. The gene is also referred to as proto-oncogene B-Raf and v-Raf murine sarcoma viral oncogene homolog B, while the protein is more formally known as serine/threonine-protein kinase B-Raf. BRAF is found mutated in 5-10% of all cancers and few drugs have been recently approved for the V600E/V600K mutation.

It may be appreciated that specialized PEF energy may be delivered with a variety of different types of KIs, alone or in combination with other agents, such as chemotherapeutic and/or immunotherapeutic agents, or other non-surgical therapies, such as neoadjuvant and adjuvant therapies such as radiotherapy, chemotherapy, targeted therapy/immunotherapy, focal therapy, gene therapy, plasmid therapy, to name a few. Example focal therapies include microwave ablation, radiofrequency ablation, cryoablation, high intensity focused ultrasound (HIFU), and other pulsed electric field ablation therapies. Such combination may condition the tissue for improved responsiveness and in some cases a synergistic response that is greater than either of the therapies alone. In addition, the PEF treatments described herein may lead to an abscopal effect due to the nature of the therapy.

It has been determined that the refined dose of specialized energy generates a treatment lesion that induces an immune response that is superior to conventional PEF treatments. When the energy is used to treat cancerous tumors, this immune response harnesses the body to further eliminate the cancerous cells such as residual cancer cells, metastatic cancer cells or later developing cancer cells. This has been studied in multiple murine models of cancer wherein the specialized PEF treatment elicits a tumor specific immune response. For example, data has been generated from a syngeneic, orthotopic model of triple-negative breast cancer (EMT6 Tumor) and a metastatic model of melanoma (B16-F10/B16-OVA Tumors). To understand the impact of this specialized PEF treatment on tumor suppression, a survival study was performed in EMT6 tumor bearing mice. Next, anti-tumor mechanisms were identified that are mediated by PEF to better describe the tumor suppression observed in the EMT6 model. Further, studies were performed to determine that the tumor antigen release induced by PEF was competent enough to drive a tumor specific T cell response.

Combination with Immunotherapy

In the last decade, a paradigm shift has occurred in the understanding of the relationship between the immune system, cancer development, and subsequent disease progression. Immunoevasion of malignant cells, escaping detection by the immune system, is now recognized as a cornerstone of tumor development. Tumors invoke a complex network of immune suppression, or immunological pressure, making it difficult for immune effectors to mount a meaningful anti-tumor response. Recently, a tremendous amount of research has investigated the immunosuppressive networks dictated by the tumor microenviroment (TME). One of the most important discoveries in oncology has been understanding the role of immune checkpoints in cancer. Immune checkpoints are inhibitory or stimulatory molecules present on the surface of T cells and antigen-presenting cells (APCs), whose direct interaction modulate the duration and response of a T cell against a foreign body. This is particularly important for maintaining self-tolerance, as it prevents T cells from damaging healthy tissues and creating an autoimmune response.

In the context of cancer, tumor cells may upregulate immune checkpoints to bind to partner receptors on T cells and evade detection. One such immune checkpoint, programmed cell death protein 1 (PD-1) and its ligand PD-L1, has been identified as a significant regulator of immune evasion in numerous cancers. PD1 is a transmembrane protein that is transcriptionally upregulated in activated T cells, B cells and myeloid cells. Therefore, activated T cells that are infiltrating a tumor by an inflammatory response of the immune system often express PD-1 on their surface.

PD-L1 is its ligand and it is found on some tumor cells, such as a variety of head and neck carcinomas, lung cancer and melanoma, to name a few. When PD-1 is bound to PD-L1, it prevents the T cells from killing the tumor cell, inducing T cell suppression upon their interaction. Specifically, the PD-1/PD-L1 interaction has been found to mediate T cell immune suppression through the following mechanisms: induce apoptosis in activated T cells, facilitate T cell anergy and exhaustion, enhance the immunosuppression of regulatory T cells (Tregs), limit T cell proliferation, and restrain T cell activation and production of interleukin-2 (IL-2).

Recently, antibodies targeting the PD-1/PD-L1 interaction (Nivolumab, Pembrolizumab, Atezolizumab, Durvalumab) have been FDA approved. For example, Nivolumab is a human immunoglobulin G4 (IgG4) monoclonal antibody that binds to the PD-1 receptor and blocks its interaction with PD-L1, releasing the PD-1 pathway-mediated inhibition of the immune response. This results in decreased tumor growth. Atezolizumab is a fully humanized, engineered monoclonal antibody of IgG1 isotype against PD-L1. Thus, Atezolizumab blocks the interaction of PD-L1 with PD-1. While promising, these drugs have limited efficacy as monotherapies. For example, in non-small-cell-lung-cancer (NSCLC), e.g. any type of epithelial lung cancer other than small cell lung cancer (SCLC), only 20% of patients achieve an objective clinical response to PD-1 blockade. Further, for the patients that do respond, the anti-tumor response is transient, as the tumor develops drug resistance. This low response rate is due to a combination of factors that include PD-L1 expression and the fraction of tumor immune cell infiltrate.

A tumor that is PD-L1 negative and has a low tumor immune cell infiltrate is known as a "cold" tumor. A tumor that is PD-L1 positive and has a high tumor immune cell infiltrate is known as a "hot" tumor. Patients that have cold tumors will be unresponsive to the checkpoint therapy because the PD-1/PD-L1 interaction that it is designed to inhibit is not present. Patients that have hot tumors, as mentioned in the latter, often develop resistance to the therapy over time. This is because the tumor cells that express PD-L1 are eliminated due to blocking of the interaction with PD-1. The remaining tumor cells are a more resistant cancer clone population which are left behind.

Therefore, improved treatments are desired, such as to increase the number of patients that are responsive to immunotherapy and to increase the clinical response of such patients. Such treatments should be safe, effective, and lead to improved outcomes. Combining immunotherapy with the specialized PEF energy described herein meets these objectives.

The devices, systems and methods described herein utilize specialized pulsed electric field energy to treat patients in a manner which utilizes aspects of the immune system, such as aspects of the immune checkpoint system. In some instances, improved outcomes in cancer immunotherapy patients are achieved, particularly for patients that have limited response to some immunotherapy treatments or acquired resistance over time. In some embodiments, the PD-1/PD-L1 interaction is targeted for treatment. In other instances, other pathways of the immune system are involved in the treatment, additionally or independent of PD-1/PD-L1.

Combination with Immunotherapy and Chemotherapy

Anti-PD1 and systemic chemotherapy, with or without resection, is the standard of care for many tumor types. However, many tumors do not respond to immunotherapy or the combination. Immune "cold" tumors may become immune "hot" under the influence of specialized pulsed electric field (PEF) therapy, inducing an adaptive immune response and an abscopal effect. The addition of chemotherapy has a synergistic effect that improves outcomes beyond any two therapy combination of specialized PEF therapy, checkpoint inhibitor therapy and chemotherapy. For example, the following study determines that adding specialized PEF to an anti-PD1 and cisplatin regimen improves outcomes in an immune cold tumor model.

Figure 31A:
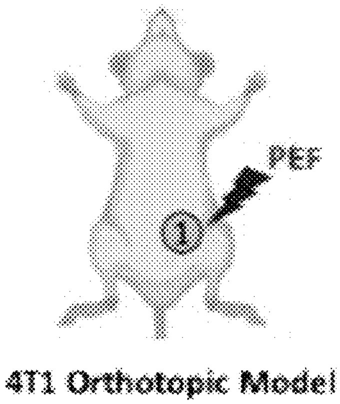
FIG. 31 illustrates a study design wherein anti-PD1 (200 μg, IP) and cisplatin (2 mg/kg, IV) were administered once weekly for eight weeks, starting on the PEF day.
Figure 31B:
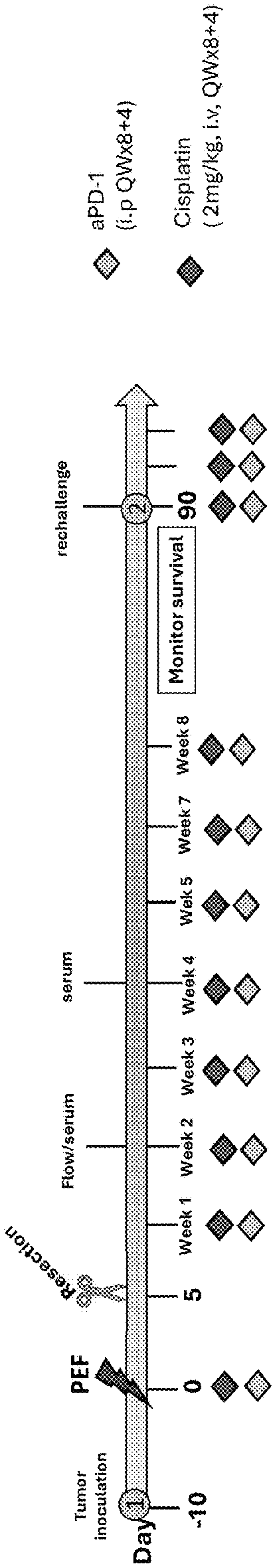

Methods:

Twenty female Balb/c mice were inoculated in the mammary fat pad with 200,000 4T1 cells, a highly aggressive syngeneic orthotopic triple negative breast cancer 4T1 mouse model that is non-responsive to anti-PD1 and only marginally responsive to cisplatin for each treatment group. Once tumors were established (5 mm diameter), animals were randomized to systemic-only Cisplatin+anti-PD1 (SOC) or PEF+Cisplatin+anti-PD1 (PEF+SOC) treatment groups. Anti-PD1 (200 μg, IP) and Cisplatin (2 mg/kg, IV) were administered once weekly for eight weeks, starting on the PEF day (FIGS. 31A-31B). Primary tumors were measured three times per week, while overall health, metastases, and survival of the mice was monitored until either death by natural causes or until tumor volume necessitated euthanasia ($\geq 2000\ mm^3$). Flow cytometry on blood collected at day 14 evaluated the systemic immune response.

Results

Figure 32A:
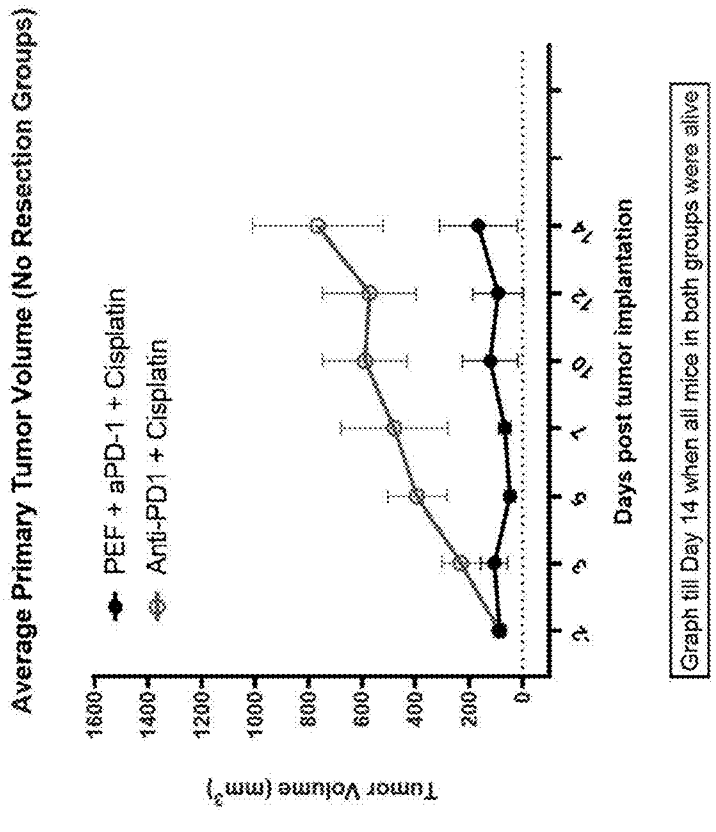
FIGS. 32A-32B illustrate that the addition of specialized PEF to the systemic therapy resulted in prolonged survival, with 44.4% of the specialized PEF-inclusive group surviving to Day 55, while all mice in the systemic-only therapy group were euthanized by day 24 due to large tumor size.
Figure 32B:
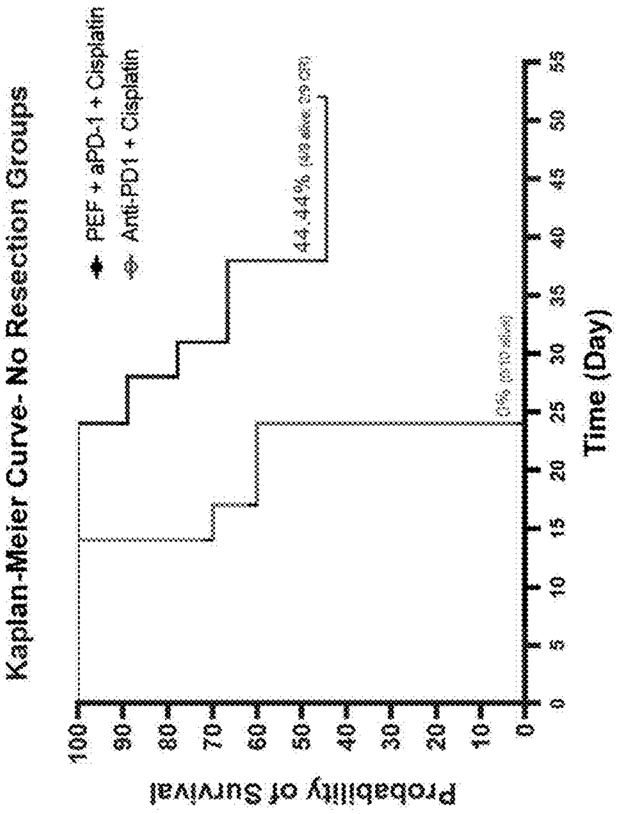
Figure 33A:
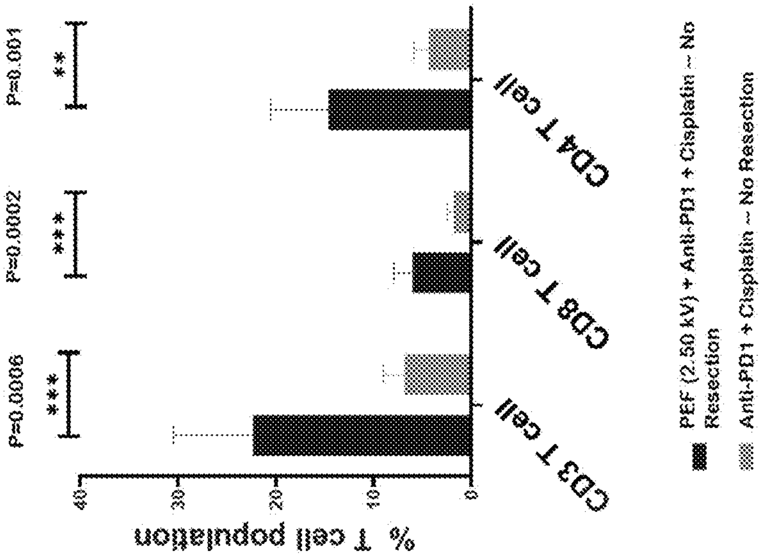
FIGS. 33A-33C illustrates that circulating immunocyte analysis at day 14 indicated markedly higher CD3, CD4, and CD8 T cells in the specialized PEF-inclusive group versus the systemic-only therapy group, with increases of 3.2× and significant increase of central memory t cell.
Figure 33B:
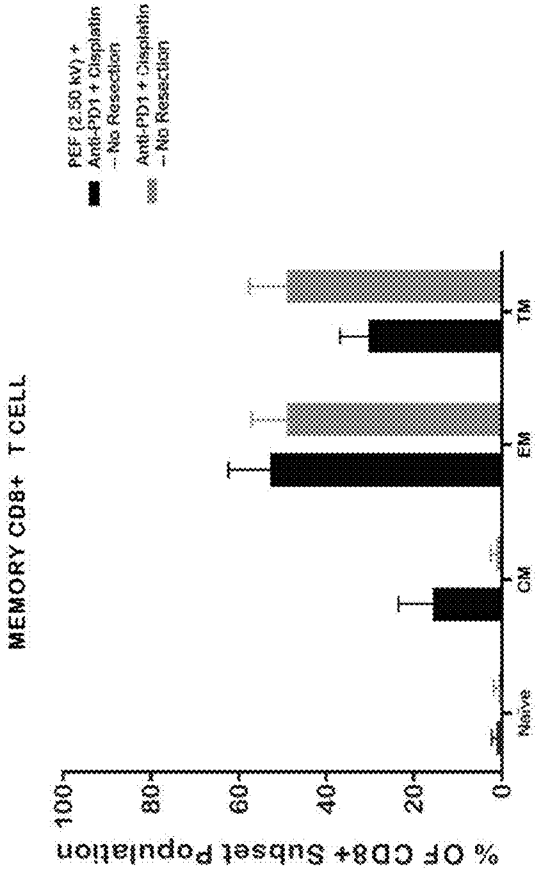
Figure 33C:
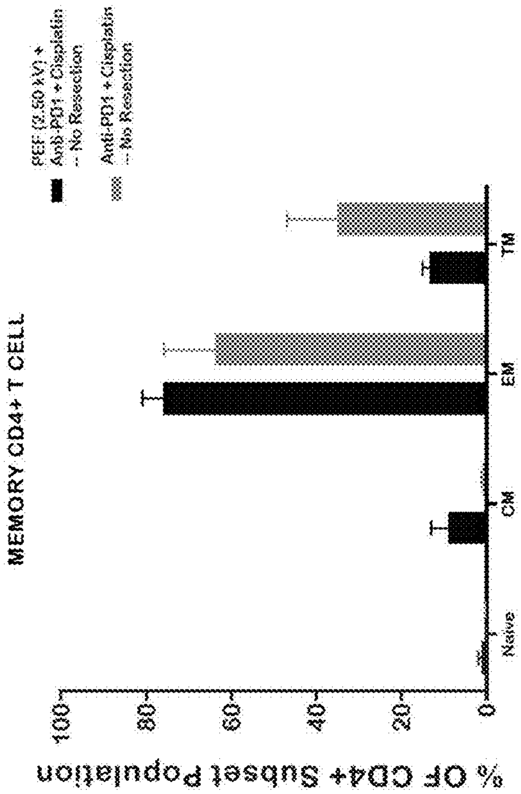
Figure 34A:
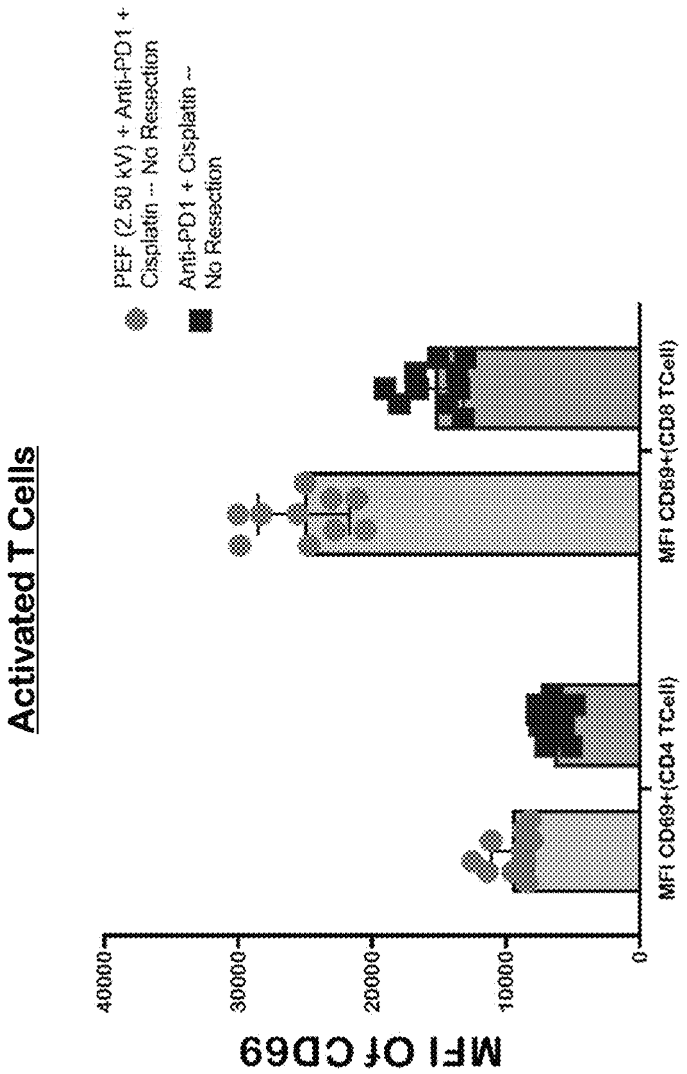
FIGS. 34A-34B illustrate that CD8 T-cells had increased CD69 MFI "activated" and reduced PD-1 "exhausted" T-cell markers in the specialized PEF-inclusive group versus systemic-only therapy group.
Figure 34B:
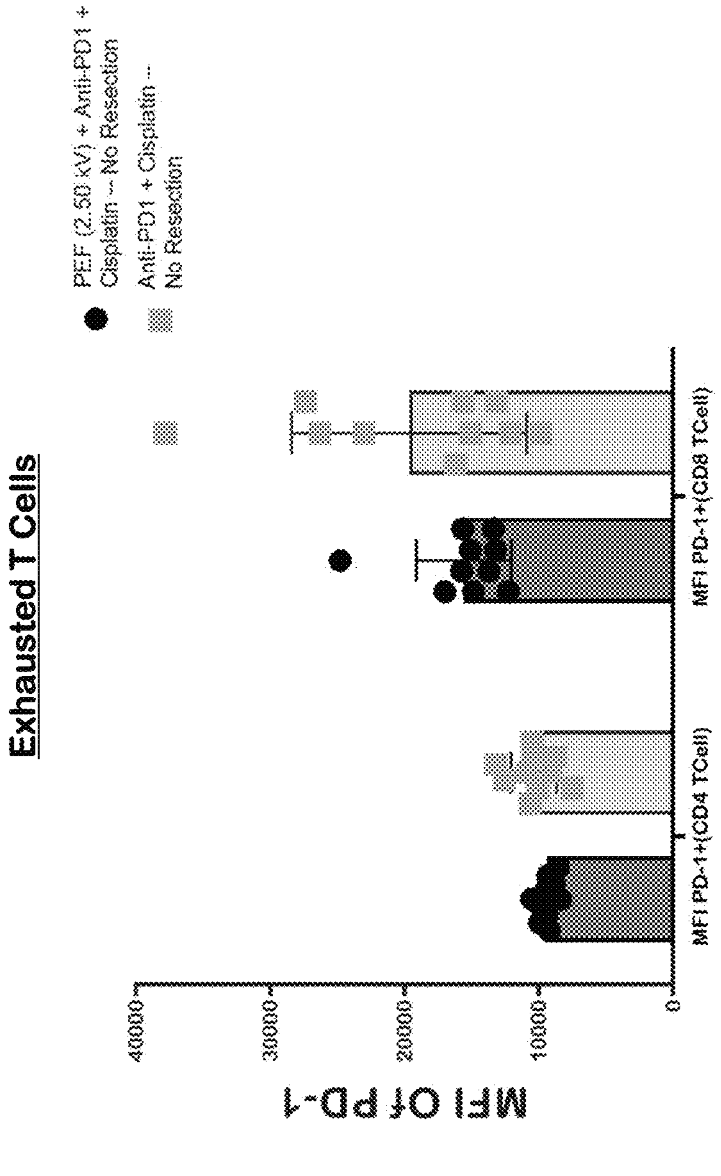

The addition of PEF to the systemic therapy resulted in prolonged survival, with 44.4% of the PEF-inclusive group surviving to Day 55, while all mice in the systemic-only therapy group were euthanized by day 24 due to large tumor size (FIGS. 32A-32B). The rank-log p-value for the Kaplan-Meier survival curve was statistically significant, P=0.0002. Circulating immunocyte analysis at day 14 indicated markedly higher CD3, CD4, and CD8 T cells in the PEF-inclusive group versus the systemic-only therapy group, with increases of 3.2× (FIG. 33A) and significant increase of central memory t cell (FIGS. 33B-33C). CD8 T-cells had increased CD69 MFI "activated" and reduced PD-1 "exhausted" T-cell markers in the PEF-inclusive group versus systemic-only therapy group (FIGS. 34A-34B).

Conclusions

Figure 35A:
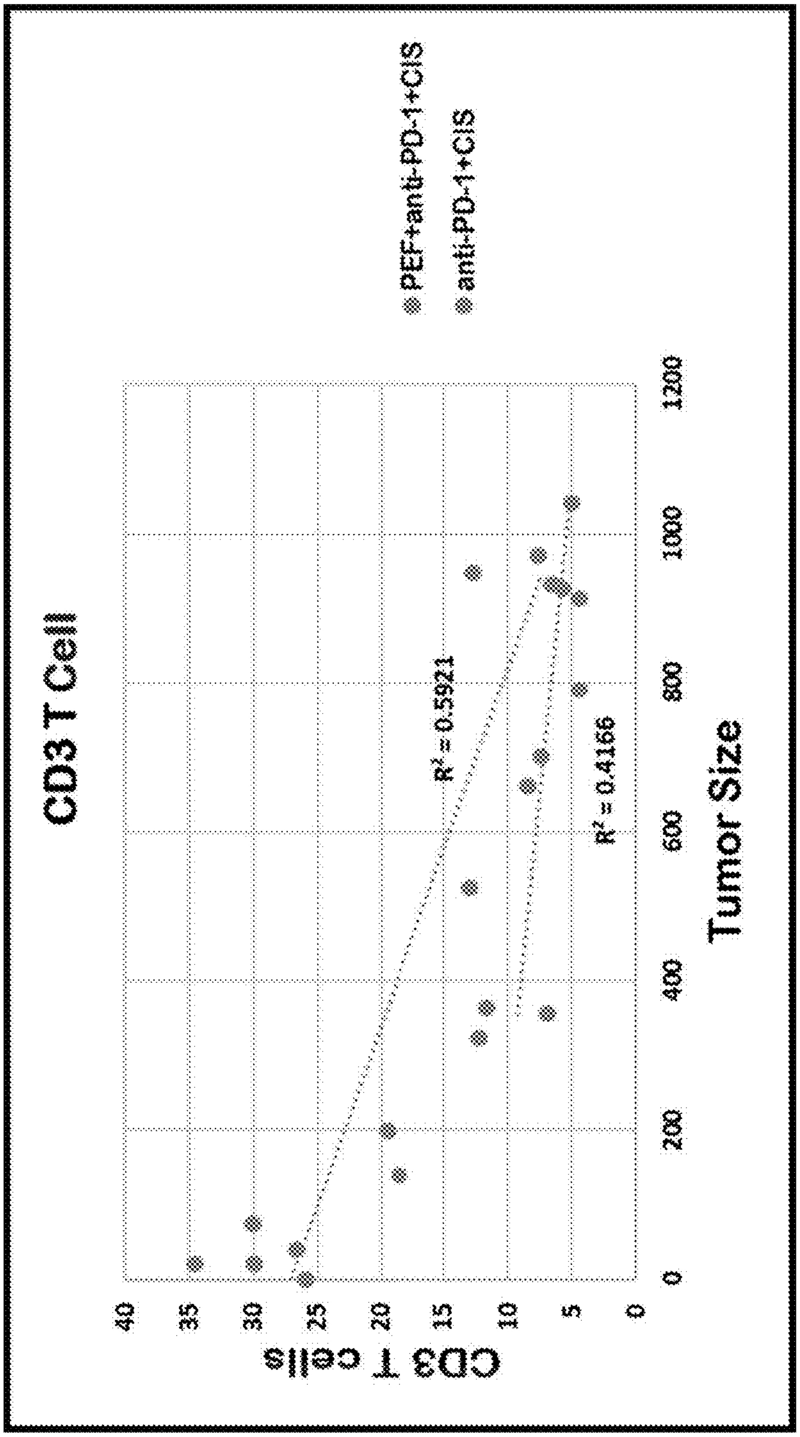
FIGS. 35A-35B illustrate that, in a murine model, adding specialized PEF to typical systemic therapy options increases circulating T-cells, with a direct correlation between immunocyte increases and primary tumor response.
Figure 35B:
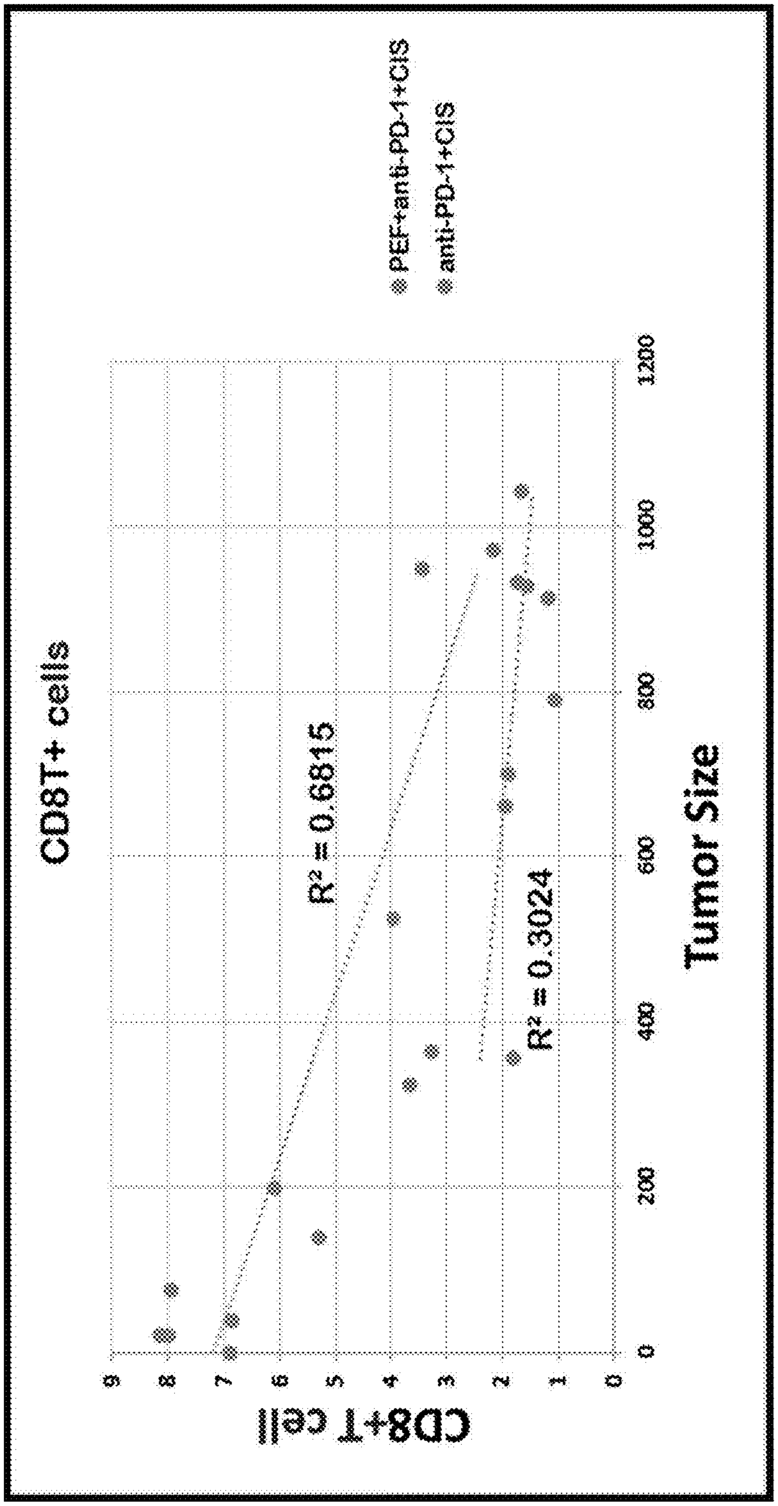

In a murine model, adding specialized PEF to typical systemic therapy options increases circulating T-cells, with a direct correlation between immunocyte increases and primary tumor response (FIGS. 35A-35B). Collectively, the results demonstrate that adding specialized PEF to anti-PD1 and Cisplatin therapy reduces tumor growth, prolongs survival, and activates an adaptive immune response in an immune "cold" tumor.

Figure 36:
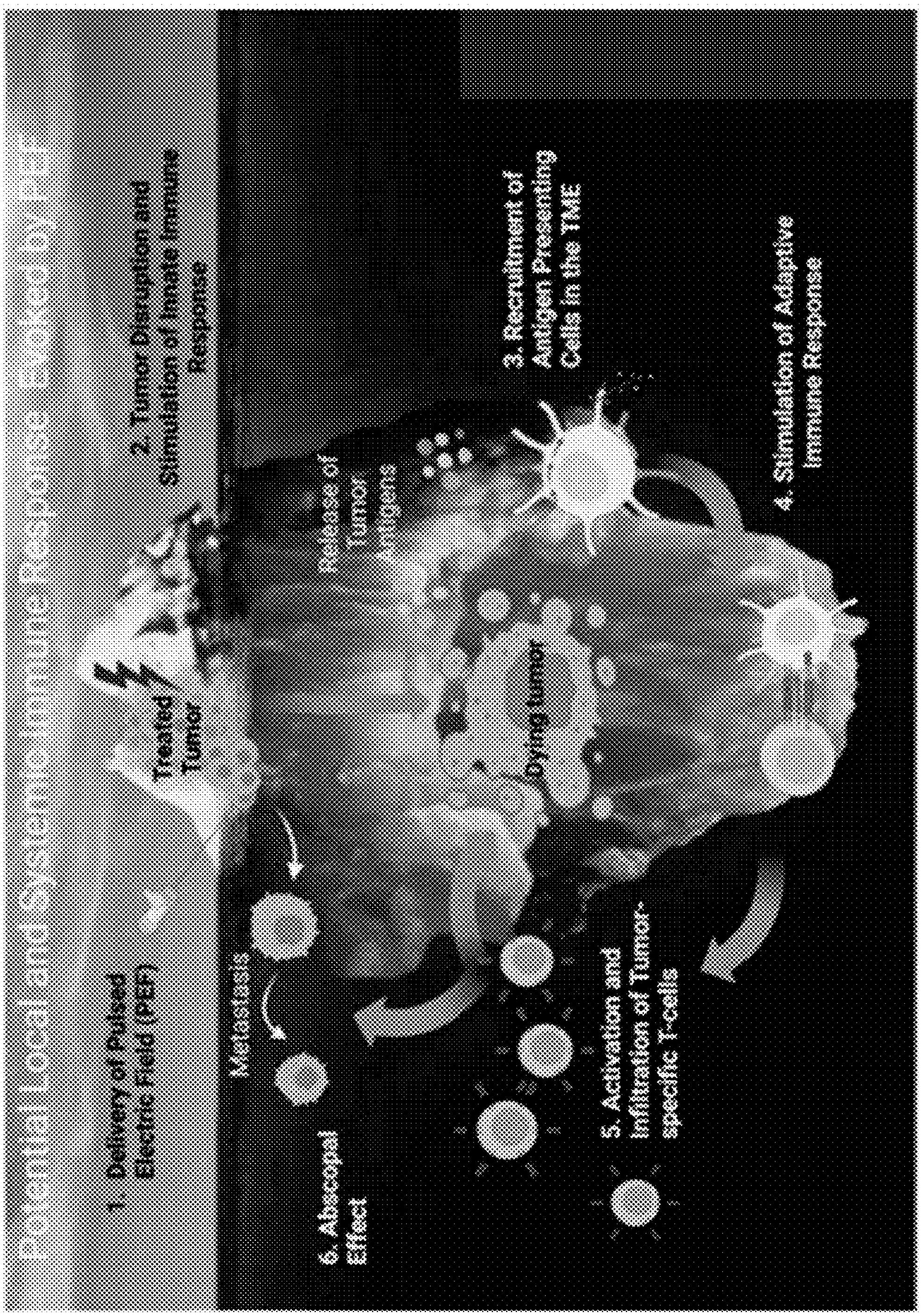
FIG. 36 illustrates local and systemic immune response evoked by specialized PEF.

As mentioned, PEF energy uses short duration, high voltage, electrical pulses to create an electric field that destabilizes cells through multiple biochemical processes. Because PEF does not rely on thermal changes to alter cells, it can be delivered to the target without damaging interstitial proteins. Also, specialized PEF induces immunogenic cell death. Its mechanism induces proinflammatory signaling as well as viable antigen presentation within the tumor microenvironment to promote a tumor-specific immune response (FIG. 36). As shown, the biologic activity of specialized PEF energy: a) Triggers immunogenic cell death (release of HMGB1); b) Releases tumor antigens to promote tumor-specific T-cell response; c) Recruits T-cells to tumors;

d) Alone and in combination with aPD-1 promotes abscopal effects on contralateral tumors.

Checkpoint blockade immunotherapy engages the immune system to attack the tumor and has transformed cancer treatment outcomes for select groups of patients with CPI-responsive tumors. However, "cold" tumors lacking T-cell infiltrates represent a therapeutic challenge for immunotherapy and concomitant therapies such as platinum-based chemotherapies are often included. Adding specialized PEF has the potential to further improve outcomes. The following preclinical study evaluated the management of metastatic burden (abscopal effect) obtained from the use of specialized PEF with inclusion of checkpoint inhibition (PD-1 blocking antibodies) and Cisplatin administration in a metastatic breast cancer mouse model (4T1).

Methods

Figure 39:
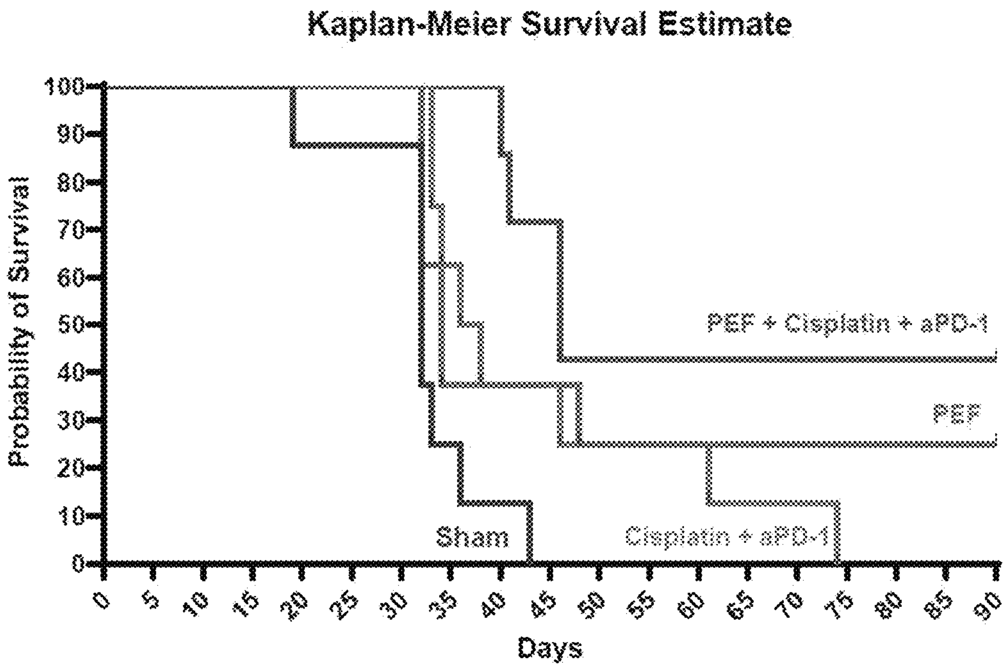
FIG. 39 illustrates a Kaplan-Meier survival curve.

Thirty-two (32) Balb/c mice were inoculated in the mammary fat pad with 200,000 4T1 cells, a highly metastatic breast cancer model of "cold" tumor that marginally responds to PD-1 blockade. Once reaching 5 mm in diameter, tumors were assigned to the following groups: (a) Sham/IgG control (n=8; needle inserted, no PEF energy delivered), (b) specialized PEF only (n=8), (c) Cisplatin+anti PD-1 (n=8) and (d) specialized PEF+Cisplatin+anti PD-1 (n=8). Tumors in the PEF groups (b, d) were treated with a single application of PEF delivered through a needle placed in the center of the tumor (FIGS. 37A-37B). PEF was administered only once (day 0) while Cisplatin and anti PD-1 were given on day 0, 7, 14 and 21. The graph of FIG. 38 shows the average tumor growth for each experimental group until the day of resection. PEF dosing was established to target approximately 80% of the tumor volume (FIG. 39). The tumor sizes were measured 3 times per week until the day of resection. All the tumors were resected when the volume reached 100-200 mm3 to recapitulate post-resection metastatic relapse. The Sham and aPD-1+Cisplatin groups underwent resection on day 5 post-treatment, the PEF and PEF+aPD-1+Cisplatin groups underwent resection on day 11 post-treatment (FIG. 37). Upon resection of the primary tumor the mice were monitored until spontaneous death or euthanasia due to extensive metastatic burden. The survival data were used to produce a Kaplan-Meier survival curve as illustrated in FIG. 39. At 90 days post-treatment, 23% of specialized PEF treated mice and 43% of specialized PEF+cis+aPD-1 were alive. The Log-Rank p-value of the curve was statistically significant (p=0.0038) between specialized PEF and specialized PEF+aPD-1+Cisplatin.

The monoclonal antibody targeting PD-1 (and the IgG non-targeting antibody) was administered once weekly (200 g, i.p) for four weeks, starting the day of PEF treatment (d=0). Cisplatin was administered (2 mg/kg, i.v) once weekly for four weeks starting on the day of PEF (d=0). Mice were followed until metastatic burden required euthanasia per IACUC guidelines. Tumors and lung samples were fixed in formalin and paraffin embedded for histology by hematoxylin & Eosin (H&E).

Figure 40A:
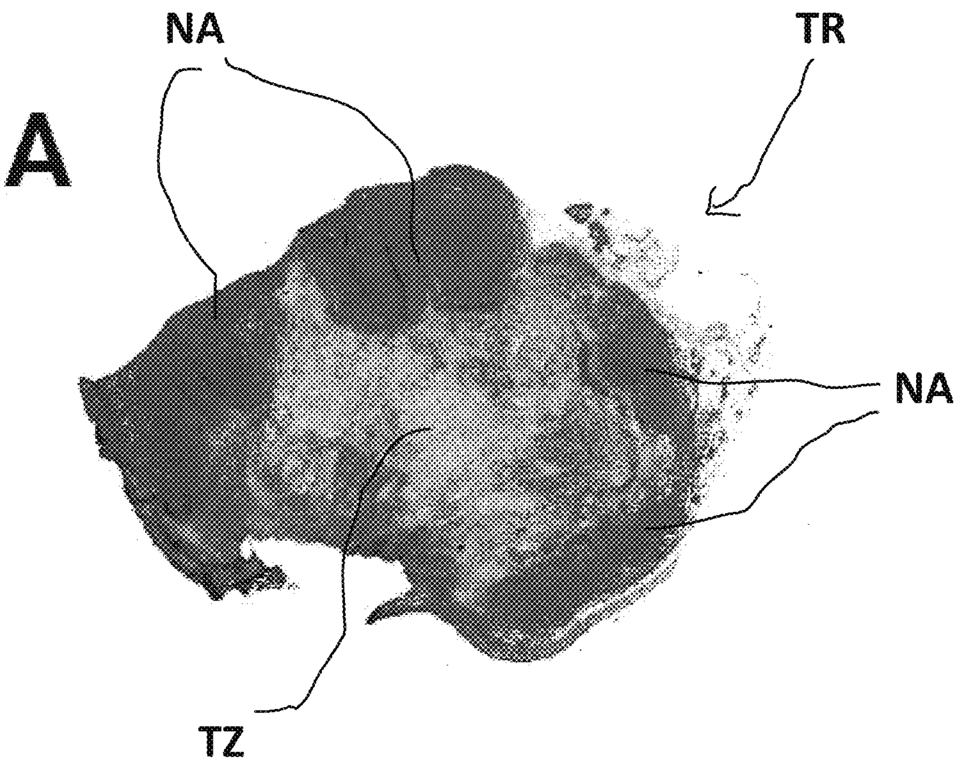
FIGS. 40A-40D show H&E staining of various tissues.
Figure 40B:
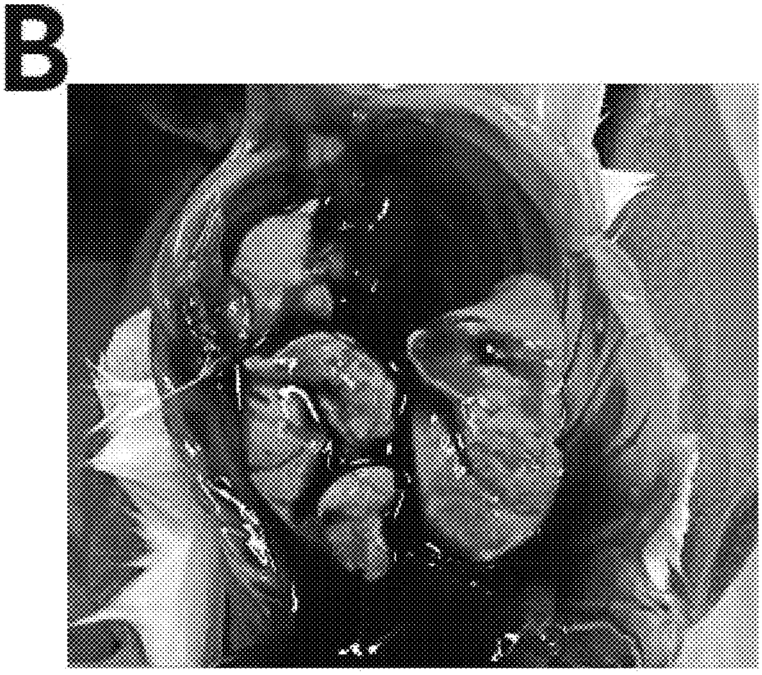
Figure 40C:
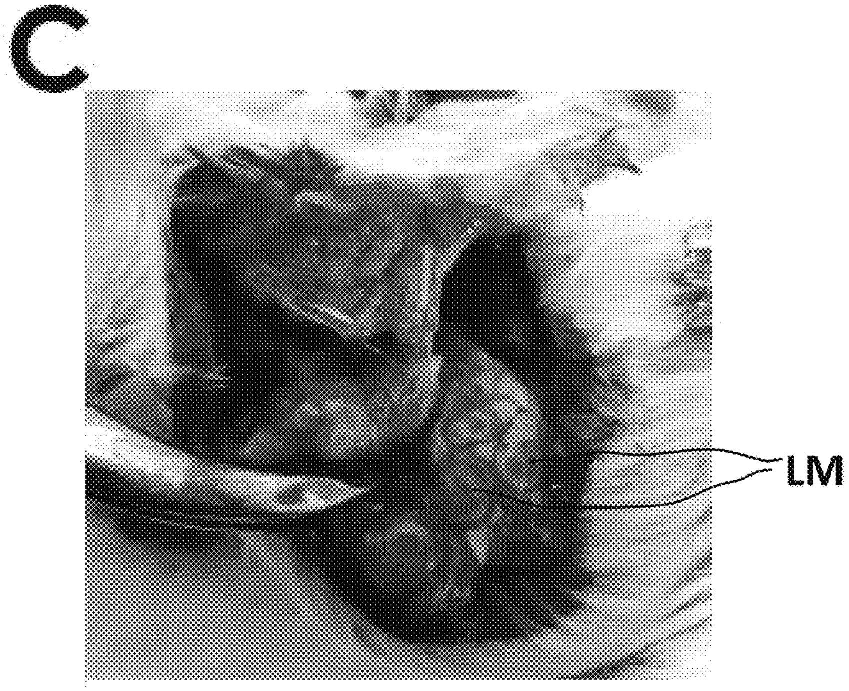
Figure 40D:
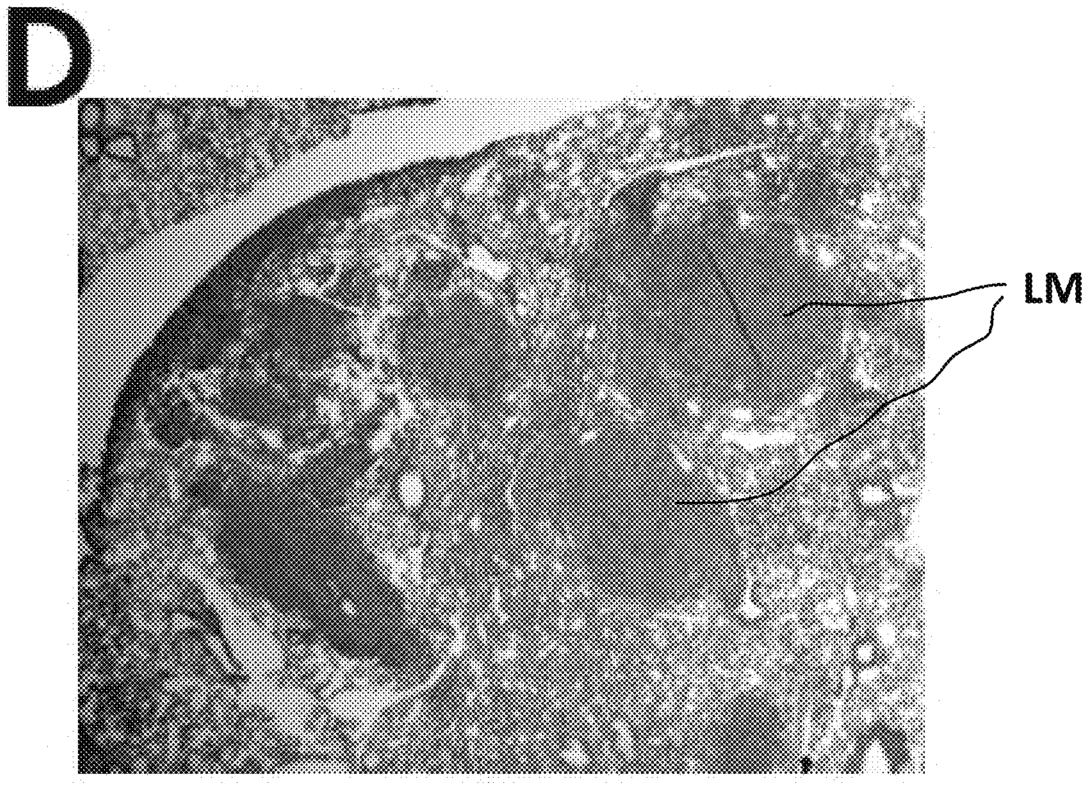

FIG. 40A shows H&E staining of a representative tumor TR harvested 3 days post PEF. The treated necrotic area NA (light grey) and untreated tumor zone TZ (dark grey) confirm the intentional subtotal ablation of the tumors with the given specialized PEF protocol. FIG. 40B shows that the absence of lung metastasis was confirmed in the mice that survived up to 90 days as a proof of abscopal effect that took place in PEF treated mice. The photo of FIG. 40C shows the extent of lung metastasis LM in a representative mouse that was euthanized from a Sham-treated group. FIG. 40D illustrates H&E staining of lungs collected from euthanized mice in Sham-treated group confirming the presence of extensive lung metastasis LM in lungs.

Results

Specialized PEF treatment strongly affected primary tumor growth compared to Sham and Cisplatin+aPD-1 treatment prior to resection (FIG. 38). Upon resection of the primary tumor the mice were monitored for health decline due to the development of micrometastases that left the primary tumor bed before surgery. Mice exhibiting significant health declines were euthanized. FIG. 40C shows the lung of a representative mouse that was euthanized due to metastatic burden. H&E staining conducted on lung samples of euthanized mice confirmed extensive metastases as shown in FIG. 40D. On the other end, FIG. 40B shows lungs free of metastases from a representative survivor mouse at the end of the study (day 90) from the specialized PEF treated groups. The Kaplan-Meier curve in FIG. 39 shows that all mice in the Sham/IgG group perished by day 43 due to metastasis affecting several organs including lungs, bones, liver and brain. All mice in the Cisplatin+anti PD-1 group perished by day 74. Within the specialized PEF-only and specialized PEF+anti PD-1+Cisplatin groups the survival at 90 days was 28% and 43%, respectively.

Conclusion

The addition of specialized PEF to a surrogate of standard of care regimen (Cisplatin+anti PD-1 followed by resection) resulted in a greater survival rate through 90 days in an immune-cold metastatic breast cancer mouse model.

XII. Conditioning

It may be appreciated that although the PEF ablation treatments provided by the systems 100 may be used as conditioning for other treatments, the target tissue cells may alternatively be conditioned prior to the PEF ablation treatments provided by the systems 100.

In some embodiments, cells targeted for treatment are conditioned so as to modify the behavior of the cells in response to the delivery of the energy signals. Such conditioning may occur prior to, during, or after delivery of the energy signals. In some embodiments, conditioning prior to energy delivery is considered pre-conditioning and conditioning after energy delivery is considered post-conditioning. Such differentiation is simply based on timing rather than on how the conditioning treatment affects the cells. In other embodiments, pre-conditioning relates to affecting what happens to the cells during energy delivery, such as how the cells uptake the energy, and post-conditioning relates to affecting what happens to the cells after energy delivery, such as how the cells behave after receiving the energy. Such differentiation may be less relevant to timing since in some instances conditioning may occur prior to energy delivery but only affect the cellular response following the energy delivery. Therefore, it may be appreciated that "conditioning" may be considered to apply to each of these situations unless otherwise noted.

Typically, conditioning is achieved by delivering a conditioning solution. In the case of intra-luminal therapy, the conditioning solution may be delivered via the luminal structure. The conditioning solution may alternatively or additionally be delivered via direct fluid injection of the conditioning solution into the targeted region, either from an endoluminal or other approach. In some embodiments, the conditioning solution selectively alters the electrical properties of the target cells, such as to affect the way the pulsed energy delivery gets distributed. In other embodiments, the conditioning solution influences the activity of the target cells. For example, in the lung such conditioning solution may promote basal cell differentiation into ciliated cells and/or downregulate goblet cells and submucosal gland cells. In other embodiments, the conditioning solution increases the likelihood of the target cells to expire following pulsed energy delivery. In still other embodiments, the conditioning solution alters the responses of non-targeted cells to the pulsed electric fields. In alternate embodiments, conditioning is performed via non-solution-based exposure of the tissues. This includes radiation therapy, radiotherapy, proton beam therapy, etc. In some embodiments, the conditioning will impact the enzymatic and energy-producing components of the cellular infrastructure.

The conditioning solution may be comprised of a variety of agents, such as drugs, genetic material, bioactive compounds, and antimicrobials, to name a few. For embodiments where the conditioning solution increases the likelihood of the target cells to expire following pulsed energy delivery, the conditioning solution may comprise chemotherapy drugs (e.g. cisplatin, doxorubicin, paclitaxel, bleomycin, carboplatin, etc), calcium, antibiotics, or toxins, to name a few. For embodiments where the conditioning solution alters the responses from non-targeted cells to the pulsed electric fields, the conditioning solution may comprise cytokines (e.g. immunostimulants, such as interleukins), genes, VEGF (e.g. to encourage more vessel growth into area), cellular differentiating factors (e.g. molecules to promote conversion of goblet cells into ciliated cells), and/or other small molecules that interact with cells, such as agonists and antagonists for receptors such as programmed death (PD-1) or programmed death ligand (PD-L1). Conditioning solutions may be delivered at the targeted site to directly interact at the site of PEF energy delivery. They may also be delivered systemically (e.g., intravenously, intraperitoneally) or regionally (e.g., intravenously to feeding arterial supplies for the targeted region, higher feeding airway generations, intraparenchymally to tissue around the tissue directly affected by the PEF treatment).

In some embodiments, the conditioning solution includes cells, such as stem cells, autograft cells, allograft cells or other cell types. In these embodiments, the cells may be used to alter the tissue response to the pulsed electric fields. In other embodiments, the cells may be used to repopulate the affected area with healthy or desirable cells. For example, once target cells have been weakened or killed by the delivered pulsed energy treatment, the cells from the conditioning solution may move into the vacancies, such as a decellularized extracellular matrix. In some embodiments, the area is washed out to remove the dead cells, such as with a mild detergent, surfactant or other solution, prior to delivery of the conditioning solution containing the new cells. In other embodiments, mechanical stimulation, such as suction, debriding, or ultrasonic hydrodissection, is used to physically remove the dead cells prior to delivery of the conditioning solution containing the new cells.

In some embodiments, the conditioning provided may invoke a targeted immune response. The immune response may result in a number of factors that alter the treatment effect outcome. This may result in an increase in the systemic immunity upregulation using specific markers associated with some targeted tissue, such as a tumor or bacteria or virus associated with an infection. It may also result in an upregulation of the innate immunity that broadly affects the immune system functionality to detect general abnormal cells, bacteria, or other infectious organisms residing within the body, which may occur locally, regionally, or systemically.

In some embodiments, the conditioning solution is warmed or chilled to alter how the target cells respond. Generally, warmed solutions promote increased treatment effects (e.g. increased susceptibility to cell death), while chilled solutions would reduce the extent of treatment effect or increase cell survival after exposure to a reversibly-designed protocol. In some embodiments, a chilled conditioning solution comprised of genes and or drugs is used to precondition cells to survive energy delivery treatment, increasing the number of cells that survive the treatment. In some embodiments, the effects of the warmed/chilled conditioning solution is compounded with the general effects caused by the other agents in the solution (e.g. warmed calcium solution, chilled gene containing solution). In other embodiments, the warmed/chilled conditioning solution does not provide effects other than temperature changes. In such embodiments, the conditioning solution is typically comprised of isotonic saline, phosphate buffered solution or other benign solution.

It may be appreciated that such heating or cooling may alternatively be achieved by other methods that do not involve delivery of a conditioning solution. For example, the target tissue may be heated or cooled by contacting the tissue with a warmed/cooled device, deliberately warming/cooling the pulsed electric field delivery catheter, delivering mild cryotherapy, or delivering mild radiofrequency or microwave energy. As previously described, this could promote enhanced lethality or permeability effects to the tissue or it could provide protective aspects to the cells that enable them to survive the procedure and exude the desired change as was targeted for them as a result of the therapy.

In some embodiments, a conditioning solution is delivered systemically, such as by intravenous injection, ingestion or other systemic methods. In other embodiments, the conditioning solution is delivered locally in the area of the targeted cells, such as through a delivery device or the instrument 102 itself.

It may be appreciated that although the examples described herein are in relation to tumors such as in the treatment of cancer, the devices, systems and methods are not so limited. For example, signaling regulated by the PD-1/PD-L pathway is also associated with substantial inflammatory effects that can resemble those in autoimmune responses, chronic infection, and sepsis, consistent with the role of this pathway in balancing protective immunity and immunopathology, as well as in homeostasis and tolerance. Therefore, the devices, systems and methods may be used to target this pathway in autoimmune and inflammatory disorders, chronic infections, and sepsis. Other conditions and disorders that may be treated include ischemia-reperfusion injury (IRI), stroke, Alzheimer's disease (AD), and pain due to the immunoregulatory role of the PD-1/PD-L pathway in these disorders. Similarly, post-stroke inflammation may be treated due to the involvement of the PD-1/PD-L.

As used herein, the terms "about" and/or "approximately" when used in conjunction with numerical values and/or ranges generally refer to those numerical values and/or ranges near to a recited numerical value and/or range. In some instances, the terms "about" and "approximately" can mean within ±10% of the recited value. For example, in some instances, "about 100 [units]" can mean within ±10% of 100 (e.g., from 90 to 110). The terms "about" and "approximately" can be used interchangeably.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of treating metastatic cancer in a subject in need thereof, the method comprising:

advancing a distal end of an instrument into a local treatment area comprising a tumor, wherein the instrument comprises an energy delivery body disposed at or near the distal end, the energy delivery body electrically coupled to a generator programmed with an energy delivery algorithm for delivering pulsed electric field (PEF) energy in packets comprising biphasic pulses; and destabilizing cancer cells of the tumor by delivering the PEF energy from the energy delivery body to the local treatment area comprising the tumor to induce immunogenic cell death of the cancer cells of the tumor in a non-thermal manner and further cause cancer shrinking in an untreated area of the subject, thereby treating the metastatic cancer.

2. The method of claim 1, wherein the induced cell death causes internal cellular components to be released, thereby exposing DNA and other cellular components of the cancer cells for identification by an immune system of the subject.

3. The method of claim 2, wherein the internal cellular components are released upon cell death.

4. The method of claim 2, wherein the internal cellular components are carried to a lymph system of the subject which assists in the identification.

5. The method of claim 1, wherein delivering the PEF energy generates a systemic immune response in the subject.

6. The method of claim 1, wherein delivering the PEF energy induces the cell death while maintaining non-cancerous, non-cellular elements in the local treatment area.

7. The method of claim 6, wherein the non-cancerous, non-cellular elements comprise collagen, elastin, and/or matrix proteins.

8. The method of claim 1, wherein delivering the PEF energy causes an abscopal effect in the subject.

9. The method of claim 1, wherein advancing the distal end of the instrument into the local treatment area comprises penetrating tissue.

10. The method of claim 1, further comprising advancing a percutaneous needle into the local treatment area, wherein advancing the distal end of the instrument comprises advancing the distal end of the instrument through the percutaneous needle.

11. The method of claim 1, wherein the energy delivery body comprises an electrode.

12. The method of claim 11, further comprising positioning a return electrode on the subject, wherein delivering the PEF energy comprises delivering the PEF energy in a monopolar fashion while utilizing the return electrode.

13. The method of claim 1, wherein advancing the distal end of the instrument comprises advancing the distal end of the instrument through an endoscope.

14. The method of claim 1, wherein the local treatment area is within a lung of the subject.

15. The method of claim 1, wherein advancing the distal end of the instrument comprises advancing the distal end of the instrument through a luminal structure.

16. The method of claim 15, wherein the PEF energy destroys at least some of the tumor while maintaining physiological function of the luminal structure.

17. The method of claim 15, wherein the luminal structure comprises a blood vessel, an esophagus, a stomach, a pancreatic duct, a biliary duct, a small intestine, a large intestine, a colon, a rectum, a bladder, a urethra, a urinary collecting duct, a uterus, a vagina, a fallopian tube, a ureter, a renal tubule, a spinal canal, a spinal cord, an airway, a nasal cavity, a mouth, a heart chamber, a heart lumen, a kidney lumen, or an organ lumen.

18. The method of claim 1, wherein cycles of the biphasic pulses are separated by a dead time so as to reduce biphasic cancellation.

19. The method of claim 18, wherein the dead time is up to 100 milliseconds.

20. The method of claim 1, wherein each packet is separated by a rest period in a range of 0.001 to 10 seconds.

21. The method of claim 1, wherein the biphasic pulses have a voltage in a range of 500 to 10,000 V.

22. The method of claim 1, wherein the biphasic pulses have a frequency in a range of 100 to 600 KHz.

23. The method of claim 1, wherein delivering the PEF energy alters a resting transmembrane potential (TMP) of the cancer cells.

24. The method of claim 1, wherein delivering the PEF energy comprises delivering the PEF energy in combination with additional therapy to administered before, during, or after delivering the PEF energy.

25. The method of claim 24, wherein the additional therapy comprises chemotherapy.

26. The method of claim 24, wherein the additional therapy comprises immunotherapy.

27. The method of claim 26, wherein the immunotherapy comprises a checkpoint inhibitor.

28. The method of claim 24, wherein the additional therapy comprises anti-PD1.

29. The method of claim 28, wherein the additional therapy further comprises cisplatin.

30. The method of claim 24, wherein the additional therapy comprises a conditioning solution comprising cytokines, genes, VEGF, cellular differentiating factors, agonists, or antagonists.

31. The method of claim 24, wherein the additional therapy comprises antibodies targeting PD-1/PD-L1 interaction.

32. The method of claim 24, wherein the additional therapy comprises surgical resection and/or debulking of the tumor.

33. The method of claim 1, wherein delivering the PEF energy induces the immunogenic cell death of the cancer cells to treat non-small cell lung cancer (NSCLC).

34. The method of claim 33, wherein delivering the PEF energy comprises delivering the PEF energy in combination with tyrosine kinase inhibitors (TKIs).

35. The method of claim 34, wherein the TKIs comprise epidermal growth factor receptor (EGFR) inhibitors.

36. The method of claim 1, wherein delivering the PEF energy is configured to cause immune system priming by a presence of antigenetic tumor cellular components.

37. The method of claim 1, wherein delivering the PEF energy induces the immunogenic cell death of the cancer cells by necroptosis and/or pyroptosis.

38. The method of claim 1, wherein delivering the PEF energy disrupts an immunosuppressive tumor immune microenvironment (TME).

39. The method of claim 1, wherein delivering the PEF energy causes tumor antigen release to promote a tumor-specific T-cell response.

40. The method of claim 1, wherein delivering the PEF energy causes release of HMGB1.

41. The method of claim 1, wherein delivering the PEF energy causes recruitment of T-cells to tumors.

* * * * *